(12) United States Patent
Jaminet et al.

(10) Patent No.: US 12,428,477 B2
(45) Date of Patent: *Sep. 30, 2025

(54) ANTIBODY-DRUG CONJUGATES COMPRISING ANTI-TM4SF1 ANTIBODIES AND METHODS OF USING THE SAME

(71) Applicant: ANGIEX, INC., Cambridge, MA (US)

(72) Inventors: Paul A. Jaminet, Sudbury, MA (US); Shou-Ching S. Jaminet, Sudbury, MA (US); Edward H. Ha, Cambridge, MA (US); Leonard G. Presta, San Francisco, CA (US); Manish S. Hudlikar, Brookline, MA (US)

(73) Assignee: ANGIEX, INC., Cambridge, MA (US)

( * ) Notice: Subject to any disclaimer, the term of this patent is extended or adjusted under 35 U.S.C. 154(b) by 878 days.

This patent is subject to a terminal disclaimer.

(21) Appl. No.: 17/434,315

(22) PCT Filed: Feb. 27, 2020

(86) PCT No.: PCT/US2020/020207
§ 371 (c)(1),
(2) Date: Aug. 26, 2021

(87) PCT Pub. No.: WO2020/176794
PCT Pub. Date: Sep. 3, 2020

(65) Prior Publication Data
US 2023/0096824 A1 Mar. 30, 2023

Related U.S. Application Data

(60) Provisional application No. 62/811,411, filed on Feb. 27, 2019, provisional application No. 62/967,377, filed on Jan. 29, 2020.

(51) Int. Cl.
*C07K 16/28* (2006.01)
*A61K 39/00* (2006.01)
*A61K 47/68* (2017.01)

(52) U.S. Cl.
CPC ........ *C07K 16/28* (2013.01); *A61K 47/68033* (2023.08); *A61K 47/6849* (2017.08); *A61K 2039/505* (2013.01); *C07K 2317/21* (2013.01); *C07K 2317/52* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,225,539 A | 7/1993 | Winter |
| 5,500,362 A | 3/1996 | Robinson et al. |
| 5,530,101 A | 6/1996 | Queen et al. |
| 5,565,332 A | 10/1996 | Hoogenboom et al. |
| 5,571,894 A | 11/1996 | Wels et al. |
| 5,585,089 A | 12/1996 | Queen et al. |
| 5,587,458 A | 12/1996 | King et al. |
| 5,624,821 A | 4/1997 | Winter et al. |
| 5,648,260 A | 7/1997 | Winter et al. |
| 5,693,761 A | 12/1997 | Queen et al. |
| 5,693,762 A | 12/1997 | Queen et al. |
| 5,821,337 A | 10/1998 | Carter et al. |
| 5,869,046 A | 2/1999 | Presta et al. |
| 6,180,370 B1 | 1/2001 | Queen et al. |
| 6,194,551 B1 | 2/2001 | Idusogie et al. |
| 6,737,056 B1 | 5/2004 | Presta |
| 6,982,321 B2 | 1/2006 | Winter |
| 7,087,409 B2 | 8/2006 | Barbas, III et al. |
| 7,332,581 B2 | 2/2008 | Presta |
| 7,361,740 B2 | 4/2008 | Hinton et al. |
| 7,371,826 B2 | 5/2008 | Presta |
| 7,527,791 B2 | 5/2009 | Adams et al. |
| 8,088,387 B2 | 1/2012 | Steeves et al. |
| 8,163,888 B2 | 4/2012 | Steeves et al. |
| 8,198,417 B2 | 6/2012 | Steeves et al. |
| 8,969,526 B2 | 3/2015 | Baehner et al. |
| 9,803,023 B2 | 10/2017 | Chamberlain et al. |
| 10,155,812 B2 * | 12/2018 | Jaminet .................. C07K 16/28 |
| 10,745,479 B2 * | 8/2020 | Chun .................. C23C 18/1651 |
| 10,844,135 B2 | 11/2020 | Chari et al. |
| 11,208,495 B2 * | 12/2021 | Jaminet .................. A61P 35/04 |
| 2004/0214872 A1 | 10/2004 | Suto et al. |
| 2005/0014934 A1 | 1/2005 | Hinton et al. |
| 2005/0054832 A1 | 3/2005 | Lazar et al. |
| 2009/0136494 A1 | 5/2009 | Ponath et al. |
| 2012/0004117 A1 | 1/2012 | Aburatani et al. |
| 2012/0070379 A1 | 3/2012 | Black et al. |

(Continued)

FOREIGN PATENT DOCUMENTS

| | | |
|---|---|---|
| EP | 0239400 B1 | 8/1994 |
| EP | 0592106 B1 | 11/2004 |

(Continued)

OTHER PUBLICATIONS

Rudikoff et al., PNAS 79: 1979-1983 (Year: 1982).*

(Continued)

*Primary Examiner* — Phuong Huynh
(74) *Attorney, Agent, or Firm* — Wilson Sonsini Goodrich & Rosati

(57) ABSTRACT

Antibody-drug conjugates (ADCs) are described, comprising anti-TM4SF1 antibodies, and antigen-binding fragments thereof. Methods of use of said ADCs are also described.

7 Claims, 7 Drawing Sheets

Specification includes a Sequence Listing.

(56) References Cited

U.S. PATENT DOCUMENTS

| | | | |
|---|---|---|---|
| 2012/0213705 A1* | 8/2012 | Dimasi | A61P 37/02 |
| | | | 435/69.6 |
| 2014/0170140 A1 | 6/2014 | Bennett et al. | |
| 2016/0102135 A1 | 4/2016 | Escobar-Cabrera | |
| 2016/0229910 A1 | 8/2016 | Jaminet et al. | |
| 2017/0216452 A1 | 8/2017 | Ma et al. | |
| 2018/0043033 A1* | 2/2018 | Anderl | C07K 16/30 |
| 2020/0268713 A1 | 8/2020 | Hutchinson et al. | |
| 2021/0260209 A1 | 8/2021 | Jaminet et al. | |
| 2022/0153860 A1 | 5/2022 | Jaminet et al. | |
| 2022/0267461 A1 | 8/2022 | Jaminet et al. | |
| 2023/0126271 A1 | 4/2023 | Jaminet et al. | |
| 2023/0293713 A1 | 9/2023 | Jaminet et al. | |
| 2023/0338572 A1 | 10/2023 | Jaminet et al. | |
| 2023/0372518 A1 | 11/2023 | Jaminet et al. | |

FOREIGN PATENT DOCUMENTS

| | | | |
|---|---|---|---|
| EP | 0519596 B1 | 2/2005 | |
| EP | 2235059 B1 | 2/2015 | |
| JP | 2011501945 A | 1/2011 | |
| JP | 2011507963 A | 3/2011 | |
| JP | 2014533659 A | 12/2014 | |
| JP | 2016520598 A | 7/2016 | |
| WO | WO-8807089 A1 | 9/1988 | |
| WO | WO-9109967 A1 | 7/1991 | |
| WO | WO-9209690 A2 | 6/1992 | |
| WO | WO-9316185 A1 | 8/1993 | |
| WO | WO-9429351 A2 | 12/1994 | |
| WO | WO-9951642 A1 | 10/1999 | |
| WO | WO-2004056312 A2 | 7/2004 | |
| WO | WO-2005100402 A1 | 10/2005 | |
| WO | WO-2006029879 A2 | 3/2006 | |
| WO | WO-2007059312 A2 | 5/2007 | |
| WO | WO-2007070659 A2 | 6/2007 | |
| WO | WO-2007079130 A2 | 7/2007 | |
| WO | WO-2007094916 A2 | 8/2007 | |
| WO | WO-2008077079 A1 | 6/2008 | |
| WO | WO-2008083346 A1 | 7/2008 | |
| WO | WO-2009086320 A1 | 7/2009 | |
| WO | WO-2009100309 A3 | 12/2009 | |
| WO | WO-2010037062 A1 | 4/2010 | |
| WO | WO-2011028195 A2 | 3/2011 | |
| WO | WO-2012166559 A1 | 12/2012 | |
| WO | WO-2012166560 A1 | 12/2012 | |
| WO | WO-2014190441 A1 | 12/2014 | |
| WO | WO-2015054427 A1 * | 4/2015 | A61K 47/6849 |
| WO | WO-2015184099 A1 | 12/2015 | |
| WO | WO-2019046338 A1 | 3/2019 | |
| WO | WO-2019241430 A2 | 12/2019 | |

OTHER PUBLICATIONS

Wu et al., J. Mol. Biol. 294: 151-162 (Year: 1999).*
Strop et al., Chemistry and Biology 20: 161-167 (Year: 2013).*
Grevys et al., J Immunology 194: 5497-5508, (Year: 2015).*
Piche-Nicholas et al., MABS 10(1): 81-94 (Year: 2018).*
Extended European Search Report for EP Patent Application No. 20762413.1 dated Feb. 21, 2023.
Oganesyan et al.: Structural characterization of a human Fc fragment engineered for extended serum half-life. Molecular Immunology. 46(8-9): 1750-1755 (2009).
Rahim et al.: Three Members of Transmembrane-4-Superfamily, TM4SF1, TM4SF4, and TM4SF5, as Emerging Anticancer Molecular Targets against Cancer Phenotypes and Chemoresistance. Pharmaceuticals. 16(110):1-27 (2023).
U.S. Appl. No. 17/532,660 Final Office Action dated Nov. 30, 2023.
U.S. Appl. No. 17/532,660 Office Action dated Jun. 26, 2023.
U.S. Appl. No. 17/532,664 Office Action dated Aug. 18, 2023.
U.S. Appl. No. 17/532,664 Restriction Requirement dated May 15, 2023.
U.S. Appl. No. 17/532,665 Final Office Action dated Jan. 22, 2024.

Yu et al.: Safety, Tolerability, and Pharmacokinetics of MEDI4893, an Investigational, Extended-Half-Life, Anti-Staphylococcus aureus Alpha-Toxin Human Monoclonal Antibody, in Healthy Adults. Antimicrobial Agents and Chemotherapy. 61(1):e01020-16 (2017).
Agard NJ, Bertozzi CR. Chemical approaches to perturb, profile, and perceive glycans. Acc Chem Res. Jun. 16, 2009;42(6):788-97.
Almagro et al. Humanization of antibodies. Front Biosci 13:1619-1633 (2008).
Altschul et al., Gapped BLAST and PSI-BLAST: a new generation of protein database search programs. Nucleic Acids Res. 25(17) 3389-3402 (1997).
An Z. et al. IgG2m4, an engineered antibody isotype with reduced Fc function. MAbs. Nov.-Dec. 2009; 1(6):572-9.
Angal, et al. A single amino acid substitution abolishes the heterogeneity of chimeric mouse/human (IgG4) antibody.Mol Immunol. Jan. 1993;30(1):105-108.
Baca et al. Antibody humanization using monovalent phage display. J Biol Chem 272(16):10678-10684 (1997).
Bass, et al. Hormone phage: an enrichment method for variant proteins with altered binding properties. Proteins. 1990;8(4):309-314.
Boeggeman E. et al. Direct identification of nonreducing GlcNAc residues on N-glycans of glycoproteins using a novel chemoenzymatic method. Bioconjug Chem. May-Jun. 2007;18(3):806-14.
Brennan et al. Preparation of bispecific antibodies by chemical recombination of monoclonal immunoglobulin fragments. Science 229:81-83 (1985).
Brodeur, et al. In: Monoclonal Antibody Production Techniques and Applications. New York: Marcel Dekker; 1987:51-63.
Brown et al. Tolerance of single, but not multiple, amino acid replacements in antibody Vh Cdr 2: a means of minimizing B cell wastage from somatic hypermutation? J Immunol 156(9):3285-3291 (1996).
Bruggemann, M., et al., Comparison of the Effector Functions of Human Immunoglobulins Using a Matched Set of Chimeric Antibodies, J. Exp. Med. 166 (1987) 1351-1361).
Campbell CT. et al. Metabolic oligosaccharide engineering: perspectives, applications, and future directions. Mol Biosyst. Mar. 2007;3(3):187-94.
Canfield, et al. The binding affinity of human IgG for its high affinity Fc receptor is determined by multiple amino acids in the CH2 domain and is modulated by the hinge region. Exp Med. Jun. 1, 1991;173(6):1483-91.
Carter et al., Bio/Technology 10: 163-167 (1992).
Carter et al. Humanization of an anti-p185HER2 antibody for human cancer therapy. Pnas USA 89(10):4285-4289 (1992).
Chang et al., CD13 (Aminopeptidase N) Can Associate With Tumor-Associated Antigen L6 and Enhance the Motility of Human Lung Cancer Cells, Int J Cancer. 1 16: 243-252, 2005.
Chappel et al. Identification of the Fcγ receptor class I binding site in human IgG through the use of recombinant IgG1/IgG2 hybrid and point-mutated antibodies, PNAS, Oct. 1991, 88:9036-9040.
Chaudhary, V.K., et al., A Rapid Method of Cloning Functional Variable-Region Antibody Genes in Escherichia coli as Single-Chain Immunotoxins, 1990 Proc. Natl. Acad. Sci. USA 87:1066.
Chen, et al. Selection and analysis of an optimized anti-VEGF antibody: crystal structure of an affinity-matured Fab in complex with antigen. J Mol Biol. Nov. 5, 1999;293(4):865-81.
Chothia et al. Canonical structures for the hypervariable regions of immunoglobulins. J Mol Biol 196:901-917 (1987).
Chothia, et al. Conformations of immunoglobulin hypervariable regions. Nature 342(6252):877-83 (1989).
"Sciuto et al., Intracellular distribution of TM4SF1 and internalization of TM4SF1-antibody complex in vascular endothelial cells Biochem Biophys Res Commun, vol. 465, pp. 338-343 (2015)."
Clark, et al. Direct in-gel fluorescence detection and cellular imaging of O-GlcNAc-modified proteins. J Am Chem Soc. Sep. 3, 2008;130(35):11576-11577. doi: 10.1021/ja8030467. Epub Aug. 7, 2008.
Clynes, et al. Fc receptors are required in passive and active immunity to melanoma. Proc Natl Acad Sci U S A. Jan. 20, 1998;95(2):652-6.

(56) References Cited

OTHER PUBLICATIONS

Cragg, et al. Complement-mediated lysis by anti-CD20 mAb correlates with segregation into lipid rafts. Blood. Feb. 1, 2003;101(3):1045-1052.

Cragg, M. S, and M. J. Glennie, Antibody specificity controls in vivo effector mechanisms of aniti-CD20 reagents, Blood 103:2738-2743 (2004).

Dall'Acqua WF. et al. Properties of human IgG1s engineered for enhanced binding to the neonatal Fc receptor (FcRn). J Biol Chem. Aug. 18, 2006;281(33):23514-24.

Dall'Acqua, et al. Antibody humanization by framework shuffling. Methods. May 2005;36(1):43-60.

Duncan and Winter, The binding site for Clq and IgG. Nature, 322:738-40, 1988.

Edwards, C P et al., "Cloning of the Murine Counterpart of the Tumor-Associated Antigen H-L6: Epitope Mapping of the Human and Murine L6 Antigens", Biochemistry, vol. 34, Jan. 1, 1995, pp. 12653-12660.

"Extended European search Report for corresponding EP Application No. 18849908.1 issued Apr. 28, 2021".

"Fell, H P et al., "Chimeric L6 antitumore antibody", Journal of Biological Chemistry, american Society for Biochesmistry and Molecular Biology, vo. 267, No. 22, Aug. 5, 1992, pp. 15552-15558".

Gazzano-Santoro et al. A non-radioactive complement-dependent cytotoxicity assay for anti-CD20 monoclonal antibody. J Immunol Methods 202(2):163-171 (Mar. 28, 1997).

Geuijen et al. Affinity ranking of antibodies using flow cytometry: application in antibody phage display-based target discovery. Journal of Immunological Methods 302(1): 68-77 (2005).

Goding J. Production of monoclonal antibodies. In: Monoclonal Antibodies: Principles and Practice. London; New York: Academic Press; 1986:59-103.

Griffiths et al. Human anti-self antibodies with high specificity from phage display libraries. Embo J. 12(2):725-734 (1993).

Grimm HP. Gaining insights into the consequences of target-mediated drug disposition of monoclonal antibodies using quasi-steady-state approximations. J Pharmacokinet Pharmacodyn. Oct. 2009;36(5):407-20.

Grisham R. et al. Clinical trial experience with CA4P anticancer therapy: focus on efficacy, cardiovascular adverse events, and hypertension management. Gynecol Oncol Res Pract. Jan. 5, 2018;5:1.

Guex and Peitsch, Swiss-Model and the Swiss-PdbViewer: An environment for comparative protein modeling, 1997, Electrophoresis 18:2714-23.

Guyer, et al. Immunoglobulin binding by mouse intestinal epithelial cell receptors. J Immunol. Aug. 1976;117(2):587-593.

Hamblett KJ. et al. Altering Antibody-Drug Conjugate Binding to the Neonatal Fc Receptor Impacts Efficacy and Tolerability. Mol Pharm. Jul. 5, 2016;13(7):2387-96.

"Hellstrom, I et al., "Antitumor effects of L6, and IgG2a antibody that reacts with most human carcinomas", Proceedings of the National Academy of Sciences, National Academy of Sciences, US, Vo. 83, No. 18, Sep. 1, 1986, pp. 7059-7063".

Hellstrom, I, et al. "Monoclonal Mouse Antibodies Raised Against Human Lung Carcinoma", Cancer Research, Vo. 46, No. 8, Aug. 1, 1986, pp. 3917-3923.

Hellstrom, I., et al., Strong antitumor activities of IgG3 antibodies to a human melanoma- associated ganglioside, Proc. Nat'l Acad. Sci. USA 82 (1985) 1499-1502.

Hezareh M. et al. Effector function activities of a panel of mutants of a broadly neutralizing antibody against human immunodeficiency virus type 1. J Virol. Dec. 2001;75(24):12161-8.

Hinton, et al. Engineered human IgG antibodies with longer serum half-lives in primates. J Biol Chem. Feb. 20, 2004;279(8):6213-6. Epub Dec. 29, 2003.

Hinton PR. et al. An engineered human IgG1 antibody with longer serum half-life. J Immunol. Jan. 1, 2006;176(1):346-56.

Honegger et al.: Yet another numbering scheme for immunoglobulin variable domains: an automatic modeling and analysis tool. J Mol Biol 309(3):657-70 (2001).

Hoogenboom, et al. By-passing immunisation. Human antibodies from synthetic repertoires of germline VH gene segments rearranged in vitro. J Mol Biol. Sep. 20, 1992;227(2):381-8.

Idusogie, et al. Mapping of the C1q binding site on rituxan, a chimeric antibody with a human IgG1 Fc. J Immunol. Apr. 15, 2000;164(8):4178-84.

Idusogie, et al. Mapping of the C1q binding site on rituxan, a chimeric antibody with a human lgG1 Fc. J Immunol. Apr. 1, 20005;164(8):4178-84.

Jones, et al. Replacing the complementarity-determining regions in a human antibody with those from a mouse. Nature. May 29-Jun 4, 1986;321(6069):522-5.

Karlin, S. et al., "Applications and statistics for multiple high-scoring segments in molecular sequences", PNAS, 1993, vol. 90, pp. 5873-5877.

Kashmiri et al., SDR grafting—a new approach to antibody humanization, Methods vol. 36, No. 1, pp. 25-34, May 2005.

Khanna and Hunter, Modeling Metastais In Vivo, Carcinogenesis, Mar. 205:26(3):513-23.

Khidekel, et al. A Chemoenzymatic Approach toward the Rapid and Sensitive Detection of O-GlcNAc Posttranslational Modifications. J. Am. Chem. Soc. 2003; 125(52):16162-16163.

Kida S. et al., Studies on heterobifunctional cross-linking reagents, 6-maleimidohexanoic acid active esters. Chem Pharm Bull (Tokyo). Apr. 2007;55(4):685-7.

Klimka et al., Human anti-CD30 recombinant antibodies by guided phage antibody selection using cell panning, Br. J. Cancer, 83:252-260 (2000).

Kohler and Milstein, "Continuous cultures of fused cells secreting antibody of predefined specificity", Nature, Aug. 7, 1975;256(5517):495-7.

Kozbor, A human hybrid myeloma for production of human monoclonal antibodies, 1984, Immunol. 133:3001-05.

Lai AC, Crews CM. Induced protein degradation: an emerging drug discovery paradigm. Nat Rev Drug Discov. Feb. 2017; 16(2):101-114. doi: 10.1038/nrd.2016.211. Epub Nov. 25, 2016.

Le Gall et al. Immunosuppressive properties of anti-CD3 single-chain Fv and diabody. J Immunol Methods 285(1):111-127 (2004).

Levengood MR et al. Orthogonal Cysteine Protection Enables Homogeneous Multi-Drug Antibody-Drug Conjugates. Angew Chem Int Ed Engl. Jan. 16, 2017;56(3):733-737.

Li X. et al. Preparation of well-defined antibody-drug conjugates through glycan remodeling and strain-promoted azide-alkyne cycloadditions. Angew Chem Int Ed Engl. Jul. 7, 2014;53(28):7179-82.

"Lin et al. TM4SF1: a new vascular therapeutic target in cancer, Angiogenesis vol. 17, pp. 897-907 (2014)".

"Liu, A Y et al., "Chimeric Mouse-Human IGG1 Antibody That can Mediate Lysis of Cancer Cells" Proceedings of the National Academy of Sciences, National Academy of Sciences, US, vol. 84, May 1, 1987, pp. 3439-3443".

Liu et al. Adding new chemistries to the genetic code. Annu Rev Biochem 79:413-444 (2010).

Lowenthal MS et al. Identification of Novel N-Glycosylation Sites at Noncanonical Protein Consensus Motifs. J Proteome Res. Jul. 1, 2016;15(7):2087-101.

Maccallum et al.: Antibody-antigen interactions: contact analysis and binding site topography. J Mol Biol. 262(5):732-745 (1996).

"Markens, John S, et al., "Membrane Topology of the L6 Antigen an dIdentification of the Protein Epitope Recognized by the L6 Monoclonal Antibody" INC the Journal of Biological Chemistry, vo. 269, No. 10, Mar. 11, 1994, pp. 7397-7401".

Marks et al. By-passing immunization: building high affinity human antibodies by chain shuffling. Biotechnology (NY) 10(7):779-783 (1992).

Morimoto K, Inouye K. Single-step purification of F(ab')2 fragments of mouse monoclonal antibodies (immunoglobulins G1) by hydrophobic interaction high performance liquid chromatography using TSKgel Phenyl-5PW. J Biochem Biophys Methods. Mar. 1992;24(1-2):107-17.

(56) References Cited

OTHER PUBLICATIONS

Morrison et al. Chimeric human antibody molecules: mouse antigen-binding domains with human constant region domains. PNAS USA 81(21):6851-6855 (1984).
Munson et al. Ligand: a versatile computerized approach for characterization of ligand-binding systems. Anal Biochem. 107(1):220-239 (Sep. 1, 1980).
O'Shannessy DJ et al. A novel procedure for labeling immunoglobulins by conjugation to oligosaccharide moieties. Immunol Lett. 1984;8(5):273-7.
Osbourn, et al. From rodent reagents to human therapeutics using antibody guided selection. Methods. May 2005;36(1):61-68.
Padlan, et al., A possible procedure for reducing the immunogenicity of antibody variable domains while preserving their ligand-binding properties. Mol Immunol 28(4-5):489-498 (1991).
Padlan, et al. Identification of specificity-determining residues in antibodies. FASEB J. 1995; 9(1):133-9.
PCT/US2020/020207 International Preliminary Report on Patentability dated Aug. 25, 2021.
PCT/US2020/020207 International Search Report and Written Opinion dated Aug. 10, 2020.
Pearson, W.R. Using the FASTA Program to Search Protein and DNA Sequence Databases. Meth. Mol. Biol. 1994; 24:307-331.
Petkova, et al. Enhanced half-life of genetically engineered human IgG1 antibodies in a humanized FcRn mouse model: potential application in humorally mediated autoimmune disease. Int Immunol. Dec. 2006;18(12):1759-1769.
Pluckthun, A. Mono- and bivalent antibody fragments produced in *Escherichia coli:* engineering, folding and antigen binding. Immunol Rev. Dec. 1992; 130: 151-188.
Presta et al. Humanization of an antibody directed against IgE. J Immunol 151:2623-2632 (1993).
Queen C., et al., "A humanized antibody that binds to the interleukin 2 receptor," Dec. 1989, Proceedings of the National Academy of Sciences, National Academy of Sciences, vol. 86, No. 24, pp. 10029-10033, XP002614478.
Rabuka, David et al. Site-Specific chemical protein conjugation using genetically encoded aldehyde tags. Nat. Protoc. 7(6):1052-1067 (2012).
Richman et al. Radioimmunotherapy for breast cancer using escalating fractionated doses of 131I-labeled chimeric L6 antibody with peripheral blood progenitor cell transfusions. Cancer Res 55(23 Suppl):5916s-5920s (Dec. 1, 1995).
Riechmann et al. Reshaping human antibodies for therapy. Nature, 332.6162:323-7 (1988).
Roberts et al. Chemistry for peptide and protein PEGylation. Adv Drug Deliv Rev 54: 459-476 (2002).
Roguska et al. Humanization of murine monoclonal antibodies through variable domain resurfacing. PNAS 91:969-973 (1994).
Rosok et al. A Combinatorial Library Strategy for the Rapid Humanization of Anticarcinoma BR96 Fab. J Biol Chem 271:22611-22618 (1996).
Rychly, et al., Therapeutic Strategies in Autoimmune Diseases by Interfering With Leukocyte Endothelium Interaction Curr Pharm Des. 2006;12(29):3799-806.
Sali, Andrej and Blundell, T., Comparative Protein Modelling by Satisfaction of Spatial Restraints, 1993, J. Mol. Biol. 234:779-815).
Saxena and Christofori, Rebuilding cancer metastasis in the mouse, Mol Oncol. Apr. 2013;7(2):283-96.
Saxena et al., Advances in Therapeutic Fc Engineering—Modulation of IgG-Associated Effector Functions and Serum Half-life, Front Immunol. Dec. 1, 20162;7:580, | https://doi.org/10.3389/fimmu.2016.00580.
Shields et al. High Resolution Mapping of the Binding Site on Human IgG1 for FcγRI, FcγRII, FcγRIII, and FcRn and Design of IgG1 Variants with Improved Binding to the FcγR. J Biol Chem 276(9):6591-6604 (2001).
Shih, et al., The L6 Protein TM4SF1 is Critical for Endothelial Cell Function and Tumor Angiogenesis, Available in PMC Apr. 15, 2010, published in final edited form as: Cancer Res. 69(8):3272-3277 (2009) (12 pages).
Silva et al., The S228P Mutation Prevents in Vivo and in Vitro IgG4 Fab-arm Exchange as Demonstrated using a Combination of Novel Quantitative Immunoassays and Physiological Matrix Preparation (J Biol Chem. Feb. 27, 2015;290(9):5462-9).
Sims et al., 1993, A humanized CD18 antibody can block function without cell destruction., J. Immunol. 151:2296-308.
Skerra, A. Bacterial expression of immunoglobulin fragments. Curr Opin Immunol. Apr. 1993;5(2):256-262.
Sondermann, et al. The 3.2-A crystal structure of the human IgG1 Fc fragment-Fc gammaRIII complex. Nature. Jul. 20, 2000;406(6793):267-73.
Strop P. Versatility of microbial transglutaminase. Bioconjug Chem. May 21, 2014;25(5):855-62.
Studnicka et al.: Human-engineered monoclonal antibodies retain full specific binding activity by preserving non-CDR complementarity-modulating residues. Protein Eng. 7(6):805-814 (1994).
"Stenzel-Johnson, P R, et al., "Identification of Residues in the Monoclonal Antitumore Antibody L6 Important for Binding to its Tumor Antigen", Biochemistry, Vo. 33, Jan. 1, 1994, pp. 14400-14406".
Vajdos et al. Comprehensive functional maps of the antigen-binding site of an anti-ErbB2 antibody obtained with shotgun scanning mutagenesis. J Mol Biol. 320(2):415-28 (2002).
Valliere-Douglass JF et al. Asparagine-linked oligosaccharides present on a non- consensus amino acid sequence in the CH1 domain of human antibodies. J Biol Chem. Nov. 20, 2009;284(47):32493-506.
Verhoeyen et al. Reshaping human antibodies: Grafting an antilysozyme activity. Science 239:1534-1536 (1988).
Vidarsson G, Dekkers G, Rispens T. IgG subclasses and allotypes: from structure to effector functions. Front Immunol. Oct. 20, 2014;5:520. doi: 10.3389/fimmu.2014.00520.
"Visintin et al., Novel Anti-TM4SF1 Antibody-Drug Conjugates with Activity against Tumor Cells and Tumor Vasculature Mol Cancer Ther, vol. 14, No. 8, pp. 1868-1876 (2015)."
Wang et al. Expanding the genetic code. Angew Chem Int Ed, 2005, , pp. 34-66, vol. 44, No. 1, e-pub Dec. 17, 2004.
Watt GM, et al., Site-specific glycosylation of an aglycosylated human IgG1-Fc antibody protein generates neoglycoproteins with enhanced function. Chem Biol. Sep. 2003;10(9):807-14. doi: 10.1016/j.chembiol.2003.08.006.
Whitelegg et al. : WAM: an improved algorithm for modelling antibodies on the WEB. Protein Eng. 13:819-24 (2000).
Winter et al., Making Antibodies by Phage Display Technology, 1994, Ann. Rev. Immunol. 12:433-55.
Wright, et al., The L6 membrane proteins—A new four-transmembrane superfamily, Protein Sci. 9: 1594-1600, 2000.
Yang NJ et al. Cytosolic delivery of siRNA by ultra-high affinity dsRNA binding proteins. Nucleic Acids Res. Jul. 27, 2017;45(13):7602-7614.
Zhou Q. et al. Site-specific antibody-drug conjugation through glycoengineering. Bioconjug Chem. Mar. 19, 2014;25(3):510-20.
Zuberbühler K. et al. Fucose-specific conjugation of hydrazide derivatives to a vascular-targeting monoclonal antibody in IgG format. Chem Commun (Camb). Jul. 18, 2012;48(56):7100-2.
Zukauskas et al., TM4SF1: A tetraspanin-like protein necessary for nanopodia formation and endothelial cell migration, Available in PMC Mar. 11, 2012, published in final edited form as: Angiogenesis. 14(3):345-354 (2011) (16 pages).
Japanese Application No. 2021-550149 Office Action dated Jan. 31, 2024.
U.S. Appl. No. 17/532,660 Office Action dated Apr. 30, 2024.
Gao, Caiyun et al. TM4SF1 is a Potential Target for Anti-invasion and Metastasis in Ovarian Cancer. BMC Cancer 19(1)237, 1-12 (2019).
U.S. Appl. No. 17/532,664 Office Action dated Jul. 19, 2024.

* cited by examiner

*BrAc-Peg4-Ahx-N-Methyl-Alanine-Maytansine*

*Maleimide-Ahx-N-Methyl-Alanine-Maytansine*
*"MC-DM-1"*

SEQUENCE LISTING

<160> NUMBER OF SEQ ID NOS: 163

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Phe
            20                  25                  30

Ala Met Ser Trp Val Arg Gln Thr Pro Glu Lys Arg Leu Glu Trp Val
        35                  40                  45

Ala Thr Ile Ser Ser Gly Ser Ile Tyr Ile Tyr Tyr Thr Asp Gly Val
    50                  55                  60

Lys Gly Arg Phe Thr Ile Ser Arg Asp Asn Ala Lys Asn Thr Val His
65                  70                  75                  80

Leu Gln Met Ser Ser Leu Arg Ser Glu Asp Thr Ala Met Tyr Tyr Cys
                85                  90                  95

Ala Arg Arg Gly Ile Tyr Tyr Gly Tyr Asp Gly Tyr Ala Met Asp Tyr
            100                 105                 110

Trp Gly Gln Gly Thr Ser Val Thr Val Ser
        115                 120

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Met Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Ile Tyr Phe Cys Ser Gln Ser
                85                  90                  95

Thr His Ile Pro Leu Ala Phe Gly Ala Gly Thr Lys Leu Glu Leu Lys
            100                 105                 110

<210> SEQ ID NO 3
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ser Phe Arg Asp Tyr
            20                  25                  30

Gly Met Asn Trp Val Lys Gln Ala Pro Gly Arg Thr Phe Lys Trp Met
        35                  40                  45

Gly Trp Ile Asn Thr Tyr Thr Gly Ala Pro Val Tyr Ala Ala Asp Phe
    50                  55                  60

Lys Gly Arg Phe Ala Phe Ser Leu Asp Thr Ser Ala Ser Ala Ala Phe
65                  70                  75                  80

Leu Gln Ile Asn Asn Leu Lys Asn Glu Asp Thr Ala Thr Tyr Phe Cys
                85                  90                  95

Ala Arg Trp Val Ser Tyr Gly Asn Asn Arg Asn Trp Phe Phe Asp Phe
            100                 105                 110

Trp Gly Ala Gly Thr Thr Val Thr Val Ser Ser
        115                 120

<210> SEQ ID NO 4
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cagatccagt tggtgcagtc tggacctgag ctgaagaagc ctggagagac agtcaagatc     60

```
tcctgcaagg cttctgggta ttccttcaga gactatggaa tgaactgggt gaagcaggct      120
ccaggaagga cttttaagtg gatgggctgg ataaacacct acactggagc gccagtatat      180
gctgctgact tcaagggacg gtttgccttc tctttggaca cctctgccag cgctgccttt      240
ttgcagatca caacctcaa aaatgaagac acggctacat atttctgtgc aagatgggtc       300
tcctacggta ataaccgcaa ctggttcttc gattttgggg gcgcaggac cacggtcacc       360 gtctcctca                                                              369
```

<210> SEQ ID NO 5
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
caaattcagt tggttcaatc cggccctgag ctcaagaagc tggagagac agtgaagata       60 agttgtaagg ctagtggcta ttcatttcga gattatggga tgaattgggt caagcaggcc     120
ccagggcgga ccttcaaatg gatggggtgg atcaatactt acactggcgc accagtatat     180
gcagctgatt ttaagggtcg ctttgcattt tcacttgata cttcagccag tgccgctttt     240
ttgcaaatca caatctcaa aaatgaagac actgctacat atttctgcgc caggtgggtg      300
agctatggca ataacagaaa ttggttcttt gacttttggg gcgcaggcac caccgtcact     360
gtctcatca                                                              369
```

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Tyr Ser Phe Arg Asp Tyr Gly Met Asn
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Ile Asn Thr Tyr Thr Gly Ala Pro Val Tyr Ala Ala Asp Phe Lys
1               5                   10                  15

Gly

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Val Ser Tyr Gly Asn Asn Arg Asn Trp Phe Phe Asp Phe
1               5                   10

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Val Leu Met Thr Gln Thr Pro Leu Ser Leu Pro Val Arg Leu Gly
1               5                   10                  15

Asp Gln Ala Ser Ile Ser Cys Arg Ser Ser Gln Thr Leu Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Val Tyr Tyr Cys Phe Gln Gly
                85                  90                  95

Ser His Gly Pro Trp Thr Phe Gly Gly Gly Thr Lys Leu Glu Ile Lys
            100                 105                 110

<210> SEQ ID NO 10
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gatgttttga tgacccaaac tccactctcc ctgcctgtcc gtcttggaga tcaggcctcc     60
atctcttgta gatctagtca gacccttgta catagtaatg gaaacaccta tttagaatgg    120
tacctgcaga accaggcca gtctccaaaa ctcttgatct acaaagtttc caatcgactt    180
tctggggtcc cagacaggtt cagtggcagt ggatcaggga cagatttcac actcaagatc    240
agcagagtgg agactgagga tctgggagtt tattactgct ttcaaggttc acatggtccg    300
tggacgttcg gtggaggcac caagctggaa atcaaa                              336

<210> SEQ ID NO 11
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gacgtactta tgacacaaac tcccttgagc ttgccagtac ggcttggcga tcaagcttca     60
atttcatgtc gttcttctca aacacttgtc cactcaaatg gaatacata tttgaatgg    120 tatctccaaa agcccggcca atccccaaaa ttgttgattt acaaggtgtc taatcgactc    180
tcaggcgtcc ccgaccgatt ctccgggagc gggtccggta cagacttcac cttgaaaatc    240
tccagggtag aaactgaaga cctcggagtc tactattgtt tccaggggtc acacggcccc    300
tggacatttg gaggaggaac taagctcgag atcaaa 336

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ser Ser Gln Thr Leu Val His Ser Asn Gly Asn Thr Tyr Leu Glu
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Val Ser Asn Arg Leu Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Gln Gly Ser His Gly Pro Trp Thr
1               5

<210> SEQ ID NO 15
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Asp Tyr
            20                  25                  30

Thr Met His Trp Val Arg Gln Ser His Gly Lys Ser Leu Glu Trp Ile
        35                  40                  45

Gly Ser Phe Asn Pro Asn Asn Gly Gly Leu Thr Asn Tyr Asn Gln Lys
    50                  55                  60

Phe Lys Gly Lys Ala Thr Leu Thr Val Asp Lys Ser Ser Ser Thr Val
65                  70                  75                  80

Tyr Met Asp Leu Arg Ser Leu Thr Ser Glu Asp Ser Ala Val Tyr Tyr
                85                  90                  95

Cys Thr Arg Ile Arg Ala Thr Gly Phe Asp Ser Trp Gly Gln Gly Thr
            100                 105                 110

Thr Leu Thr Val Ser Ser
        115

<210> SEQ ID NO 16
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gaggtccagc tgcaacagtc tggacctgag ctggtgaagc ctggggcttc agtgaagata      60
tcctgcaaga cttctggata cacattcact gattacacca tgcactgggt gaggcagagc     120
catggaaaga gccttgagtg gattggaagt tttaatccta acaatggtgg tcttactaac     180
tacaaccaga gttcaaggg caaggccaca ttgactgtgg acaagtcttc cagcacagtg      240
tacatggacc tccgcagcct gacatctgag gattctgcag tctattactg tacaagaatc     300
cgggctacgg gctttgactc ctggggccag ggcaccactc tcacagtctc ctca           354

<210> SEQ ID NO 17
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gaggtacaac tgcaacagag tggacctgaa cttgtcaaac ctggagcaag tgtgaagatt      60
agctgtaaaa ccagtggcta cacatttacc gattatacta tgcactgggt aagacagagc     120
cacggaaaat cactggagtg gattggtagt ttcaatccta acaacggagg attgacaaat     180
tacaaccaga gttcaaagg gaaagccacc ttgacagttg ataagtcctc aagtaccgtg      240
tatatggatc tgcgttctct cacaagtgaa gatagcgcag tttactactg tacccgcatc     300
cgagccaccg ggttcgattc atggggtcag gggacaacac tgactgtttc ttct           354

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Tyr Thr Phe Thr Asp Tyr Thr Met His
1               5                   10

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Phe Asn Pro Asn Asn Gly Gly Leu Thr Asn Tyr Asn Gln Lys Phe
1               5                   10                  15

Lys Gly

<210> SEQ ID NO 20
<211> LENGTH: 8

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Arg Ala Thr Gly Phe Asp Ser
1               5

<210> SEQ ID NO 21
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Asn Val Gln Ala Glu Asp Leu Thr Val Tyr Tyr Cys Lys Gln
                85                  90                  95

Ser Tyr Asn Pro Pro Trp Thr Phe Gly Gly Gly Thr Lys Leu Glu Ile
            100                 105                 110

Lys

<210> SEQ ID NO 22
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gacattgtga tgtcacagtc tccatcctcc ctggctgtgt cagcaggaga gaaggtcact      60
atgagctgca aatccagtca gagtctgctc aacagtagaa cccgaaagaa ctacttggct     120
tggtaccagc agaaaccagg gcagtctcct aaactgctga tctactgggc atccactagg     180
gaatctgggg tccctgatcg cttcacaggc agtggatctg gacagatttt cactctcacc     240
atcagcaatg tgcaggctga agacctgaca gtttattact gcaagcaatc ttataatcct     300
ccgtggacgt tcggtggagg caccaagctg gaaatcaaa                            339

<210> SEQ ID NO 23
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
gacatagtta tgtcccagtc tccatccagc ttggctgtca gcgccggaga gaaagtgact      60
atgagttgta atcttccca gtccctgctt aactcacgta ctcggaagaa ttatcttgcc      120
tggtatcaac aaaagccagg tcaaagtcct aagctcctta tttactgggc ctcaacacgg    180
gagtcaggtg tccccgatcg cttcacaggt agtgggagtg gtactgactt cactctcacc    240
atttcaaatg tccaagcaga agacttgact gtgtattact gtaagcagag ttacaaccct    300
ccttggacct ttggtgggggg gaccaaactg gagatcaag                          339
```

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Lys Ser Ser Gln Ser Leu Leu Asn Ser Arg Thr Arg Lys Asn Tyr Leu
1               5                   10                  15

Ala
```

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Trp Ala Ser Thr Arg Glu Ser
1               5
```

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Lys Gln Ser Tyr Asn Pro Pro Trp Thr
1               5
```

<210> SEQ ID NO 27
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Glu Val Gln Val Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Asn Asn Asp Asn Ile Asn Tyr Asn Glu Lys Phe
    50                  55                  60
```

Lys Gly Lys Ala Ser Leu Thr Ser Asp Lys Ser Ser Asn Thr Val Tyr
65                  70                  75                  80

Met Glu Leu Ser Ser Leu Thr Ser Glu Asp Ser Ala Val Tyr Tyr Cys
                85                  90                  95

Ala Gly Tyr Gly Asn Ser Gly Ala Asn Trp Gly Gln Gly Thr Leu Val
            100                 105                 110

Thr Val Ser Ala
        115

<210> SEQ ID NO 28
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gaggtccagg tacagcagtc tggacctgaa ctggtaaagc ctggggcttc agtgaagatg      60
tcctgtaagg cttctggata cacattcact agctatgtca tgcactgggt gaagcagaag     120
cctgggcagg gccttgagtg gattggatat attaatccta acaatgataa tattaactac     180
aatgagaagt tcaaaggcaa ggcctcactg acttcagaca atcctccaa cacagtctac      240 atggagctca gcagcctgac ctctgaggac tctgcggtct attactgtgc aggctatggt     300
aactccggag ctaactgggg ccaagggact ctggtcactg tctctgca                  348

<210> SEQ ID NO 29
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gaagttcaag ttcagcaaag cgggcctgag cttgtcaagc caggcgcatc agtcaaaatg      60
agctgtaagg cttccgggta caccttcacc agttatgtca tgcattgggt aaaacaaaag     120
ccaggacagg gactcgagtg gataggatac attaacccaa ataacgacaa cattaactac     180
aacgagaaat tcaagggcaa agcatcattg acttccgata atcctctaa caccgtgtac      240 atggagctga gttcattgac cagcgaggat tctgccgtgt actactgtgc aggttatggc     300
aactctggtg ctaactgggg gcaggggact ctggtcacag tcagcgca                  348

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Tyr Thr Phe Thr Ser Tyr Val Met His
1               5                   10

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 31

Tyr Ile Asn Pro Asn Asn Asp Asn Ile Asn Tyr Asn Glu Lys Phe Lys
1               5                   10                  15

Gly

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Gly Asn Ser Gly Ala Asn
1               5

<210> SEQ ID NO 33
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Gln Met Thr Gln Ser Pro Ala Ser Leu Ser Ala Ser Val Gly
1               5                   10                  15

Glu Thr Val Thr Ile Thr Cys Arg Thr Ser Lys Asn Ile Phe Asn Phe
            20                  25                  30

Leu Ala Trp Tyr His Gln Lys Gln Gly Arg Ser Pro Arg Leu Leu Val
        35                  40                  45

Ser His Thr Lys Thr Leu Ala Ala Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ile Tyr Tyr Cys Gln His Tyr Gly Thr Pro Trp
                85                  90                  95

Thr Phe Gly Gly Gly Thr Lys Leu Glu Ile Lys
            100                 105

<210> SEQ ID NO 34
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gacatccaga tgactcagtc tccagcctcc ctatctgcat ctgtgggaga aactgtcacc      60
atcacatgtc gaacaagtaa aaatattttc aattttttag catggtatca ccagaaacag    120
ggaagatctc ctcgactcct ggtctctcat acaaaaacct tagcagcagg tgtgccatca    180
aggttcagtg gcagtggctc aggcacacag ttttctctga agatcaacag cctgcagcct    240
gaagattttg ggatttatta ctgtcaacat cattatggta ctccgtggac gttcggtgga    300
ggcaccaaac tggaaatcaa a                                              321

```
<210> SEQ ID NO 35
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gacattcaga tgacccagtc accagcatct tgagcgcat ccgttgggga gactgtgaca      60
atcacatgcc gaaccagtaa gaacatcttc aacttcctcg catggtacca tcaaaagcag    120
ggcaggtctc ccagactgct tgtctctcac accaagacac tggcagcagg cgtccccagc    180
cggtttagtg gtagtggatc tggcacacag tttagtttga aaatcaattc cctgcaaccc    240
gaagacttcg gcatatacta ttgccagcac cactatggga caccttggac tttcggaggt    300
ggtactaaac ttgagattaa a                                              321

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Thr Ser Lys Asn Ile Phe Asn Phe Leu Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

His Thr Lys Thr Leu Ala Ala
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln His His Tyr Gly Thr Pro Trp Thr
1               5

<210> SEQ ID NO 39
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
```

```
            20              25                  30
Gly Val Lys Trp Val Lys Gln Ala Pro Gly Lys Asp Leu Lys Trp Met
        35                  40                  45

Gly Trp Ile Asn Thr Tyr Thr Gly Asn Pro Ile Tyr Ala Ala Asp Phe
    50                  55                  60

Lys Gly Arg Phe Ala Phe Ser Leu Glu Thr Ser Ala Ser Thr Ala Phe
65                  70                  75                  80

Leu Gln Ile Asn Asn Leu Lys Asn Glu Asp Thr Ala Thr Tyr Phe Cys
                85                  90                  95

Val Arg Phe Gln Tyr Gly Asp Tyr Arg Tyr Phe Asp Val Trp Gly Ala
            100                 105                 110

Gly Thr Thr Val Thr Val Ser Ser
            115                 120

<210> SEQ ID NO 40
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
cagatccagt tggtgcagtc tggacctgag ctgaagaagc tggagagaca agtcaagatc      60
tcctgcaagg cttctgggta taccttcaca aactatggag tgaagtgggt gaagcaggct     120
ccaggaaagg atttaaagtg gatgggctgg ataaacacct acactggaaa tccaattat     180 gctgctgact tcaagggacg gtttgccttc tctttggaga cctctgccag cactgccttt     240
ttgcagatca acaacctcaa aaatgaggac acggctacat atttctgtgt aagattccaa     300
tatggcgatt accggtactt cgatgtctgg ggcgcaggga ccacggtcac cgtctcctca     360

<210> SEQ ID NO 41
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
caaatccaac ttgtccagag cggtcccgag ttgaagaagc tggcgaaac cgtgaaaatc       60 tcatgcaagg ccagtggata tacatttaca aactatggcg tcaagtgggt gaaacaagcc     120
ccaggtaaag acttgaaatg gatgggatgg atcaacacat acacagggaa tcctatctat     180
gcagccgact ttaaaggcag atttgccttc agtttggaga catctgcctc caccgctttc     240
ctgcaaataa ataacctgaa aaatgaagat accgctacat acttctgtgt acggttccag     300
tacggagatt accgctattt cgatgtgtgg ggcgcaggta ccacagtaac cgtctcctca     360

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Tyr Thr Phe Thr Asn Tyr Gly Val Lys
1               5                   10
```

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Ile Asn Thr Tyr Thr Gly Asn Pro Ile Tyr Ala Ala Asp Phe Lys
1               5                   10                  15

Gly

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Phe Gln Tyr Gly Asp Tyr Arg Tyr Phe Asp Val
1               5                   10

<210> SEQ ID NO 45
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Ile Ile Leu Ser Gln Ser Pro Ala Ile Leu Ser Ala Ser Pro Gly
1               5                   10                  15

Glu Lys Val Thr Met Thr Cys Arg Ala Asn Ser Gly Ile Ser Phe Ile
            20                  25                  30

Asn Trp Tyr Gln Gln Lys Pro Gly Ser Ser Pro Lys Pro Trp Ile Tyr
        35                  40                  45

Gly Thr Ala Asn Leu Ala Ser Gly Val Pro Ala Arg Phe Gly Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Arg
            100                 105

<210> SEQ ID NO 46
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
caaattattc tctcccagtc tccagcaatc ctgtctgcat ctccagggga gaaggtcacg      60
atgacttgca gggccaactc aggtattagt ttcatcaact ggtaccagca gaagccagga     120
tcctccccca aaccctggat ttatggcaca gccaacctgg cttctggagt ccctgctcgc     180

```
ttcggtggca gtgggtctgg gacttcttac tctctcacaa tcagcagagt ggaggctgaa    240
gacgctgcca cttattactg ccagcagtgg agtagtaacc cgctcacgtt cggtgctggg    300
accaagctgg agttgaga                                                   318
```

<210> SEQ ID NO 47
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
caaataattc tgtcacagtc ccccgctata cttagtgctt caccaggaga aaaagtgacc     60
atgacttgta gagctaattc tggcatatca ttcatcaact ggtatcaaca aaagccaggt    120
tcctccccca agccatggat ttacgggacc gccaaccttg cttctggggt acccgctcgt    180
ttcggcggat caggttcagg aacttcctat agcctcacta tcagtcgggt tgaagctgag    240
gatgccgcta catattactg ccagcaatgg tctagtaatc cacttacctt tggagctggc    300
accaaattgg aacttcgt                                                  318
```

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

```
Arg Ala Asn Ser Gly Ile Ser Phe Ile Asn
1               5                   10
```

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

```
Gly Thr Ala Asn Leu Ala Ser
1               5
```

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

```
Gln Gln Trp Ser Ser Asn Pro Leu Thr
1               5
```

<210> SEQ ID NO 51
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

Glu Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Ser Asp Val Thr Asn Cys Asn Glu Lys Phe
50                  55                  60

Lys Gly Lys Ala Thr Leu Thr Ser Asp Lys Thr Ser Thr Ala Tyr
65                  70                  75                  80

Met Glu Leu Ser Ser Leu Thr Ser Glu Asp Ser Ala Val Tyr Tyr Cys
            85                  90                  95

Ser Ser Tyr Gly Gly Gly Phe Ala Tyr Trp Gly Gln Gly Thr Leu Val
            100                 105                 110

Thr Val Ser Ala
        115

<210> SEQ ID NO 52
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
gaggtccagc tgcagcagtc tggacctgag ctggtaaagc ctggggcttc agtgaagctg    60
tcctgcaagg cttctggata cacagtcact agctatgtta tgcactgggt gaagcagaag   120
cctgggcagg gccttgagtg gattggatat attaatcctt acagtgatgt tactaactgc   180
aatgagaagt tcaaaggcaa ggccacactg acttcagaca aaacctccag cacagcctac   240
atggagctca gcagcctgac ctctgaggac tctgcggtct attactgttc ctcctacggt   300 gggggtttg cttactgggg ccaagggact ctggtcactg tctctgca                 348

<210> SEQ ID NO 53
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gaagtccagc ttcagcaatc cggcccagaa ctggtaaaac caggcgcaag tgttaagttg    60
agttgcaaag ccagtggtta taccgttact tcatacgtca tgcattgggt aaaacaaaag   120
cccggccaag ggcttgaatg gatcggctac atcaacccctt actctgacgt caccaactgc   180
aacgagaaat tcaaagggaa agccacattg acctctgaca agacaagcag taccgcctac   240
atggagcttt ctagtttgac ttctgaagac tctgctgtct actactgtag cagctacggc   300
ggcggctttg cttactgggg ccagggtaca ttggtgactg tgagtgca                348

<210> SEQ ID NO 54
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 54

Gly Tyr Thr Val Thr Ser Tyr Val Met His
1               5                   10

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Tyr Ile Asn Pro Tyr Ser Asp Val Thr Asn Cys Asn Glu Lys Phe Lys
1               5                   10                  15

Gly

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Tyr Gly Gly Gly Phe Ala Tyr
1               5

<210> SEQ ID NO 57
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Gln Met Thr Gln Ser Pro Ala Ser Leu Ser Ala Ser Val Gly
1               5                   10                  15

Glu Pro Val Thr Ile Thr Cys Arg Ala Ser Lys Asn Ile Tyr Thr Tyr
            20                  25                  30

Leu Ala Trp Tyr His Gln Lys Gln Gly Lys Ser Pro Gln Phe Leu Val
        35                  40                  45

Tyr Asn Ala Arg Thr Leu Ala Gly Gly Val Pro Ser Arg Leu Ser Gly
    50                  55                  60

Ser Gly Ser Val Thr Gln Phe Ser Leu Asn Ile Asn Thr Leu His Arg
65                  70                  75                  80

Glu Asp Leu Gly Thr Tyr Phe Cys Gln His His Tyr Asp Thr Pro Tyr
                85                  90                  95

Thr Phe Gly Gly Gly Thr Asn Leu Glu Ile Lys
            100                 105

<210> SEQ ID NO 58
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 58

```
gacatccaga tgactcagtc tccagcctcc ctatctgcat ctgtgggaga acctgtcacc      60
atcacatgtc gagcaagtaa gaatatttac acatatttag catggtatca ccagaaacag     120
ggaaaatctc ctcagttcct ggtctataat gcaagaacct tagcaggagg tgtgccatca     180
aggctcagtg gcagtggatc agtcacgcag tttctctaa acatcaacac cttgcatcga      240
gaagatttag ggacttactt ctgtcaacat cattatgata ctccgtacac gttcggaggg     300
gggaccaacc tggaaataaa a                                               321
```

<210> SEQ ID NO 59
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
gacatccaga tgacacagtc accagcatcc ctgtccgcct cagttgggga gcctgttacc      60
ataacttgtc gggcaagcaa aaacatatac acctatttgg cttggtatca ccaaaagcaa     120
ggtaagtcac ctcagtttct tgtatataat gcccgcacac ttgctggcgg agtaccctct     180
cgattgtctg gatctggcag cgttacccaa ttcagcctga acatcaacac cctccatcgg     240
gaagatttgg gtacctattt ctgtcaacat cactacgaca ccccatacac cttcggaggc     300
ggcacaaatt tggaaattaa a                                               321
```

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Arg Ala Ser Lys Asn Ile Tyr Thr Tyr Leu Ala
1               5                   10
```

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Asn Ala Arg Thr Leu Ala Gly
1               5
```

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Gln His His Tyr Asp Thr Pro Tyr Thr
1               5
```

<210> SEQ ID NO 63
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 63

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Ser Asp Val Thr Asn Tyr Asn Glu Lys Phe
    50                  55                  60

Lys Gly Lys Ala Thr Leu Thr Ser Asp Arg Ser Ser Asn Thr Ala Tyr
65                  70                  75                  80

Met Glu Leu Ser Ser Leu Thr Ser Glu Asp Ser Ala Val Tyr Tyr Cys
                85                  90                  95

Ala Arg Asn Tyr Phe Asp Trp Gly Arg Gly Thr Leu Val Thr Val Ser
            100                 105                 110

Ala

<210> SEQ ID NO 64
<211> LENGTH: 339
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 64
gaggtccagc tgcagcagtc tggacctgag ctggtaaagc ctggggcttc agtgaagatg      60
tcctgcaagg cttctggata cacattctct agctatgtta tgcactgggt gaagcagaag     120
cctgggcagg gccttgagtg gattggatat attaatcctt acagtgatgt cactaactac     180
aatgagaagt tcaaaggcaa ggccacactg acttcagaca gatcctccaa cacagcctac     240
atggaactca gcagcctgac ctctgaggac tctgcggtct attactgtgc aagaaattac     300
ttcgactggg gccgagggac tctggtcaca gtctctgca                            339

<210> SEQ ID NO 65
<211> LENGTH: 339
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 65
gaggtacagc ttcagcagag tggtccagaa ctcgtcaagc ctggggcaag cgttaagatg      60
agttgtaaag catccggtta cacattcagt agctatgtta tgcactgggt caaacagaag     120
cctgggcagg ggttggagtg gatcggatat ataaatccct attcagacgt aactaattat     180
aatgaaaagt tcaaggggaa agcaaccttg acaagtgacc ggtcatctaa taccgcatac     240
atggagctga gctcattgac aagtgaggac tctgctgtgt attactgtgc ccggaactac     300
ttcgactggg gtaggggcac actggtaact gttagtgca                           339

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Tyr Thr Phe Ser Ser Tyr Val Met His
1               5                   10

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Tyr Ile Asn Pro Tyr Ser Asp Val Thr Asn Tyr Asn Glu Lys Phe Lys
1               5                   10                  15

Gly

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asn Tyr Phe Asp
1

<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Gln Met Thr Gln Ser Pro Ala Ser Leu Ser Ala Ser Val Gly
1               5                   10                  15

Glu Thr Val Thr Ile Thr Cys Arg Ala Ser Lys Asn Val Tyr Ser Tyr
                20                  25                  30

Leu Ala Trp Phe Gln Gln Lys Gln Gly Lys Ser Pro Gln Leu Leu Val
            35                  40                  45

Tyr Asn Ala Lys Thr Leu Ala Glu Gly Val Pro Ser Arg Phe Ser Gly
        50                  55                  60

Gly Gly Ser Gly Thr Gln Phe Ser Leu Lys Ile Asn Ser Leu Gln Pro
65                  70                  75                  80

Ala Asp Phe Gly Ser Tyr Tyr Cys Gln His His Tyr Asn Ile Pro Phe
                85                  90                  95

Thr Phe Gly Ser Gly Thr Lys Leu Glu Ile Lys
                100                 105

```
<210> SEQ ID NO 70
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
gacatccaga tgactcagtc tccagcctcc ctatctgcat ctgtgggaga aactgtcacc      60
atcacatgtc gagcaagtaa aaatgtttac agttatttag catggtttca acagaaacag     120
gggaaatctc ctcagctcct ggtctataat gctaaaacct tagcagaagg tgtgccatca     180
aggttcagtg gcgggggatc aggcacacag ttttctctga agatcaacag cctgcagcct     240
gcagattttg ggagttatta ctgtcaacat cattataata ttccattcac gttcggctcg     300
gggacaaagt tggaaataaa a                                               321

<210> SEQ ID NO 71
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gacatacaaa tgacacaaag tcccgctagt ctttcagcca gtgttggtga gactgtgaca      60
ataacctgta gagctagcaa aaatgtctac tcctatctgg cttggttcca gcagaaacaa     120
ggaaagagtc ctcagttgct cgtatataat gctaaaactt tggcagaagg cgtcccttct     180
cgtttcagtg gcggaggaag tgggactcaa ttctcactga agatcaatag cctccagccc     240
gccgactttg ggagctacta ttgccaacat cattacaaca taccattcac ctttggctca     300
ggtactaaac tcgaaattaa a                                               321

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Ala Ser Lys Asn Val Tyr Ser Tyr Leu Ala
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asn Ala Lys Thr Leu Ala Glu
1               5

<210> SEQ ID NO 74
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 74

Gln His His Tyr Asn Ile Pro Phe Thr
1               5

<210> SEQ ID NO 75
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr Asn Tyr
            20                  25                  30

Pro Met His Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Gly Tyr Asp Gly Ser Arg Glu Phe Ala Tyr Trp Gly Gln
            100                 105                 110

Gly Thr Leu Val Thr Val Ser
        115

<210> SEQ ID NO 76
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
cagatccagt tggtgcagtc tggacctgag ctgaagaagc ctggagagac agtcaagatc      60
tcctgcaagg cttctgggtt taccttcaca aactatccaa tgcactgggt gaagcaggct    120
ccaggaaagg gtttaaagtg gatgggctgg ataaacacct actctggagt gccaacatat    180
gcagatgact caagggacg gtttgccttc tctttggaaa cctctgccag cactgcatat     240
ttgcagatca acaacctcaa aaatgaggac atggctacat atttctgtgc aagaggggc     300 tacgatggta gcagggagtt tgcttactgg ggccaaggga ctctggtcac tgtctct       357

<210> SEQ ID NO 77
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
cagatacaac tcgtccagtc aggtccagag ttgaagaaac ccggagaaac tgtgaagata      60

```
tcctgtaaag ccagcggctt tactttcaca aactacccca tgcattgggt gaagcaggcc    120
cccggaaaag gactcaaatg gatgggatgg atcaacacat acagtggggt gcctacttac    180
gcagacgatt tcaaaggaag gttcgcattt agcttggaaa ctagcgcatc tacagcatat    240
ctccagatta acaatcttaa aaatgaggat atggcaacat acttctgcgc taggggaggt    300
tacgatggga gcagggagtt cgcttattgg gggcaaggga ctcttgtgac tgtaagt      357
```

```
<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Phe Thr Phe Thr Asn Tyr Pro Met His
1               5                   10

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Trp Ile Asn Thr Tyr Ser Gly Val Pro Thr Tyr Ala Asp Asp Phe Lys
1               5                   10                  15

Gly

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Gly Tyr Asp Gly Ser Arg Glu Phe Ala Tyr
1               5                   10

<210> SEQ ID NO 81
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Val Leu Thr Gln Ser Pro Ala Ser Leu Ala Ala Ser Leu Gly
1               5                   10                  15

Gln Arg Ala Thr Thr Ser Tyr Arg Ala Ser Lys Ser Val Ser Thr Ser
                20                  25                  30

Gly Tyr Ser Tyr Met His Trp Asn Gln Gln Lys Pro Gly Gln Pro Pro
            35                  40                  45

Arg Leu Leu Ile Tyr Leu Val Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80
```

Pro Val Glu Glu Glu Asp Ala Ala Thr Tyr Tyr Cys Gln His Ile Arg
                85                  90                  95

Glu Leu Thr Thr Phe Gly Gly Gly Thr Lys Leu Glu Ile Lys
            100                 105                 110

<210> SEQ ID NO 82
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
gacattgtgc tgacacagtc tcctgcttcc ttagctgcat ctctggggca gagggccacc     60
acctcataca gggccagcaa aagtgtcagt acatctggct atagttatat gcactggaac    120
caacagaaac caggacagcc acccagactc ctcatctatc ttgtatccaa cctagaatct    180
ggggtccctg ccaggttcag tggcagtggg tctgggacag acttcaccct caacatccat    240
cctgtggagg aggaggatgc tgcaacctat tactgtcagc acattaggga gcttaccacg    300
ttcggagggg ggaccaagct ggaaataaaa                                      330

<210> SEQ ID NO 83
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
gacatagtgc tcactcagag ccctgcatcc cttgccgcct ccctcggaca acgagctact     60
acaagctacc gggcatcaaa gtccgttagc acatcaggat acagctatat gcactggaat    120
cagcaaaagc caggccaacc accccgtctt ctcatctacc tcgtaagtaa tctggaatca    180
ggcgtgccag cccgattcag tgggtcaggg tctgggacag atttcaccct caacatccat    240
ccagtagagg aagaggacgc agcaacatat tactgccaac acattagaga acttaccact    300
ttcggaggag gaactaaatt ggagatcaaa                                      330

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ala Ser Lys Ser Val Ser Thr Ser Gly Tyr Ser Tyr Met His
1               5                   10                  15

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Val Ser Asn Leu Glu Ser

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln His Ile Arg Glu Leu Thr Thr
1               5

<210> SEQ ID NO 87
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe

```
            275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 88
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 89
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 90
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Val Lys Trp Val Arg Gln Ala Pro Gly Gln Asp Leu Glu Trp Met
            35                  40                  45

Gly Trp Ile Asn Thr Tyr Thr Gly Asn Pro Ile Tyr Ala Ala Asp Phe
        50                  55                  60

Lys Gly Arg Val Thr Met Thr Thr Asp Thr Ser Thr Ser Thr Ala Phe
65                  70                  75                  80

Met Glu Leu Arg Ser Leu Arg Ser Asp Thr Ala Val Tyr Tyr Cys
                85                  90                  95

Val Arg Phe Gln Tyr Gly Asp Tyr Arg Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
        180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Ala Ala Gly Ala
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
        260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
        340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
        420                 425                 430
Glu Ala Leu His Asn His Tyr Thr Gln Lys Ser Leu Ser Leu Ser Pro
        435                 440                 445
Gly Lys
    450

<210> SEQ ID NO 91
<211> LENGTH: 1362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
tctaccggac aggtgcagtt ggttcagtct ggcgccgaag tgaagaaacc tggcgcttct     60
gtgaaggtgt cctgcaaggc ctctggctac acctttacca actacggcgt gaaatgggtc    120
cgacaggctc ctggacagga tctggaatgg atgggctgga tcaacaccta caccggcaat    180
cctatctacg ccgccgactt caagggcaga gtgaccatga ccaccgacac ctctacctcc    240
accgccttca tgaactgcg gtccctgaga tctgacgaca ccgccgtgta ctactgcgtg    300
cggtttcagt acggcgacta ccggtacttt gatgtgtggg gccagggcac actggtcacc    360
```

```
gtttcttccg cttctaccaa gggacccagc gtgttcctc tggctccttc ctctaaatcc    420
acctctggcg gaaccgctgc tctgggctgt ctggtcaagg attacttccc tgagcctgtg    480
accgtgtcct ggaactctgg tgctctgaca tccggcgtgc acacctttcc agctgtgctg    540
cagtcctctg gcctgtactc tctgtcctct gtcgtgaccg tgccttctag ctctctgggc    600
acccagacct acatctgcaa cgtgaaccac aagccttcca acaccaaggt ggacaagaag    660
gtggaaccca gtcctgcga caagacccac acctgtcctc catgtcctgc tccagaagct    720
gctggcgctc cctctgtgtt cctgtttcct ccaaagccta aggacaccct gatgatctct    780
cggacccctg aagtgacctg cgtggtggtg gatgtgtctc acgaggaccc agaagtgaag    840
ttcaattggt acgtggacgg cgtggaagtg cacaacgcca gaccaagcc tagagaggaa    900 cagtacaact ccacctacag agtggtgtcc gtgctgaccg tgctgcacca ggattggctg    960
aacggcaaag agtacaagtg caaggtgtcc aacaaggcac tgcccgctcc tatcgaaaag    1020
accatctcca aggctaaggg ccagcctcgg gaacctcagg tttacaccct gcctccatct    1080
cgggaagaga tgaccaagaa ccaggtgtcc ctgacctgcc tcgtgaaggg cttctaccct    1140
tccgatatcg ccgtggaatg ggagtccaat ggccagcctg agaacaacta caagacaacc    1200
cctcctgtgc tggactccga cggctcattc ttcctgtact ccaagctgac agtggacaag    1260
tctcggtggc agcagggcaa cgtgttctcc tgttctgtga tgcacgaggc cctgcacaac    1320
cactacacac agaagtccct gtctctgtcc cctggcaagt ga                       1362
```

<210> SEQ ID NO 92  
<211> LENGTH: 450  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 92

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Lys Trp Val Arg Gln Ala Pro Gly Gln Gly Leu Glu Trp Met
        35                  40                  45

Gly Trp Ile Asn Thr Tyr Thr Gly Asn Pro Ile Tyr Ala Ala Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Val Arg Phe Gln Tyr Gly Asp Tyr Arg Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 93
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
gaagtgcagt tggtgcagtc tggcgccgaa gtgaagaaac tggcgcttc tgtgaaggtg      60 tcctgcaagg cctctggcta cacctttacc aactacggcg tgaaatgggt ccgacaggct    120
cctggacaag gcctggaatg gatgggctgg atcaacacct acaccggcaa tcctatctac    180
gccgccgact tcaagggcag agtgaccatg accaccgaca cctctacctc caccgcctac    240
atggaactgc ggtccctgag atctgacgac accgccgtgt actactgcgt gcggtttcag    300
tacggcgact accggtactt tgatgtgtgg ggccagggca cactggtcac cgtttcttcc    360
gcttctacca agggacccag cgtgttccct ctggctcctt cctctaaatc cacctctggc    420
```

```
ggaaccgctg ctctgggctg tctggtcaag gattacttcc ctgagcctgt gaccgtgtcc    480
tggaattctg gtgctctgac atccggcgtg cacacctttc cagctgtgct gcagtcctct    540
ggcctgtact ctctgtcctc tgtcgtgacc gtgccttcta gctctctggg cacccagacc    600
tacatctgca acgtgaacca caagccttcc aacaccaagg tggacaagaa ggtggaaccc    660
aagtcctgcg acaagaccca cacctgtcct ccatgtcctg ctccagaagc tgctggcgct    720
ccctctgtgt tcctgtttcc tccaaagcct aaggacaccc tgatgatctc tcggacccct    780
gaagtgacct gcgtggtggt ggatgtgtct cacgaggacc cagaagtgaa gttcaattgg    840
tacgtggacg gcgtggaagt gcacaacgcc aagaccaagc ctagagagga acagtacaac    900
tccacctaca gagtggtgtc cgtgctgacc gtgctgcacc aggattggct gaacggcaaa    960
gagtacaagt gcaaggtgtc caacaaggca ctgcccgctc ctatcgaaaa gaccatctcc   1020
aaggctaagg gccagcctcg ggaacctcag gtttacaccc tgcctccatc tcgggaagag   1080
atgaccaaga accaggtgtc cctgacctgc ctcgtgaagg gcttctaccc ttccgatatc   1140
gccgtggaat gggagtccaa tggccagcct gagaacaact acaagacaac ccctcctgtg   1200
ctggactccg acggctcatt cttcctgtac tccaagctga cagtggacaa gtctcggtgg   1260
cagcagggca acgtgttctc ctgttctgtg atgcacgagg ccctgcacaa ccactacaca   1320
cagaagtccc tgtctctgtc ccctggcaag tga                                1353
```

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Tyr Thr Phe Thr Asn Tyr Gly Val Lys
1               5                   10

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Trp Ile Asn Thr Tyr Thr Gly Asn Pro Ile Tyr Ala Ala Asp Phe Lys
1               5                   10                  15

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Phe Gln Tyr Gly Asp Tyr Arg Tyr Phe Asp Val
1               5                   10

<210> SEQ ID NO 97
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Glu Ile Ile Leu Thr Gln Ser Pro Ala Thr Leu Ser Leu Ser Pro Gly
1               5                   10                  15

Glu Arg Ala Thr Leu Ser Cys Arg Ala Asn Ser Gly Ile Ser Phe Ile
            20                  25                  30

Asn Trp Tyr Gln Gln Lys Pro Gly Gln Ala Pro Arg Leu Leu Ile Tyr
        35                  40                  45

Gly Thr Ala Asn Leu Ala Ser Gly Ile Pro Ala Arg Phe Gly Gly Ser
65              55                  55                  60

Gly Ser Gly Arg Asp Phe Thr Leu Thr Ile Ser Ser Leu Glu Pro Glu
65              70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 98
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

```
aagcttgcca ccatggaaac cgacacactg ctgctgtggg tgctgttgtt gtgggtgcca      60
ggatctaccg gagagatcat cctgacacag agccccgcca cattgtctct gagtcctggc     120
gagagagcta ccctgtcctg tagagccaac tccggcatct ccttcatcaa ctggtatcag     180
cagaagcccg gccaggctcc tagactgctg atctatggca ccgctaacct ggcctctggc     240
atccctgcta gatttggcgg ctctggctct ggcagagact tcaccctgac catctctagc     300
ctggaacctg aggacttcgc cgtgtactac tgccagcagt ggtctagcaa ccctctgacc     360
tttggcggag gcaccaaggt ggaaatcaag agaaccgtgg ccgctccttc cgtgttcatc     420
ttcccaccat ctgacgagca gctgaagtct ggcacagcct ctgtcgtgtg cctgctgaac     480
aacttctacc ctcgggaagc caaggtgcag tggaaggtgg acaatgccct gcagtccggc     540
aactcccaag agtctgtgac cgagcaggac tccaaggact ctacctacag cctgtcctcc     600
```
acactgaccc tgtctaaggc cgactacgag aagcacaagg tgtacgcctg tgaagtgacc    660
caccagggac tgtctagccc cgtgaccaag tctttcaacc ggggcgagtg ctga          714

<210> SEQ ID NO 99
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Ile Val Leu Thr Gln Ser Pro Ala Thr Leu Ser Leu Ser Pro Gly
1               5                   10                  15

Glu Arg Ala Thr Leu Ser Cys Arg Ala Asn Ser Gly Ile Ser Phe Ile
            20                  25                  30

Asn Trp Tyr Gln Gln Lys Pro Gly Gln Ala Pro Arg Leu Leu Ile Tyr
        35                  40                  45

Gly Thr Ala Asn Leu Ala Ser Gly Ile Pro Ala Arg Phe Ser Gly Ser
    50                  55                  60

Gly Ser Gly Arg Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 100
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
tctacaggcg agatcgtgct gacccagtct cctgccacat tgtctctgag tcctggcgag    60
agagctaccc tgtcctgtag agccaactcc ggcatctcct tcatcaactg gtatcagcag    120
aagcccggcc aggctcctag actgctgatc tatggcaccg ctaacctggc ctctggcatc    180
cctgctagat tttccggctc tggctctggc agagacttca ccctgaccat ctctagcctg    240
gaacctgagg acttcgccgt gtactactgc cagcagtggt ctagcaaccc tctgaccttt    300
ggcggaggca ccaaggtgga aatcaagaga accgtggccg ctccttccgt gttcatcttc    360

```
ccaccatctg acgagcagct gaagtctggc acagcctctg tcgtgtgcct gctgaacaac    420
ttctaccctc gggaagccaa ggtgcagtgg aaggtggaca atgccctgca gtccggcaac    480
tcccaagagt ctgtgaccga gcaggactcc aaggactcta cctacagcct gtcctccaca    540
ctgaccctgt ctaaggccga ctacgagaag cacaaggtgt acgcctgtga agtgacccac    600
cagggactgt ctagccccgt gaccaagtct ttcaaccggg gcgagtgctg a             651
```

<210> SEQ ID NO 101
<211> LENGTH: 213
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

```
Glu Ile Val Leu Thr Gln Ser Pro Ala Thr Leu Ser Leu Ser Pro Gly
1               5                   10                  15

Glu Arg Ala Thr Leu Ser Cys Arg Ala Gln Ser Gly Ile Ser Phe Ile
            20                  25                  30

Asn Trp Tyr Gln Gln Lys Pro Gly Gln Ala Pro Arg Leu Leu Ile Tyr
        35                  40                  45

Gly Thr Ala Asn Leu Ala Ser Gly Ile Pro Ala Arg Phe Ser Gly Ser
    50                  55                  60

Gly Ser Gly Arg Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 102
<211> LENGTH: 651
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 102

```
tctacaggcg agatcgtgct gacccagtct cctgccacat tgtctctgag tcctggcgag    60
agagctaccc tgtcttgtag agcccagtcc ggcatctcct tcatcaactg gtatcagcag   120
```

```
aagcccggcc aggctcctag actgctgatc tatggcaccg ctaacctggc ctctggcatc    180
cctgctagat tttccggctc tggctctggc agagacttca ccctgaccat ctctagcctg    240
gaacctgagg acttcgccgt gtactactgc cagcagtggt ctagcaaccc tctgaccttt    300
ggcggaggca ccaaggtgga aatcaagaga accgtggccg ctccttccgt gttcatcttc    360
ccaccatctg acgagcagct gaagtctggc acagcctctg tcgtgtgcct gctgaacaac    420
ttctaccctc gggaagccaa ggtgcagtgg aaggtggaca atgccctgca gtctggcaac    480
tcccaagagt ctgtgaccga gcaggactcc aaggactcta cctacagcct gtcctccaca    540
ctgaccctgt ctaaggccga ctacgagaag cacaaggtgt acgcctgtga agtgacccac    600
cagggactgt ctagccccgt gaccaagtct ttcaaccggg gcgagtgctg a              651
```

<210> SEQ ID NO 103
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

```
Glu Ile Val Leu Thr Gln Ser Pro Ala Thr Leu Ser Leu Ser Pro Gly
1               5                   10                  15

Glu Arg Ala Thr Leu Ser Cys Arg Ala Asn Ser Gly Ile Ser Phe Ile
            20                  25                  30

Asn Trp Tyr Gln Gln Lys Pro Gly Gln Ala Pro Arg Leu Leu Ile Tyr
        35                  40                  45

Gly Thr Ala Asn Leu Ala Ser Gly Ile Pro Ala Arg Phe Ser Gly Ser
    50                  55                  60

Gly Ser Gly Arg Asp Phe Thr Leu Thr Ile Ser Ser Leu Glu Pro Glu
65                  70                  75                  80

Asp Phe Ala Val Tyr Tyr Cys Gln Gln Tyr Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 104
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

```
tctacaggcg agatcgtgct gacccagtct cctgccacat tgtctctgag tcctggcgag      60
agagctaccc tgtcctgtag agccaactcc ggcatctcct tcatcaactg gtatcagcag     120
aagcccggcc aggctcctag actgctgatc tatggcaccg ctaacctggc ctctggcatc     180
cctgctagat tttccggctc tggctctggc agagacttca ccctgaccat ctctagcctg     240
gaacctgagg acttcgccgt gtactactgc cagcagtaca gcagcaaccc tctgaccttt     300
ggcggaggca ccaaggtgga aatcaagaga accgtggccg ctccttccgt gttcatcttc     360
ccaccatctg acgagcagct gaagtctggc acagcctctg tcgtgtgcct gctgaacaac     420
ttctaccctc gggaagccaa ggtgcagtgg aaggtggaca atgccctgca gtccggcaac     480
tcccaagagt ctgtgaccga gcaggactcc aaggactcta cctacagcct gtcctccaca     540
ctgaccctgt ctaaggccga ctacgagaag cacaaggtgt acgcctgtga agtgacccac     600
cagggactgt ctagccccgt gaccaagtct ttcaaccggg gcgagtgctg a              651
```

<210> SEQ ID NO 105
<211> LENGTH: 213
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys Arg Ala Gln Ser Gly Ile Ser Phe Ile
            20                  25                  30

Asn Trp Tyr Gln Gln Lys Pro Gly Gln Ala Pro Arg Leu Leu Ile Tyr
        35                  40                  45

Gly Thr Ala Asn Leu Ala Ser Gly Ile Pro Ala Arg Phe Ser Gly Ser
    50                  55                  60

Gly Ser Gly Arg Asp Phe Thr Leu Thr Ile Ser Ser Leu Glu Pro Glu
65                  70                  75                  80

Asp Phe Ala Val Tyr Tyr Cys Gln Gln Tyr Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 106
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

```
tctacaggcg agatcgtgct gacccagtct cctgccacat tgtctctgag tcctggcgag    60
agagctaccc tgtcttgtag agcccagtcc ggcatctcct tcatcaactg gtatcagcag   120
aagcccggcc aggctcctag actgctgatc tatggcaccg ctaacctggc ctctggcatc   180
cctgctagat tttccggctc tggctctggc agagacttca ccctgaccat ctctagcctg   240
gaacctgagg acttcgccgt gtactactgc cagcagtaca gcagcaaccc tctgaccttt   300
ggcggaggca ccaaggtgga aatcaagaga accgtggccg ctccttccgt gttcatcttc   360
ccaccatctg acgagcagct gaagtctggc acagcctctg tcgtgtgcct gctgaacaac   420
ttctaccctc gggaagccaa ggtgcagtgg aaggtggaca atgccctgca gtctggcaac   480
tcccaagagt ctgtgaccga gcaggactcc aaggactcta cctacagcct gtcctccaca   540
ctgaccctgt ctaaggccga ctacgagaag cacaaggtgt acgcctgtga agtgacccac   600
cagggactgt ctagccccgt gaccaagtct ttcaaccggg gcgagtgctg a             651
```

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Ala Asn Ser Gly Ile Ser Phe Ile Asn
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Ala Gln Ser Gly Ile Ser Phe Ile Asn
1               5                   10

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Thr Ala Asn Leu Ala Ser
1               5

<210> SEQ ID NO 110
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 110

Gln Gln Trp Ser Ser Asn Pro Leu Thr
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Gln Tyr Ser Ser Asn Pro Leu Thr
1               5

<210> SEQ ID NO 112
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Lys | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Phe |
| | | 20 | | | | | 25 | | | | | 30 | | | |
| Ala | Met | Ser | Trp | Val | Arg | Gln | Ala | Pro | Gly | Lys | Gly | Leu | Glu | Trp | Val |
| | | 35 | | | | 40 | | | | | 45 | | | | |
| Ser | Thr | Ile | Ser | Ser | Gly | Ser | Ile | Tyr | Ile | Tyr | Tyr | Thr | Asp | Gly | Val |
| 50 | | | | | 55 | | | | | 60 | | | | | |
| Lys | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Arg | Gly | Ile | Tyr | Tyr | Gly | Tyr | Asp | Gly | Tyr | Ala | Met | Asp | Tyr |
| | | | 100 | | | | | 105 | | | | | 110 | | |
| Trp | Gly | Gln | Gly | Thr | Leu | Val | Thr | Val | Ser | Ser | Ala | Ser | Thr | Lys | Gly |
| | | | 115 | | | | | 120 | | | | | 125 | | |
| Pro | Ser | Val | Phe | Pro | Leu | Ala | Pro | Ser | Ser | Lys | Ser | Thr | Ser | Gly | Gly |
| | | 130 | | | | | 135 | | | | | 140 | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Gln | Thr | Tyr | Ile | Cys | Asn | Val |
| | | | 195 | | | | | 200 | | | | | 205 | | |
| Asn | His | Lys | Pro | Ser | Asn | Thr | Lys | Val | Asp | Lys | Lys | Val | Glu | Pro | Lys |
| | | 210 | | | | | 215 | | | | | 220 | | | |
| Ser | Cys | Asp | Lys | Thr | His | Thr | Cys | Pro | Pro | Cys | Pro | Ala | Pro | Glu | Ala |
| 225 | | | | | 230 | | | | | 235 | | | | | 240 |

```
Ala Gly Ala Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 113
<211> LENGTH: 1362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
gaggtgcagc tggttgaatc tggcggagga cttgtgaagc ctggcggctc tctgagactg     60
tcttgtgccg cctctggctt caccttctcc agctttgcca tgtcctgggt ccgacaggct    120
cctggcaaag gactggaatg ggtgtccacc atctcctccg gctccatcta catctactac    180
accgacggcg tgaagggcag attcaccatc agcagagaca cgccaagaa ctccctgtac     240 ctgcagatga acagcctgag agccgaggac accgccgtgt actattgtgc agacggggc    300 atctactatg gctacgacgg ctacgctatg gactattggg gacagggcac actggtcacc    360
gtgtcctctg cttctaccaa gggacccagc gtgttccctc tggctccttc ctctaaatcc    420
acctctggcg gaaccgctgc tctgggctgt ctggtcaagg attacttccc tgagcctgtg    480
accgtgtcct ggaactctgg tgctctgaca tccggcgtgc acacctttcc agctgtgctg    540
cagtcctctg gcctgtactc tctgtcctct gtcgtgaccg tgccttctag ctctctgggc    600
acccagacct acatctgcaa cgtgaaccac aagccttcca caccaaggt ggacaagaag    660 gtggaaccca gtcctgcga caagacccac acctgtcctc catgtcctgc tccagaagct    720
gctggcgctc cctctgtgtt cctgtttcct ccaaagccta aggacaccct gatgatctct    780
```

```
cggacccctg aagtgacctg cgtggtggtg gatgtgtctc acgaggaccc agaagtgaag    840
ttcaattggt acgtggacgg cgtggaagtg cacaacgcca agaccaagcc tagagaggaa    900
cagtacaact ccacctacag agtggtgtcc gtgctgaccg tgctgcacca ggattggctg    960
aacggcaaag agtacaagtg caaggtgtcc aacaaggcac tgcccgctcc tatcgaaaag   1020
accatctcca aggctaaggg ccagcctcgg aacctcagg tttacaccct gcctccatct    1080
cgggaagaga tgaccaagaa ccaggtgtcc ctgacctgcc tcgtgaaggg cttctaccct   1140
tccgatatcg ccgtggaatg ggagtccaat ggccagcctg agaacaacta caagacaacc   1200
cctcctgtgc tggactccga cggctcattc ttcctgtact ccaagctgac agtggacaag   1260
tctcggtggc agcagggcaa cgtgttctcc tgttctgtga tgcacgaggc cctgcacaac   1320
cactacacac agaagtccct gtctctgtcc cctggcaagt ga                      1362
```

<210> SEQ ID NO 114
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe
                20                  25                  30

Ala Met Ser Trp Val Arg Gln Ala Pro Gly Lys Gly Leu Glu Trp Val
            35                  40                  45

Ser Thr Ile Ser Ser Gly Ser Ile Tyr Ile Tyr Tyr Thr Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Ile Tyr Tyr Gly Tyr Glu Gly Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Ala
225                 230                 235                 240

Ala Gly Ala Pro Ser Val Phe Leu Phe Pro Pro Lys Pro Lys Asp Thr
                245                 250                 255
```

Leu Met Ile Ser Arg Thr Pro Glu Val Thr Cys Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Phe Thr Phe Ser Ser Phe Ala Met Ser
1               5                   10

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Thr Ile Ser Ser Gly Ser Ile Tyr Ile Tyr Tyr Thr Asp Gly Val Lys
1               5                   10                  15

Gly

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Thr Ile Ser Ser Gly Ser Ile Tyr Ile Tyr Tyr Thr Asp Ser Val Lys
1               5                   10                  15

Gly

<210> SEQ ID NO 118
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Gly Ile Tyr Tyr Gly Tyr Asp Gly Tyr Ala Met Asp Tyr
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Gly Ile Tyr Tyr Gly Tyr Glu Gly Tyr Ala Met Asp Tyr
1               5                   10

<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Gly Ile Tyr Tyr Gly Tyr Ser Gly Tyr Ala Met Asp Tyr
1               5                   10

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Gly Ile Tyr Tyr Gly Tyr Ala Gly Tyr Ala Met Asp Tyr
1               5                   10

<210> SEQ ID NO 122
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ala Ile Val Leu Thr Gln Ser Pro Gly Thr Leu Ser Leu Ser Pro Gly
1               5                   10                  15

Glu Arg Ala Thr Leu Ser Cys Arg Ser Ser Gln Ser Leu Val His Ser
            20                  25                  30

Asn Gly Asn Thr Tyr Leu His Trp Tyr Met Gln Lys Pro Gly Gln Ala
            35                  40                  45

Pro Arg Val Leu Ile Tyr Lys Val Ser Asn Arg Phe Ser Gly Ile Pro
 50                  55                  60

Asp Arg Phe Ser Gly Ser Gly Ser Gly Thr Asp Phe Thr Leu Thr Ile
 65                  70                  75                  80

Ser Arg Leu Glu Pro Asp Asp Phe Ala Ile Tyr Tyr Cys Ser Gln Ser
                 85                  90                  95

Thr His Ile Pro Leu Ala Phe Gly Gln Gly Thr Lys Leu Glu Ile Lys
             100                 105                 110

Arg Thr Val Ala Ala Pro Ser Val Phe Ile Phe Pro Pro Ser Asp Glu
         115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 123
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
gccatcgtgt tgacccagtc tccaggcaca ttgtctctga gccctggcga gagagctacc        60
ctgtcctgca gatcttctca gtccctggtg cactccaacg caacaccta cctgcactgg       120 tacatgcaga agcccggaca ggctcccaga gtgctgatct acaaggtgtc caaccggttc       180
tctggcatcc ccgacagatt ttccggctct ggctctggca ccgacttcac cctgaccatc       240
tctagactgg aacccgacga cttcgccatc tactactgct cccagtccac acacatccct       300
ctggcttttg gccagggcac caagctggaa atcaagagaa ccgtggccgc tccttccgtg       360
ttcatcttcc caccatctga cgagcagctg aagtccggca gcttctgt cgtgtgcctg        420 ctgaacaact ctaccctcg ggaagccaag gtgcagtgga aggtggacaa tgccctgcag       480
tccggcaact cccaagagtc tgtgaccgag caggactcca aggactctac ctacagcctg       540
tcctccacac tgaccctgtc taaggccgac tacgagaagc acaaggtgta cgcctgtgaa       600
gtgacccacc agggcctgtc tagccctgtg accaagtctt tcaaccgggg cgagtgttga       660

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Ser Ser Gln Ser Leu Val His Ser Asn Gly Asn Thr Tyr Leu His
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Ser Ser Gln Ser Leu Val His Ser Ser Gly Asn Thr Tyr Leu His
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Arg Ser Ser Gln Ser Leu Val His Ser Thr Gly Asn Thr Tyr Leu His
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Ser Ser Gln Ser Leu Val His Ser Gln Gly Asn Thr Tyr Leu His
1               5                   10                  15

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Lys Val Ser Asn Arg Phe Ser
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Gln Ser Thr His Ile Pro Leu Ala
1               5

<210> SEQ ID NO 130
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Lys Trp Val Arg Gln Ala Pro Gly Gln Gly Leu Glu Trp Met
        35                  40                  45

Gly Trp Ile Asn Thr Tyr Thr Gly Asn Pro Ile Tyr Ala Ala Asp Phe
50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Val Arg Phe Gln Tyr Gly Asp Tyr Arg Tyr Phe Asp Val Trp Gly Gln
            100                 105                 110

Gly Thr Leu Val Thr Val Ser Ser
        115                 120
```

<210> SEQ ID NO 131
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

```
Glu Ile Val Leu Thr Gln Ser Pro Ala Thr Leu Ser Leu Ser Pro Gly
1               5                   10                  15

Glu Arg Ala Thr Leu Ser Cys Arg Ala Gln Ser Gly Ile Ser Phe Ile
            20                  25                  30

Asn Trp Tyr Gln Gln Lys Pro Gly Gln Ala Pro Arg Leu Leu Ile Tyr
        35                  40                  45

Gly Thr Ala Asn Leu Ala Ser Gly Ile Pro Ala Arg Phe Ser Gly Ser
50                  55                  60

Gly Ser Gly Arg Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105
```

<210> SEQ ID NO 132
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

Gly Val Lys Trp Val Arg Gln Ala Pro Gly Gln Asp Leu Glu Trp Met
            35                  40                  45

Gly Trp Ile Asn Thr Tyr Thr Gly Asn Pro Ile Tyr Ala Ala Asp Phe
    50                  55                  60

Lys Gly Arg Val Thr Met Thr Thr Asp Thr Ser Thr Ser Thr Ala Phe
65                  70                  75                  80

Met Glu Leu Arg Ser Leu Arg Ser Asp Thr Ala Val Tyr Tyr Cys
                85                  90                  95

Val Arg Phe Gln Tyr Gly Asp Tyr Arg Tyr Phe Asp Val Trp Gly Gln
            100                 105                 110

Gly Thr Leu Val Thr Val Ser Ser
            115                 120

<210> SEQ ID NO 133
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Ile Ile Leu Thr Gln Ser Pro Ala Thr Leu Ser Leu Ser Pro Gly
1               5                   10                  15

Glu Arg Ala Thr Leu Ser Cys Arg Ala Asn Ser Gly Ile Ser Phe Ile
            20                  25                  30

Asn Trp Tyr Gln Gln Lys Pro Gly Gln Ala Pro Arg Leu Leu Ile Tyr
            35                  40                  45

Gly Thr Ala Asn Leu Ala Ser Gly Ile Pro Ala Arg Phe Gly Gly Ser
    50                  55                  60

Gly Ser Gly Arg Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 134
<211> LENGTH: 202
<212> TYPE: PRT
<213> ORGANISM: Homo sapiens

<400> SEQUENCE: 134

Met Cys Tyr Gly Lys Cys Ala Arg Cys Ile Gly His Ser Leu Val Gly
1               5                   10                  15

Leu Ala Leu Leu Cys Ile Ala Ala Asn Ile Leu Leu Tyr Phe Pro Asn
            20                  25                  30

Gly Glu Thr Lys Tyr Ala Ser Glu Asn His Leu Ser Arg Phe Val Trp
            35                  40                  45

Phe Phe Ser Gly Ile Val Gly Gly Leu Leu Met Leu Leu Pro Ala
    50                  55                  60

Phe Val Phe Ile Gly Leu Glu Gln Asp Asp Cys Cys Gly Cys Cys Gly
65                  70                  75                  80

His Glu Asn Cys Gly Lys Arg Cys Ala Met Leu Ser Ser Val Leu Ala
                85                  90                  95

Ala Leu Ile Gly Ile Ala Gly Ser Gly Tyr Cys Val Ile Val Ala Ala
            100                 105                 110

```
Leu Gly Leu Ala Glu Gly Pro Leu Cys Leu Asp Ser Leu Gly Gln Trp
            115                 120                 125

Asn Tyr Thr Phe Ala Ser Thr Glu Gly Gln Tyr Leu Leu Asp Thr Ser
        130                 135                 140

Thr Trp Ser Glu Cys Thr Glu Pro Lys His Ile Val Glu Trp Asn Val
145                 150                 155                 160

Ser Leu Phe Ser Ile Leu Leu Ala Leu Gly Ile Glu Phe Ile Leu
                165                 170                 175

Cys Leu Ile Gln Val Ile Asn Gly Val Leu Gly Gly Ile Cys Gly Phe
            180                 185                 190

Cys Cys Ser His Gln Gln Gln Tyr Asp Cys
            195                 200

<210> SEQ ID NO 135
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

Asn Tyr Lys Thr Thr Pro Pro Val Leu Asp Ser Asp Gly Ser Phe Phe
              275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
              325                 330

<210> SEQ ID NO 136
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
              20                  25                  30

Phe Pro Glu Pro Val Thr Val Ser Trp Asn Ser Gly Ala Leu Thr Ser
           35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Cys Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn

```
            290                 295                 300
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 137
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Gly Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

Gln Lys Ser Leu Ser Leu Ser Pro Gly Lys
            325                 330

<210> SEQ ID NO 138
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Cys Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Gly Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 139

<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Gly Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 140
<211> LENGTH: 330
<212> TYPE: PRT
<213> ORGANISM: Artificial Sequence
<220> FEATURE:
<223> OTHER INFORMATION: Description of Artificial Sequence: Synthetic

<400> SEQUENCE: 140

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Gly Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 141
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ala Ser Thr Lys Gly Pro Ser Val Phe Pro Leu Ala Pro Ser Ser Lys

```
                1               5                  10                 15
            Ser Thr Ser Gly Gly Thr Ala Ala Leu Gly Cys Leu Val Lys Asp Tyr
                            20                  25                  30

Phe Pro Glu Pro Val Thr Val Ser Trp Asn Ser Gly Ala Leu Thr Ser
                            35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Leu Gly Thr Gln Thr
             65                  70                  75                  80

Tyr Ile Cys Asn Val Asn His Lys Pro Ser Asn Thr Lys Val Asp Lys
                            85                  90                  95

Lys Val Glu Pro Lys Ser Cys Asp Lys Thr His Thr Cys Pro Pro Cys
                            100                 105                 110

Pro Ala Pro Glu Ala Ala Gly Ala Pro Ser Val Phe Leu Phe Pro Pro
                            115                 120                 125

Lys Pro Lys Asp Thr Leu Met Ile Ser Arg Thr Pro Glu Val Thr Cys
             130                 135                 140

Val Val Val Asp Val Ser His Glu Asp Pro Glu Val Lys Phe Asn Trp
             145                 150                 155                 160

Tyr Val Asp Gly Val Glu Val His Asn Ala Lys Thr Lys Pro Arg Glu
                            165                 170                 175

Glu Gln Tyr Cys Ser Thr Tyr Arg Val Val Ser Val Leu Thr Val Leu
                            180                 185                 190

His Gln Asp Trp Leu Asn Gly Lys Glu Tyr Lys Cys Lys Val Ser Asn
                            195                 200                 205

Lys Ala Leu Pro Ala Pro Ile Glu Lys Thr Ile Ser Lys Ala Lys Gly
                            210                 215                 220

Gln Pro Arg Glu Pro Gln Val Tyr Thr Leu Pro Pro Ser Arg Glu Glu
             225                 230                 235                 240

Met Thr Lys Asn Gln Val Ser Leu Thr Cys Leu Val Lys Gly Phe Tyr
                            245                 250                 255

Pro Ser Asp Ile Ala Val Glu Trp Glu Ser Asn Gly Gln Pro Glu Asn
                            260                 265                 270

Asn Tyr Lys Thr Thr Pro Pro Val Leu Asp Ser Asp Gly Ser Phe Phe
                            275                 280                 285

Leu Tyr Ser Lys Leu Thr Val Asp Lys Ser Arg Trp Gln Gln Gly Asn
                            290                 295                 300

Val Phe Ser Cys Ser Val Met His Glu Ala Leu His Asn His Tyr Thr
             305                 310                 315                 320

Gln Lys Ser Leu Ser Leu Ser Pro Gly Lys
                            325                 330

<210> SEQ ID NO 142
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30
```

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Cys Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
            195                 200                 205

Lys Ala Leu Pro Ala Gly Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 143
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Cys Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Gly Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 144
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys 85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Cys Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
            195                 200                 205

Lys Ala Leu Pro Ala Gly Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 145
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Cys Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Gly Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Lys Pro
                325                 330

<210> SEQ ID NO 146
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Lys Trp Val Arg Gln Ala Pro Gly Gln Gly Leu Glu Trp Met
        35                  40                  45

Gly Trp Ile Asn Thr Tyr Thr Gly Asn Pro Ile Tyr Ala Ala Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Val Arg Phe Gln Tyr Gly Asp Tyr Arg Tyr Phe Asp Val Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140
```

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 147
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Lys Trp Val Arg Gln Ala Pro Gly Gln Gly Leu Glu Trp Met
            35                  40                  45

Gly Trp Ile Asn Thr Tyr Thr Gly Asn Pro Ile Tyr Ala Ala Asp Phe

```
            50                  55                  60
Lys Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                     85                  90                  95
Val Arg Phe Gln Tyr Gly Asp Tyr Arg Tyr Phe Asp Val Trp Gly Gln
                    100                 105                 110
Gly Thr Leu Val Thr Val Ser Ser Ala Ser Thr Lys Gly Pro Ser Val
                    115                 120                 125
Phe Pro Leu Ala Pro Cys Ser Arg Ser Thr Ser Glu Ser Thr Ala Ala
                    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                    165                 170                 175
Leu Gln Ser Ser Gly Leu Tyr Ser Leu Ser Ser Val Val Thr Val Pro
                    180                 185                 190
Ser Ser Ser Leu Gly Thr Lys Thr Tyr Thr Cys Asn Val Asp His Lys
                    195                 200                 205
Pro Ser Asn Thr Lys Val Asp Lys Arg Val Glu Ser Lys Tyr Gly Pro
                    210                 215                 220
Pro Cys Pro Pro Cys Pro Ala Pro Glu Phe Glu Gly Gly Pro Ser Val
225                 230                 235                 240
Phe Leu Phe Pro Pro Lys Pro Lys Asp Thr Leu Met Ile Ser Arg Thr
                    245                 250                 255
Pro Glu Val Thr Cys Val Val Val Asp Val Ser Gln Glu Asp Pro Glu
                    260                 265                 270
Val Gln Phe Asn Trp Tyr Val Asp Gly Val Glu Val His Asn Ala Lys
                    275                 280                 285
Thr Lys Pro Arg Glu Glu Gln Phe Asn Ser Thr Tyr Arg Val Val Ser
                    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                    325                 330                 335
Ser Lys Ala Lys Gly Gln Pro Arg Glu Pro Gln Val Tyr Thr Leu Pro
                    340                 345                 350
Pro Ser Gln Glu Glu Met Thr Lys Asn Gln Val Ser Leu Thr Cys Leu
                    355                 360                 365
Val Lys Gly Phe Tyr Pro Ser Asp Ile Ala Val Glu Trp Glu Ser Asn
                    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                    405                 410                 415
Trp Gln Glu Gly Asn Val Phe Ser Cys Ser Val Met His Glu Ala Leu
                    420                 425                 430
His Asn His Tyr Thr Gln Lys Ser Leu Ser Leu Ser Leu Gly Lys
                    435                 440                 445

<210> SEQ ID NO 148
<211> LENGTH: 447
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 148

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Lys Trp Val Arg Gln Ala Pro Gly Gln Gly Leu Glu Trp Met
        35                  40                  45

Gly Trp Ile Asn Thr Tyr Thr Gly Asn Pro Ile Tyr Ala Ala Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Val Arg Phe Gln Tyr Gly Asp Tyr Arg Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Cys Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
```

-continued

```
            385                 390                 395                 400
Asp Gly Ser Phe Phe Leu Tyr Ser Arg Leu Thr Val Asp Lys Ser Arg
                    405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445

<210> SEQ ID NO 149
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Lys Trp Val Arg Gln Ala Pro Gly Gln Gly Leu Glu Trp Met
        35                  40                  45

Gly Trp Ile Asn Thr Tyr Thr Gly Asn Pro Ile Tyr Ala Ala Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Val Arg Phe Gln Tyr Gly Asp Tyr Arg Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Cys Ser Thr Tyr Arg Val Val Ser
    290                 295                 300
```

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 150
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Lys Trp Val Arg Gln Ala Pro Gly Gln Gly Leu Glu Trp Met
            35                  40                  45

Gly Trp Ile Asn Thr Tyr Thr Gly Asn Pro Ile Tyr Ala Ala Asp Phe
50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Val Arg Phe Gln Tyr Gly Asp Tyr Arg Tyr Phe Asp Val Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

```
Pro Cys Pro Pro Cys Pro Ala Pro Glu Phe Glu Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
            275                 280                 285

Thr Lys Pro Arg Glu Glu Gln Phe Cys Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Lys
            435                 440                 445

Pro

<210> SEQ ID NO 151
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Tyr Ile Thr Arg Glu Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 152
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Gln Leu Met Ile Ser Arg Thr Pro Glu Val Thr Cys
    130                 135                 140

Val Val Val Asp Val Ser His Glu Asp Pro Glu Val Lys Phe Asn Trp
```

```
                145                 150                 155                 160
Tyr Val Asp Gly Val Glu Val His Asn Ala Lys Thr Lys Pro Arg Glu
                    165                 170                 175

Glu Gln Tyr Asn Ser Thr Tyr Arg Val Val Ser Val Leu Thr Val Leu
                    180                 185                 190

His Gln Asp Trp Leu Asn Gly Lys Glu Tyr Lys Cys Lys Val Ser Asn
                    195                 200                 205

Lys Ala Leu Pro Ala Pro Ile Glu Lys Thr Ile Ser Lys Ala Lys Gly
                    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
                    290                 295                 300

Val Phe Ser Cys Ser Val Leu His Glu Ala Leu His Asn His Tyr Thr
305                 310                 315                 320

Gln Lys Ser Leu Ser Leu Ser Pro Gly Lys
                    325                 330

<210> SEQ ID NO 153
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
                    35                  40                  45

Gly Val His Thr Phe Pro Ala Val Leu Gln Ser Ser Gly Leu Tyr Ser
                    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                    100                 105                 110

Pro Ala Pro Glu Leu Leu Gly Gly Pro Ser Val Phe Leu Phe Pro Pro
                    115                 120                 125

Lys Pro Lys Asp Thr Leu Met Ile Ser Arg Thr Pro Glu Val Thr Cys
                    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                    165                 170                 175
```

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
            325                 330

<210> SEQ ID NO 154
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Lys Trp Val Arg Gln Ala Pro Gly Gln Gly Leu Glu Trp Met
        35                  40                  45

Gly Trp Ile Asn Thr Tyr Thr Gly Asn Pro Ile Tyr Ala Ala Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Val Arg Phe Gln Tyr Gly Asp Tyr Arg Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

-continued

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Gln Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Leu His Glu Ala Leu
            420                 425                 430

His Asn His Tyr Thr Gln Lys Ser Leu Ser Leu Ser Leu Gly Lys
        435                 440                 445

<210> SEQ ID NO 155
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Lys Trp Val Arg Gln Ala Pro Gly Gln Gly Leu Glu Trp Met
        35                  40                  45

Gly Trp Ile Asn Thr Tyr Thr Gly Asn Pro Ile Tyr Ala Ala Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Val Arg Phe Gln Tyr Gly Asp Tyr Arg Tyr Phe Asp Val Trp Gly Gln
            100                 105                 110

Gly Thr Leu Val Thr Val Ser Ser Ala Ser Thr Lys Gly Pro Ser Val 115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Leu His Glu Ala Leu
            420                 425                 430

His Ser His Tyr Thr Gln Lys Ser Leu Ser Leu Ser Leu Gly Lys
        435                 440                 445

<210> SEQ ID NO 156
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

```
Gly Val Lys Trp Val Arg Gln Ala Pro Gly Gln Gly Leu Glu Trp Met
             35                  40                  45
Gly Trp Ile Asn Thr Tyr Thr Gly Asn Pro Ile Tyr Ala Ala Asp Phe
 50                  55                  60
Lys Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
             85                  90                  95
Val Arg Phe Gln Tyr Gly Asp Tyr Arg Tyr Phe Asp Val Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Tyr Ile
            245                 250                 255
Thr Arg Glu Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
```

```
<210> SEQ ID NO 157
<211> LENGTH: 48
<212> TYPE: PRT
<213> ORGANISM: Homo sapiens

<400> SEQUENCE: 157

Glu Gly Pro Leu Cys Leu Asp Ser Leu Gly Gln Trp Asn Tyr Thr Phe
1               5                   10                  15

Ala Ser Thr Glu Gly Gln Tyr Leu Leu Asp Thr Ser Thr Trp Ser Glu
                20                  25                  30

Cys Thr Glu Pro Lys His Ile Val Glu Trp Asn Val Ser Leu Phe Ser
            35                  40                  45

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Arg Glu Glu Gln Tyr Cys Ser Thr Tyr Arg Val Val
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Arg Glu Glu Gln Phe Cys Ser Thr Tyr Arg Val Val
1               5                   10

<210> SEQ ID NO 160
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Gly Gly Gly Gly Gly
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Gly Gly Gly Gly Gly Gly
1               5

<210> SEQ ID NO 162
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 162

Pro Gly Lys Lys Pro
1               5

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Leu Gly Lys Lys Pro
1               5
```

ANTIBODY-DRUG CONJUGATES COMPRISING ANTI-TM4SF1 ANTIBODIES AND METHODS OF USING THE SAME

CROSS-REFERENCE

This application is a 371 U.S. National Phase Application of International Patent Application No. PCT/US2020/020207 filed Feb. 27, 2020 which claims the benefit of U.S. Provisional Application No. 62/811,411 filed Feb. 27, 2019, and U.S. Provisional Application No. 62/967,377 filed Jan. 29, 2020, each incorporated by reference herein in its entirety.

SEQUENCE LISTING

The instant application contains a Sequence Listing which has been submitted electronically in ASCII format and is hereby incorporated by reference in its entirety. Said ASCII copy, created on Apr. 8, 2020, is named 52628-706_601_SL.txt and is 179,643 bytes in size.

BACKGROUND

There remains a need in the art for cancer therapeutics, and in particular therapeutics with improved therapeutic margins that can regress primary tumors as well as invasive tumor cells and metastases.

Cancer therapies designed to destroy tumor blood vessels have in the past failed in clinical trials due to toxicity. Examples include the vascular disrupting agents such as Combretastatin (CA4P). See, e.g., Grisham et al. Clinical trial experience with CA4P anticancer therapy: focus on efficacy, cardiovascular adverse events, and hypertension management. Gynecol Oncol Res Pract. 2018; 5:1. CA4P reduced overall survival from 16.2 to 13.6 months in the Phase II FALCON study, and seven patients have experienced heart attacks while being treated with CA4P. Id. As coronary heart disease and stroke are leading causes of death, any vascular targeted toxic therapy may lead to a risk of lethal toxicity.

TM4SF1 is an endothelial marker with a functional role in angiogenesis. See, e.g., Shih et al. The L6 protein TM4SF1 is critical for endothelial cell function and tumor angiogenesis. Cancer Res. 2009; 69(8):3272-7. Although antibody-drug conjugates targeting TM4SF1 have been considered previously, see, e.g., Visintin et al. Novel Anti-TM4SF1 Antibody—Drug Conjugates with Activity against Tumor Cells and Tumor Vasculature, Mol Cancer Ther 2015 (14) (8) 1868-1876, in order to enable anti-TM4SF1 ADCs to fulfill their promise as therapies for solid tumors, TM4SF1 targeted ADCs with reduced toxicity to normal vessels, especially arteries, are needed.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

One embodiment provides an antibody-drug conjugate comprising (i) an anti-TM4SF1 antibody or an antigen binding fragment thereof and (ii) a therapeutic molecule, wherein said anti-TM4SF1 antibody or an antigen binding fragment thereof comprises an IgG Fc region comprising a mutation at one or more positions selected from the group consisting of E233, L234, L235, G237, M252, S254, T250, T256, D265, N297, K322, P331, M428, and N434; as numbered by the EU index as set forth in Kabat. In some embodiments, said IgG Fc region comprises said mutation at position N297. In some embodiments, said mutation at position N297 comprises N297C. In some embodiments, said IgG Fc region further comprises an extended C-terminus that is positively charged, wherein said extended C-terminus comprises one or more amino acid residues after position K447, as numbered by the EU index as set forth in Kabat.

One embodiment provides an antibody-drug conjugate comprising (i) an anti-TM4SF1 antibody or an antigen binding fragment thereof and (ii) a therapeutic molecule, wherein said anti-TM4SF1 antibody or an antigen binding fragment thereof comprises an IgG Fc region comprising an extended C-terminus that is positively charged, wherein said extended C-terminus comprises one or more amino acid residues after position K447, as numbered by the EU index as set forth in Kabat. In some embodiments, said IgG Fc region further comprises a mutation at one or more positions selected from the group consisting of E233, L234, L235, G237, M252, S254, T250, T256, D265, N297, K322, P331, T356, M428, and N434; as numbered by the EU index as set forth in Kabat. In some embodiments, said IgG Fc region comprises said mutation at position N297. In some embodiments, said mutation at position N297 comprises N297C.

One embodiment provides an antibody-drug conjugate comprising (i) an anti-TM4SF1 antibody or an antigen binding fragment thereof and (ii) a therapeutic molecule, wherein said anti-TM4SF1 antibody or an antigen binding fragment thereof comprises an IgG Fc region comprising a cysteine residue at position N297, as numbered by the EU index as set forth in Kabat. In some embodiments, said IgG Fc region further comprises a mutation at one or more positions selected from the group consisting of E233, L234, L235, G237, M252, S254, T250, T256, D265, N297, K322, P331, M428, and N434; as numbered by the EU index as set forth in Kabat.

In some embodiments, said IgG Fc region further comprises an extended C-terminus that is positively charged, wherein said extended C-terminus comprises one or more amino acid residues after position K447, as numbered by the EU index as set forth in Kabat. One embodiment provides an antibody-drug conjugate comprising (i) an anti-TM4SF1 antibody or an antigen binding fragment thereof and (ii) a therapeutic molecule, wherein said anti-TM4SF1 antibody or an antigen binding fragment thereof comprises an IgG Fc region comprising a human IgG1 Fc region comprising a cysteine residue at position N297 and a mutation at one or more positions selected from the group consisting of E233, L234, L235, G237, M252, S254, T250, T256, D265, N297, K322, P331, M428, and N434; as numbered by the EU index as set forth in Kabat. In some embodiments, said IgG Fc region further comprises an extended C-terminus that is positively charged, wherein said extended C-terminus comprises one or more amino acid residues after position K447, as numbered by the EU index as set forth in Kabat.

One embodiment provides an antibody-drug conjugate comprising (i) an anti-TM4SF1 antibody or an antigen binding fragment thereof and (ii) a therapeutic molecule, wherein said anti-TM4SF1 antibody or an antigen binding fragment thereof comprises an IgG Fc region comprising a cysteine residue at position N297, as numbered by the EU index as set forth in Kabat, wherein said antibody-drug conjugate comprises a drug to antibody ratio (DAR) of greater than or equal to about 1. In some embodiments, said IgG Fc region further comprises a mutation at one or more positions selected from the group consisting of E233, L234, L235, G237, M252, S254, T250, T256, D265, N297, K322, P331, M428, and N434; as numbered by the EU index as set forth in Kabat. In some embodiments, said IgG Fc region further comprises an extended C-terminus that is positively charged, wherein said extended C-terminus comprises one or more amino acid residues after position K447, as numbered by the EU index as set forth in Kabat.

One embodiment provides an antibody-drug conjugate comprising (i) an anti-TM4SF1 antibody or an antigen binding fragment thereof and (ii) a therapeutic molecule, wherein said anti-TM4SF1 antibody or an antigen binding fragment thereof comprises an IgG Fc region comprising a cysteine residue at position N297 and an extended C-terminus that is positively charged, wherein said extended C-terminus comprises one or more amino acid residues after position K447, wherein numbering is according to the EU index as set forth in Kabat. In some embodiments, said IgG Fc region further comprises a mutation at one or more positions selected from the group consisting of E233, L234, L235, G237, M252, S254, T250, T256, D265, N297, K322, P331, M428, and N434; as numbered by the EU index as set forth in Kabat. In some embodiments, said one or more amino acid residues after position K447 are independently selected from the group consisting of: a lysine, a proline, an arginine, or any combinations thereof.

In some embodiments, said one or more amino acid residues after position K447 are independently selected from the group consisting of: said lysine and said proline. In some embodiments, said IgG Fc region comprises said mutation at position E233. In some embodiments, said mutation at position E233 comprises E233P. In some embodiments, said IgG Fc region comprises said mutation at position L234. In some embodiments, said mutation at position L234 comprises L234A. In some embodiments, said IgG Fc region comprises said mutation at position L235. In some embodiments, said mutation at position L235 comprises L235A. In some embodiments, said IgG Fc region comprises said mutation at position G237. In some embodiments, said mutation at position G237 comprises G237A. In some embodiments, said IgG Fc region comprises said mutation at position M252. In some embodiments, said mutation at position M252 comprises M252Y. In some embodiments, said IgG Fc region comprises said mutation at position S254. In some embodiments, said mutation at position S254 comprises S254T. In some embodiments, said IgG Fc region comprises said mutation at position T256. In some embodiments, said mutation at position T256 comprises T256E. In some embodiments, said IgG Fc region comprises said mutation at position M428. In some embodiments, said mutation at position M428 comprises M428L. In some embodiments, said IgG Fc region comprises said mutation at position N434. In some embodiments, said mutation at position N434 comprises N434S or N434A. In some embodiments, said IgG Fc region comprises said mutation at position T250. In some embodiments, said mutation at position T250 comprises T250Q. In some embodiments, said IgG Fc region comprises said mutation at position D265. In some embodiments, said mutation at position D265 comprises D265A. In some embodiments, said IgG Fc region comprises said mutation at position K322. In some embodiments, said mutation at position K322 comprises K322A. In some embodiments, said IgG Fc region comprises said mutation at position P331. In some embodiments, said mutation at position P331 comprises P331G. In some embodiments, said IgG Fc region comprises T250Q and M428L. In some embodiments, said IgG Fc region comprises M428L. In some embodiments, said IgG Fc region comprises M428L and N434S.

In some embodiments, said IgG Fc region comprises N434A. In some embodiments, said IgG Fc region comprises L234A, L235A, and G237A. In some embodiments, said IgG Fc region comprises L234A, L235A, G237A, and P331G. In some embodiments, said IgG Fc region comprises L234A, L235A, G237A, N297C, and P331G. In some embodiments, said IgG Fc region comprises L234A, L235A, G237A, K322A, and P331G. In some embodiments, said IgG Fc region comprises E233P, L234A, L235A, G237A, and P331G. In some embodiments, said IgG Fc region comprises E233P, L234A, L235A, G237A, and N297C. In some embodiments, said IgG Fc region comprises E233P, L234A, L235A, G237A, and N297C. In some embodiments, said IgG Fc region comprises L234A, L235A, G237A, N297C, K322A, and P331G. In some embodiments, said IgG Fc region comprises E233P, L234A, L235A, G237A, D265A, N297C, K322A, and P331G. In some embodiments, said IgG Fc region comprises E233P, L234A, L235A, G237A, D265A, N297C, K322A, and P331G. In some embodiments, said IgG Fc region comprises E233P and D265A. In some embodiments, said IgG Fc region comprises M252Y, S254T, and T256E. In some embodiments, said IgG Fc region comprises M252Y, S254T, T256E, and N297C. In some embodiments, said IgG Fc region comprises K322A and P331G, and wherein said IgG Fc region further comprises an extended C-terminus that is positively charged, wherein said extended C-terminus comprises one or more amino acid residues after position K447. In some embodiments, said IgG Fc region comprises an amino acid sequence selected from the group consisting of SEQ ID Nos. 87-88, 135-145, and 151-153. In some embodiments, said IgG Fc region exhibits reduced or ablated binding with C1q. In some embodiments, said IgG Fc region exhibits reduced or ablated binding to an Fc receptor. In some embodiments, said anti-TM4SF1 antibody exhibits reduced or ablated ADCC or CDC effector function.

One embodiment provides an antibody-drug conjugate comprising (i) an anti-TM4SF1 antibody or an antigen binding fragment thereof and (ii) a therapeutic molecule, wherein said anti-TM4SF1 antibody or an antigen binding fragment thereof comprises a human IgG4 Fc region comprising a mutation at one or more positions selected from the group consisting of S228, F234, L235, G237, P238, F243, T250, M252, S254, T256, E258, D259, V264, D265, K288, T299, T307, V308, Q311, K322, L328, P329, A330, P331, T356, K370, A378, R409, V427, M428, H433, N434, H435, and N297, as numbered by the EU index as set forth in Kabat. In some embodiments, said human IgG4 Fc region comprises said mutation at position N297. In some embodiments, said mutation at position N297 comprises N297C. In some embodiments, said human IgG4 Fc region further comprises an extended C-terminus that is positively charged, wherein said extended C-terminus comprises one or more amino acid residues after position K447, as numbered by the EU index as set forth in Kabat.

One embodiment provides an antibody-drug conjugate comprising (i) an anti-TM4SF1 antibody or an antigen binding fragment thereof and (ii) a therapeutic molecule, wherein said anti-TM4SF1 antibody or an antigen binding fragment thereof comprises a human IgG4 Fc region comprising an extended C-terminus that is positively charged, wherein said extended C-terminus comprises one or more amino acid residues after position K447, as numbered by the EU index as set forth in Kabat. In some embodiments, said human IgG4 Fc region further comprises a mutation at one or more positions selected from the group consisting of S228, F234, L235, G237, P238, F243, T250, M252, S254, T256, E258, D259, V264, D265, K288, T299, T307, V308, Q311, K322, L328, P329, A330, P331, T356, K370, A378, R409, V427, M428, H433, N434, H435, and N297, as numbered by the EU index as set forth in Kabat. In some embodiments, said human IgG4 Fc region comprises said mutation at position N297. In some embodiments, said mutation at position N297 comprises N297C.

One embodiment provides an antibody-drug conjugate comprising (i) an anti-TM4SF1 antibody or an antigen binding fragment thereof and (ii) a therapeutic molecule, wherein said anti-TM4SF1 antibody or an antigen binding fragment thereof comprises a human IgG4 Fc region comprising a cysteine residue at position N297, as numbered by the EU index as set forth in Kabat. In some embodiments, said human IgG4 Fc region further comprises a mutation at one or more positions selected from the group consisting of S228, F234, L235, G237, P238, F243, T250, M252, S254, T256, E258, D259, V264, D265, K288, T299, T307, V308, Q311, K322, L328, P329, A330, P331, T356, K370, A378, R409, V427, M428, H433, N434, and H435, as numbered by the EU index as set forth in Kabat. In some embodiments, said human IgG4 Fc region further comprises an extended C-terminus that is positively charged, wherein said extended C-terminus comprises one or more amino acid residues after position K447, as numbered by the EU index as set forth in Kabat.

One embodiment provides an antibody-drug conjugate comprising (i) an anti-TM4SF1 antibody or an antigen binding fragment thereof and (ii) a therapeutic molecule, wherein said anti-TM4SF1 antibody or an antigen binding fragment thereof comprises a human IgG4 Fc region comprising a cysteine residue at position N297 and a mutation at one or more positions selected from the group consisting of S228, F234, L235, G237, P238, F243, T250, M252, S254, T256, E258, D259, V264, D265, K288, T299, T307, V308, Q311, K322, L328, P329, A330, P331, T356, K370, A378, R409, V427, M428, H433, N434, and H435, as numbered by the EU index as set forth in Kabat. In some embodiments, said human IgG4 Fc region further comprises an extended C-terminus that is positively charged, wherein said extended C-terminus comprises one or more amino acid residues after position K447, as numbered by the EU index as set forth in Kabat.

One embodiment provides an antibody-drug conjugate comprising (i) an anti-TM4SF1 antibody or an antigen binding fragment thereof and (ii) a therapeutic molecule, wherein said anti-TM4SF1 antibody or an antigen binding fragment thereof comprises a human IgG4 Fc region comprising a cysteine residue at position N297, as numbered by the EU index as set forth in Kabat, wherein said antibody-drug conjugate comprises a drug to antibody ratio (DAR) of greater than or equal to 1. In some embodiments, said human IgG4 Fc region further comprises a mutation at one or more positions selected from the group consisting of S228, F234, L235, G237, P238, F243, T250, M252, S254, T256, E258, D259, V264, D265, K288, T299, T307, V308, Q311, K322, L328, P329, A330, P331, T356, K370, A378, R409, V427, M428, H433, N434, and H435, as numbered by the EU index as set forth in Kabat. In some embodiments, said human IgG4 Fc region further comprises an extended C-terminus that is positively charged, wherein said extended C-terminus comprises one or more amino acid residues after position K447, as numbered by the EU index as set forth in Kabat.

One embodiment provides an antibody-drug conjugate comprising (i) an anti-TM4SF1 antibody or an antigen binding fragment thereof and (ii) a therapeutic molecule, wherein said anti-TM4SF1 antibody or an antigen binding fragment thereof comprises a human IgG4 Fc region comprising a cysteine residue at position N297 and an extended C-terminus that is positively charged, wherein said extended C-terminus comprises one or more amino acid residues after position K447, wherein numbering is according to the EU index as set forth in Kabat. In some embodiments, said human IgG4 Fc region further comprises a mutation at one or more positions selected from the group consisting of S228, F234, L235, G237, P238, F243, T250, M252, S254, T256, E258, D259, V264, D265, K288, T299, T307, V308, Q311, K322, L328, P329, A330, P331, T356, K370, A378, R409, V427, M428, H433, N434, and H435, as numbered by the EU index as set forth in Kabat. In some embodiments, said one or more amino acid residues after position K447 is independently selected from the group consisting of: a lysine, a proline, an arginine, or any combinations thereof. In some embodiments, said one or more amino acid residues after position K447 is independently selected from the group consisting of: said lysine and said proline. In some embodiments, said human IgG4 Fc region comprises said mutation at position S228. In some embodiments, said mutation at position S228 comprises S228P. In some embodiments, said human IgG4 Fc region comprises said mutation at position F234. In some embodiments, said mutation at position F234 comprises F234A. In some embodiments, said human IgG4 Fc region comprises said mutation at position L235. In some embodiments, said mutation at position L235 comprises L235E. In some embodiments, said human IgG4 Fc region comprises S228P and L235E. In some embodiments, said human IgG4 Fc region comprises S228P, L235E, and N297C. In some embodiments, said human IgG4 Fc region comprises S228P, F234A, L235E, and N297C. In some embodiments, said human IgG4 Fc region comprises S228P, L235E, and N297C, and wherein said human IgG4 Fc region further comprises an extended C-terminus that is positively charged, wherein said extended C-terminus comprises one or more amino acid residues after position K447. In some embodiments, said human IgG4 Fc region comprises M428L and N434S. In some embodiments, said human IgG4 Fc region comprises mutations at L235 and F234. In some embodiments, said human IgG4 Fc region comprises mutations at positions L328, A330, and T299. In some embodiments, said human IgG4 Fc region comprises S228P, F234A, L235A, G237A, and P238S. In some embodiments, said human IgG4 Fc region comprises F243A and V264A. In some embodiments, said human IgG4 Fc region comprises S228P and L235A. In some embodiments, said human IgG4 Fc region comprises M252Y and M428L; D259I and V308F; or N434S. In some embodiments, said human IgG4 Fc region comprises T307Q and N434S; M428L and V308F; Q311V and N434S; H433K and N434F; E258F and V427T; or T256D, Q311V, and A378V. In some embodiments, said human IgG4 Fc region comprises one or more of the following properties: (i) reduced or ablated binding with C1q; (ii) reduced or ablated binding to an Fc receptor; and (iii) reduced or ablated ADCC or CDC effector function. In some embodiments, said anti-TM4SF1 antibody or an antigen binding fragment thereof comprising said human IgG4 Fc region comprises an amino acid sequence selected from the group consisting of SEQ ID Nos. 146-150, and 154-155.

In some embodiments, said anti-TM4SF1 antibody or an antigen binding fragment thereof comprises:

(a) a heavy chain comprising a CDR3 domain comprising an amino acid sequence that has at least 75% identity to a sequence selected from the group consisting of SEQ ID NO: 8, 20, 32, 44, 56, 68, 80, 96, 118, 119, 120, or 121; a CDR2 domain comprising an amino acid sequence that has at least 75% identity to a sequence selected from the group consisting of SEQ ID NO: 7, 19, 31, 43, 55, 67, 79, 95, 116, or 117; and a CDR1 domain comprising an amino acid sequence that has at least 75% identity to a sequence selected from the group consisting of SEQ ID NO: 6, 18, 30, 42, 54, 66, 78, 94, or 115; and (b) a light chain comprising a CDR3 domain comprising an amino acid sequence that has at least 75% identity to a sequence selected from the group consisting of SEQ ID NO: 14, 26, 38, 50, 62, 74, 86, 110, or 129; a CDR2 domain comprising an amino acid sequence that has at least 75% identity to a sequence selected from the group consisting of SEQ ID NO: 13, 25, 37, 49, 61, 73, 85, 109, or 128; and a CDR1 domain comprising an amino acid sequence that has at least 75% identity to a sequence selected from the group consisting of SEQ ID NO: 12, 24, 36, 48, 60, 72, or 84, 107, 108, 124, 125, 126, or 127.

In some embodiments, said heavy chain comprises an amino acid sequence that has at least 75% identity to SEQ ID NO: 3, 15, 27, 39, 51, 63, 75, 90, 92, 112, 114, 130, or 132, and a light chain comprises an amino acid sequence that has at least 75% identity to SEQ ID NO: 9, 21, 33, 45, 57, 69, 81, 97, 99, 101, 122, 131, or 133. In some embodiments, said heavy chain comprises a sequence as set forth in SEQ ID NO: 3, 15, 27, 39, 51, 63, 75, 90, 92, 112, 114, 130, or 132, and wherein said light chain variable domain comprises a sequence as set forth in SEQ ID NO: 9, 21, 33, 45, 57, 69, 81, 97, 99, 101, 122, 131, or 133. In some embodiments, said heavy chain comprises a CDR3 domain comprising the amino acid sequence as set forth in SEQ ID NO: 8, a CDR2 domain comprising the amino acid sequence as set forth in SEQ ID NO: 7, and a CDR1 domain comprising the amino acid sequence as set forth in SEQ ID NO: 6; and wherein said light chain comprises a CDR3 domain comprising the amino acid sequence as set forth in SEQ ID NO: 14, a CDR2 domain comprising the amino acid sequence as set forth in SEQ ID NO: 13, and a CDR1 domain comprising the amino acid sequence as set forth in SEQ ID NO: 12. In some embodiments, said heavy chain comprises a CDR3 domain comprising the amino acid sequence se set forth in SEQ ID NO: 20, a CDR2 domain comprising the amino acid sequence as set forth in SEQ ID NO: 19, and a CDR1 domain comprising the amino acid sequence as set forth in SEQ ID NO: 18; and wherein said light chain comprises a CDR3 domain comprising the amino acid sequence as set forth in SEQ ID NO: 26, a CDR2 domain comprising the amino acid sequence as set forth in SEQ ID NO: 25, and a CDR1 domain comprising the amino acid sequence as set forth in SEQ ID NO: 24. In some embodiments, said heavy chain comprises a CDR3 domain comprising the amino acid sequence se set forth in SEQ ID NO: 32, a CDR2 domain comprising the amino acid sequence as set forth in SEQ ID NO: 31, and a CDR1 domain comprising the amino acid sequence as set forth in SEQ ID NO: 30; and wherein said light chain comprises a CDR3 domain comprising the amino acid sequence as set forth in SEQ ID NO: 38, a CDR2 domain comprising the amino acid sequence as set forth in SEQ ID NO: 37, and a CDR1 domain comprising the amino acid sequence as set forth in SEQ ID NO: 36.

In some embodiments, said heavy chain comprises a CDR3 domain comprising the amino acid sequence se set forth in SEQ ID NO: 44, a CDR2 domain comprising the amino acid sequence as set forth in SEQ ID NO: 43, and a CDR1 domain comprising the amino acid sequence as set forth in SEQ ID NO: 42; and wherein said light chain comprises a CDR3 domain comprising the amino acid sequence as set forth in SEQ ID NO: 50, a CDR2 domain comprising the amino acid sequence as set forth in SEQ ID NO: 49, and a CDR1 domain comprising the amino acid sequence as set forth in SEQ ID NO: 48. In some embodiments, said heavy chain comprises a CDR3 domain comprising the amino acid sequence se set forth in SEQ ID NO: 56, a CDR2 domain comprising the amino acid sequence as set forth in SEQ ID NO: 55, and a CDR1 domain comprising the amino acid sequence as set forth in SEQ ID NO: 54; and wherein said light chain comprises a CDR3 domain comprising the amino acid sequence as set forth in SEQ ID NO: 62, a CDR2 domain comprising the amino acid sequence as set forth in SEQ ID NO: 61, and a CDR1 domain comprising the amino acid sequence as set forth in SEQ ID NO: 60. In some embodiments, said heavy chain comprises a CDR3 domain comprising the amino acid sequence se set forth in SEQ ID NO: 68, a CDR2 domain comprising the amino acid sequence as set forth in SEQ ID NO: 67, and a CDR1 domain comprising the amino acid sequence as set forth in SEQ ID NO: 66; and wherein said light chain comprises a CDR3 domain comprising the amino acid sequence as set forth in SEQ ID NO: 74, a CDR2 domain comprising the amino acid sequence as set forth in SEQ ID NO: 73, and a CDR1 domain comprising the amino acid sequence as set forth in SEQ ID NO: 72. In some embodiments, said heavy chain comprises a CDR3 domain comprising the amino acid sequence se set forth in SEQ ID NO: 80, a CDR2 domain comprising the amino acid sequence as set forth in SEQ ID NO: 79, and a CDR1 domain comprising the amino acid sequence as set forth in SEQ ID NO: 78; and wherein said light chain comprises a CDR3 domain comprising the amino acid sequence as set forth in SEQ ID NO: 86, a CDR2 domain comprising the amino acid sequence as set forth in SEQ ID NO: 85, and a CDR1 domain comprising the amino acid sequence as set forth in SEQ ID NO: 84. In some embodiments, said heavy chain comprises a CDR3 domain comprising the amino acid sequence se set forth in SEQ ID NO: 96, a CDR2 domain comprising the amino acid sequence as set forth in SEQ ID NO: 95, and a CDR1 domain comprising the amino acid sequence as set forth in SEQ ID NO: 94; and wherein said light chain comprises a CDR3 domain comprising the amino acid sequence as set forth in SEQ ID NO: 111 or SEQ ID NO: 110, a CDR2 domain comprising the amino acid sequence as set forth in SEQ ID NO: 109, and a CDR1 domain comprising the amino acid sequence as set forth in SEQ ID NO: 107 or SEQ ID NO: 108.

In some embodiments, said heavy chain comprises a CDR3 domain comprising the amino acid sequence se set forth in SEQ ID NO: 96, a CDR2 domain comprising the amino acid sequence as set forth in SEQ ID NO: 95, and a CDR1 domain comprising the amino acid sequence as set forth in SEQ ID NO: 94; and wherein said light chain comprises a CDR3 domain comprising the amino acid sequence as set forth in SEQ ID NO: 110, a CDR2 domain comprising the amino acid sequence as set forth in SEQ ID NO: 109, and a CDR1 domain comprising the amino acid sequence as set forth in SEQ ID NO: 107. In some embodiments, said heavy chain comprises a CDR3 domain comprising the amino acid sequence se set forth in SEQ ID NO: 96, a CDR2 domain comprising the amino acid sequence as set forth in SEQ ID NO: 95, and a CDR1 domain comprising the amino acid sequence as set forth in SEQ ID NO: 94; and wherein said light chain comprises a CDR3 domain comprising the amino acid sequence as set forth in SEQ ID NO: 110, a CDR2 domain comprising the amino acid sequence as set forth in SEQ ID NO: 109, and a CDR1 domain comprising the amino acid sequence as set forth in SEQ ID NO: 108. In some embodiments, said heavy chain comprises a CDR3 domain comprising the amino acid sequence se set forth in SEQ ID NO: 96, a CDR2 domain comprising the amino acid sequence as set forth in SEQ ID NO: 95, and a CDR1 domain comprising the amino acid sequence as set forth in SEQ ID NO: 94; and wherein said light chain comprises a CDR3 domain comprising the amino acid sequence as set forth in SEQ ID NO: 111, a CDR2 domain comprising the amino acid sequence as set forth in SEQ ID NO: 109, and a CDR1 domain comprising the amino acid sequence as set forth in SEQ ID NO: 107. In some embodiments, said heavy chain comprises a CDR3 domain comprising the amino acid sequence se set forth in SEQ ID NO: 96, a CDR2 domain comprising the amino acid sequence as set forth in SEQ ID NO: 95, and a CDR1 domain comprising the amino acid sequence as set forth in SEQ ID NO: 94; and wherein said light chain comprises a CDR3 domain comprising the amino acid sequence as set forth in SEQ ID NO: 111, a CDR2 domain comprising the amino acid sequence as set forth in SEQ ID NO: 109, and a CDR1 domain comprising the amino acid sequence as set forth in SEQ ID NO: 108. In some embodiments, said heavy chain comprises a CDR3 domain comprising the amino acid sequence se set forth in SEQ ID NO: 118, a CDR2 domain comprising the amino acid sequence as set forth in SEQ ID NO: 116, and a CDR1 domain comprising the amino acid sequence as set forth in SEQ ID NO: 115; and wherein said light chain comprises a CDR3 domain comprising the amino acid sequence as set forth in SEQ ID NO: 129, a CDR2 domain comprising the amino acid sequence as set forth in SEQ ID NO: 128, and a CDR1 domain comprising the amino acid sequence as set forth in SEQ ID NO: 124.

In some embodiments, said heavy chain comprises a CDR3 domain comprising the amino acid sequence se set forth in SEQ ID NO: 118, SEQ ID NO: 119, SEQ IN NO: 120, or SEQ ID NO: 121, a CDR2 domain comprising the amino acid sequence as set forth in SEQ ID NO: 116 or SEQ ID NO: 117, and a CDR1 domain comprising the amino acid sequence as set forth in SEQ ID NO: 115; and wherein said light chain comprises a CDR3 domain comprising the amino acid sequence as set forth in SEQ ID NO: 129, a CDR2 domain comprising the amino acid sequence as set forth in SEQ ID NO: 128, and a CDR1 domain comprising the amino acid sequence as set forth in SEQ ID NO: 124, SEQ ID NO: 125, SEQ ID NO: 126, or SEQ ID NO: 127. In some embodiments, said antigen-binding fragment comprises an Fab, an Fab', an F(ab')$_2$, an Fv, or an scFv.

One embodiment provides an anti-TM4SF1 binding protein comprising a modified human IgG1 Fc region, wherein said modified human IgG1 Fc region comprises one or more amino acid substitutions selected from the group consisting of E233, L234, L235, G237, M252, S254, T250, T256, D265, N297, K322, P331, M428, and N434, as numbered by the EU index as set forth in Kabat, wherein said anti-TM4SF1 binding protein demonstrates improved vascular safety compared to an otherwise identical binding protein that does not comprise an amino acid substitution selected from the group consisting of E233, L234, L235, G237, M252, S254, T250, T256, D265, N297, K322, P331, M428, and N434. In some embodiments said modified human IgG1 Fc region comprises a mutation at one or more positions selected from the group consisting of T250, M252, S254, T256, M428, and N434 as numbered by the EU index as set forth in Kabat. In some embodiments said modified human IgG1 Fc region comprises a mutation selected from the group consisting of T250Q, M252Y, S254T, T256E, M428L, and N434S, as numbered by the EU index as set forth in Kabat. In some embodiments, said modified human IgG1 Fc region comprises mutations T250Q and M428L. In some embodiments, said modified human IgG1 Fc region comprises mutations M252Y, S254T, and T256E. In some embodiments, said modified human IgG1 Fc region comprises mutations M428L and N434S.

One embodiment provides an anti-TM4SF1 binding protein comprising a modified human IgG4 Fc region, wherein said modified human IgG4 Fc region comprises one or more amino acid substitutions selected from the group consisting of S228, F234, L235, G237, P238, F243, T250, M252, S254, T256, E258, D259, V264, D265, K288, T299, T307, V308, Q311, K322, L328, P329, A330, P331, T356, K370, A378, R409, V427, M428, H433, N434, H435, and N297, as numbered by the EU index as set forth in Kabat, wherein said anti-TM4SF1 binding protein demonstrates improved vascular safety compared to an otherwise identical binding protein that does not comprise an amino acid substitutions selected from the group consisting of S228, F234, L235, G237, P238, F243, T250, M252, S254, T256, E258, D259, V264, D265, K288, T299, T307, V308, Q311, K322, L328, P329, A330, P331, T356, K370, A378, R409, V427, M428, H433, N434, H435, and N297. In some embodiments, said modified human IgG4 Fc region comprises a mutation at one or more positions selected from the group consisting of T250, M428, and N434 as numbered by the EU index as set forth in Kabat. In some embodiments, said modified human IgG4 Fc region comprises a mutation selected from the group consisting of T250Q, M428L, and N434S as numbered by the EU index as set forth in Kabat. In some embodiments, said modified human IgG4 Fc region comprises mutations T250Q and M428L. In some embodiments, said modified human IgG4 Fc region comprises M428L and N434S. In some embodiments, said binding protein exhibits increased affinity to FcRn as compared to a control anti-TM4SF1 binding protein comprising a wild type IgG1 Fc or IgG4 Fc. In some embodiments, said anti-TM4SF1 binding protein comprises an anti-TM4SF1 antibody or an antigen binding fragment thereof. In some embodiments, said anti-TM4SF1 antibody or an antigen binding fragment thereof is conjugated to a therapeutic molecule, wherein said therapeutic molecule comprises at least one of: a small molecule, a degrader, a nucleic acid molecule, a CRISPR-Cas9 gene editing system, and a lipid nanoparticle, or any combinations thereof.

One embodiment provides an antibody-drug conjugate comprising (i) an anti-TM4SF1 antibody or an antigen binding fragment thereof and (ii) a therapeutic molecule, wherein said anti-TM4SF1 antibody or said antigen binding fragment thereof comprises a human IgG1 Fc region comprising a mutation at one or more positions selected from the group consisting of T250, M252, S254, T256, M428, and N434 as numbered by the EU index as set forth in Kabat. In some embodiments, said human IgG1 Fc region comprises a mutation selected from the group consisting of T250Q, M252Y, S254T, T256E, M428L, and N434S, as numbered by the EU index as set forth in Kabat. In some embodiments, said human IgG1 Fc region comprises mutations at positions T250 and M428. In some embodiments, said human IgG1 Fc region comprises mutations T250Q and M428L. In some embodiments, said human IgG1 Fc region comprises mutations at positions M252, S254, and T256. In some embodiments, said human IgG1 Fc region comprises mutations M252Y, S254T, and T256E. In some embodiments, said human IgG1 Fc region comprises mutations at positions M428 and N434. In some embodiments, said human IgG1 Fc region comprises mutations M428L and N434S. In some embodiments, said human IgG1 Fc region further comprises a mutation at position N297. In some embodiments, said mutation at position N297 is N297C. In some embodiments, said human IgG1 Fc region further comprises an extended C-terminus that is positively charged, wherein said extended C-terminus comprises one or more amino acid residues after position K447, as numbered by the EU index as set forth in Kabat. In some embodiments, said human IgG1 Fc region further comprises a mutation at one or more positions selected from the group consisting of E233, L234, L235, G237, D265, N297, K322, and P331; as numbered by the EU index as set forth in Kabat. In some embodiments, said human IgG1 Fc region comprises a mutation selected from the group consisting of E233P, L234A, L235A, G237A, D265A, N297C, K322A, and P331G.

In some embodiments, said human IgG1 Fc region comprises 2, 3, 4, 5, 6, or 7 mutations selected from the group consisting of E233P, L234A, L235A, G237A, D265A, N297C, K322A, and P331G. In some embodiments, said human IgG1 Fc region comprises mutations L234A, L235A, and G237A. In some embodiments, said human IgG1 Fc region comprises mutations L234A, L235A, G237A, and P331G. In some embodiments, said human IgG1 Fc region comprises mutations L234A, L235A, G237A, K322A, and P331G. In some embodiments, said human IgG1 Fc region comprises mutations L234A, L235A, G237A, E233P, and P331G. In some embodiments, said human IgG1 Fc region comprises mutations L234A, L235A, G237A, and N297C. In some embodiments, said human IgG1 Fc region comprises mutations L234A, L235A, G237A, N297C, and P331G. In some embodiments, said human IgG1 Fc region comprises mutations L234A, L235A, G237A, N297C, K322A, and P331G. In some embodiments, said human IgG1 Fc region comprises mutations L234A, L235A, G237A, N297C, E233P, and P331G. In some embodiments, said human IgG1 Fc region comprises mutations L234A, L235A, G237A, D265A, N297C, K322A, and P331G.

One embodiment provides an antibody-drug conjugate comprising (i) an anti-TM4SF1 antibody or an antigen binding fragment thereof and (ii) a therapeutic molecule, wherein said anti-TM4SF1 antibody or said antigen binding fragment thereof comprises a human IgG4 Fc region comprising a mutation at one or more positions selected from the group consisting of T250, M428, and N434 as numbered by the EU index as set forth in Kabat. In some embodiments, said human IgG4 Fc region comprises a mutation selected from the group consisting of T250Q, M428L, and N434S as numbered by the EU index as set forth in Kabat. In some embodiments, said human IgG4 Fc region comprises mutations at positions T250 and M428. In some embodiments, said human IgG4 Fc region comprises mutations T250Q and M428L. In some embodiments, said human IgG4 Fc region comprises mutations at positions M428 and N434. In some embodiments, said human IgG4 Fc region comprises mutations M428L and N434S. In some embodiments, said human IgG4 Fc region further comprises a mutation at position N297. In some embodiments, said mutation at position N297 is N297C. In some embodiments, said human IgG4 Fc region further comprises an extended C-terminus that is positively charged, wherein said extended C-terminus comprises one or more amino acid residues after position K447, as numbered by the EU index as set forth in Kabat. In some embodiments, said human IgG4 Fc region further comprises a mutation at one or more positions selected from the group consisting of S228, F234, and L235 as numbered by the EU index as set forth in Kabat. In some embodiments, said human IgG4 Fc region comprises a mutation selected from the group consisting of S228P, F234A, L235E, and N297C as numbered by the EU index as set forth in Kabat. In some embodiments, said human IgG4 Fc region comprises 2, 3, or 4, mutations selected from the group consisting of S228P, F234A, L235E, and N297C. In some embodiments, said IgG4 Fc region comprises a mutation at position S228. In some embodiments, said mutation at position S228 is S228P. In some embodiments, said IgG4 Fc region comprises mutations at positions S228 and L235. In some embodiments, said IgG4 Fc region comprises mutations S228P and L235E. In some embodiments, said IgG4 Fc region comprises mutations at positions S228, L235, and N297. In some embodiments, said IgG4 Fc region comprises mutations S228P, L235E, and N297C. In some embodiments, said antibody drug conjugate exhibits increased affinity to FcRn as compared to a control antibody drug conjugate comprising a wild type IgG1 Fc or IgG4 Fc.

In some embodiments, said therapeutic molecule comprises at least one of: a small molecule, a degrader, a nucleic acid molecule, a CRISPR-Cas9 gene editing system, and a lipid nanoparticle, or any combinations thereof. In some embodiments, said therapeutic molecule comprises at least one of: a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a DHFR inhibitor, a nucleic acid, a CRISPR enzyme, or any combinations thereof. In some embodiments, said degrader comprises an agent that induces protein degradation. In some embodiments, said agent that induces protein degradation comprises a hydrophobic tag, a proteolysis inducing chimera, an HSP90 inhibitor, a selective estrogen receptor degrader (SERD), and a selective androgen receptor degrader (SARD), or any combinations thereof. In some embodiments, said lipid nanoparticle encapsulates one or more therapeutic molecules. In some embodiments, said nucleic acid molecule comprises an RNA molecule or a DNA molecule. In some embodiments, said RNA molecule comprises an siRNA, an antisense-RNA, an miRNA, an antisense miRNA, an antagomir (anti-miRNA), an shRNA, or an mRNA. In some embodiments, said anti-TM4SF1 antibody or an antigen binding fragment thereof and said therapeutic molecule are conjugated by a linker in a single or a multistep protocol. In some embodiments, said linker comprises a cleavable linker, a non-cleavable linker, a hydrophilic linker, a pro-charged linker, or a dicarboxylic acid based linker. In some embodiments, said cleavable linker comprises a cleavable covalent or non-covalent linker. In some embodiments, said linker comprises a non-cleavable covalent or non-covalent linker. In some embodiments, said cleavable linker comprises an acid-labile linker, a protease-sensitive linker, a photo-labile linker, or a disulfide-containing linker. In some embodiments, said linker comprises a cysteine linker or a non-cysteine linker. In some embodiments, said non-cysteine linker comprises a lysine linker. In some embodiments, said linker comprises a MC (6-maleimidocaproyl), a MCC (a maleimidomethyl cyclohexane-1-carboxylate), a MP (maleimidopropanoyl), a val-cit (valine-citrulline), a val-ala (valine-alanine), an ala-phe (alanine-phenylalanine), a PAB (p-aminobenzyloxycarbonyl), a SPP (N-Succinimidyl 4-(2-pyridylthio) pentanoate), 2,5-dioxopyrrolidin-1-yl 4-(pyridin-2-ylthio)hexanoate, 2,5-dioxopyrrolidin-1-yl 5-methyl-4-(pyridin-2-ylthio)hexanoate, 2,5-dioxopyrrolidin-1-yl 5-methyl-4-(pyridin-2-ylthio)heptanoate, 2,5-dioxopyrrolidin-1-yl 5-ethyl-4-(pyridin-2-ylthio)heptanoate, 2,5-dioxopyrrolidin-1-yl 4-cyclopropyl-4-(pyridin-2-ylthio)butanoate, 2,5-dioxopyrrolidin-1-yl 4-cyclobutyl-4-(pyridin-2-ylthio)butanoate, 2,5-dioxopyrrolidin-1-yl 4-cyclopentyl-4-(pyridin-2-ylthio)butanoate, 2,5-dioxopyrrolidin-1-yl 4-cyclohexyl-4-(pyridin-2-ylthio)butanoate, a SMCC (N-Succinimidyl 4-(N-maleimidomethyl)cyclohexane-1 carboxylate), or a SIAB (N-Succinimidyl (4-iodo-acetyl) aminobenzoate). In some embodiments, said linker is derived from a cross-linking reagent, wherein the cross-linking reagent comprises N-succinimidyl-3-(2-pyridyldithio)propionate (SPDP), 2,5-dioxopyrrolidin-1-yl 3-cyclopropyl-3-(pyridin-2-yldisulfaneyl)propanoate, 2,5-dioxopyrrolidin-1-yl 3-cyclobutyl-3-(pyridin-2-yldisulfaneyl)propanoate, N-succinimidyl 4-(2-pyridyldithio)pentanoate (SPP), 2,5-dioxopyrrolidin-1-yl 4-cyclopropyl-4-(pyridin-2-yldisulfaneyl)butanoate, 2,5-dioxopyrrolidin-1-yl 4-cyclobutyl-4-(pyridin-2-yldisulfaneyl) butanoate, N-succinimidyl 4-(2-pyridyldithio)butanoate (SPDB), 2,5-dioxopyrrolidin-1-yl 4-cyclopropyl-4-(pyridin-2-yldisulfaneyl)butanoate, 2,5-dioxopyrrolidin-1-yl 4-cyclobutyl-4-(pyridin-2-yldisulfaneyl)butanoate, N-succinimidyl-4-(2-pyridyldithio)-2-sulfo-butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl) cyclohexanecarboxylate (SMCC), N-sulfosuccinimidyl 4-(maleimidomethyl) cyclohexanecarboxylate (sulfo-SMCC), or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

One embodiment provides a method of treating or preventing a disease or disorder in a subject, wherein the disease or disorder is characterized by abnormal endothelial cell (EC)-cell interaction, said method comprising administering to the subject an antibody-drug conjugate according to this disclosure. In some embodiments, the EC-cell interaction comprises one or more of EC-mesenchymal stem cell, EC-fibroblast, EC-smooth muscle cell, EC-tumor cell, EC-leukocyte, EC-adipose cell, and EC-neuronal cell interactions. In some embodiments, the disease or disorder comprises an inflammatory disease or a cancer. One embodiment provides a method of treating or preventing inflammation in a subject, said method comprising administering to the subject an antibody-drug conjugate according to this disclosure. One embodiment provides a method of treating or preventing metastasis in a subject, said method comprising administering to the subject an antibody-drug conjugate according to this disclosure, wherein the subject is in partial or complete remission from a cancer. One embodiment provides a method of treating a subject having a cancer which is associated with a high risk of metastasis, said method comprising administering an antibody-drug conjugate according to this disclosure, to the subject having the cancer which is associated with the high risk of metastasis. One embodiment provides a method of treating or preventing metastasis in a subject having a cancer, said method comprising administering an antibody-drug conjugate according to this disclosure, to the subject having the cancer. In some embodiments, the subject is undergoing a treatment which may induce metastasis. In some embodiments, the treatment comprises surgery, radiation treatment and chemotherapy. In some embodiments, the subject is a human. In some embodiments, the cancer is a carcinoma or a sarcoma. In some embodiments, the carcinoma comprises breast cancer, lung cancer, colon cancer, prostate cancer, pancreatic cancer, liver cancer, gastric cancer, renal cancer, bladder cancer, uterine cancer, cervical cancer, ovarian cancer. In some embodiments, the sarcoma comprises an angiosarcoma, an osteosarcoma, or a soft tissue sarcoma. In some embodiments, the cancer is a glioblastoma. One embodiment provides a method of treating or preventing lymphatic or hematogenous metastasis in a human subject comprising administering to the human subject an antibody-drug conjugate according to this disclosure. In some embodiments, the antibody drug conjugate exhibits longer serum half-life after administration as compared to a control antibody drug conjugate comprising a wild type IgG1 Fc or IgG4 Fc.

One embodiment provides a pharmaceutical composition comprising (i) an antibody-drug conjugate according to this disclosure and (ii) a pharmaceutically acceptable carrier. One embodiment provides a pharmaceutical composition comprising the binding protein according to this disclosure.

One embodiment provides an antibody drug conjugate comprising an anti-TM4SF1 antibody or an antigen binding fragment thereof comprising a modified IgG Fc region comprising one or more mutations selected from the group consisting of: (i) S228, F234, L235, G237, P238, F243, T250, M252, S254, T256, E258, D259, V264, D265, K288, T299, T307, V308, Q311, K322, L328, P329, A330, P331, T356, K370, A378, R409, V427, M428, H433, N434, H435, and N297; or (ii) E233, L234, L235, G237, M252, S254, T250, T256, D265, N297, K322, P331, M428, and N434, conjugated to a therapeutic molecule via a linker, wherein said linker is derived from a compound of Formula:

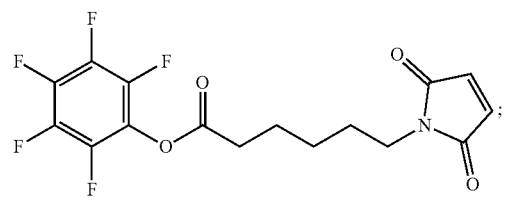

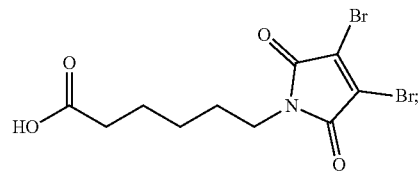

15
-continued

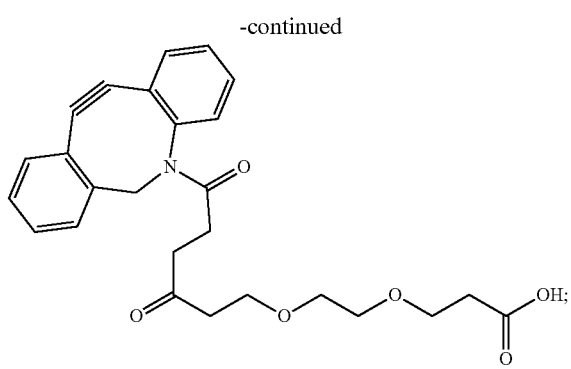

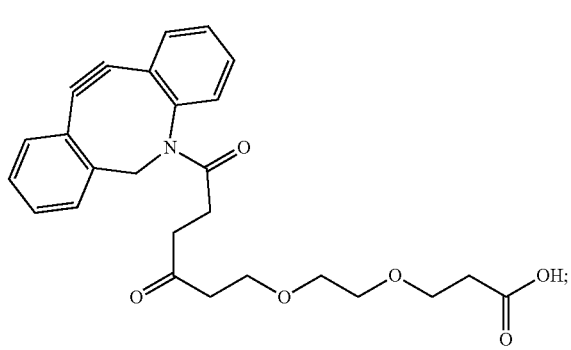

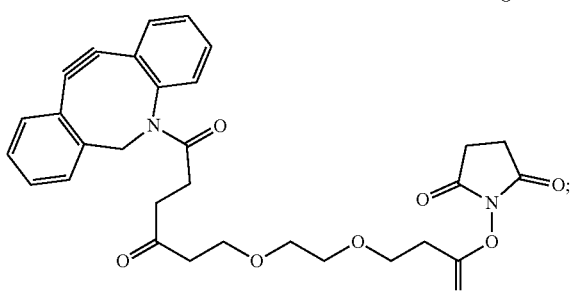

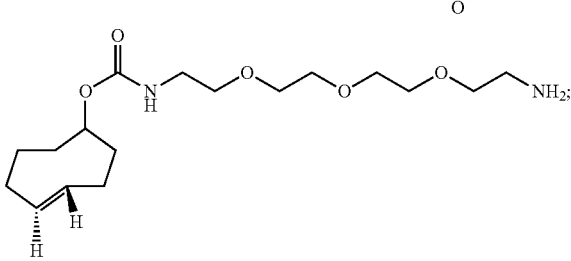

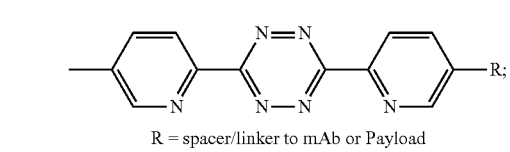

R = spacer/linker to mAb or Payload

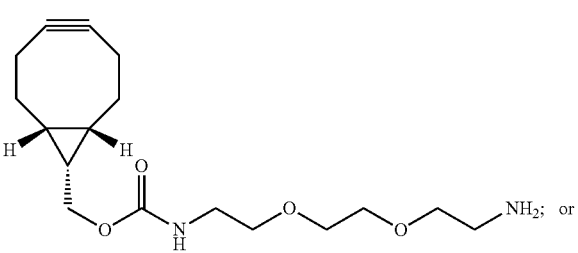

16
-continued

DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

Figure 13:
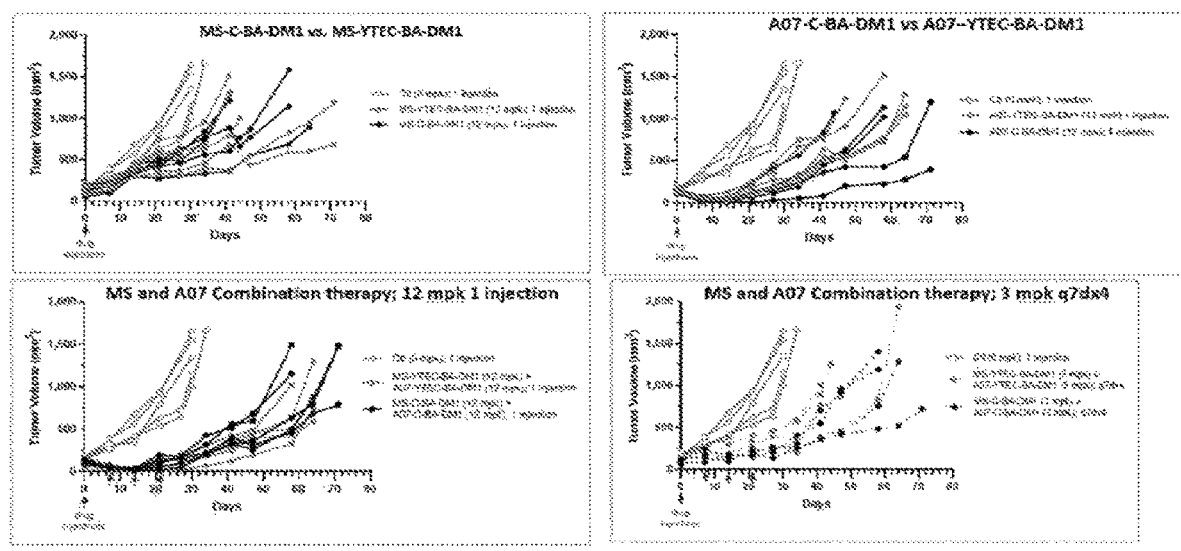

FIG. 13 provides the results of an in vivo study assessing the efficacy of ADCs containing anti-TM4SF1 antibodies (murine surrogate, MS; anti-human TM4SF1 antibodies (AGX-A07); or combinations of both) containing various Fc region mutations, administered at varying doses (3 mg/kg and 12 mg/kg), in regression of tumor growth in a xenograft model.

DETAILED DESCRIPTION OF THE INVENTION

Transmembrane-4 L six family member-1 (TM4SF1) is a small membrane glycoprotein with tetraspanin topology that is highly expressed on many human epithelial tumor cells and in endothelial cells, especially endothelial cells in angiogenic vessels.

Provided herein in one embodiment, is an antibody-drug conjugate (ADC) for a vascular-targeted therapy that, e.g., can regress primary tumors by killing the endothelial cells of tumor blood vessels. This therapy may include various attractive features. Notably, (1) angiogenesis is a hallmark of cancer and a therapy that destroys angiogenic vessels can be a universal treatment for solid tumors; (2) the vascular endothelium is an unmutated host system and might be unable to evolve resistance to therapy. Thus, a vascular-targeted therapy may be able to overcome a common problem with tumor cell targeted therapies, wherein a target tissue evolves and becomes resistant to therapy; and (3) the vascular endothelium of tumors is directly exposed to intravenously (IV)-infused drugs and therefore can be accessible to drugs that cannot reach tumor cells. The inaccessibility of tumor cells can be a major problem in cancers such as pancreatic cancer which have a dense fibrotic stroma which limits access of drugs to tumor cells. A vascular targeted therapy, using an ADC that comprises an anti-TM4SF1 antibody, can advantageously reach the vascular endothelium of tumors.

In one embodiment, the disclosure provides antibody-drug conjugates (ADCs) comprising TM4SF1 binding proteins, such as anti-TM4SF1 antibodies, and antigen-binding fragments thereof. The disclosure includes, in some examples, methods of using the ADCs for treating or preventing cancer. The disclosure includes, in some embodiments, ADCs in which the drug payload conjugated to the antibody is comprised of a small molecule, RNA, DNA, degrader, protein, or combinations thereof.

I. Definitions

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting.

Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the present disclosure may be more readily understood, select terms are defined below. The terms "transmembrane-4 L six family member-1" or "TM4SF1", as used herein refer to a polypeptide of the transmembrane 4 superfamily/tetraspanin family, which is highly expressed on tumor vasculature endothelial cells (ECs), tumor cells (TCs), ECs of developing retinal vasculature, and angiogenic blood vessels. TM4SF1 has two extracellular loops (ECL1 and ECL2) that are separated by four transmembrane domains (M1, M2, M3, and M4), the N- and C-termini, and the intracellular loop (ICL). ECL2 contains two N-glycosylation sites. The amino acid sequence of human TM4SF1 (hTM4SF1) is described in SEQ ID NO: 134 (see also NCBI Ref Seq No. NP_055035.1).

The term "antibody", as used herein, means any antigen-binding molecule comprising at least one complementarity determining region (CDR) that specifically binds to or interacts with a particular antigen (e.g., TM4SF1). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-TMS4F1 antibody (or antigen-binding portion thereof) may be identical to the human germline sequences, or may be naturally or artificially modified. An amino acid consensus sequence may be defined based on a side-by-side analysis of two or more CDRs.

The term "intact antibody" refers to an antibody comprising four polypeptide chains, two heavy (H) chains and two light (L) chains inter-connected by disulfide bonds. In one embodiment, the anti-TM4SF1 antibody is an intact antibody. In one embodiment, the intact antibody is an intact human IgG1, IgG2 or IgG4 isotype. In certain embodiments, the anti-TM4SF1 antibody, or antigen-binding fragment thereof, is a human IgG1, IgG2, or IgG4 isotype.

The terms "antigen-binding portion" of an antibody, "antigen-binding fragment," or "antibody-fragment," of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from intact antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide.

The term "variable region" or "variable domain" of an antibody, or fragment thereof, as used herein refers to the portions of the light and heavy chains of antibody molecules that include amino acid sequences of complementarity determining regions (CDRs; i.e., CDR-1, CDR-2, and CDR-3), and framework regions (FRs). VH refers to the variable domain of the heavy chain. VL refers to the variable domain of the light chain. According to the methods used in this disclosure, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

The term "complementarity determining regions" or "CDRs" as used herein refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia et al., J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

The term "framework regions" (hereinafter FR) as used herein refers to those variable domain residues other than the CDR residues. Each variable domain typically has four FRs identified as FR1, FR2, FR3 and FR4. Common structural features among the variable regions of antibodies, or functional fragments thereof, are well known in the art. The DNA sequence encoding a particular antibody can generally be found following well known methods such as those described in Kabat, et al. 1987 Sequence of Proteins of Immunological Interest, U.S. Department of Health and Human Services, Bethesda Md., which is incorporated herein as a reference. In addition, a general method for cloning functional variable regions from antibodies can be found in Chaudhary, V. K., et al., 1990 Proc. Natl. Acad. Sci. USA 87:1066, which is incorporated herein as a reference.

The term "Fc region" herein is used to define a C-terminal region of an antibody heavy chain, including, for example, native sequence Fc regions, recombinant Fc regions, and variant Fc regions. Although the boundaries of the Fc region of an antibody heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system as in Kabat et al.) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Further, a composition of intact antibodies in this disclosure may comprise antibody populations with extension of residues after the C-terminal lysine, K447.

The term "humanized antibody" as used herein refers to an antibody or a variant, derivative, analog or fragment thereof, which immunospecifically binds to an antigen of interest (e.g., human TM4SF1), and which comprises a framework (FR) region having substantially the amino acid sequence of a human antibody and a complementary determining region (CDR) having substantially the amino acid sequence of a non-human antibody. Humanized forms of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332, all of which are hereby incorporated by reference in their entireties.

The term "monoclonal antibody" as used herein refers to an antibody obtained from a population of substantially homogeneous antibodies, i.e., the individual antibodies comprising the population are identical except for possible mutations, e.g., naturally occurring mutations that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. In contrast to polyclonal antibody preparations, which typically include different antibodies directed against different determinants (epitopes), each monoclonal antibody of a monoclonal-antibody preparation is directed against a single epitope on an antigen.

The term "chimeric antibody" as used herein refers to antibodies (immunoglobulins) that have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

The term "epitope" as used herein refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The terms "payload," "drug payload," "therapeutic molecule," therapeutic payload", "therapeutic agents," "therapeutic moieties," as used interchangeably herein, refers to a chemical or biological moiety that is conjugated to an anti-TMSF1 antibody or antigen binding fragment (e.g., an anti-TM4SF1 antibody or antigen binding fragment disclosed herein), and can include any therapeutic or diagnostic agent, for example, but not limited to, small molecules, both for cancer and for non-cancer angiogenic indications; a V-ATPase inhibitor; a pro-apoptotic agent; a Bcl2 inhibitor; an MCL1 inhibitor; a HSP90 inhibitor; an IAP inhibitor; an mTor inhibitor; a microtubule stabilizer; a microtubule destabilizer; an auristatin; a dolastatin; a maytansinoid; a MetAP (methionine aminopeptidase); an inhibitor of nuclear export of proteins CRM1; a DPPIV inhibitor; proteasome inhibitors; inhibitors of phosphoryl transfer reactions in mitochondria; a protein synthesis inhibitor; a kinase inhibitor (such as, a CDK2 inhibitor, a CDK9 inhibitor); a kinesin inhibitor, an HDAC inhibitor, a DNA damaging agent, a DNA alkylating agent, a DNA intercalator, a DNA minor groove binder, a DHFR inhibitor, a nucleic acid, a CRISPR enzyme; degraders (such as agents that induce protein degradation, (e.g., HSP90 inhibitor, selective estrogen receptor degraders (SERDs), selective androgen receptor degraders (SARDs); hydrophobic tags that can be used to recruit chaperones to a protein of interest, e.g., Adamantane, Arg-Boc3; E3 ligase recruiting ligands, e.g., Nutlin-3a (MDM2 ligand), Bestatin (cIAP ligand), VHL ligand, Pomalidomide (CRBN ligand); proteolysis-targeting chimeras (PROTACs) that may utilize different D3 ligases to target a protein of interest for degradation)) (see, e.g., Lai A C, Crews C M. Induced protein degradation: an emerging drug discovery paradigm. Nat Rev Drug Discov. 2016; 16(2):101-114); antisense oligonucleotides; RNAi agents (such as siRNA), CRISPR-Cas9 gene editing systems; RNA molecules; DNA e.g., plasmids; an anti-cancer agent, an anti-inflammatory agent, an anti-infective agent (e.g., antifungal, antibacterial, anti-parasitic, anti-viral), an anesthetic agent; RNA polymerase II inhibitor; a DNA intercalating agent, a DNA cross-linking agent; an anti-tubulin agent; a cytotoxic drug, a tumor vaccine, an antibody, a peptide, pepti-bodies, a chemotherapeutic agent, a cytotoxic agent; a cytostatic agent; an immunological modifiers, an interferon, an interleukin, an immuno stimulatory growth hormone, a cytokine, a vitamin, a mineral, an aromatase inhibitor, a Histone Deacetylase (HDAC), an HDAC inhibitor; a lipid nanoparticle to encapsulate one or more therapeutic molecules.

The term "drug-to-antibody ratio" or "DAR" can refer to the number of drugs (also referred to herein as therapeutic molecules, therapeutic agents, or therapeutic moieties), attached to an anti-TM4SF1 antibody or antigen binding fragments thereof, of the ADCs disclosed herein. The DAR of an ADC typically ranges from 1 to 12, although higher loads, e.g., 16, are also possible depending on the number of linkage sites on an antibody or the use of multivalent linkages in which multiple drug payloads are attached to one linkage site. The term DAR may be used in reference to the number of drug molecules loaded onto an individual antibody, or, alternatively, may be used in reference to the average or mean DAR of a group of ADCs to reflect average drug loading. Compositions, batches, and/or formulations of a plurality of ADCs may be characterized by an average DAR. DAR and average DAR can be determined by various conventional means such as UV spectroscopy, mass spectroscopy, ELISA assay, radiometric methods, hydrophobic interaction chromatography (HIC), electrophoresis and HPLC.

The term "binding affinity" generally refers to the strength of the sum total of noncovalent interactions between a single binding site of a molecule (e.g., a binding protein such as an antibody) and its binding partner (e.g., an antigen). The affinity of a binding molecule X (e.g., anti-TM4SF1 antibody) for its binding partner Y (e.g., human TM4SF1) can generally be represented by the dissociation constant ($K_D$).

Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments include the following. In one embodiment, the "$K_D$" or "$K_D$ value" may be measured by assays known in the art, for example by a binding assay. The $K_D$ may be measured in a RIA, for example, performed with the Fab version of an antibody of interest and its antigen (Chen et al., 1999, J. Mol Biol 293:865-81). The $K_D$ may also be measured by using FACS or surface plasmon resonance assays by BIACORE, using, for example, a BIACORE 2000 or a BIACORE 3000, or by biolayer interferometry using, for example, the OCTET QK384 system. In certain embodiments, the $K_D$ of an anti-TM4SF1 antibody is determined using a standard flow cytometry assay with HUVEC cells. An "on-rate" or "rate of association" or "association rate" or "$k_{on}$" and an "off-rate" or "rate of dissociation" or "dissociation rate" or "$k_{off}$" may also be determined with the same surface plasmon resonance or biolayer interferometry techniques described above using, for example, a BIACORE 2000 or a BIACORE 3000, or the OCTET QK384 system.

The term "$k_{on}$", as used herein, is intended to refer to the on rate constant for association of an antibody to the antigen to form the antibody/antigen complex, as is known in the art.

The term "$k_{off}$", as used herein, is intended to refer to the off rate constant for dissociation of an antibody from the antibody/antigen complex, as is known in the art.

The term "inhibition" or "inhibit," when used herein, refers to partial (such as, 1%, 2%, 5%, 10%, 20%, 25%, 50%, 75%, 90%, 95%, 99%) or complete (i.e., 100%) inhibition.

The term "cancer" as used herein, refers to or describes the physiological condition in mammals that is typically characterized by unregulated cell growth.

The term "cancer which is associated with a high risk of metastasis", as used herein, refers to a cancer that is associated with at least one factor known to increase the risk that a subject having the cancer will develop metastatic cancer. Examples of factors associated with increased risk for metastasis include, but are not limited to, the number of cancerous lymph nodes a subject has at the initial diagnosis of cancer, the size of the tumor, histological grading, and the stage of the cancer at initial diagnosis.

The term "hematogenous metastasis" as used herein refers to the ability of cancer cells to penetrate the walls of blood vessels, after which they are able to circulate through the bloodstream (circulating tumor cells) to other sites and tissues in the body.

The term "lymphatic metastasis" as used herein refers to the ability of cancer cells to penetrate lymph vessels and drain into blood vessels.

In the context of the disclosure, the term "treating" or "treatment", as used herein, means reversing, alleviating, inhibiting the progress of, or preventing the disorder or condition to which such term applies, or one or more symptoms of such disorder or condition. By the term "treating cancer" as used herein is meant the inhibition of the growth and/or proliferation of cancer cells. In one embodiment, the compositions and methods described herein are used to treat metastasis in a subject having metastatic cancer.

The term "preventing cancer" or "prevention of cancer" refers to delaying, inhibiting, or preventing the onset of a cancer in a mammal in which the onset of oncogenesis or tumorigenesis is not evidenced but a predisposition for cancer is identified whether determined by genetic screening, for example, or otherwise. The term also encompasses treating a mammal having premalignant conditions to stop the progression of, or cause regression of, the premalignant conditions towards malignancy. Examples of premalignant conditions include hyperplasia, dysplasia, and metaplasia. In some embodiments, preventing cancer is used in reference to a subject who is in remission from cancer.

A variety of cancers, including malignant or benign and/or primary or secondary, may be treated or prevented with a method according to the disclosure. Examples of such cancers are known to those skilled in the art and listed in standard textbooks such as the Merck Manual of Diagnosis and Therapy (published by Merck).

The term "subject" as used herein, refers to a mammal (e.g., a human).

The term "administering" as used herein refers to a method of giving a dosage of an antibody or fragment thereof, or a composition (e.g., a pharmaceutical composition) to a subject. The method of administration can vary depending on various factors (e.g., the binding protein or the pharmaceutical composition being administered and the severity of the condition, disease, or disorder being treated).

The term "effective amount" as used herein refers to the amount of an antibody or pharmaceutical composition provided herein which is sufficient to result in the desired outcome.

The terms "about" and "approximately" mean within 20%, within 15%, within 10%, within 9%, within 8%, within 7%, within 6%, within 5%, within 4%, within 3%, within 2%, within 1%, or less of a given value or range.

The term "identity," or "homology" as used interchangeable herein, may be to calculations of "identity," "homology," or "percent homology" between two or more nucleotide or amino acid sequences that can be determined by aligning the sequences for optimal comparison purposes (e.g., gaps can be introduced in the sequence of a first sequence). The nucleotides at corresponding positions may then be compared, and the percent identity between the two sequences may be a function of the number of identical positions shared by the sequences (i.e., % homology=# of identical positions/total # of positions×100). For example, a position in the first sequence may be occupied by the same nucleotide as the corresponding position in the second sequence, then the molecules are identical at that position. The percent homology between the two sequences may be a function of the number of identical positions shared by the sequences, taking into account the number of gaps, and the length of each gap, which need to be introduced for optimal alignment of the two sequences. In some embodiments, the length of a sequence aligned for comparison purposes may be at least about: 30%, 40%, 50%, 60%, 65%, 70%, 75%, 80%, 85%, 90%, 91%, 92%, 93%, 94%, 95%, 96%, 97%, 98%, or 95%, of the length of the reference sequence. A BLAST® search may determine homology between two sequences. The two sequences can be genes, nucleotides sequences, protein sequences, peptide sequences, amino acid sequences, or fragments thereof. The actual comparison of the two sequences can be accomplished by well-known methods, for example, using a mathematical algorithm. A non-limiting example of such a mathematical algorithm may be described in Karlin, S. and Altschul, S., Proc. Natl. Acad. Sci. USA, 90-5873-5877 (1993). Such an algorithm may be incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In another embodiment, the percent identity between two amino acid sequences can be accomplished using, for example, the GAP program in the GCG software package (Accelrys, Cambridge, UK).

The term "manufacturability," as used herein, refers to the stability of a particular protein during recombinant expression and purification of that protein. Manufacturability is believed to be due to the intrinsic properties of the molecule under conditions of expression and purification. Examples of improved manufacturability characteristics include uniform glycosylation of a protein, increased cell titer, growth and protein expression during recombinant production of the protein, improved purification properties, less propensity of aggregation or non-aggregation, and improved stability, including, but not limited to, thermal stability and stability at low pH. In some embodiments are provided TM4SF1 binding proteins that demonstrate the manufacturability, along with retention of in vitro and in vivo activity, compared with other TM4SF1 antibodies. In some embodiments, humanization of a parent TM4SF1 binding protein, by making amino acid substitutions in the CDR or framework regions, can confer additional manufacturability benefits.

In some embodiments are provided TM4SF1 binding proteins that demonstrate improved developability characteristics, including, but not limited to improved purification yield, for example, after protein A purification or size exclusion chromatography, improved homogeneity after purification, improved thermal stability. In some cases, the improvement is with respect to an anti-TM4SF1 antibody produced by a hybridoma mouse cell line 8G4-5-13-13F (PTA-120523), as determined by HLA molecule binding.

In some examples, binding affinity is determined by Scatchard analysis, which comprises generating a Scatchard plot, which is a plot of the ratio of concentrations of bound ligand to unbound ligand versus the bound ligand concentration.

The term "vascular toxicity" refers to any effect of an anti-TM4SF1 antibody-therapeutic molecule conjugate (also referred to herein as anti-TM4SF1 ADC or TM4SF1 targeted ADC) which leads to vascular injury either directly due to the antibody or the therapeutic molecule effects on antigen-bearing cells or indirectly through activation of the immune system and resulting inflammation. Such vascular injury may include, but is not limited to, damage or inflammation affecting vascular endothelial cells or underlying smooth muscle cells or pericytes or the basement membrane of any blood vessel, including the endocardium (lining of the heart). Such vascular injury may affect arteries, including major arteries such as the aorta, elastic arteries (such as the aorta), muscuar arteries of varying sizes, such as coronary artery, pulmonary artery, carotid artery, arterioles, capillaries, arteries of the brain or retina; venues, veins; or it may affect angiogenic vessels including vessels serving hair follicles, the digestive tract, and bone marrow. Such vascular injury may include microvascular dysfunction or damage in the heart, lung, kidney, retina, brain, skin, liver, digestive tract, bone marrow, endocrine glands, testes or ovaries, endometrium, and other target organs and may include renal, retinal or cerebrovascular circulation dysfunction.

The term "antibody-dependent cell-mediated cytotoxicity (ADCC)" as used herein refers to the killing of an antibody-coated target cell by a cytotoxic effector cell through a nonphagocytic process, characterized by the release of the content of cytotoxic granules or by the expression of cell death-inducing molecules. ADCC is triggered through interaction of target-bound antibodies (belonging to IgG or IgA or IgE classes) with certain Fc receptors (FcRs), glycoproteins present on the effector cell surface that bind the Fc region of immunoglobulins (Ig). Effector cells that mediate ADCC include natural killer (NK) cells, monocytes, macrophages, neutrophils, eosinophils and dendritic cells. ADCC is a rapid effector mechanism whose efficacy is dependent on a number of parameters (density and stability of the antigen on the surface of the target cell; antibody affinity and FcR-binding affinity). PBMC-based ADCC assays and natural kill cell-based ADCC assays can be used to detect ADCC. The readout in these assays is endpoint-driven (target cell lysis).

The term "complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay (See, e.g., Gazzano-Santoro et al., 1996, J. Immunol. Methods 202: 163) may be performed. Polypeptide variants with altered Fc region amino acid sequences (polypeptides with a variant Fc region) and increased or decreased C1q binding capability have been described (see, e.g., U.S. Pat. No. 6,194,551; WO 1999/51642; Idusogie et al., 2000, J. Immunol. 164: 4178-84). Antibodies (or fragments) with little or no CDC activity may be selected for use.

The term "effector function" as used herein refers to a function contributed by an Fc effector domain(s) of an IgG (e.g., the Fc region of an immunoglobulin). Such function can be effected by, for example, binding of an Fc effector domain(s) to an Fc receptor on an immune cell with phagocytic or lytic activity or by binding of an Fc effector domain(s) to components of the complement system. Examples of antibody effector functions include: C1q binding and complement dependent cytotoxicity (CDC); Fc receptor binding; antibody-dependent cell-mediated cytotoxicity (ADCC); phagocytosis (ADCP); down regulation of cell surface receptors (e.g. B cell receptor); and B cell activation.

The terms "reduce" or "ablate" as used herein refers to the ability to cause an overall decrease preferably of 20% or greater, more preferably of 50% or greater, and most preferably of 75%, 85%, 90%, 95%, or greater. Reduce or ablate can refer to binding affinity of two molecules, for example the binding of immunoglobulins to C1q or to Fc receptors; or can refer to the symptoms of the disorder (e.g., cancer) being treated, such as the presence or size of metastases or the size of the primary tumor.

The term "reduced ADCC/CDC function," as used herein refers to a reduction of a specific effector function, e.g. ADCC and/or CDC, in comparison to a control (for example an antibody with a Fc region not including the mutation(s)), by at least about 5%, at least about 10%, at least about 15%, at least about 20%, at least about 30%, at least about 40%, at least about 50%, at least about 60%, at least about 70%, at least about 80% at least, at least about 90% or more.

For all amino acid positions discussed in the present disclosure, in the context of antibodies or antigen binding fragments thereof, numbering is according to the EU index.

The "EU index" or "EU index as in Kabat et al." or "EU numbering scheme" refers to the numbering of the EU antibody (See Edelman et al., 1969; Kabat et al., 1991).

II. Antibody-Drug Conjugates Containing Anti-TM4SF1 Antibodies or Antigen Binding Fragments Thereof, with Modified Fc Regions and/or CDR Regions One embodiment of the disclosure provides antibody-drug conjugates (ADCs) comprising an anti-TM4SF1 antibody or an antigen binding fragment thereof linked to a therapeutic molecule, wherein the anti-TM4SF1 antibody or antigen binding fragment thereof comprises a modified Fc region, such as a modified IgG region (e.g., IgG1, IgG2, IgG3, IgG4) comprising one or more mutations. In some cases, said one or more mutations in the Fc region leads to improvements in a drug comprising such a modified Fc region, in areas of improvement such as: 1) reduction of effector functions, 2) half-life modulation, 3) stability, and 4) downstream processes. In some cases, the modified Fc region can comprise one or more mutations that will reduce or ablate interactions between the antibodies and the immune system. Key interactions may include interactions of the antibody Fc with Fcγ receptors on white blood cells and platelets, and with C1q of the complement system leading to complement dependent cytotoxicity.

The present disclosure provides, in some cases, an ADC comprising an anti-TM4SF1 antibody or an antigen binding fragment thereof that includes immune ablating mutations, for example, in the Fc region which in such cases is a modified Fc region, for example, a modified IgG Fc region. In some embodiments, the modified Fc region comprises a modification at position N297. In some embodiments, the modified Fc region comprises a modified IgG Fc region (e.g., a modified IgG1, IgG2, IgG3, or IgG4 Fc region) comprising one or more mutations at positions E233, L234 or F234, L235, G237, P238, F243, T250, M252, S254, T256, E258, D259, V264, D265, K288, N297, T299, T307, V308, Q311, K322, L328, P329, A330, P331, T356, K370, A378, R409, V427, M428, H433, N434, and H435, or any combinations thereof. In some embodiments, the Fc region comprises an extension of residues at its C-terminus, such that positive charge is maintained at the C-terminus (e.g., in some cases, if the anti-TM4SF1 antibody or antigen binding fragment comprises two heavy chains then at least one heavy chain comprises an extension of residues at the C-terminus). Such extension of residues can comprises addition of one or more amino acids, such as, arginine, lysine, proline, or any combinations thereof. In some examples, the extended C-terminus of the Fc regions leads to reduced CDC function of the anti-TM4SF1 antibody or antigen binding fragment thereof, and that of an ADC comprising the anti-TM4SF1 antibody or antigen binding fragment thereof. Such an effect is seen, in some cases, by addition of KP residues after K447 of Fc in IgG1 or IgG4, alone or in combination with other mutations (e.g., K322A, P331G-IgG1).

In some embodiments, an anti-TM4SF1 antibody or an antigen binding fragment thereof can comprise an antibody with reduced effector function, including substitution of one or more of Fc region residues 238, 265, 269, 270, 297, 327 and 329 (See, e.g., U.S. Pat. No. 6,737,056). In some cases, such mutations in the Fc region may comprise substitutions at two or more of amino acid positions 265, 269, 270, 297 and 327, for example, substitution of residues 265 and 297 to alanine (DANA mutations, i.e., D265A and N297A) (See, e.g., U.S. Pat. No. 7,332,581). In some cases, mutations in the Fc region may comprises substitutions at one or more amino acid positions E233, L234, L235, G237, D265, N297, K322, and P331. In some cases, mutations in the Fc region may comprises at least one of E233P, L234A, L235A, G237A, D265A, N297A, K322A, and P331G, or any combinations thereof. For instance, the mutations in the Fc region can comprise L234A/L235A/G237A (IgG1), or F234A/L235E (IgG4), and an anti-TM4SF1 antibody or antigen binding fragment comprising such mutations may exhibit altered FcgRI interactions.

In some embodiments, an anti-TM4SF1 antibody or antigen binding fragment thereof may include an Fc variant comprising the following mutations: an amino acid substitution at position M428 and N434 (M428L, N434S) (See, e.g., U.S. Pat. No. 9,803,023). In some embodiments, an anti-TM4SF1 antibody or antigen binding fragment thereof may include an Fc variant comprising the following mutations: an amino acid substitution at position T250 and M428 (T250Q, M428L) (See, e.g., U.S. Pat. No. 9,803,023).

In some embodiments, the TM4SF1 antibody or antigen binding fragment thereof may comprise mutations D265A and N297A. In some cases, the proline at position 329 (P329) of a wild-type human Fc region may be substituted with glycine or arginine or an amino acid residue large enough to destroy the proline sandwich within the Fc/Fcγ receptor interface, that is formed between the P329 of the Fc and tryptophan residues W87 and WHO of FcgRIII (See, e.g., Sondermann et al., Nature 406, 267-273 (20 Jul. 2000)). In a further embodiment, the mutations in the Fc region may comprise one or more amino acid substitutions such as S228P (IgG4), E233P, L234A, L235A, L235E, N297A, N297D, or P331S and in still in other embodiments: L234A and L235A of the human IgG1 Fc region or S228P and F234A, L235A, or L235E of the human IgG4 Fc region.

In some embodiments, an anti-TM4SF1 antibody or antigen binding fragment thereof may include a modified Fc region which is an Fc variant of a wild-type human IgG Fc region wherein P329 of the human IgG Fc region substituted with glycine and wherein the Fc variant comprises at least two further amino acid substitutions at L234A and L235A of the human IgG1 Fc region or S228P and L235E of the human IgG4 Fc region, and wherein the residues are numbered according to the EU numbering (See, e.g., U.S. Pat. No. 8,969,526). The polypeptide comprising the P329G, L234A and L235A substitutions may exhibit a reduced affinity to the human FcγRIIIA and FcγRIIA, for down-modulation of ADCC to at least 20% of the ADCC induced by the polypeptide comprising the wildtype human IgG Fc region, and/or for down-modulation of ADCP (See, e.g., U.S. Pat. No. 8,969,526).

In some embodiments, an anti-TM4SF1 antibody or antigen binding fragment thereof may include an Fc variant comprising triple mutations: an amino acid substitution at position P329, a L234A and a L235A mutation (P329/LALA) (See, e.g., U.S. Pat. No. 8,969,526).

Certain anti-TM4SF1 antibodies or antigen binding fragments of this disclosure, in some embodiments, can comprise mutations that exhibit improved or diminished binding to FcRs. (See, e.g., U.S. Pat. No. 6,737,056; WO 2004/056312, and Shields et al., J. Biol. Chem. 9(2): 6591-6604 (2001).)

In some instances, an anti-TM4SF1 antibody or antigen binding fragment may include an Fc region with one or more amino acid substitutions which improve ADCC, e.g., substitutions at positions 298, 333, and/or 334 of the Fc region. Alterations may be made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. (2000) J. Immunol. 164: 4178-4184.

Antibodies with increased half-lives and improved binding to the neonatal Fc receptor (FcRn). FcRn, named after its function for the transfer of maternal IgGs to the fetus, also serves to prevent antibodies from being degraded in lysosomes, by capturing them in endosomes and returning them to circulation. (See, e.g., Guyer et al., J. Immunol. 117:587 (1976) and Kim et al., J. Immunol. 24:249 (1994)), are described in US2005/0014934. Without being bound by any particular theory, it is contemplated that antibodies with improved binding to FcRn detach from TM4SF1 and bind to FcRn, which then recycles the ADC back to circulation, thus reducing vascular toxicity. In some embodiments herein are provided anti-TM4SF1 antibodies or antigen binding fragments that comprise an Fc region with one or more substitutions that enhance FcRn recycling. In some embodiments herein are provided anti-TM4SF1 antibodies or antigen binding fragments thereof that comprise an Fc region with one or more substitutions therein which improve binding of the Fc region to FcRn, such as, substitutions at one or more of positions: 238, 250, 252, 254, 256, 265, 272, 286, 303, 305, 307, 311, 312, 317, 340, 356, 360, 362, 376, 378, 380, 382, 413, 428, 424, 434, and 435, e.g., substitution of Fc region residue 434 (U.S. Pat. No. 7,371,826) according to EU numbering. See also Duncan & Winter, Nature 322:738-40 (1988); U.S. Pat. Nos. 5,648,260; 5,624,821; US2005/0014934 and WO 94/29351 concerning other examples of Fc region variants, the entirety of which are incorporated herein by reference.

In some embodiments, provided herein are anti-TM4SF1 antibodies or antigen binding fragments thereof that have pH dependent FcRn binding affinities. Without being bound by any particular theory, it is contemplated that ADC antibodies or antigen binding fragments thereof with pH dependent FcRn binding affinity detach from FcRn at pH >7, and bind to FcRn at pH 6. Accordingly, FcRn in acidic pH subcellular organelles, e.g. endosomes, binds such antibodies and carries the antibodies back to the cell membrane, and release the antibodies into plasma at pH >7, recycling the antibody and avoiding lysosomal release of ADC payloads.

In certain embodiments, herein are provided anti-TM4SF1 antibodies or antigen binding fragments thereof that comprise an Fc region with one or more substitutions therein which modulate FcRn recycling. In some embodiments herein are provided anti-TM4SF1 antibodies or antigen binding fragments thereof that comprise one or more substitutions that enhance FcRn binding at acidic pH, e.g., pH 6, and does not affect FcRn binding at neutral or basic pH, e.g. pH 7. In some embodiments, an anti-TM4SF1 antibody or antigen binding fragment thereof may comprise substitutions at one or more of positions 250, 252, 254, 256, 428, and 434 according to EU numbering. In some embodiments, an anti-TM4SF1 antibody or antigen binding fragment thereof may include an Fc variant comprising one or more of substitutions T250Q, M252Y, S254T, T256E, M428L, and N434S. In some embodiments, an anti-TM4SF1 antibody or antigen binding fragment thereof may include an IgG1 Fc variant comprising substitutions T250Q and M428L (the "QL mutant"). In some embodiments, an anti-TM4SF1 antibody or antigen binding fragment thereof may include an IgG4 Fc variant comprising substitutions T250Q and M428L (the "QL mutant"). In some embodiments, an anti-TM4SF1 antibody or antigen binding fragment thereof may include an IgG1 Fc variant comprising substitutions M252Y, S254T, and T256E (the "YTE mutant"). In some embodiments, an anti-TM4SF1 antibody or antigen binding fragment thereof may include an IgG1 Fc variant comprising substitutions M428L and N434S (the "LS mutant"). In some embodiments, an anti-TM4SF1 antibody or antigen binding fragment thereof may include an IgG4 Fc variant comprising substitutions M428L and N434S (the "LS mutant"). Effects of amino acid substitutions in the Fc region that modulate FcRn recycling are described in, e.g. Hamblen et al., Mol. Pharm. 13(7): 2387-96 (2016); Dall'Acqua et al., J. Biol. Chem. 281(33): 23514-24 (2006), Hinton et al., J. Biol. Chem. 279(8): 6213-6 (2003), Hinton et al., J. Immunol., 176(1): 346-56 (2006), US20080181887, U.S. Pat. No. 7,361,740, and EP2235059, the entirety of which are incorporated herein by reference.

In certain embodiments, an anti-TM4SF1 antibody, or antigen-binding fragment thereof, is an IgG1 isotype and comprises an Fc region comprising one or more substitutions selected from the group consisting of T250Q, M252Y, S254T, T256E, M428L, and N434S. In some embodiments, an anti-TM4SF1 antibody, or antigen binding fragment thereof, is an IgG4 isotype and comprises an Fc region comprising one or more substitutions selected from the group consisting of T250Q, M252Y, S254T, T256E, M428L, and N434S. In some embodiments, an anti-TM4SF1 antibody or antigen binding fragment thereof is an IgG1 isotype and comprises an Fc region comprising substitutions T250Q and M428L. In some embodiments, an anti-TM4SF1 antibody or antigen binding fragment thereof is an IgG1 isotype and comprises an Fc variant comprising substitutions M252Y, S254T, and T256E. In some embodiments, an anti-TM4SF1 antibody or antigen binding fragment thereof is an IgG4 isotype and comprises an Fc variant comprising substitutions M252Y, S254T, and T256E. In some embodiments, an anti-TM4SF1 antibody or antigen binding fragment thereof is an IgG1 isotype and comprises an Fc variant comprising substitutions M428L and N434S. In some embodiments, an anti-TM4SF1 antibody or antigen binding fragment thereof is an IgG4 isotype and comprises an Fc variant comprising substitutions M428L and N434S.

In certain embodiments, the ADCs disclosed herein exhibit reduced vascular toxicity, reduced lysosomal toxicity, improved efficacy, and/or improved therapeutic margin. In some embodiments, the ADCs disclosed herein comprise anti-TM4SF1 antibodies or antigen binding fragments thereof comprising mutated Fc regions that have increased FcRn binding affinity and increased serum half life. In certain embodiments, an anti-TM4SF1 antibody or antigen binding fragment thereof comprising mutated Fc regions have serum half life of at least 10 days, at least 15 days, at least 20 days, at least 25 days, at least 30 days, at least 35 days, at least 40 days, at least 50 days, at least 60 days, at least 70 days, at least 80 days, at least 90 days, at least 100 days or more. In some embodiments, In certain embodiments, the ADCs of this disclosure exhibit reduced vascular toxicity, improved therapeutic margin, or both. In certain embodiments the ADCs of this disclosure comprise anti-TM4SF1 antibodies or antigen binding fragments thereof comprising mutated Fc regions that have reduced or ablated affinity for an Fc ligand responsible for facilitating effector function compared to an antibody having the same amino acid sequence as the antibody of the disclosure but not comprising the addition, substitution, or deletion of at least one amino acid residue to the Fc region (also referred to herein as an "unmodified antibody").

In one embodiment, an anti-TM4SF1 antibody, or antigen-binding fragment thereof comprises an Fc region comprising at least two mutations that reduce or ablate ADCC and/or CDC effector function of the antibody, or antigen-binding fragment thereof. In further embodiments, the anti-TM4SF1 antibody, or antigen-binding fragment thereof, comprises an Fc region comprising at least three, at least four, at least five, at least six, at least seven, at least eight, at least nine, at least ten or more mutations that reduce or ablate ADCC and/or CDC effector function of the antibody, or antigen-binding fragment thereof.

In certain embodiments, an anti-TM4SF1 antibody, or antigen-binding fragment thereof, is an IgG1 isotype and comprises an Fc region comprising one or more mutations selected from the group consisting of E233P, L234V, L234A, L235A, G236Delta (deletion), G237A, V263L, N297A, N297D, N297G, N297Q, K322A, A327G, P329A, P329G, P329R, A330S, P331A, P331G, and P331S.

In one embodiment, an anti-TM4SF1 antibody, or antigen-binding fragment thereof, is an IgG1 isotype and comprises an Fc region comprising an L234A/L235A mutation, with or without a G237A mutation. In one embodiment, the anti-TM4SF1 antibody, or antigen-binding fragment thereof, is an IgG1 isotype and comprises an Fc region comprising L234A, L235A, and G237A mutations.

In one embodiment, an anti-TM4SF1 antibody, or antigen-binding fragment thereof, is an IgG1 isotype and comprises an Fc region comprising an A327G/A330S/P331S mutation.

In one embodiment, an anti-TM4SF1 antibody, or antigen-binding fragment thereof, is an IgG1 isotype and comprises an Fc region comprising an E233P/L234V/L235A/delta G236 (deletion) mutation, which provides reduced binding to FcγRI (also referred to herein as FcgRI), FcγRIIA (also referred to herein as FcgRIIA), FcγRIIIA (also referred to herein as FcgRIIIAI) and reduced ADCC and CDC effector function, as described, for example, in An Z et al. Mabs 2009 November-Ec; 1(6):572-9, incorporated by reference in its entirety herein.

In one embodiment, an anti-TM4SF1 antibody, or antigen-binding fragment thereof, is an IgG1 isotype and comprises an Fc region comprising an N297x mutation, where x=A, D, G, Q.

In one embodiment, an anti-TM4SF1 antibody, or antigen-binding fragment thereof, is an IgG1 isotype and comprises an Fc region comprising an A327G/A330S/P331S mutation.

In one embodiment, an anti-TM4SF1 antibody, or antigen-binding fragment thereof, is an IgG1 isotype and comprises an Fc region comprising a mutation in one or more of K322A, P329A, and P331A, which provides reduced binding to C1q, as described, for example, in Canfield & Morrison. J Exp Med (1991) 173(6):1483-91.10.1084, incorporated by reference in its entirety herein.

In one embodiment, an anti-TM4SF1 antibody, or antigen-binding fragment thereof, is an IgG1 isotype and comprises an Fc region comprising a V263L mutation, which provides enhanced binding to FcγRIIB (also referred to herein as FcgRIIB) and enhanced ADCC, as described in, for example, Hezareh et al. J Virol. 2001 December; 75(24): 12161-8, incorporated by reference in its entirety herein.

In other embodiments, an anti-TM4SF1 antibody or antigen-binding fragment thereof is an IgG1 isotype and comprises an Fc region comprising a L234A/L235A, G237A or L235E mutation.

In other embodiments, an anti-TM4SF1 antibody, or antigen-binding fragment thereof, is an IgG1 isotype and comprises an Fc region comprising a L234F, L235E or P331S mutation.

In certain embodiments, an anti-TM4SF1 antibody, or antigen-binding fragment thereof, is an IgG2 isotype and comprises an Fc region comprising a one or more mutations selected from the group consisting of V234A, G237A, P238S, H268A or H268Q, V309L, A330S and P331S.

In one embodiment, an anti-TM4SF1 antibody, or antigen-binding fragment thereof, is an IgG2 isotype and comprises an Fc region comprising an A330S/P331S mutation.

In one embodiment, an anti-TM4SF1 antibody, or antigen-binding fragment thereof, is an IgG2 isotype and comprises an Fc region comprising an A330S/P331S, V234A/G237A/P238S/H268A/V309L/A330S/P331S or H268Q/V309L/A330S/P331S mutation.

In other embodiments, an anti-TM4SF1 antibody, or antigen-binding fragment thereof, is an IgG4 isotype and comprises an Fc region comprising a one or more mutations selected from the group consisting of S228P, E233P, F234A, F234V, L235E, L235A, G236Delta (deletion), N297A, N297D, N297G, N297Q, P329G, P329R.

In certain embodiments, an anti-TM4SF1 antibody, or antigen-binding fragment thereof, is an IgG4 isotype and comprises an Fc region comprising an S228P mutation, which provides reduced Fab-arm exchange and reduced aggregation, as described for example in Chappel et al. Proc Natl Acad Sci USA (1991) 88(20):9036-40, incorporated by reference in its entirety herein.

In one embodiment, an anti-TM4SF1 antibody, or antigen-binding fragment thereof, is an IgG4 isotype and comprises an Fc region comprising an S228P/L235E mutation.

In one embodiment, an anti-TM4SF1 antibody, or antigen-binding fragment thereof, is an IgG4 isotype and comprises an Fc region comprising an S228P/E233P/F234V/L235A/delta G236 (deletion) mutation.

In one embodiment, an anti-TM4SF1 antibody, or antigen-binding fragment thereof, is an IgG4 isotype and comprises an Fc region comprising an N297x mutation, where x=A, D, G, Q.

In one embodiment, an anti-TM4SF1 antibody, or antigen-binding fragment thereof, is an IgG4 isotype and comprises an Fc region comprising an S228P/F234A/L235A mutation.

In one embodiment, an anti-TM4SF1 antibody, or antigen-binding fragment thereof, is an IgG4 isotype and comprises an Fc region comprising a L235E mutation, which provides reduced binding to FcγR1, FcγRIIA, FcγRIIIA and reduced ADCC and CDC effector activity, as described in, for example, Saxena et al. Front Immunol. 2016 Dec. 12; 7:580.

In other embodiments, an anti-TM4SF1 antibody, or antigen-binding fragment thereof, is an IgG4 isotype and comprises an Fc region comprising a S228P/F234A/L235A or E233P/L235A/G236Delta mutation.

In one embodiment, an anti-TM4SF1 antibody, or antigen-binding fragment thereof, is an IgG4 isotype and comprises an Fc region comprising at least a S228P mutation. See, e.g., Angal et al. (Mol Immunol. 1993 January; 30(1): 105-8) describe an analysis of the hinge sequences of human IgG4 heavy chains to determine that the presence of serine at residue 241 (according to EU numbering system, and now corresponding to residue 228 in Kabat numbering,) as the cause of heterogeneity of the inter-heavy chain disulphide bridges in the hinge region in a proportion of secreted human IgG4. Silva et al. (J Biol Chem. 2015 Feb. 27; 290(9):5462-

9) describe the S228P mutation in human IgG4 that prevents in vivo and in vitro IgG4 Fab-arm exchange.

In other embodiments, an anti-TM4SF1 antibody, or antigen-binding fragment thereof, is an IgG4 isotype and comprises an Fc region comprising a L235E or S228P mutation.

In other embodiments, the anti-TM4SF1 antibody, or antigen-binding fragment thereof, is an IgG4 or IgG1 isotype and comprises an Fc region comprising a N297A, N297D or N297G mutation.

In other embodiments, an anti-TM4SF1 antibody, or antigen-binding fragment thereof, is an IgG4 or IgG1 isotype and comprises an Fc region comprising a P329G, P329R mutation.

In one exemplary embodiment, the mutated Fc region of any IgG isotype comprises one or more mutations at positions 234, 235, 236, 237, 297, 318, 320, 322 (as described in WO1988007089, incorporated by reference in its entirety herein). Other possible mutations in the Fc region, including substitutions, deletions and additions are also described in, for example, US20140170140, WO2009100309, US20090136494 and U.S. Pat. No. 8,969,526, incorporated by reference in their entireties herein.

In vitro and/or in vivo cytotoxicity assays can be conducted to confirm the reduction or ablation of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, RII and RIII. Non-limiting examples of in vitro assays to assess ADCC activity of a molecule of interest is described in U.S. Pat. No. 5,500,362 (see, e.g. Hellstrom, I., et al., Proc. Nat'l Acad. Sci. USA 83 (1986) 7059-7063) and Hellstrom, I., et al., Proc. Nat'l Acad. Sci. USA 82 (1985) 1499-1502; U.S. Pat. No. 5,821,337 (see Bruggemann, M., et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, et al., Proc. Nat'l Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, et al., J. Immunol. Methods 202 (1996) 163; Cragg, M. S., et al., Blood 101 (2003) 1045-1052; and Cragg, M. S., and Glennie, M. J., Blood 103 (2004) 2738-2743). FcRn binding and in vivo clearance/half-life determinations can also be performed using methods known in the art (see, e.g., Petkova, S. B., et al., Int'l. Immunol. 18(12) (2006) 1759-1769).

In some embodiments, the mutated Fc region of any IgG isotype comprises a mutation at position L328, such as L328 M, L328D, L328E, L328N, L328Q, L328F, L328I, L328V, L328T, L328H, L328A (see e.g., US20050054832)

In one embodiment, antibodies, or antigen-binding fragments thereof, of the disclosure exhibit reduced or ablated ADCC effector function as compared to unmodified antibodies. In another embodiment, antibodies, or antigen-binding fragments thereof, of the disclosure exhibit reduced ADCC effector function that is at least 2 fold, or at least 3 fold, or at least 5 fold or at least 10 fold or at least 50 fold or at least 100 fold less than that of an unmodified antibody. In still another embodiment, antibodies of the disclosure exhibit ADCC effector function that is reduced by at least 10%, or at least 20%, or by at least 30%, or by at least 40%, or by at least 50%, or by at least 60%, or by at least 70%, or by at least 80%, or by at least 90%, or by at least 100%, relative to an unmodified antibody. In a further aspect of the disclosure the reduction or down-modulation of ADCC effector function induced by the antibodies, or antigen-binding fragments thereof, of the present disclosure, is a reduction to 0, 2.5, 5, 10, 20, 50 or 75% of the value observed for induction of ADCC by unmodified antibodies. In certain embodiments, the reduction and/or ablation of ADCC activity may be attributed to the reduced affinity of the antibodies, or antigen-binding fragments thereof, of the disclosure for Fc ligands and/or receptors.

CDR Substitutions that Modulate pH-Dependent TM-4SF1 Binding of an Anti-TM4SF1 Antibody or Antigen Binding Fragment Thereof One embodiment of the disclosure provides ADCs comprising an anti-TM4SF1 antibody or an antigen binding fragment thereof linked to a therapeutic molecule or a payload, wherein the anti-TM4SF1 antibody or antigen binding fragment thereof exhibit pH dependent binding affinity to TM4SF1. In some instances, an anti-TM4SF1 antibody or antigen binding fragment thereof binds to TM4SF1 with higher affinity at certain pH range as compared to other pH ranges. For example, an anti-TM4SF1 antibody or antigen binding fragment thereof may bind to TM4SF1 with different affinity at an acidic pH than at a neutral pH or a basic pH. In some embodiments, an anti-TM4SF1 antibody or antigen binding fragment thereof binds to TM4SF1 with higher affinity at an acidic pH than at a neutral or basic pH. In some embodiments, an anti-TM4SF1 antibody or antigen binding fragment thereof binds to TM4SF1 with lower affinity at an acidic pH than at a neutral or basic pH. In some embodiments, an anti-TM4SF1 antibody or antigen binding fragment thereof binds to TM4SF1 at acidic pH and dissociates from TM4SF1 at neutral or basic pH. In some embodiments, an anti-TM4SF1 antibody or antigen binding fragment thereof binds to TM4SF1 at pH7 or higher and detaches from TM4SF1 at pH6 or lower. In subcellular compartments such as plasma, cytosol, and nucleus, the pH is neutral or basic. In lysosomes or endosomes, the pH is acidic. Without being bound by any theory, an anti-TM4SF1 antibody or antigen binding fragment thereof bind to the antigen and subsequently internalized in the membrane of an endosome. A pH-dependent anti-TM4SF1 antibody or antigen binding fragment thereof can detach from TM4SF1 in an endosome and bind to FcRn receptors within the endosome, and can be recycled by the FcRn receptor back into circulation rather than degraded in a lysosome that the endosome progresses to. Accordingly, a pH dependent anti-TM4SF1 antibody or antigen binding fragment thereof can bind to TM4SF1 antigen multiple times. Accordingly, a pH dependent anti-TM4SF1 antibody and the associated therapeutic molecule or payload therewith can be recycled by FcRn receptors, without releasing the payload in the lysosome.

Target-mediated drug disposition, or TMDD, occurs when an antigen carries a bound antibody and/or any associated ADC payload to the lysosome, wherein the ADC is degraded and the payload is released. Lysosome toxicity related to TMDD as described in Grimm et al., J. Pharmacokinet. Pharmacodyn. 36(5): 407-20 (2009) is incorporated herein by reference in its entirety. In some embodiments, provided herein are ADCs comprising an anti-TM4SF1 antibody or antigen binding fragment thereof linked to a therapeutic molecule that exhibit reduced vascular toxicity, increased serum half-life, and/or improved therapeutic margin. In some embodiments, an anti-TM4SF1 antibody or antigen binding fragment thereof comprises one or more histidine amino acid residue substitutions in CDR residues. Not intended to be bound by any particular theory, the introduction of a histidine residue at a suitable position of an anti-TM4SF1 antibody may allow pH-regulatable binding affinity to TM4SF1. For example, an ADC with a pH-dependent anti-TM4SF1 antibody may dissociate from TM4SF1 in acidic lysosome or endosome environment, and subsequently be recycled into circulation via FcRn binding. As compared to an otherwise comparable wild type anti-TM4SF1 antibody or antigen binding fragment thereof, a pH-dependent ant-TM4SF1 antibody may exhibit increased serum half-life and reduced degradation rate or payload release rate in lysosomes. In some cases, the ADCs comprising a pH-dependent anti-TM4SF1 antibody or antigen binding fragment thereof may demonstrate increased half-life, reduced vascular toxicity, improved therapeutic window, and/or improved or at least about equivalent in vivo potency.

Disclosed herein are methods of making an ADC comprising an anti-TM4SF1 antibody or antigen binding fragment thereof that has increased half-life and/or pharmacodynamic effect by regulating antibody-TM4SF1 binding affinity in a pH dependent manner, comprising selecting for antibody CDR histidine residues or other residues that optimize the microenvironment affecting pKa of the antibody, such that the antibody-TM4SF1 binding has a Kd ratio and/or Koff ratio at pH6.0/pH7.4 that is at least 2, 3, 4, 8, 10, 16, or more, or ranges between 2, 3, 4, 8, 10, 16, or more. In some embodiments, the method comprises introducing amino acid substitutions into an anti-TM4SF1 antibody or antigen binding fragment thereof to achieve TM4SF1 affinity with a $K_D$ at pH 7.4 of at least 100 nM as measured at 25° C. In certain embodiments, said method comprises generating an antibody library enriched for histidines in CDR residues or other residues that optimize the microenvironment affecting pKa. In some embodiments, the antibody library comprises anti-TM4SF1 antibodies or antigen binding fragments thereof with histidine residues introduced into a CDR position. In some embodiments, the antibody library comprises a series of anti-TM4SF1 antibodies or antigen binding fragments thereof, wherein each anti-TM4SF1 antibody in the antibody library comprises a single histidine substitution at a different CDR position. In some embodiments, the antibody library comprises a series of anti-TM4SF1 antibodies or antigen binding fragments thereof, each comprising 1, 2, 3, 4, 5, 6, 7, 8, 9, 10, 11, 12, 13, 14, 15, 16, or 17 mutations to histidine residues. In some embodiments, every CDR position is mutated to histidine in at least one of the TM4SF1 antibodies or antigen fragments of the antibody library.

In some embodiments, an anti-TM4SF1 antibody or antigen binding fragment thereof comprises 1, 2, 3, 4, 5, or more histidine substitutions in a CDR region. A histidine residue can be engineered into different positions of an anti-TM4SF1 antibody light chain (LC) or heavy chain (HC) for pH dependent binding affinity. Accordingly, in some embodiments, provided herein are ADCs with histidine engineered anti-TM4SF1 antibody or antigen binding fragment thereof. In some embodiments, an anti-TM4SF1 antibody or antigen binding fragment thereof comprises one or more histidine residues in CDR1, CDR2, and/or CDR3 of the light chain variable region (VL). In some embodiments, an anti-TM4SF1 antibody or antigen binding fragment thereof comprises one or more histidine residues in CDR1 of the light chain variable region (VL). In some embodiments, an anti-TM4SF1 antibody or antigen binding fragment thereof comprises one or more histidine residues in CDR2 of the light chain variable region (VL). In some embodiments, an anti-TM4SF1 antibody or antigen binding fragment thereof comprises one or more histidine residues in CDR3 of the light chain variable region (VL). In some embodiments, an anti-TM4SF1 antibody or antigen binding fragment thereof comprises one or more histidine residues in CDR1, CDR2, and/or CDR3 of the heavy chain variable region (VH). In some embodiments, an anti-TM4SF1 antibody or antigen binding fragment thereof comprises one or more histidine residues in CDR1 of the heavy chain variable region (VH). In some embodiments, an anti-TM4SF1 antibody or antigen binding fragment thereof comprises one or more histidine residues in CDR2 of the heavy chain variable region (VH). In some embodiments, an anti-TM4SF1 antibody or antigen binding fragment thereof comprises one or more histidine residues in CDR3 of the heavy chain variable region (VH). Accordingly, in some embodiments, the ADCs of the present disclosure comprise a histidine engineered anti-TM4SF1 antibody or antigen binding fragment thereof.

In some embodiments, an anti-TM4SF1 antibody or antigen binding fragment thereof comprises one or more histidine residues in CDR1, CDR2, and/or CDR3 of the light chain, for instance, in one or more of positions 30 (S30H), 92 (S92H), and 93 (N93H) of SEQ ID No. 101 or SEQ ID No. 131. In some embodiments, an anti-TM4SF1 antibody or antigen binding fragment thereof comprises one or more histidine residues in CDR1, CDR2, and/or CDR3 of the heavy chain, for instance in one or more of positions 28 (T28H), 31 (N31H), 32 (Y32H), 52 (N52H), 54 (Y54H), 57 (N57H), 100 (Q100H), and 101 (Y101H), of SEQ ID No. 92 or SEQ ID No. 130.

Substitution at Position N297(Asn 297) and Conjugation of One or More Therapeutic Molecules to an Anti-TM4SF1 Antibody or Antigen Binding Fragment Thereof Human IgG molecules have a conserved glycosylation site at each N297 residue in the CH2 domain, making these pendant N-glycans a convenient target for site-specific conjugation. This glycosylation site is sufficiently far from the variable region that conjugation of drug moieties to attached glycans should not impact antigen binding. In some embodiments of this disclosure, therapeutic molecules are linked to the glycans, using exemplary methods that include oxidative cleavage of the vicinal diol moieties contained in these glycans with periodate to generate aldehydes that can be reductively aminated and conjugated to hydrazide and aminooxy compounds. (See, e.g., O'Shannessy, et al. (1984) Immunol. Lett. 8:273-77).

Another method may include increasing the fucosylation of the N-acetylglucosamine residues in these glycans. Oxidation of these fucose residues can produce carboxylic acid and aldehyde moieties that can be used to link drugs and fluorophores to these specific sites on the antibody (See, e.g., Zuberbuhler, et al. (2012) Chem. Commun. 48:7100-02). Another method may include modifying sialic acid in these glycans (as well as increasing the sialic acid content in these glycans) followed by oxidation of the sialic acid and conjugation with aminooxy-drugs to form oxime-linked conjugates (See, e.g., Zhou, et al. (2014) Bioconjugate Chem. 25:510-20).

Alternatively, a sialyltransferase may be used to incorporate a modified sialic acid residue containing a bioorthogonal functional group into these glycans. The bioorthogonal functional group may then be modified to attach therapeutic molecules to the site of the glycan (See, e.g. Li, et al. (2014) Angew. Chem. Int. 53:7179-82). Another approach to modifying these glycan sites is the use of glycosyltransferases to link galactose, or galactose analogues containing ketones or azides, to the N-acetylglucosamine in these glycans, and linking drugs or radionucleotides to the galactose molecules (See, e.g. Khidekel, et al., (2003) J. Am. Chem. Soc. 125: 16162-63; Clark, et al., (2008) J. Am. Chem. Soc. 130: 11576-77; Boeggeman, et al. (2007) Bioconjugate Chem. 18:806-14). Another approach relies on the introduction of modified sugars into these glycans at the time of expression of the antibody by metabolic oligosaccharide engineering (See, e.g. Campbell, et al. (2007) Mol. BioSyst. 3: 187-94; Agard, et al., (2009) Acc. Chem. Res. 42:788-97).

In some embodiments, the anti-TM4SF1 antibody or antigen binding fragment thereof is conjugated to a therapeutic molecule, by site-specific conjugation. Several native or engineered amino acids, including cysteines and glutamines, can be selected as the sites for conjugation.

In some instances, a cysteine residue can be engineered into different positions of antibody heavy chain (HC) or light chain (LC) for coupling, such as at position N297, i.e., N297C. Thus, in some embodiments, the ADCs of the present disclosure comprise a cysteine engineered anti-TM4SF1 antibody or an antigen binding fragment thereof.

The introduction of a cysteine residue at a suitable position of the anti-TM4SF1 antibody may allow control of the site of conjugation and the obtained site-specific conjugates may be more homogeneous than the conjugates obtained via wild-type conjugation, i.e. conjugation via reduced interchain cysteines. In some cases, the ADCs comprising at least one conjugation via cysteine may demonstrate at least equivalent in vivo potency, improved pharmacokinetics (PK), and an expanded therapeutic window compared to wild-type conjugates. The ADC, in some embodiments, comprises a cleavable dipeptide linker (i.e., valine-alanine) and a DNA-cross-linking pyrrolobenzodiazepine (PBD) dimer as the drug, which is linked to a cysteine at heavy chain position N297C in the Fc part of the anti-TM4SF1 antibody or antigen binding fragment thereof. In some cases, the ADCs have an average drug-to-antibody ratio (DAR) of greater than or equal to 1, such as a DAR of about 2, 6, 10 etc.

Without being bound by any particular theory, it is contemplated that site-specific conjugation through unpaired cysteine can be relatively simple and scalable. For instance, the therapeutic molecule coupling can be done without the need of special reagents. In some cases, ADCs prepared through site-specific cysteines can show stronger in vivo antitumor activities and could be better tolerated than the conventional conjugates. In some embodiments, position N297 of the anti-TM4SF1 antibody or an antigen binding fragment thereof can be mutated to cysteine, i.e., N297C, and the cysteine residue can be conjugated to a therapeutic molecule. In some instances, the N297C mutation is combined with additional mutations in nearby residues, to add stabilizing residues (e.g., arginine, lysine) and/or remove glutamic acid. In some cases, one or more positions from residue 292-303 are modified, in addition to N297C. The sequence for positions 292-303 can be REEQYCSTYRVV (SEQ ID NO: 158) (in IgG1), and REEQFCSTYRVV (SEQ ID NO: 159) (in IgG4).

In some embodiments, the anti-TM4SF1 antibody or antigen binding fragment thereof is conjugated to a therapeutic molecule, by site-specific conjugation through a glutamine residue. In some cases, microbial transglutaminase (mTG) can be used to transfer an amine containing drug-linker or a reactive spacer into Q295 residue in the heavy chain of an anti-TM4SF1 antibody or an antigen binding fragment thereof, for example, a deglycosylated anti-TM4SF1 antibody or an antigen binding fragment thereof. The conjugation can be optimized using a two-step chemoenzymatic approach whereby a reactive spacer containing a bioorthogonal azido or thiol functional linker is attached to the antibody by mTG and subsequently reacted with either dibenzocyclooctynes (DBCO) or maleimide containing MMAE. By using strain-promoted azide-alkyne cycloaddition (SPAAC) or thiol-maleimide chemistry, ADCs can be generated with DAR, for example, at about 2.

In some instances, the anti-TM4SF1 antibody or antigen binding fragment thereof is conjugated to a therapeutic molecule, by site-specific conjugations through a glutamine residue (e.g., Q295) as well as cysteine at position 297, N297C. This combination of mutations can open up two conjugation handles in the anti-TM4SF1 antibody or an antigen binding fragment thereof, and ADCs of highers DAR can be obtained. Thus, in some embodiments of this disclosure, ADCs are provided wherein more than one therapeutic molecules (e.g., two therpeutic molecules) are conjugated to an anti-TM4SF1 antibody or antigen-binding fragment thereof via site specific conjugations at N297C and Q295. The cysteine conjugation can be, for example, to maleimide, haloacetamide, or another partner.

Increased DAR could lead to efficient ADC construction, minimal destabilization of the antibody structure, and enhanced ADC efficacy. A cysteine conjugation-based dual-loading linker enabling modular payload installation was recently developed (Levengood et al., 2017). Thus, there remains a need for ADCs capable of delivering multiple payloads.

In addition, the ADC linker structure and antibody-payload conjugation modality impact ADC homogeneity, cytotoxic potency, tolerability, and pharmacokinetics (PK). These key parameters may critically contribute to overall in vivo therapeutic efficacy (See, e.g., Lu et al., 2016, Hamblen et al., 2004, Junutula et al., 2008, and Behrens et al., 2015). Thus, refining linker and conjugation chemistries is of crucial importance to maximize the therapeutic potential and safety profiles of ADCs.

Bioconjugation modality and method may be optimized for improved ADC stability and efficacy. In some embodiments, one or more therapeutic agents and/or diagnostic agents are conjugated to anti-TM4SF1 antibodies or antigen binding fragments via maleimide, e.g., cysteine-maleimide conjugation. Other functional groups besides maleimide, which in some instances are reactive with an anti-TM4SF1 antibody, such as a thiol group of a cysteine engineered anti-TM4SF1 antibody, include iodoacetamide, bromoacetamide, vinyl pyridine, disulfide, pyridyl disulfide, isocyanate, and isothiocyanate. In some embodiments, the therapeutic agents and/or diagnostic agents are conjugated to anti-TM4SF1 antibodies or antigen binding fragments thereof via acetamide. For example, a therapeutic agent may be conjugated to an anti-TM4SF1 antibody or antigen binding fragment thereof via bromoacetamide conjugation. In some cases, an ADC comprising a bromoacetamide conjugated anti-TM4SF1 antibody or antigen binding fragment thereof exhibits increased stability, increased half-life, reduced toxicity, and/or improved therapeutic margin. Exemplary ADC structures are provided in FIGS. 1 and 2.

III. Anti-TM4SF1 Antibody or Antigen Binding Fragments Thereof

TM4SF1 is a small plasma membrane glycoprotein (NCBI Ref Seq No. N P_055035.1) with tetraspanin topology but not homology (Wright et al. Protein Sci. 9: 1594-1600, 2000). It forms TM4SF1-enriched domains (TMED) on plasma membranes, where, like genuine tetraspanins, it serves as a molecular facilitator that recruits functionally related membrane and cytosolic molecules (Shih et al. Cancer Res. 69: 3272-3277, 2009; Zukauskas et al., Angiogenesis. 14: 345-354, 201 1), and plays important roles in cancer cell growth (Hellstrom et al. Cancer Res. 46: 391 7-3923, 1986), motility (Chang et al. Int J Cancer. 1 16: 243-252, 2005), and metastasis (Richman et al. Cancer Res. 5916s-5920s, 1995). The amino acid sequence of human TM4SF1 protein (NCBI RefSeq No. NP_055035.1) is shown below as SEQ ID NO: 134.

```
                                        (SEQ ID NO: 134)
MCYGKCARCIGHSLVGLALLCIAANILLYF PNGETKYASE

NHLSRFVWFF SGIVGGGLLM LLPAFVFIGLEQDDCCGCCG

HENCGKRCAM LSSVLAALIG IAGSGYCVIV

AALGLAEGPLCLDSLGQWNYTFASTEGQYLLDTSTWSECTEPK

HIVEWNVSLFSILLALG

GIEFILCLIQVINGVLGGIC GFCCSHQQQY DC
```

In some embodiments, the anti-TM4SF1 antibodies and antigen binding fragments thereof, of the disclosure are specific to the ECL2 domain of TM4SF1. The amino acid sequence of human TM4SF1 ECL2 domain is

```
                                        (SEQ ID NO: 157)
EGPLCLDSLGQWNYTFASTEGQYLLDTSTWSECTEPKHIVEWNVSLFS.
```

As described in Table 1 below, included in the disclosure are novel antibodies that are specific to TM4SF1. The antibodies described in Table 1 are monoclonal murine antibodies AGX-A03, AGX-A04, AGX-A05, AGX-A07, AGX-A08, AGX-A09, and AGX-A11, each of which were identified in the screen described in the Examples and bind the ECL2 region of TM4SF1. Further provided in Table 1 below are humanized antibodies h AGX-A07 and h AGX-A01.

In some embodiments, the anti-TM4SF1 antibodies or antigen-binding fragments thereof, comprise an IgG heavy chain constant region comprising an amino acid sequence set forth in SEQ ID NO: 87 or 88, or a sequence that is at least about 60%, at least about 65%, at least about 70%, at least about 75%, at least about, at least about 80%, at least about 85%, at least about 90%, at least about 95%, at least about 96%, at least about 97%, at least about 98%, at least about 99%, or 100% identical to SEQ ID NO: 73 or 74.

In another embodiment, the anti-TM4SF1 antibody or antigen-binding fragment thereof, comprises a light chain constant region comprising the amino acid sequence set forth in SEQ ID NO: 89, or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 89.

In another embodiment, the anti-TM4SF1 antibody or antigen-binding fragment thereof, comprises a heavy chain variable domain comprising the amino acid sequence set forth in SEQ ID NO: 3, 15, 27, 39, 51, 63, or 75, or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 3, 15, 27, 39, 51, 63, or 75.

In another embodiment, the anti-TM4SF1 antibody or antigen-binding fragment thereof is humanized and, comprises a heavy chain comprising the amino acid sequence set forth in SEQ ID NO: 90 or 92 or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 90 or 92.

In another embodiment, the anti-TM4SF1 antibody or antigen-binding fragment thereof is humanized and, comprises a heavy chain comprising the amino acid sequence set forth in SEQ ID NO: 112 or 114, or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 112 or 114.

In another embodiment, the anti-TM4SF1 antibody or antigen-binding fragment thereof, comprises a light chain variable domain comprising the amino acid sequence set forth in SEQ ID NO: 9, 21, 33, 45, 57, 69, or 81, or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 9, 21, 33, 45, 57, 69, or 81.

In another embodiment, the anti-TM4SF1 antibody or antigen-binding fragment thereof is humanized and, comprises a light chain variable domain comprising the amino acid sequence set forth in SEQ ID NO: 97, 99, 101, 103, or 105 or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 97, 99, 101, 103 or 105. In another embodiment, the antibody or antigen-binding fragment thereof is humanized and, comprises a light chain variable domain comprising the amino acid sequence set forth in SEQ ID NO: 97, 99, or 101 or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 97, 99, or 101.

In another embodiment, the anti-TM4SF1 antibody or antigen-binding fragment thereof is humanized and, comprises a light chain variable domain comprising the amino acid sequence set forth in SEQ ID NO: 122, or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 122.

In some embodiments, the anti-TM4SF1 antibody or antigen binding fragment thereof comprises a heavy chain CDR1 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 6, 18, 30, 42, 54, 66, or 78. In some embodiments, the anti-TM4SF1 antibody or antigen binding fragment thereof comprises a heavy chain CDR2 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 7, 19, 31, 43, 55, 67, or 79. In some embodiments, the anti-TM4SF1 antibody or antigen binding fragment thereof comprises a heavy chain CDR3 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 8, 20, 32, 44, 56, 68, or 80.

In some embodiments, the anti-TM4SF1 antibody or antigen binding fragment thereof comprises a light chain CDR1 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 12, 24, 36, 48, 60, 72, or 84. In some embodiments, the anti-TM4SF1 antibody or antigen binding fragment thereof comprises a light chain CDR2 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 13, 25, 37, 49, 61, 73, or 85. In some embodiments, the anti-TM4SF1 antibody or antigen binding fragment thereof comprises a light chain CDR3 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 14, 26, 38, 50, 62, 74, or 86.

In some embodiments, the anti-TM4SF1 antibody or antigen binding fragment thereof is humanized and comprises a heavy chain CDR1 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 94 or SEQ ID NO: 115. In some embodiments, the anti-TM4SF1 antibody or antigen binding fragment thereof is humanized and comprises a heavy chain CDR2 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 95, SEQ ID NO: 116, or SEQ ID NO: 117. In some embodiments, the anti-TM4SF1 antibody or antigen binding fragment thereof is humanized and comprises a heavy chain CDR3 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 96, SEQ ID NO: 118, SEQ ID NO: 119, SEQ ID NO: 120, or SEQ ID NO: 121.

In some embodiments, the anti-TM4SF1 antibody or antigen binding fragment thereof is humanized and comprises a light chain CDR1 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 107, SEQ ID NO: 108, SEQ ID NO: 124, SEQ ID NO: 125, SEQ ID NO: 126, or SEQ ID NO: 127. In some embodiments, the anti-TM4SF1 antibody or antigen binding fragment thereof is humanized comprises a light chain CDR2 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 109 or SEQ ID NO: 128. In some embodiments, the anti-TM4SF1 antibody or antigen binding fragment thereof is humanized and comprises a light chain CDR3 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 110, SEQ ID NO: 111, or SEQ ID NO: 129. In some embodiments, the anti-TM4SF1 antibody or antigen binding fragment thereof is humanized and comprises a light chain CDR3 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 110, or SEQ ID NO: 129.

The amino acid sequences of murine monoclonal antibody AGX-A03 are described in Table 1. Specifically, the heavy chain CDR sequences are set forth in SEQ ID Nos: 6, 7, and 8 (CDR1, CDR2, and CDR3), and the light chain CDR amino acid sequences are set forth in SEQ ID Nos: 12, 13, and 14 (CDR1, CDR2, and CDR3). Included in the disclosure are anti-TM4SF1 antibodies, or antigen binding fragments comprising a heavy chain variable region comprising CDRs as set forth in the amino acid sequences of SEQ ID Nos: 6, 7, and 8 and/or a light chain variable region comprising CDRs as set forth in the amino acid sequences of SEQ ID Nos: 12, 13, and 14. Included in the disclosure are humanized antibodies or antigen binding fragments comprising the CDRs of AGX-A03. Further, the heavy chain variable amino acid sequences and the light chain variable amino acid sequences of AGX-A03 are described in SEQ ID NOS: 3 and 9, respectively.

The amino acid sequences of murine monoclonal antibody AGX-A04 are described in Table 1. Specifically, the heavy chain CDR sequences are set forth in SEQ ID Nos: 18, 19, and 20 (CDR1, CDR2, and CDR3), and the light chain CDR amino acid sequences are set forth in SEQ ID Nos: 24, 25, and 26 (CDR1, CDR2, and CDR3). Included in the disclosure are anti-TM4SF1 antibodies, or antigen binding fragments comprising a heavy chain variable region comprising CDRs as set forth in the amino acid sequences of SEQ ID Nos: 18, 19, and 20 and/or a light chain variable region comprising CDRs as set forth in the amino acid sequences of SEQ ID Nos: 24, 25, and 26. Included in the disclosure are humanized antibodies or antigen binding fragments comprising the CDRs of AGX-A04. Further, the heavy chain variable amino acid sequences and the light chain variable amino acid sequences of AGX-A04 are described in SEQ ID NOS: 15 and 21, respectively.

The amino acid sequences of murine monoclonal antibody AGX-A05 are described in Table 1. Specifically, the heavy chain CDR sequences are set forth in SEQ ID Nos: 30, 31, and 32 (CDR1, CDR2, and CDR3), and the light chain CDR amino acid sequences are set forth in SEQ ID Nos: 36, 37, and 38 (CDR1, CDR2, and CDR3). Included in the disclosure are anti-TM4SF1 antibodies, or antigen binding fragments comprising a heavy chain variable region comprising CDRs as set forth in the amino acid sequences of SEQ ID Nos: 30, 31, and 32 and/or a light chain variable region comprising CDRs as set forth in the amino acid sequences of SEQ ID Nos: 36, 37, and 38. Included in the disclosure are humanized antibodies or antigen binding fragments comprising the CDRs of AGX-A05. Further, the heavy chain variable amino acid sequences and the light chain variable amino acid sequences of AGX-A05 are described in SEQ ID NOS: 27 and 33, respectively. The amino acid sequences of murine monoclonal antibody AGX-A07 are described in Table 1. Specifically, the heavy chain CDR sequences are set forth in SEQ ID Nos: 42, 43, and 44 (CDR1, CDR2, and CDR3), and the light chain CDR amino acid sequences are set forth in SEQ ID Nos: 48, 49, and 50 (CDR1, CDR2, and CDR3). Included in the disclosure are anti-TM4SF1 antibodies, or antigen binding fragments comprising a heavy chain variable region comprising CDRs as set forth in the amino acid sequences of SEQ ID Nos: 42, 43, and 44 and/or a light chain variable region comprising CDRs as set forth in the amino acid sequences of SEQ ID Nos: 48, 49, and 50. Included in the disclosure are humanized antibodies or antigen binding fragments comprising the CDRs of AGX-A07. Further, the heavy chain variable amino acid sequences and the light chain variable amino acid sequences of AGX-A07 are described in SEQ ID NOs: 39 and 45, respectively.

In one embodiment, a humanized AGX-A07 (h AGX-A07) antibody or antigen binding fragments thereof is provided, comprising a heavy chain sequence as forth in the amino acid sequence of SEQ ID NO: 90. In some embodiments, the humanized AGX-A07 antibody or antigen binding fragments thereof is a humanized mutated AGX-A07 (hm AGX-A07) antibody or antigen binding fragments thereof, comprising a heavy chain sequence comprising one or more substitutions in the sequence as set forth in the amino acid sequence of SEQ ID NO: 90. As shown in Table 6, the heavy chain sequence set forth in SEQ ID NO: 90 is also referred to herein as AGX-A07 H2. In some embodiments, the humanized AGX-A07 antibody or antigen binding fragments thereof is a humanized mutated AGX-A07 antibody or antigen binding fragments thereof, comprising a heavy chain sequence comprising one or more substitutions in the sequence as set forth in the amino acid sequence of SEQ ID NO: 90, wherein the one or more substitutions are in amino acid positions 1, 44, and 80 of SEQ ID NO: 90. In some cases, the humanized mutated AGX-A07 antibody or antigen binding fragments thereof comprises an E1Q (glutamic acid to glutamine substitution at position 1 of the heavy chain, SEQ ID NO: 90). In some cases, the humanized mutated AGX-A07 antibody or antigen binding fragments thereof comprises a D44G (aspartate to glycine substitution at position 44 of the heavy chain, SEQ ID NO: 90). In some cases, the humanized mutated AGX-A07 antibody or antigen binding fragments thereof comprises a F80Y (phenyl alanine to tyrosine substitution at position 80 of the heavy chain, SEQ ID NO: 90). In some embodiments, a humanized mutated AGX-A07 antibody or antigen binding fragments is provided, comprising a heavy chain sequence as forth in the amino acid sequence of SEQ ID NO: 92. As shown in Table 6, the heavy chain sequence set forth in SEQ ID NO: 92 is also referred to herein as AGX-A07 H2v1. In some embodiments, humanized AGX-A07 antibodies or antigen binding fragments are provided, comprising a light chain sequence as forth in the amino acid sequence of SEQ ID NO: 97. As shown in Table 6, the light chain sequence set forth in SEQ ID NO: 97 is also referred to herein as AGX-A07 L5. In some embodiments, the humanized AGX-A07 antibody or antigen binding fragments thereof is a humanized mutated AGX-A07 antibody or antigen binding fragments thereof, comprising a light chain sequence comprising one or more substitutions in the sequence as set forth in the amino acid sequence of SEQ ID NO: 97. In some embodiments, the humanized AGX-A07 antibodies or antigen binding fragments thereof is a humanized mutated AGX-A07 antibody or antigen binding fragments thereof, comprising a light chain sequence comprising one or more substitutions in the sequence as set forth in the amino acid sequence of SEQ ID NO: 97, wherein the one or more substitutions are in amino acid positions 3, 26, 62, and 90 of SEQ ID NO: 97. In some cases, the humanized mutated AGX-A07 antibody or antigen binding fragments thereof comprises an I3V (isoleucine to valine substitution at position 3 of the light chain, SEQ ID NO: 97). In some cases, the humanized mutated AGX-A07 antibody or antigen binding fragments thereof comprises a N26Q (asparagine to glutamine substitution at position 26 of the light chain, SEQ ID NO: 97). In some cases, the humanized mutated AGX-A07 antibody or antigen binding fragments thereof comprises a N26S (asparagine to serine substitution at position 26 of the light chain, SEQ ID NO: 97). In some cases, the humanized mutated AGX-A07 antibody or antigen binding fragments thereof comprises a G62S (glycine to serine substitution at position 62 of the light chain, SEQ ID NO: 97). In some cases, the humanized mutated AGX-A07 antibody or antigen binding fragments thereof comprises a W90Y (tryptophan to tyrosine substitution at position 90 of the light chain, SEQ ID NO: 97). In some embodiments, humanized mutated AGX-A07 antibodies or antigen binding fragments are provided, comprising a light chain sequence as forth in an amino acid sequence selected from the group consisting of SEQ ID NO: 99, SEQ ID NO: 101, SEQ ID NO: 103, and SEQ ID NO: 105. As shown in Table 6, the light chain sequence set forth in SEQ ID NO: 99 is also referred to herein as AGX-A07 L5v1, the light chain sequence set forth in SEQ ID NO: 101 is also referred to herein as AGX-A07 L5v2, the light chain sequence set forth in SEQ ID NO: 103 is also referred to herein as AGX-A07 L5v3, and the light chain sequence set forth in SEQ ID NO: 105 is also referred to herein as AGX-A07 L5v4. Exemplary coding sequence for the heavy chain of a humanized AGX-A07 antibody or antigen binding fragment thereof is provided in SEQ ID NO: 91. Exemplary coding sequence for the heavy chain of a humanized mutated AGX-A07 antibody or antigen binding fragment thereof is provided in SEQ ID NO: 93. Exemplary coding sequence for the light chain of a humanized AGX-A07 antibody or antigen binding fragment thereof is provided in SEQ ID NO: 98 (AGX-A07 L5). Exemplary coding sequences for the light chain of a humanized mutated AGX-A07 antibody or antigen binding fragment thereof are provided in SEQ ID NO: 100 (AGX-A07 L5v1), SEQ ID NO: 102 (AGX-A07 L5v2), SEQ ID NO: 104 (AGX-A07 L5v3), and SEQ ID NO: 106 (AGX-A07 L5v4).

In one embodiment, a humanized AGX-A07 antibody or antigen binding fragments thereof is provided, comprising a heavy chain variable domain sequence as forth in the amino acid sequence of SEQ ID NO: 130 or SEQ ID NO: 132. In some embodiments, the humanized AGX-A07 antibody or antigen binding fragments thereof is a humanized mutated AGX-A07 antibody or antigen binding fragments thereof, comprising a heavy chain variable domain sequence comprising one or more substitutions in the sequence as set forth in the amino acid sequence of SEQ ID NO: 130 or SEQ ID NO: 132. In one embodiment, a humanized AGX-A07 antibody or antigen binding fragments thereof is provided, comprising a light chain variable domain sequence as forth in the amino acid sequence of SEQ ID NO: 131 or SEQ ID NO: 133. In some embodiments, the humanized AGX-A07 antibody or antigen binding fragments thereof is a humanized mutated AGX-A07 antibody or antigen binding fragments thereof, comprising a light chain variable domain sequence comprising one or more substitutions in the sequence as set forth in the amino acid sequence of SEQ ID NO: 131 or SEQ ID NO: 133.

In some embodiments, the humanized AGX-A07 antibody or antigen binding fragment thereof is a humanized mutated AGX-A07 antibody or antigen binding fragment thereof comprising a light chain variable domain sequence comprising the sequence as set forth in the amino acid sequence of SEQ ID NO: 131 and a heavy chain variable domain sequence comprising the sequence as set forth in the amino acid sequence of SEQ ID NO: 130. In some embodiments, the humanized AGX-A07 antibody or antigen binding fragment thereof is a humanized mutated AGX-A07 antibody or antigen binding fragments thereof, comprising a light chain variable domain sequence comprising one or more substitutions in the sequence as set forth in the amino acid sequence of SEQ ID NO: 131 and a heavy chain variable domain sequence comprises one or more substitutions in the sequence as set forth in the amino acid sequence of SEQ ID NO: 130. In some embodiments, the humanized AGX-A07 antibody or antigen binding fragments thereof is a humanized mutated AGX-A07 antibody or antigen binding fragments thereof comprising a light chain variable domain sequence comprising the sequence as set forth in the amino acid sequence of SEQ ID NO: 133 and a heavy chain variable domain sequence comprising the sequence as set forth in the amino acid sequence of SEQ ID NO: 132. In some embodiments, the humanized AGX-A07 antibody or antigen binding fragments thereof is a humanized mutated AGX-A07 antibody or antigen binding fragments thereof, comprising a light chain variable domain sequence comprising one or more substitutions in the sequence as set forth in the amino acid sequence of SEQ ID NO: 133 and a heavy chain variable domain sequence comprises one or more substitutions in the sequence as set forth in the amino acid sequence of SEQ ID NO: 132. In some embodiments, the humanized AGX-A07 antibody or antigen binding fragments thereof is a humanized mutated AGX-A07 antibody or antigen binding fragments thereof comprising a heavy chain sequence comprising the sequence as set forth in the amino acid sequence of SEQ ID NO: 156, or a sequence comprising one of more substitutions in the amino acid sequence of SEQ ID NO: 156.

In some cases, the humanized AGX-A07 antibodies or antigen binding fragments thereof comprise heavy chain CDR sequences as set forth in SEQ ID Nos: 94, 95, and 96 (CDR1, CDR2, and CDR3), or CDR sequences comprising one or more substitutions in the sequences as set forth in SEQ ID Nos: 94, 95, and 96 (CDR1, CDR2, and CDR3). In some cases, the humanized mutated AGX-A07 antibodies or antigen binding fragments thereof comprises heavy chain CDR sequences as set forth in SEQ ID Nos: 94, 95, and 96 (CDR1, CDR2, and CDR3), or CDR sequences comprising one or more substitutions in the sequences as set forth in SEQ ID Nos: 94, 95, and 96 (CDR1, CDR2, and CDR3).

In some cases, the humanized mutated AGX-A07 antibodies or antigen binding fragments thereof comprise heavy chain CDR1 sequence as set forth in SEQ ID NO: 94, or a heavy chain CDR1 sequence comprising one or more substitutions in the sequences as set forth in SEQ ID NO: 94. In some cases, the humanized mutated AGX-A07 antibodies or antigen binding fragments thereof comprise a heavy chain CDR2 sequence as set forth in SEQ ID NO: 95, or a heavy chain CDR2 sequence comprising one or more substitutions in the sequences as set forth in SEQ ID NO: 95. In some cases, the humanized mutated AGX-A07 antibodies or antigen binding fragments thereof comprise a heavy chain CDR3 sequence as set forth in SEQ ID NO: 96, or a heavy chain CDR3 sequence comprising one or more substitutions in the sequences as set forth in SEQ ID NO: 96.

In some cases, the humanized AGX-A07 antibodies or antigen binding fragments thereof comprise light chain CDR sequences as set forth in SEQ ID Nos: 107, 109, and 110 (CDR1, CDR2, and CDR3), or CDR sequences comprising one or more substitutions in the sequences as set forth in SEQ ID Nos: 107, 109, and 110 (CDR1, CDR2, and CDR3). In some cases, the humanized AGX-A07 antibodies or antigen binding fragments thereof comprise light chain CDR sequences as set forth in SEQ ID Nos: 107, 109, and 111 (CDR1, CDR2, and CDR3), or CDR sequences comprising one or more substitutions in the sequences as set forth in SEQ ID Nos: 107, 109, and 111 (CDR1, CDR2, and CDR3). In some cases, the humanized AGX-A07 antibodies or antigen binding fragments thereof comprise light chain CDR sequences as set forth in SEQ ID Nos: 108, 109, and 110 (CDR1, CDR2, and CDR3), or CDR sequences comprising one or more substitutions in the sequences as set forth in SEQ ID Nos: 108, 109, and 110 (CDR1, CDR2, and CDR3). In some cases, the humanized AGX-A07 antibodies or antigen binding fragments thereof comprise light chain CDR sequences as set forth in SEQ ID Nos: 108, 109, and 111 (CDR1, CDR2, and CDR3), or CDR sequences comprising one or more substitutions in the sequences as set forth in SEQ ID Nos: 108, 109, and 111 (CDR1, CDR2, and CDR3).

In some cases, the humanized mutated AGX-A07 antibodies or antigen binding fragments thereof comprise light chain CDR1 sequence as set forth in SEQ ID Nos: 107 or 108, or light chain CDR1 sequence comprising one or more substitutions in the sequences as set forth in SEQ ID Nos: 107 or 108. In some cases, the humanized mutated AGX-A07 antibodies or antigen binding fragments thereof comprise light chain CDR2 sequence as set forth in SEQ ID NO: 109, or light chain CDR2 sequence comprising one or more substitutions in the sequences as set forth in SEQ ID NO: 109. In some cases, the humanized mutated AGX-A07 antibodies or antigen binding fragments thereof comprise light chain CDR3 sequence as set forth in SEQ ID NO: 110 or 111, or light chain CDR1 sequence comprising one or more substitutions in the sequences as set forth in SEQ ID Nos: 110 or 111. In some cases, the humanized mutated AGX-A07 antibodies or antigen binding fragments thereof comprise light chain CDR3 sequence as set forth in SEQ ID NO: 110, or light chain CDR1 sequence comprising one or more substitutions in the sequences as set forth in SEQ ID Nos: 110.

In some embodiments, the humanized mutated AGX-A07 comprises a heavy chain variable region comprising the following amino acid substitutions: Q1E, D44G, F80Y in SEQ ID NO: 132 (also referred to herein as AGX-A07 H2), and a light chain variable region comprising the following amino acid substitutions: I3V, N26Q, G62S in SEQ ID NO: 133 (also referred to herein as AGX-A07 L5). In some embodiments, the humanized mutated AGX-A07 comprises a heavy chain variable region comprising the following amino acid substitutions: Q1E, D44G, F80Y in SEQ ID NO: 132, and a light chain variable region comprising the following amino acid substitutions: I3V, N26Q, G62S in SEQ ID NO: 133, wherein the heavy chain comprises CDR1 (SEQ ID NO: 94), CDR2 (SEQ ID NO: 95), and CDR3 (SEQ ID NO: 96), and the light chain comprises CDR1 (SEQ ID NO: 108), CDR2 (SEQ ID NO: 109), and CDR3 (SEQ ID NO: 110). In some embodiments, the humanized mutated AGX-A07 is AGX-A07 H2v1L5v2 and comprises a heavy chain comprising the amino acid sequence as set forth in SEQ ID NO: 130 (also referred to herein as AGX-A07 H2v1), and a light chain comprising the amino acid sequence as set forth in SEQ ID NO: 131 (also referred to herein as AGX-A07 L5v2). In some embodiments, the humanized mutated AGX-A07 comprises a heavy chain comprising the amino acid sequence as set forth in SEQ ID NO: 92, and a light chain comprising the amino acid sequence as set forth in SEQ ID NO: 101.

The amino acid sequences of murine monoclonal antibody AGX-A08 are described in Table 1. Specifically, the heavy chain CDR sequences are set forth in SEQ ID Nos: 54, 55, and 56 (CDR1, CDR2, and CDR3), and the light chain CDR amino acid sequences are set forth in SEQ ID Nos: 60, 61, and 62 (CDR1, CDR2, and CDR3). Included in the disclosure are anti-TM4SF1 antibodies, or antigen binding fragments comprising a heavy chain variable region comprising CDRs as set forth in the amino acid sequences of SEQ ID Nos: 54, 55, and 56 and/or a light chain variable region comprising CDRs as set forth in the amino acid sequences of SEQ ID Nos: 60, 61, and 62. Included in the disclosure are humanized antibodies or antigen binding fragments comprising the CDRs of AGX-A08. Further, the heavy chain variable amino acid sequences and the light chain variable amino acid sequences of AGX-A08 are described in SEQ ID NOs: 51 and 57, respectively.

The amino acid sequences of murine monoclonal antibody AGX-A09 are described in Table 1. Specifically, the heavy chain CDR sequences are set forth in SEQ ID Nos: 66, 67, and 68 (CDR1, CDR2, and CDR3), and the light chain CDR amino acid sequences are set forth in SEQ ID Nos: 72, 73, and 74 (CDR1, CDR2, and CDR3). Included in the disclosure are anti-TM4SF1 antibodies, or antigen binding fragments comprising a heavy chain variable region comprising CDRs as set forth in the amino acid sequences of SEQ ID Nos: 66, 67, and 68 and/or a light chain variable region comprising CDRs as set forth in the amino acid sequences of SEQ ID Nos: 72, 73, and 74. Included in the disclosure are humanized antibodies or antigen binding fragments comprising the CDRs of AGX-A09. Further, the heavy chain variable amino acid sequences and the light chain variable amino acid sequences of AGX-A09 are described in SEQ ID NOs: 63 and 69, respectively.

The amino acid sequences of murine monoclonal antibody AGX-A11 are described in Table 1. Specifically, the heavy chain CDR sequences are set forth in SEQ ID Nos: 78, 79, and 80 (CDR1, CDR2, and CDR3), and the light chain CDR amino acid sequences are set forth in SEQ ID Nos: 84, 85, and 86 (CDR1, CDR2, and CDR3). Included in the disclosure are anti-TM4SF1 antibodies, or antigen binding fragments comprising a heavy chain variable region comprising CDRs as set forth in the amino acid sequences of SEQ ID Nos: 78, 79, and 80 and/or a light chain variable region comprising CDRs as set forth in the amino acid sequences of SEQ ID Nos: 84, 85, and 862. Included in the disclosure are humanized antibodies or antigen binding fragments comprising the CDRs of AGX-A11. Further, the heavy chain variable amino acid sequences and the light chain variable amino acid sequences of AGX-A11 are described in SEQ ID NOS: 75 and 81, respectively.

The amino acid sequences of a humanized antibody AGX-A01 (h AGX-A01) are described in Table 6. As shown in Table 6, the heavy chain sequence set forth is SEQ ID NO: 112 is also referred to herein as AGX-A01 H1. Specifically, the heavy chain CDR sequences are set forth in SEQ ID Nos: 115, 116, and 118 (CDR1, CDR2, and CDR3) and the light chain CDR amino acid sequences are set forth in SEQ ID Nos: 124, 128, and 129 (CDR1, CDR2, and CDR3). Further, exemplary heavy chain amino acid sequence and the light chain amino acid sequence of the humanized AGX-A01 are described in SEQ ID Nos: 112 and 122, respectively. Exemplary coding sequences for the heavy chain and the light chain of the humanized AGX-A01 are described in SEQ ID Nos: 113 and 123, respectively In some embodiments, the humanized AGX-A01 antibody or antigen binding fragments thereof is a humanized mutated AGX-A01 (hm AGX-A01) antibody or antigen binding fragments thereof, comprising a heavy chain sequence comprising one or more substitutions in the sequence as set forth in the amino acid sequence of SEQ ID NO: 112. In some embodiments, the humanized AGX-A01 antibody or antigen binding fragments thereof is a humanized mutated AGX-A01 antibody or antigen binding fragments thereof, comprising a heavy chain sequence comprising one or more substitutions in the sequence as set forth in the amino acid sequence of SEQ ID NO: 112, wherein the one or more substitutions are in amino acid positions 63 and 106 of SEQ ID NO: 112. In some cases, the humanized mutated AGX-A01 antibody or antigen binding fragments thereof comprises a G63S (glycine to serine substitution at position 63 of the heavy chain, SEQ ID NO: 112). In some cases, the humanized mutated AGX-A01 antibody or antigen binding fragments thereof comprises a D106E (aspartate to glutamic acid substitution at position 106 of the heavy chain, SEQ ID NO: 112). In some cases, the humanized mutated AGX-A01 antibody or antigen binding fragments thereof comprises a D106S (aspartate to serine substitution at position 106 of the heavy chain, SEQ ID NO: 112). In some embodiments, a humanized mutated AGX-A01 antibody or antigen binding fragments is provided, comprising a heavy chain sequence as forth in the amino acid sequence of SEQ ID NO: 114. As shown in Table 6, the heavy chain sequence set forth is SEQ ID NO: 114 is also referred to herein as AGX-A01 H1v1.

In some embodiments, humanized AGX-A01 antibodies or antigen binding fragments are provided, comprising a light chain sequence as forth in the amino acid sequence of SEQ ID NO: 122. As shown in Table 6, the light chain sequence set forth is SEQ ID NO: 122 is also referred to herein as AGX-A01 L10. In some embodiments, the humanized AGX-A01 antibody or antigen binding fragments thereof is a humanized mutated AGX-A01 antibody or antigen binding fragments thereof, comprising a light chain sequence comprising one or more substitutions in the sequence as set forth in the amino acid sequence of SEQ ID NO: 122. In some embodiments, the humanized mutated AGX-A01 antibody or antigen binding fragments thereof is a humanized mutated AGX-A01 antibody or antigen binding fragments thereof, comprising a light chain sequence comprising one or more substitutions in the sequence as set forth in the amino acid sequence of SEQ ID NO: 122, wherein the one or more substitutions are in one or more amino acid positions selected from amino acid positions 1, 33, 42, 51, 86, and 90 of SEQ ID NO: 122. In some embodiments, the humanized mutated AGX-A01 antibody or antigen binding fragments thereof is a humanized mutated AGX-A01 antibody or antigen binding fragments thereof, comprising a light chain sequence comprising one or more substitutions in the sequence as set forth in the amino acid sequence of SEQ ID NO: 122, wherein the one or more substitutions are in one or more amino acid positions selected from amino acid positions 1, 33, 42, 51, and 86 of SEQ ID NO: 122. In some cases, the humanized mutated AGX-A01 antibody or antigen binding fragments thereof comprises an A1E (alanine to glutamic acid substitution at position 1 of the light chain, SEQ ID NO: 122). In some cases, the humanized mutated AGX-A01 antibody or antigen binding fragments thereof comprises a N33S (asparagine to serine substitution at position 33 of the light chain, SEQ ID NO: 122). In some cases, the humanized mutated AGX-A01 antibody or antigen binding fragments thereof comprises a M42Q (methionine to glutamine substitution at position 42 of the light chain, SEQ ID NO: 122). In some cases, the humanized mutated AGX-A01 antibody or antigen binding fragments thereof comprises a V51L (valine to leucine substitution at position 51 of the light chain, SEQ ID NO: 122). In some cases, the humanized mutated AGX-A01 antibody or antigen binding fragments thereof comprises a D86E (aspartate to glutamic acid substitution at position 86 of the light chain, SEQ ID NO: 122). In some cases, the humanized mutated AGX-A01 antibody or antigen binding fragments thereof comprises an I90V (isoleucine to valine substitution at position 90 of the light chain, SEQ ID NO: 122).

In some cases, the humanized AGX-A01 antibodies or antigen binding fragments thereof comprise heavy chain CDR sequences as set forth in SEQ ID Nos: 115 (CDR1); 116 (CDR2); and 118 (CDR3), or CDR sequences comprising one or more substitutions in the sequences as set forth in SEQ ID Nos: 115 (CDR1); 116 (CDR2); and 118 (CDR3). In some cases, the humanized mutated AGX-A01 antibodies or antigen binding fragments thereof comprise heavy chain CDR sequences as set forth in SEQ ID Nos: 115 (CDR1); 116 or 117 (CDR2); and 118, 119, 120, or 121 (CDR3), or CDR sequences comprising one or more substitutions in the sequences as set forth in SEQ ID Nos: 115 (CDR1); 116 or 117 (CDR2); and 118, 119, 120, or 121 (CDR3).

In some cases, the humanized mutated AGX-A01 antibodies or antigen binding fragments thereof comprise heavy chain CDR1 sequence as set forth in SEQ ID NO: 115, or a heavy chain CDR1 sequence comprising one or more substitutions in the sequences as set forth in SEQ ID NO: 115. In some cases, the humanized mutated AGX-A01 antibodies or antigen binding fragments thereof comprise a heavy chain CDR2 sequence as set forth in SEQ ID NO: 116, or a heavy chain CDR2 sequence comprising one or more substitutions in the sequences as set forth in SEQ ID NO: 116. In some cases, the humanized mutated AGX-A01 antibodies or antigen binding fragments thereof comprise a heavy chain CDR2 sequence as set forth in SEQ ID NO: 117, or a heavy chain CDR2 sequence comprising one or more substitutions in the sequences as set forth in SEQ ID NO: 117. In some cases, the humanized mutated AGX-A01 antibodies or antigen binding fragments thereof comprise a heavy chain CDR3 sequence as set forth in a sequence selected from SEQ ID Nos: 118, 119, 120 and 121, or a heavy chain CDR3 sequence comprising one or more substitutions in a sequence selected from SEQ ID Nos: 118, 119, 120, and 121.

In some cases, the humanized AGX-A01 antibodies or antigen binding fragments thereof comprise light chain CDR sequences as set forth in SEQ ID Nos: 124 (CDR1); 128 (CDR2); and 129 (CDR3), or CDR sequences comprising one or more substitutions in the sequences as set forth in SEQ ID Nos: 124 (CDR1); 128 (CDR2); and 129 (CDR3). In some cases, the humanized mutated AGX-A01 antibodies or antigen binding fragments thereof comprise light chain CDR sequences as set forth in SEQ ID Nos: 124, 125, 126, or 127 (CDR1); 128 (CDR2); and 129 (CDR3), or CDR sequences comprising one or more substitutions in the sequences as set forth in SEQ ID Nos: 124, 125, 126, or 127 (CDR1); 128 (CDR2); and 129 (CDR3).

In some cases, the humanized mutated AGX-A01 antibodies or antigen binding fragments thereof comprise light chain CDR1 sequence as set forth in SEQ ID Nos: 125, 126, 127, or 128, or light chain CDR1 sequence comprising one or more substitutions in the sequences as set forth in SEQ ID Nos: 125, 126, 127, or 128. In some cases, the humanized mutated AGX-A01 antibodies or antigen binding fragments thereof comprise light chain CDR2 sequence as set forth in SEQ ID NO: 129, or light chain CDR2 sequence comprising one or more substitutions in the sequences as set forth in SEQ ID NO: 129. In some cases, the humanized mutated AGX-A01 antibodies or antigen binding fragments thereof comprise light chain CDR3 sequence as set forth in SEQ ID Nos: 130, or light chain CDR1 sequence comprising one or more substitutions in the sequences as set forth in SEQ ID Nos: 130.

In one embodiment, the disclosure provides an anti-TM4SF1 antibody, or antigen-binding fragment thereof, that comprises a heavy chain variable domain encoded by a nucleic acid sequence as set forth in SEQ ID NO: 3, and a light chain variable domain encoded by a nucleic acid sequence as set forth in SEQ ID NO: 9. In one embodiment, the disclosure provides an anti-TM4SF1 antibody, or antigen-binding fragment thereof, that comprises a heavy chain variable domain encoded by a nucleic acid sequence as set forth in SEQ ID NO: 15, and a light chain variable domain encoded by a nucleic acid sequence as set forth in SEQ ID NO: 21 In one embodiment, the disclosure provides an anti-TM4SF1 antibody, or antigen-binding fragment thereof, that comprises a heavy chain variable domain encoded by a nucleic acid sequence as set forth in SEQ ID NO: 27, and a light chain variable domain encoded by a nucleic acid sequence as set forth in SEQ ID NO: 33. In one embodiment, the disclosure provides an anti-TM4SF1 antibody, or antigen-binding fragment thereof, that comprises a heavy chain variable domain encoded by a nucleic acid sequence as set forth in SEQ ID NO: 39, and a light chain variable domain encoded by a nucleic acid sequence as set forth in SEQ ID NO: 45. In one embodiment, the disclosure provides an anti-TM4SF1 antibody, or antigen-binding fragment thereof, that comprises a heavy chain variable domain encoded by a nucleic acid sequence as set forth in SEQ ID NO: 51, and a light chain variable domain encoded by a nucleic acid sequence as set forth in SEQ ID NO: 57. In one embodiment, the disclosure provides an anti-TM4SF1 antibody, or antigen-binding fragment thereof, that comprises a heavy chain variable domain encoded by a nucleic acid sequence as set forth in SEQ ID NO: 63, and a light chain variable domain encoded by a nucleic acid sequence as set forth in SEQ ID NO: 69. In one embodiment, the disclosure provides an anti-TM4SF1 antibody, or antigen-binding fragment thereof, that comprises a heavy chain variable domain encoded by a nucleic acid sequence as set forth in SEQ ID NO: 75, and a light chain variable domain encoded by a nucleic acid sequence as set forth in SEQ ID NO: 81. In one embodiment, the disclosure provides an anti-TM4SF1 antibody, or antigen-binding fragment thereof, that comprises a heavy chain variable domain encoded by a nucleic acid sequence as set forth in SEQ ID NO: 90, and a light chain variable domain encoded by a nucleic acid sequence as set forth in SEQ ID NO: 97. In one embodiment, the disclosure provides an anti-TM4SF1 antibody, or antigen-binding fragment thereof, that comprises a heavy chain variable domain encoded by a nucleic acid sequence as set forth in SEQ ID NO: 90, and a light chain variable domain encoded by a nucleic acid sequence as set forth in SEQ ID NO: 99. In one embodiment, the disclosure provides an anti-TM4SF1 antibody, or antigen-binding fragment thereof, that comprises a heavy chain variable domain encoded by a nucleic acid sequence as set forth in SEQ ID NO: 90, and a light chain variable domain encoded by a nucleic acid sequence as set forth in SEQ ID NO: 101. In one embodiment, the disclosure provides an anti-TM4SF1 antibody, or antigen-binding fragment thereof, that comprises a heavy chain variable domain encoded by a nucleic acid sequence as set forth in SEQ ID NO: 90, and a light chain variable domain encoded by a nucleic acid sequence as set forth in SEQ ID NO: 103. In one embodiment, the disclosure provides an anti-TM4SF1 antibody, or antigen-binding fragment thereof, that comprises a heavy chain variable domain encoded by a nucleic acid sequence as set forth in SEQ ID NO: 90, and a light chain variable domain encoded by a nucleic acid sequence as set forth in SEQ ID NO: 105. In one embodiment, the disclosure provides an anti-TM4SF1 antibody, or antigen-binding fragment thereof, that comprises a heavy chain variable domain encoded by a nucleic acid sequence as set forth in SEQ ID NO: 92, and a light chain variable domain encoded by a nucleic acid sequence as set forth in SEQ ID NO: 97. In one embodiment, the disclosure provides an anti-TM4SF1 antibody, or antigen-binding fragment thereof, that comprises a heavy chain variable domain encoded by a nucleic acid sequence as set forth in SEQ ID NO: 92, and a light chain variable domain encoded by a nucleic acid sequence as set forth in SEQ ID NO: 99. In one embodiment, the disclosure provides an anti-TM4SF1 antibody, or antigen-binding fragment thereof, that comprises a heavy chain variable domain encoded by a nucleic acid sequence as set forth in SEQ ID NO: 92, and a light chain variable domain encoded by a nucleic acid sequence as set forth in SEQ ID NO: 101. In one embodiment, the disclosure provides an anti-TM4SF1 antibody, or antigen-binding fragment thereof, that comprises a heavy chain variable domain encoded by a nucleic acid sequence as set forth in SEQ ID NO: 92, and a light chain variable domain encoded by a nucleic acid sequence as set forth in SEQ ID NO: 103. In one embodiment, the disclosure provides an anti-TM4SF1 antibody, or antigen-binding fragment thereof, that comprises a heavy chain variable domain encoded by a nucleic acid sequence as set forth in SEQ ID NO: 92, and a light chain variable domain encoded by a nucleic acid sequence as set forth in SEQ ID NO: 105.

In one embodiment, the present disclosure provides an anti-TM4SF1 antibody, or antigen-binding fragment thereof, that has a heavy chain variable domain sequence that is at least 95% identical, at least 96% identical, at least 97% identical, at least 98% identical, at least 99% identical, or 100% identical to an amino acid sequence selected from SEQ ID NO: 3, SEQ ID NO: 15, SEQ ID NO: 27, SEQ ID NO: 39, SEQ ID NO: 51, SEQ ID NO: 63, SEQ ID NO: 75, SEQ ID NO: 90, SEQ ID NO: 92, SEQ ID NO: 112, or SEQ ID NO: 114; and that has a light chain variable domain sequence that is at least 95% identical, at least 96% identical, at least 97% identical, at least 98% identical, at least 99% identical, or 100% identical to an amino acid sequence selected from SEQ ID NO: 9, SEQ ID NO: 21, SEQ ID NO: 33, SEQ ID NO: 45, SEQ ID NO: 57, SEQ ID NO: 69, SEQ ID NO: 81, SEQ ID NO: 97, SEQ ID NO: 99, SEQ ID NO: 101, SEQ ID NO: 103, SEQ ID NO: 105, or SEQ ID NO: 122. In one embodiment, the present disclosure provides an anti-TM4SF1 antibody, or antigen-binding fragment thereof, that has a heavy chain variable domain sequence that is at least 95% identical, at least 96% identical, at least 97% identical, at least 98% identical, at least 99% identical, or 100% identical to an amino acid sequence selected from SEQ ID NO: 3, SEQ ID NO: 15, SEQ ID NO: 27, SEQ ID NO: 39, SEQ ID NO: 51, SEQ ID NO: 63, SEQ ID NO: 75, SEQ ID NO: 90, SEQ ID NO: 92, SEQ ID NO: 112, or SEQ ID NO: 114; and that has a light chain variable domain sequence that is at least 95% identical, at least 96% identical, at least 97% identical, at least 98% identical, at least 99% identical, or 100% identical to an amino acid sequence selected from SEQ ID NO: 9, SEQ ID NO: 21, SEQ ID NO: 33, SEQ ID NO: 45, SEQ ID NO: 57, SEQ ID NO: 69, SEQ ID NO: 81, SEQ ID NO: 97, SEQ ID NO: 99, SEQ ID NO: 101, or SEQ ID NO: 122.

In one embodiment, the disclosure includes an anti-TM4SF1 antibody which is an IgG and comprises four polypeptide chains including two heavy chains each comprising a heavy chain variable domain and heavy chain constant regions CH1, CH2 and CH3, and two light chains each comprising a light chain variable domain and a light chain constant region (CL). In certain embodiments, the antibody is a human IgG1, IgG2, or an IgG4. In certain embodiments, the antibody is a human IgG1. In other embodiments, the antibody is an IgG2. The heavy and light chain variable domain sequences may contain CDRs as set forth in Table 6.

Complementarily determining regions (CDRs) are known as hypervariable regions both in the light chain and the heavy chain variable domains. The more highly conserved portions of variable domains are called the framework (FR). CDRs and framework regions (FR) of a given antibody may be identified using the system described by Kabat et al. supra; Lefranc et al., supra and/or Honegger and Pluckthun, supra. Also familiar to those in the art is the numbering system described in Kabat et al. (1991, NIH Publication 91-3242, National Technical Information Service, Springfield, Va.). In this regard Kabat et al. defined a numbering system for variable domain sequences, including the identification of CDRs, that is applicable to any antibody.

One or more CDRs may be incorporated into a molecule either covalently or noncovalently to make it an antigen binding protein.

An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest. The CDR3, in particular, is known to play an important role in antigen binding of an antibody or antibody fragment.

In one embodiment, the disclosure provides an anti-TM4SF1 antibody, or an antigen-binding fragment thereof, comprising a heavy chain comprising a CDR3 domain as set forth in any one of SEQ ID NO: 8, SEQ ID NO: 20, SEQ ID NO: 32, SEQ ID NO: 44, SEQ ID NO: 56, SEQ ID NO: 68, or SEQ ID NO: 80 and comprising a variable domain comprising an amino acid sequence that has at least about 60%, at least about 65%, at least about 70%, at least about 75%, at least about 80%, at least about 85%, at least about 90%, at least about 95%, at least about 96%, at least about 97%, at least about 98%, at least about 99%, or 100% identical to a sequence as set forth in any one of SEQ ID NO: 3, SEQ ID NO: 15, SEQ ID NO: 27, SEQ ID NO: 39, SEQ ID NO: 51, SEQ ID NO: 63, or SEQ ID NO: 75. In one embodiment, the disclosure provides an anti-TM4SF1 antibody, or an antigen-binding fragment thereof, comprising a light chain comprising a CDR3 domain as set forth in any one of SEQ ID NO: 14, SEQ ID NO: 26, SEQ ID NO: 38, SEQ ID NO: 50, SEQ ID NO: 62, SEQ ID NO: 74, or SEQ ID NO: 86, and having a light chain variable domain comprising an amino acid sequence that has at least at least about 60%, at least about 65%, at least about 70%, at least about 75%, at least about 80%, at least about 85%, at least about 90%, at least about 95%, at least about 96%, at least about 97%, at least about 98%, or at least about 99%, or 100% identical to a sequence as set forth in any one of SEQ ID NO: 9, SEQ ID NO: 21, SEQ ID NO: 33, SEQ ID NO: 45, SEQ ID NO: 57, SEQ ID NO: 69, or SEQ ID NO: 81. Thus, in certain embodiments, the CDR3 domain is held constant, while variability may be introduced into the remaining CDRs and/or framework regions of the heavy and/or light chains, while the antibody, or antigen binding fragment thereof, retains the ability to bind to TM4SF1 and retains the functional characteristics, e.g., binding affinity, of the parent, or has improved functional characteristic, e.g., binding affinity, compared to the parent.

In one embodiment, the disclosure provides an anti-TM4SF1 antibody, or an antigen-binding fragment thereof, comprising a heavy chain comprising a CDR2 domain as set forth in any one of SEQ ID NO: 7, SEQ ID NO: 19, SEQ ID NO: 31, SEQ ID NO: 43, SEQ ID NO: 55, SEQ ID NO: 67, or SEQ ID NO: 79 and comprising a variable domain comprising an amino acid sequence that has at least at least about 60%, at least about 65%, at least about 70%, at least about 75%, at least about 80%, at least about 85%, at least about 90%, at least about 95%, at least about 96%, at least about 97%, at least about 98%, or at least about 99%, or 100% identical to a sequence as set forth in any one of SEQ ID NO: 3, SEQ ID NO: 15, SEQ ID NO: 27, SEQ ID NO: 39, SEQ ID NO: 51, SEQ ID NO: 63, or SEQ ID NO: 75. In one embodiment, the disclosure provides an anti-TM4SF1 antibody, or an antigen-binding fragment thereof, comprising a light chain comprising a CDR2 domain as set forth in any one of SEQ ID NO: 13, SEQ ID NO: 25, SEQ ID NO: 37, SEQ ID NO: 49, SEQ ID NO: 61, SEQ ID NO: 73, or SEQ ID NO: 85, and having a light chain variable domain comprising an amino acid sequence that has at least at least about 60%, at least about 65%, at least about 70%, at least about 75%, at least about 80%, at least about 85%, at least about 90%, at least about 95%, at least about 96%, at least about 97%, at least about 98%, or at least about 99%, or 100% identical to a sequence as set forth in any one of SEQ ID NO: 9, SEQ ID NO: 21, SEQ ID NO: 33, SEQ ID NO: 45, SEQ ID NO: 57, SEQ ID NO: 69, or SEQ ID NO:

81. Thus, in certain embodiments, the CDR2 domain is held constant, while variability may be introduced into the remaining CDRs and/or framework regions of the heavy and/or light chains, while the antibody, or antigen binding fragment thereof, retains the ability to bind to TM4SF1 and retains the functional characteristics, e.g., binding affinity, of the parent, or has improved functional characteristic, e.g., binding affinity, compared to the parent.

In one embodiment, the disclosure provides an anti-TM4SF1 antibody, or an antigen-binding fragment thereof, comprising a heavy chain comprising a CDR1 domain as set forth in any one of SEQ ID NO: 6, SEQ ID NO: 18, SEQ ID NO: 30, SEQ ID NO: 42, SEQ ID NO: 54, SEQ ID NO: 66, or SEQ ID NO: 78 and comprising a variable domain comprising an amino acid sequence that has at least at least about 60%, at least about 65%, at least about 70%, at least about 75%, at least about 80%, at least about 85%, at least about 90%, at least about 95%, at least about 96%, at least about 97%, at least about 98%, or at least about 99%, or 100% identical to a sequence as set forth in any one of SEQ ID NO: 3, SEQ ID NO: 15, SEQ ID NO: 27, SEQ ID NO: 39, SEQ ID NO: 45, SEQ ID NO: 69, or SEQ ID NO: 81. In one embodiment, the disclosure provides an anti-TM4SF1 antibody, or an antigen-binding fragment thereof, comprising a light chain comprising a CDR1 domain as set forth in any one of SEQ ID NO: 12, SEQ ID NO: 24, SEQ ID NO: 36, SEQ ID NO: 48, SEQ ID NO: 60, SEQ ID NO: 72, or SEQ ID NO: 84, and having a light chain variable domain comprising an amino acid sequence that has at least at least about 60%, at least about 65%, at least about 70%, at least about 75%, at least about 80%, at least about 85%, at least about 90%, at least about 95%, at least about 96%, at least about 97%, at least about 98%, or at least about 99%, or 100% identical to a sequence a set forth in any one of SEQ ID NO: 9, SEQ ID NO: 21, SEQ ID NO: 33, SEQ ID NO: 45, SEQ ID NO: 57, SEQ ID NO: 69, or SEQ ID NO: 81. Thus, in certain embodiments, the CDR1 domain is held constant, while variability may be introduced into the remaining CDRs and/or framework regions of the heavy and/or light chains, while the antibody, or antigen binding fragment thereof, retains the ability to bind to TM4SF1 and retains the functional characteristics, e.g., binding affinity, of the parent.

In some embodiments, an anti-TM4SF1 antibody of this disclosure comprises a heavy chain comprising an Fc region, wherein said Fc region comprises a sequence selected from the group consisting of: SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 151, SEQ ID NO: 152, and SEQ ID NO: 153; or wherein said Fc region comprises a sequence comprising one or more substitutions in a sequence selected from the group consisting of: SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 151, SEQ ID NO: 152, and SEQ ID NO: 153. For instance, in some embodiments, an anti-TM4SF1 antibody of this disclosure comprises an Fc region, wherein said Fc region comprises a sequence that is at least about 70% to about 100%, such as at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to a sequence selected from the group consisting of: SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 151, SEQ ID NO: 152, and SEQ ID NO: 153.

In some embodiments, an anti-TM4SF1 antibody of this disclosure comprises a heavy chain comprising a sequence selected from the group consisting of: SEQ ID NO: 146, SEQ ID NO: 147, SEQ ID NO: 148, SEQ ID NO: 149, SEQ ID NO: 150, SEQ ID NO: 154, SEQ ID NO: 155, and SEQ ID NO: 156; or wherein said heavy chain comprises a sequence comprising one or more substitutions in a sequence selected from the group consisting of: SEQ ID NO: 146, SEQ ID NO: 147, SEQ ID NO: 148, SEQ ID NO: 149, SEQ ID NO: 150, SEQ ID NO: 154, SEQ ID NO: 155, and SEQ ID NO: 156. For instance, in some embodiments, an anti-TM4SF1 antibody of this disclosure comprises a heavy chain comprising a sequence that is at least about 70% to about 100%, such as at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to a sequence selected from the group consisting of: SEQ ID NO: 146, SEQ ID NO: 147, SEQ ID NO: 148, SEQ ID NO: 149, SEQ ID NO: 150, SEQ ID NO: 154, SEQ ID NO: 155, and SEQ ID NO: 156.

The anti-TM4SF1 antibodies and fragments described in Table 1 may also be humanized. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization may be performed, for example, following the method of Jones et al., 1986, Nature 321:522-25; Riechmann et al., 1988, Nature 332:323-27; and Verhoeyen et al., 1988, Science 239:1534-36), by substituting hypervariable region sequences for the corresponding sequences of a human antibody.

In some cases, the humanized antibodies are constructed by CDR grafting, in which the amino acid sequences of the six CDRs of the parent non-human antibody (e.g., rodent) are grafted onto a human antibody framework. For example, Padlan et al. determined that only about one third of the residues in the CDRs actually contact the antigen, and termed these the "specificity determining residues," or SDRs (Padlan et al., 1995, FASEB J. 9:133-39). In the technique of SDR grafting, only the SDR residues are grafted onto the human antibody framework (See, e.g., Kashmiri et al., 2005, Methods 36:25-34).

The choice of human variable domains, both light and heavy, to be used in making the humanized antibodies can be important to reduce antigenicity. For example, according to the so-called "best-fit" method, the sequence of the variable domain of a non-human (e.g., rodent) antibody is screened against the entire library of known human variable-domain sequences. The human sequence that is closest to that of the rodent may be selected as the human framework for the humanized antibody (Sims et al., 1993, J. Immunol.

151:2296-308; and Chothia et al., 1987, J. Mol. Biol. 196:901-17). Another method uses a particular framework derived from the consensus sequence of all human antibodies of a particular subgroup of light or heavy chains. The same framework may be used for several different humanized antibodies (Carter et al., 1992, Proc. Natl. Acad. Sci. USA 89:4285-89; and Presta et al., 1993, J. Immunol. 151:2623-32). In some cases, the framework is derived from the consensus sequences of the most abundant human subclasses, VL6 subgroup I (VL6 I) and VH subgroup III (VHIII). In another method, human germline genes are used as the source of the framework regions.

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, 2000, Protein Eng. 13:819-24), Modeller (Sali and Blundell, 1993, J. Mol. Biol. 234:779-815), and Swiss PDB Viewer (Guex and Peitsch, 1997, Electrophoresis 18:2714-23). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human framework regions that may be used for humanization include but are not limited to: framework regions selected using the "best-fit" method (see, e.g., Sims, et al., J. Immunol. 151 (1993) 2296); framework regions derived from the consensus sequence of human antibodies of a particular subgroup of light or heavy chain variable regions (see, e.g., Carter, et al., Proc. Natl. Acad. Sci. USA, 89 (1992) 4285; and Presta, et al., J. Immunol., 151 (1993) 2623); human mature (somatically mutated) framework regions or human germline framework regions (see, e.g., Almagro, and Fransson, Front. Biosci. 13 (2008) 1619-1633); and framework regions derived from screening FR libraries (see, e.g., Baca, et al., J. Biol. Chem. 272 (1997) 10678-10684 and Rosok, et al., J. Biol. Chem. 271 (1996) 22611-22618).

Humanized antibodies and methods of making them are reviewed, e.g., in Almagro, and Fransson, Front. Biosci. 13 (2008) 1619-1633, and are further described, e.g., in Riechmann, et al., Nature 332 (1988) 323-329; Queen, et al., Proc. Nat'l Acad. Sci. USA 86 (1989) 10029-10033; U.S. Pat. Nos. 5,821,337, 7,527,791, 6,982,321, and 7,087,409; Kashmiri, et al., Methods 36 (2005) 25-34 (describing SDR (a-CDR) grafting); Padlan, Mol. Immunol. 28 (1991) 489-498 (describing "resurfacing"); Dall'Acqua, et al., Methods 36 (2005) 43-60 (describing "FR shuffling"); and Osbourn, et al., Methods 36 (2005)61-68 and Klimka, et al., Br. J. Cancer, 83 (2000) 252-260 (describing the "guided selection" approach to FR shuffling).

In one embodiment, an anti-TM4SF1 antibody, or antigen-binding fragment thereof, of the disclosure binds to cynomolgus TM4SF1 with a $K_D$ about $1 \times 10^{-6}$ M or less.

An anti-TM4SF1 antibody, or antigen-binding fragment thereof, of the disclosure, in certain embodiments, binds to an epitope on the ECL2 loop of human TM4SF1 with a $K_D$ about $5 \times 10^{-8}$ M or less as determined in a standard flow cytometry assay using HUVEC cells.

An anti-TM4SF1 antibody, or antigen-binding fragment thereof, of the disclosure, in certain embodiments, binds to human TM4SF1 with a $K_D$ of about $1 \times 10^{-8}$ M or less in a standard flow cytometry assay using HUVEC cells.

An anti-TM4SF1 antibody, or antigen-binding fragment thereof, of the disclosure, in certain embodiments, binds to human TM4SF1 with a $K_D$ of about $1 \times 10^{-3}$ M to about $1 \times 10^{-4}$ M, about $1 \times 10^{-4}$ M to about $1 \times 10^{-5}$ M, about $1 \times 10^{-5}$ M to about $1 \times 10^{-6}$ M, about $1 \times 10^{-6}$ to about $1 \times 10^{-7}$ M, about $1 \times 10^{-7}$ to about $1 \times 10^{-8}$ M, about $1 \times 10^{-8}$ M to about $1 \times 10^{-9}$ M, about $1 \times 10^{-9}$ M to about $1 \times 10^{-10}$ M, about $1 \times 10^{-10}$ M to about $1 \times 10^{-11}$ M, about $1 \times 10^{-11}$ M to about $1 \times 10^{-12}$ M, about $2 \times 10^{-3}$ M to about $2 \times 10^{-4}$ M, about $2 \times 10^{-4}$ M to about $2 \times 10^{-5}$ M, about $2 \times 10^{-5}$ M to about $2 \times 10^{-6}$ M, about $2 \times 10^{-6}$ to about $2 \times 10^{-7}$ M, about $2 \times 10^{-7}$ to about $2 \times 10^{-8}$ M, about $2 \times 10^{-8}$ M to about $2 \times 10^{-9}$ M, about $2 \times 10^{-9}$ M to about $2 \times 10^{-10}$ M, about $2 \times 10^{-10}$ M to about $2 \times 10^{-11}$ M, about $2 \times 10^{-11}$ M to about $2 \times 10^{-12}$ M, about $3 \times 10^{-3}$ M to about $3 \times 10^{-4}$ M, about $3 \times 10^{-4}$ M to about $3 \times 10^{-5}$ M, about $3 \times 10^{-5}$ M to about $3 \times 10^{-6}$ M, about $3 \times 10^{-6}$ to about $3 \times 10^{-7}$ M, about $3 \times 10^{-7}$ to about $3 \times 10^{-8}$ M, about $3 \times 10^{-8}$ M to about $3 \times 10^{-9}$ M, about $3 \times 10^{-9}$ M to about $3 \times 10^{-10}$ M, about $3 \times 10^{-10}$ M to about $3 \times 10^{-11}$ M, about $3 \times 10^{-11}$ M to about $3 \times 10^{-12}$ M, about $4 \times 10^{-3}$ M to about $4 \times 10^{-4}$ M, about $4 \times 10^{-4}$ M to about $4 \times 10^{-5}$ M, about $4 \times 10^{-5}$ M to about $4 \times 10^{-6}$ M, about $4 \times 10^{-6}$ to about $4 \times 10^{-7}$ M, about $4 \times 10^{-7}$ to about $4 \times 10^{-8}$ M, about $4 \times 10^{-8}$ M to about $4 \times 10^{-9}$ M, about $4 \times 10^{-9}$ M to about $4 \times 10^{-10}$ M, about $4 \times 10^{-10}$ M to about $4 \times 10^{-11}$ M, about $4 \times 10^{-11}$ M to about $4 \times 10^{-12}$ M, about $5 \times 10^{-3}$ M to about $5 \times 10^{-4}$ M, about $5 \times 10^{-4}$ M to about $5 \times 10^{-5}$ M, about $5 \times 10^{-5}$ M to about $5 \times 10^{-6}$ M, about $5 \times 10^{-6}$ to about $5 \times 10^{-7}$ M, about $5 \times 10^{-7}$ to about $5 \times 10^{-8}$ M, about $5 \times 10^{-8}$ M to about $5 \times 10^{-9}$ M, about $5 \times 10^{-9}$ M to about $5 \times 10^{-10}$ M, about $5 \times 10^{-10}$ M to about $5 \times 10^{-11}$ M, about $5 \times 10^{-11}$ M to about $5 \times 10^{-12}$ M, about $5 \times 10^{-7}$ M to about $5 \times 10^{-11}$ M, about $5 \times 10^{-7}$ M to about $1 \times 10^{-7}$ M, about $5 \times 10^{-8}$ M, about $1 \times 10^{-8}$ M, about $5 \times 10^{-9}$ M, about $1 \times 10^{-9}$ M, about $5 \times 10^{-10}$ M, about $1 \times 10^{-10}$ M, about $5 \times 10^{-11}$ M or about $1 \times 10^{-11}$ M. In some embodiments, the $K_D$ is determined in a standard flow cytometry assay using HUVEC cells.

An anti-TM4SF1 antibody, or antigen-binding fragment thereof, of the disclosure, in certain embodiments, binds to human TM4SF1 with a $K_D$ of about $5 \times 10^{-10}$ M or less in a standard flow cytometry assay using HUVEC cells.

An anti-TM4SF1 antibody, or antigen-binding fragment thereof, of the disclosure, in certain embodiments, binds to cynomolgus TM4SF1 with a $K_D$ about $1 \times 10^{-6}$ M or less in a standard flow cytometry assay using HEK293 overexpressing cells. In one embodiment, the HEK293 cells are transfected to express cynomolgus TM4SF1. In a further embodiment, HEK293 cells express cynomolgus TM4SF1 at about 600 mRNA copies per $10^6$ copies 18S rRNA.

Methods of determining the $K_D$ of an antibody or antibody fragment are known in the art. For example, surface plasmon resonance may be used to determine the $K_D$ of the antibody to the antigen (e.g., using a BIACORE 2000 or a BIACORE 3000 (BIAcore, Inc., Piscataway, N.J.) at 25° C. with immobilized antigen or Fc receptor CM5 chips at about 10 response units (RU)). In certain embodiments FACS or flow cytometry is used to determine the $K_D$, whereby cells, such as HEK293 cells or HUVEC cells, that express TM4SF1 are used to bind the antibody or fragment and measure the $K_D$ according to standard methods. Affinity determination of antibodies using flow cytometry is described, for example, in Geuijen et al (2005) *J Immunol Methods*. 302(1-2):68-77. In certain embodiments, FACS is used to determine affinity of antibodies.

In one embodiment, the disclosure features an anti-TM4SF1 antibody or antigen binding fragment thereof, having CDR amino acid sequences described herein with conservative amino acid substitutions, such that the anti-TM4SF1 antibody or antigen binding fragment thereof comprises an amino acid sequence of a CDR that is at least 95% identical (or at least 96% identical, or at least 97% identical, or at least 98% identical, or at least 99% identical) to a CDR amino acid sequence set forth in Table 1. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

The disclosure further features in one aspect an anti-TM4SF1 antibody, or antigen-binding fragment thereof, that binds to an epitope on the ECL2 loop of human TM4SF1 with a $K_D$ of about $5 \times 10^{-8}$ M or less as determined in a standard flow cytometry assay using HUVEC cells, wherein the anti-TM4SF1 antibody, or antigen-binding fragment thereof, comprises a light chain variable region comprising a human IgG framework region and comprises a heavy chain variable region comprising a human IgG framework region. In one embodiment, the anti-TM4SF1 antibody, or antigen-binding fragment thereof, is humanized. In one embodiment, the anti-TM4SF1 antibody, or antigen-binding fragment thereof, cross reacts with cynomolgus TM4SF1.

In another aspect of the disclosure, the anti-TM4SF1 antibody, or antigen-binding fragment thereof, is a humanized anti-TM4SF1 antibody, or antigen-binding fragment thereof, that binds to an epitope on the ECL2 loop of human TM4SF1 with a $K_D$ about $5 \times 10^{-8}$ M or less as determined in a standard flow cytometry assay using HUVEC cells. In one embodiment, the anti-TM4SF1 antibody, or antigen-binding fragment thereof, binds to cynomolgus TM4SF1 with a $K_D$ about $1 \times 10^{-6}$ M or less in a standard flow cytometry assay using HEK293 overexpressing cells. In one embodiment, the anti-TM4SF1 antibody, or antigen-binding fragment thereof, binds to human TM4SF1 with a $K_D$ of about $1 \times 10^{-8}$ M or less in a standard flow cytometry assay using HUVEC cells. In one embodiment, the anti-TM4SF1 antibody, or antigen-binding fragment thereof, binds to human TM4SF1 with a $K_D$ of $1 \times 10^{-3}$ M to about $1 \times 10^{-4}$ M, about $1 \times 10^{-4}$ M to about $1 \times 10^{-5}$ M, about $1 \times 10^{-5}$ M to about $1 \times 10^{-6}$ M, about $1 \times 10^{-6}$ to about $1 \times 10^{-7}$ M, about $1 \times 10^{-7}$ to about $1 \times 10^{-8}$ M, about $1 \times 10^{-8}$ M to about $1 \times 10^{-9}$ M, about $1 \times 10^{-9}$ M to about $1 \times 10^{-10}$ M, about $1 \times 10^{-10}$ M to about $1 \times 10^{-11}$ M, about $1 \times 10^{-11}$ M to about $1 \times 10^{-12}$ M, about $2 \times 10^{-3}$ M to about $2 \times 10^{-4}$ M, about $2 \times 10^{-4}$ M to about $2 \times 10^{-5}$ M, about $2 \times 10^{-5}$ M to about $2 \times 10^{-6}$ M, about $2 \times 10^{-6}$ to about $2 \times 10^{-7}$ M, about $2 \times 10^{-7}$ to about $2 \times 10^{-8}$ M, about $2 \times 10^{-8}$ M to about $2 \times 10^{-9}$ M, about $2 \times 10^{-9}$ M to about $2 \times 10^{-10}$ M, about $2 \times 10^{-10}$ M to about $2 \times 10^{-11}$ M, about $2 \times 10^{-11}$ M to about $2 \times 10^{-12}$ M, about $3 \times 10^{-3}$ M to about $3 \times 10^{-4}$ M, about $3 \times 10^{-4}$ M to about $3 \times 10^{-5}$ M, about $3 \times 10^{-5}$ M to about $3 \times 10^{-6}$ M, about $3 \times 10^{-6}$ to about $3 \times 10^{-7}$ M, about $3 \times 10^{-7}$ to about $3 \times 10^{-8}$ M, about $3 \times 10^{-8}$ M to about $3 \times 10^{-9}$ M, about $3 \times 10^{-9}$ M to about $3 \times 10^{-10}$ M, about $3 \times 10^{-10}$ M to about $3 \times 10^{-11}$ M, about $3 \times 10^{-11}$ M to about $3 \times 10^{-12}$ M, about $4 \times 10^{-3}$ M to about $4 \times 10^{-4}$ M, about $4 \times 10^{-4}$ M to about $4 \times 10^{-5}$ M, about $4 \times 10^{-5}$ M to about $4 \times 10^{-6}$ M, about $4 \times 10^{-6}$ to about $4 \times 10^{-7}$ M, about $4 \times 10^{-7}$ to about $4 \times 10^{-8}$ M, about $4 \times 10^{-8}$ M to about $4 \times 10^{-9}$ M, about $4 \times 10^{-9}$ M to about $4 \times 10^{-10}$ M, about $4 \times 10^{-10}$ M to about $4 \times 10^{-11}$ M, about $4 \times 10^{-11}$ M to about $4 \times 10^{-12}$ M, about $5 \times 10^{-3}$ M to about $5 \times 10^{-4}$ M, about $5 \times 10^{-4}$ M to about $5 \times 10^{-5}$ M, about $5 \times 10^{-5}$ M to about $5 \times 10^{-6}$ M, about $5 \times 10^{-6}$ to about $5 \times 10^{-7}$ M, about $5 \times 10^{-7}$ to about $5 \times 10^{-8}$ M, about $5 \times 10^{-8}$ M to about $5 \times 10^{-9}$ M, about $5 \times 10^{-9}$ M to about $5 \times 10^{-10}$ M, about $5 \times 10^{-10}$ M to about $5 \times 10^{-11}$ M, about $5 \times 10^{-11}$ M to about $5 \times 10^{-12}$ M, about $5 \times 10^{-7}$ M to about $5 \times 10^{-11}$ M, about $5 \times 10^{-7}$ M, about $1 \times 10^{-7}$ M, about $5 \times 10^{-8}$ M, about $1 \times 10^{-8}$ M, about $5 \times 10^{-9}$ M, about $1 \times 10^{-9}$ M, about $5 \times 10^{-10}$ M, about $1 \times 10^{-10}$ M, about $5 \times 10^{-11}$ M or about $1 \times 10^{-11}$ M. In some embodiments, the $K_D$ is determined in a standard flow cytometry assay using HUVEC cells. In one embodiment, the anti-TM4SF1 antibody, or antigen-binding fragment thereof, binds to human TM4SF1 with a $K_D$ of about $5 \times 10^{-10}$ M or less in a standard flow cytometry assay using TM4SF1 expressing HUVEC cells.

In one embodiment, binding of an anti-TM4SF1 antibody, or antigen binding fragment, of the disclosure to human TM4SF1 is not dependent on glycosylation of the ECL2 loop of human TM4SF1, i.e., binding of the antibody is independent of glycosylation of TM4SF1 within the ECL2 loop (SEQ ID NO: 77).

The anti-TM4SF1 antibodies, or antigen-binding fragments thereof, of the disclosure may be any of any isotype (for example, but not limited to IgG, IgM, and IgE). In certain embodiments, antibodies, or antigen-binding fragments thereof, of the disclosure are IgG isotypes. In a specific embodiment, antibodies, or antigen-binding fragments thereof, of the disclosure are of the IgG1, IgG2 or IgG4 isotype. In certain embodiments, the anti-TM4SF1 antibody, or antigen-binding fragment thereof, are human IgG1, human IgG2, or human IgG4 isotype.

IgG2 is naturally the lowest in ADCC and/or CDC activity (An et al., MAbs. 2009 November-December; 1(6): 572-579). Accordingly, in certain embodiments it IgG2 is advantageously used. However, IgG2 has two extra cysteines (leading to 4 inter-hinge disulfide bonds) which make it prone to aggregation via formation of inter-antibody disulfide bonds. In a related embodiment, mutations to the IgG2 cysteines are made to decrease aggregation.

The present disclosure provides antibody fragments that bind to TM4SF1. In certain circumstances there are advantages of using antibody fragments, rather than whole antibodies. The smaller size of the fragments allows for rapid clearance, and may lead to improved access to cells, tissues, or organs. For a review of certain antibody fragments, see Hudson et al., 2003, Nature Med. 9:129-34.

Various techniques have been developed for the production of antibody fragments. Traditionally, these fragments were derived via proteolytic digestion of intact antibodies (see, e.g., Morimoto et al., 1992, J. Biochem. Biophys. Methods 24:107-17; and Brennan et al., 1985, Science 229:81-83). However, these fragments can now be produced directly by recombinant host cells. Fab, Fv, and scFv antibody fragments can all be expressed in and secreted from *E. coli* or yeast cells, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')2 fragments (Carter et al., 1992, Bio/Technology 10:163-67). According to another approach, F(ab')2 fragments can be isolated directly from recombinant host cell culture. Fab and F(ab')2 fragment with increased in vivo half-life comprising salvage receptor binding epitope residues are described in, for example, U.S. Pat. No. 5,869,046. Other techniques for the production of antibody fragments will be apparent to the skilled practitioner. In certain embodiments, an antibody is a single chain Fv fragment (scFv) (see, e.g., WO 93/16185; U.S. Pat. Nos. 5,571,894 and 5,587,458). Fv and scFv have intact combining sites that are devoid of constant regions; thus, they may be suitable for reduced nonspecific binding during in vivo use. scFv fusion proteins may be constructed to yield fusion of an effector protein at either the amino or the carboxy terminus of an scFv (See, e.g., Borrebaeck ed., supra). The antibody fragment may also be a "linear antibody," for example, as described in the references cited above. Such linear antibodies may be monospecific or multi-specific, such as bispecific.

In certain embodiments, the antigen binding fragment is selected from the group consisting of a Fab, a Fab', a F(ab')2, an Fv, and an scFv.

Anti-TM4SF1 antibodies (and fragments) that, for example, have a high affinity for human TM4SF1, can be identified using screening techniques known in the art. For example, monoclonal antibodies may be made using the hybridoma method first described by Kohler et al., 1975, Nature 256:495-97, or may be made by recombinant DNA methods (see, e.g., U.S. Pat. No. 4,816,567).

In the hybridoma method, a mouse or other appropriate host animal, such as a hamster, is immunized using, for example, the ECL2 loop of human TM4SF1 or cells expressing TM4SF1 (whereby the ECL2 loop is expressed on the cell surface), to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice 59-103 (1986)).

The hybridoma cells thus prepared are seeded and grown in a suitable culture medium which, in certain embodiments, contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which prevent the growth of HGPRT-deficient cells.

Exemplary fusion partner myeloma cells are those that fuse efficiently, support stable high-level production of antibody by the selected antibody-producing cells, and are sensitive to a selective medium that selects against the unfused parental cells. Exemplary myeloma cell lines are murine myeloma lines, such as SP-2 and derivatives, for example, X63-Ag8-653 cells available from the American Type Culture Collection (Manassas, Va.), and those derived from MOPC-21 and MPC-11 mouse tumors available from the Salk Institute Cell Distribution Center (San Diego, Calif.). Human myeloma and mouse-human heteromyeloma cell lines also have been described for the production of human monoclonal antibodies (Kozbor, 1984, Immunol. 133:3001-05; and Brodeur et al., Monoclonal Antibody Production Techniques and Applications 51-63 (1987)).

Culture medium in which hybridoma cells are growing is assayed for production of monoclonal antibodies directed against the antigen. The binding specificity of monoclonal antibodies produced by hybridoma cells is determined by immunoprecipitation or by an in vitro binding assay, such as RIA or ELISA. The binding affinity of the monoclonal antibody can, for example, be determined by the Scatchard analysis described in Munson et al., 1980, Anal. Biochem. 107:220-39.

Once hybridoma cells that produce antibodies of the desired specificity, affinity, and/or activity are identified, the clones may be subcloned by limiting dilution procedures and grown by standard methods (Goding, supra). Suitable culture media for this purpose include, for example, DMEM or RPMI-1640 medium. In addition, the hybridoma cells may be grown in vivo as ascites tumors in an animal, for example, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells can serve as a source of such DNA. Once isolated, the DNA may be placed into expression vectors, which are then transfected into host cells, such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., 1993, Curr. Opinion in Immunol. 5:256-62 and Pluckthun, 1992, Immunol. Revs. 130:151-88.

In a further embodiment, monoclonal antibodies or antibody fragments can be isolated from antibody phage libraries generated using the techniques described in, for example, Antibody Phage Display: Methods and Protocols (O'Brien and Aitken eds., 2002). In principle, synthetic antibody clones are selected by screening phage libraries containing phages that display various fragments of antibody variable region (Fv) fused to phage coat protein. Such phage libraries are screened against the desired antigen. Clones expressing Fv fragments capable of binding to the desired antigen are adsorbed to the antigen and thus separated from the non-binding clones in the library. The binding clones are then eluted from the antigen and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described, for example, in Winter et al., 1994, Ann. Rev. Immunol. 12:433-55.

Repertoires of VH and VL genes can be separately cloned by PCR and recombined randomly in phage libraries, which can then be searched for antigen-binding clones as described in Winter et al., supra. Libraries from immunized sources provide high-affinity antibodies to the immunogen without the requirement of constructing hybridomas. Alternatively, the naive repertoire can be cloned to provide a single source of human antibodies to a wide range of non-self and also self-antigens without any immunization as described by Griffiths et al., 1993, EMBO J 12:725-34. Finally, naive libraries can also be made synthetically by cloning the unrearranged V-gene segments from stem cells, and using PCR primers containing random sequence to encode the highly variable CDR3 regions and to accomplish rearrangement in vitro as described, for example, by Hoogenboom and Winter, 1992, J. Mol. Biol. 227:381-88.

Screening of the libraries can be accomplished by various techniques known in the art. For example, TM4SF1 (e.g., a soluble form of the ECL2 loop or cells expressing said loop) can be used to coat the wells of adsorption plates, expressed on host cells affixed to adsorption plates or used in cell sorting, conjugated to biotin for capture with streptavidin-coated beads, or used in any other method for panning display libraries. The selection of antibodies with slow dissociation kinetics (e.g., good binding affinities) can be promoted by use of long washes and monovalent phage display as described in Bass et al., 1990, Proteins 8:309-14 and WO 92/09690, and by use of a low coating density of antigen as described in Marks et al., 1992, Biotechnol. 10:779-83.

Anti-TM4SF1 antibodies can be obtained by designing a suitable antigen screening procedure to select for the phage clone of interest followed by construction of a full length anti-TM4SF1 antibody clone using VH and/or VL sequences (e.g., the Fav sequences), or various CDR sequences from VH and VL sequences, from the phage clone of interest and suitable constant region (e.g., Fc) sequences described in Kabat et al., supra.

Screening of anti-TM4SF1 antibodies can be performed using binding assays known in the art and described herein for determining whether the antibody has a therapeutic affinity for the ECL2 loop of TM4SF1. The ability of the antibody to inhibit or decrease metastatic cell activity can be measured using standard assays in the art, as well as those described herein. Preclinical assays require use of an animal model of metastasis, commonly of one of three types: (i) injection of metastatic mouse tumor cells such as B16F10 melanoma TCs into mice, commonly via tail vein injection to generate lung metastases, via portal vein or intrasplenic injection to generate liver metastases, or via left ventricular cardiac injection to generate bone and other metastases; (ii) orthotopic transplantation of metastatic tumor cells or intact tumor fragments into mice, which methods often require later surgical resection of the primary tumor to prevent morbidity associated with primary tumor growth; and (iii) genetically engineered mouse models of spontaneous metastasis, of which the most common is the MMTV-Pyt (mouse mammary tumor virus-polyomavirus middle T Antigen) mouse mammary carcinoma model which provides a highly realistic mouse model of human cancer metastasis; greater than 85% of hemizygous MMTV-PyMT females spontaneously develop palpable mammary tumors which metastasize to the lung at age to 8-16 weeks. Quantifying the metastatic burden in the lung, either by live animal imaging or direct counting of metastatic nodules in the lungs of sacrificed animals, as a function of the degree of TM4SF1 immunoblockade and achieving a therapeutic level, e.g., at least a 50% reduction in lung metastasis, would be indicative, for example, of a therapeutic antibody that could be used in the methods of the disclosure. Further, cross-species reactivity assays are known in the art. Examples of assays that can be used are described, for example, in Khanna and Hunter (Carcinogenesis. 2005 March; 26(3):513-23) and Saxena and Christofori (Mol Oncol. 2013 April; 7(2):283-96), incorporated by reference in their entireties herein.

In some embodiments, the anti-TM4SF1 antibodies and antigen binding fragments thereof can be used, e.g., to treat or prevent cancer. In certain embodiments, the anti-TM4SF1 antibodies and antigen binding fragments of the disclosure can be used to prevent tumor cells from metastasizing. The anti-TM4SF1 antibodies and antigen binding fragments thereof, of this disclosure, in some examples, prevent tumor cell metastasis by interfering with the interaction between tumor cells and blood vessel endothelial cells.

IV. Therapeutic Molecules in the ADCs

In some embodiments, the ADCs of this disclosure comprise one or more therapeutic (also referred to herein as a therapeutic molecule or a therapeutic agent) conjugated to an anti-TM4SF1 antibody or an antigen binding fragment thereof. In some embodiments, the agent is a therapeutic agent or a diagnostic agent. In some embodiments, the therapeutic agent is a biologically active moiety. In some embodiments, the biologically active moiety comprises a radioactive isotope, a cytotoxic agent, a chemotherapeutic agent, a protein, a peptide, an antibody, a growth inhibitory agent, a prodrug activating enzyme, and an anti-hormonal agent. In some embodiments, a therapeutic molecule can be a small molecule (e.g., both for cancer and for non-cancer angiogenic indications); a V-ATPase inhibitor; a pro-apoptotic agent; a Bcl2 inhibitor; an MCL1 inhibitor; a HSP90 inhibitor; an IAP inhibitor; an mTor inhibitor; a microtubule stabilizer; a microtubule destabilizer; an auristatin; a dolastatin; a maytansinoid; a MetAP (methionine aminopeptidase); an inhibitor of nuclear export of proteins CRM1; a DPPIV inhibitor; proteasome inhibitors; inhibitors of phosphoryl transfer reactions in mitochondria; a protein synthesis inhibitor; a kinase inhibitor (such as, a CDK2 inhibitor, a CDK9 inhibitor); a kinesin inhibitor, an HDAC inhibitor, a DNA damaging agent, a DNA alkylating agent, a DNA intercalator, a DNA minor groove binder, a DHFR inhibitor, a nucleic acid, a CRISPR enzyme; degraders (such as agents that induce protein degradation, (e.g., HSP90 inhibitor, selective estrogen receptor degraders (SERDs), selective androgen receptor degraders (SARDs); hydrophobic tags that can be used to recruit chaperones to a protein of interest, e.g., Adamantane, Arg-Boc3; E3 ligase recruiting ligands, e.g., Nutlin-3a (MDM2 ligand), Bestatin (cIAP ligand), VHL ligand, Pomalidomide (CRBN ligand); proteolysis-targeting chimeras (PROTACs) that may utilize different D3 ligases to target a protein of interest for degradation)) (see, e.g., Lai A C, Crews C M. Induced protein degradation: an emerging drug discovery paradigm. Nat Rev Drug Discov. 2016; 16(2):101-114); antisense oligonucleotides; RNAi agents (such as siRNA), CRISPR-Cas9 gene editing systems; RNA molecules; DNA e.g., plasmids; an anticancer agent, an anti-inflammatory agent, an anti-infective agent (e.g., anti-fungal, antibacterial, anti-parasitic, anti-viral), an anesthetic agent; RNA polymerase II inhibitor; a DNA intercalating agent, a DNA cross-linking agent; an anti-tubulin agent; a cytotoxic drug, a tumor vaccine, an antibody, a peptide, pepti-bodies, a chemotherapeutic agent, a cytotoxic agent; a cytostatic agent; an immunological modifiers, an interferon, an interleukin, an immuno stimulatory growth hormone, a cytokine, a vitamin, a mineral, an aromatase inhibitor, a Histone Deacetylase (HDAC), an HDAC inhibitor; a lipid nanoparticle to encapsulate one or more therapeutic molecule.

In some embodiments, the radioactive isotope may be one or more kinds selected from the group consisting of $^{211}$At, $^{131}$I, $^{125}$I, $^{90}$Y, $^{186}$Re, $^{188}$Re, $^{153}$Sm, $^{212}$Bi, $^{32}$P, and radioactive isotopes of Lu, but not limited thereto. In some embodiments, the prodrug-activating enzyme is one or more kinds selected from the group consisting of: an alkaline phosphatase, an arylsulfatase, a cytosine deaminase, a protease, a D-alanylcarboxy-peptidase, a carbohydrate-cleaving enzyme, a P-lactamase and a penicillin amidase, but not limited thereto.

The cytotoxic agent, ins some embodiments, comprises one or more selected from the group consisting of: ricin, saporin, gelonin, momordin, debouganin, diphtheria toxin, pseudomonas toxin, etc., but not limited thereto. The cytotoxic agent, in some instances is one or more kinds selected from the group consisting of: cisplatin, carboplatin, oxaliplatin, paclitaxel, melphalan, doxorubicin, methotrexate, 5-fluorouracil, etoposide, mechlorethamine, cyclophosphamide, bleomycin, a calicheamicin, a maytansine, a trichothene, CC1065, diphtheria A chain, Pseudomonas aeruginosa exotoxin A chain, ricin A chain, abrin A chain, modeccin A chain, alpha-sarcin, Aleuritesfordii proteins, dianthin proteins, Phytolaca americana proteins, *Momordica charantia* inhibitors, curcin, crotin, *Sapaonaria officinalis* inhibitors, gelonin, mitogellin, restrictocin, phenomycin, enomycin, tricothecenes, ribonucleases and deoxyribonucleases, but not limited thereto. In some embodiments, the cytotoxic agent is one or more kinds selected from the group consisting of: duocarmycin, monomethyl auristatin E (MMAE), monomethyl auristatin F (MMAF), N2'-deacetyl-N2'-(3-mercapto-1-oxopropyl)maytansine (DM1), PBD (Pyrrolobenzodiazepine) dimer, duocarmycin, monomethyl auristatin E (MMAE), monomethyl auristatin F (MMAF), but not limited thereto. In some embodiments, the cytotoxic agent comprises a ribosome inactivating protein, a histone deacetylase (HDAC) inhibitor, a tubulin inhibitor, an alkylating agent, an antibiotic, an antineoplastic agent, an antiproliferative agent, an antimetabolite, a topoisomerase I or II inhibitor, a hormonal agonist or antagonist, an immunomodulator, a DNA minor groove binder, and a radioactive agent. In certain embodiments, the ribosome inactivating protein is saporin. In some embodiments, the diagnostic agent is a label. In some embodiments, the label is a fluorescent label, a chromogenic label, or a radiolabel. In some embodiments, the agent is directly conjugated to the anti-TM4SF1 antibody or antigen binding fragment thereof. In other embodiments, the agent is indirectly conjugated to the anti-TM4SF1 antibody or antigen binding fragment thereof, optionally by a linker.

In some embodiments, an ADC of this disclosure comprises an anti-TM4SF1 antibody or antigen binding fragment thereof and one or more agents (e.g., 1, 2, 3, or 4 or more agents), such as therapeutic agents, that act additively or synergistically with the anti-TM4SF1 antibody or antigen binding fragment thereof, for example, to kill or inhibit tumor cells (TCs) and/or tumor vasculature endothelial cells (ECs) in the treatment of a disorder associated with pathological angiogenesis, such as cancer. The therapeutic agent, for example, can be a biologically active moiety, such as a cytotoxic agent, a chemotherapeutic agent, a protein, a peptide, an antibody, a growth inhibitory agent, and/or an anti-hormonal agent.

Examples of tubulin inhibitors that can be conjugated, either directly or indirectly, to an anti-TM4SF1 antibody or antigen binding fragment thereof, can include, without limitation, polymerization inhibitors (e.g., vinblastine, vincristine, vinorelbine, vinflunine, cryptophycin 52, hallchondrins, dolastatins, hemiasterlins that can bind to the vinca domain of tubulin; colchine, combretastatins, 2-methoxyestradiol, E7010 that can bind to the cholchicine domain of tubulin; depolymerization inhibitors, such as paclitaxel, docetaxel, epothilon, discodermolide that can bind to the taxane site).

Exemplary chemotherapeutic agents include, but are not limited to, methotrexate, adriamicin, vinca alkaloids (vincristine, vinblastine, etoposide), doxorubicin, melphalan, mitomycin C, chlorambucil, daunorubicin or other intercalating agents; enzymes and fragments thereof such as nucleolytic enzymes, antibiotics, and toxins such as small molecule toxins or enzymatically active toxins of bacterial, fungal, plant or animal origin, including fragments and/or variants thereof. Enzymatically active toxins and fragments thereof that can be used include diphtheria A chain, non-binding active fragments of diphtheria toxin, exotoxin A chain (from Pseudomonas aeruginosa), ricin A chain, abrin A chain, modeccin A chain, alpha-sarcin, *Aleurites fordii* proteins, dianthin proteins, Phytolaca americana proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In addition, a variety of radionuclides can be used for conjugation of the anti-TM4SF1 antibodies or antigen binding fragments to the therapeutic agents, to generate the ADCs of this disclosure. Examples include At$^{211}$, I$^{131}$, I$^{125}$, Y$^{90}$, Re$^{186}$, Sm$^{153}$, Bi$^{212}$, P$^{32}$ and radioactive isotopes of Lu. Alternatively, the anti-TM4SF1 antibodies or antigen binding fragments can be conjugated to one or more smaller molecule toxins, such as a calicheamicin, maytansinoids, dolastatins, aurostatins, a trichothecene, and CC1065, and the derivatives of these toxins that have toxin activity, are also contemplated herein. Other therapeutic agents that can be conjugated to TM4SF1 binding protein of the disclosure include, in various examples, BCNU, streptozoicin, vincristine and 5-fluorouracil etc.

The diagnostic agent for conjugation, in some embodiments, is a label, such as a fluorescent label, a chromogenic label, or a radiolabel. Accordingly, the label may be used for detection purposes, and may be a fluorescent compound, an enzyme, a prosthetic group, a luminescent material, a bioluminescent material, or a radioactive material. The radiolabel, for example, may comprise a radioactive atom for scintigraphic studies, for example Tc$^{99m}$ or I$^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The one or more agents (e.g., therapeutic agents and/or diagnostic agents) may be directly conjugated to anti-TM4SF1 antibodies or antigen binding fragments (e.g., by way of a direct covalent or non-covalent interaction), such that the agent is immediately conjugated to the protein. An agent may be directly conjugated to a binding protein of the disclosure, for example, by a direct peptide bond. In other instances, the direct conjugation is by way of a direct non-covalent interaction, such as an interaction between the anti-TM4SF1 antibodies or antigen binding fragments and an agent that specifically binds to the anti-TM4SF1 antibodies or antigen binding fragments.

V. Linkers

The one or more agents (e.g., therapeutic agents and/or diagnostic agents) may be indirectly conjugated to anti-TM4SF1 antibodies or antigen binding fragments (e.g., by way of a linker with direct covalent or non-covalent interactions). Linkers can be chemical linking agents, such as homobifunctional and heterobifunctional cross-linkers, which are available from many commercial sources. Regions available for cross-linking may be found on the binding protein (e.g., anti-TM4SF1 antibodies) of the disclosure. The linker may comprise a flexible arm, e.g., 2, 3, 4, 5, 6, 7, 8, 9, 10, 11, 12, 13, 14, or 15 carbon atoms. Exemplary linkers include BS3 ([Bis(sulfosuccinimidyl) suberate];BS3 is a homobifunctional N-hydroxysuccinimideester that targets accessible primary amines), NHS/EDC (N-hydroxysuccinimide and N-ethyl-(dimethylaminopropyl)carbodimide; NHS/EDC allows for the conjugation of primary amine groups with carboxyl groups), sulfo-EMCS ([N-e-Maleimidocaproic acid]hydrazide; sulfo-EMCS are heterobifunctional reactive groups (maleimide and NHS-ester) that are reactive toward sulfhydryl and amino groups), hydrazide (most proteins contain exposed carbohydrates and hydrazide is a useful reagent for linking carboxyl groups to primary amines), and SATA (N-succinimidyl-S-acetylthioacetate; SATA is reactive towards amines and adds protected sulfhydryls groups). To form covalent bonds, a chemically reactive group a wide variety of active carboxyl groups (e.g., esters) where the hydroxyl moiety is physiologically acceptable at the levels required to modify the peptide. Particular agents include N-hydroxysuccinimide (NHS), N-hydroxysulfosuccinimide (sulfo-NHS), maleimide-benzoyl-succinimide (MBS), gamma-maleimido-butyryloxy succinimide ester (GMBS), maleimido propionic acid (MPA) maleimido hexanoic acid (MHA), and maleimido undecanoic acid (MUA). Primary amines are the principal targets for NHS esters. Accessible a-amino groups present on the N-termini of proteins and the ε-amine of lysine react with NHS esters. An amide bond is formed when the NHS ester conjugation reaction reacts with primary amines releasing N-hydroxysuccinimide. These succinimide containing reactive groups are herein referred to as succinimidyl groups. In certain embodiments of the disclosure, the functional group on the protein will be a thiol group and the chemically reactive group will be a maleimido-containing group such as gamma-maleimide-butrylamide (GMBA or MPA). Such maleimide containing groups are referred to herein as maleido groups. The maleimido group is most selective for sulfhydryl groups on peptides when the pH of the reaction mixture is 6.5-7.4. At pH 7.0, the rate of reaction of maleimido groups with sulfhydryls (e.g., thiol groups on proteins such as serum albumin or IgG) is 1000-fold faster than with amines. Thus, a stable thioether linkage between the maleimido group and the sulfhydryl can be formed.

Further exemplary linker/linker chemistry that in some embodiments is used for conjugation of an anti-TM4SF1 antibody or an antigen binding fragment thereof, as described herein, include moieties that can be used in a click conjugation, e.g., in a two-step conjugation in which a first moiety is conjugated to an engineered cysteine (e.g., at position N297 with an N297C mutation), said first moiety containing a reactive handle, and a second moiety containing the linker-payload which reacts with the first moiety. An example of a possible reaction between the first moiety's reactive handle and the second moiety is a metal free click reaction that utilizes strain-promoted azide-alkyne cycloaddition. Examples of moieties include, but are not limited to, bicyclononyne (BCN) reacting with an azide or tetrazine, dibenzocyclooctyne (DBCO) reacting with an azide, also denoted as aza-dibenzocyclooctyne (DIBAC), a transcyclooctene (TCO) reacting with a tetrazine (such as methyl tetrazine), or a methyl cyclopropene click handle reacting with tetrazine. Specific examples of such moieties are as follows, but not limited to: dibenzylcyclooctyne-PegX-carboxylic acid, perfluorophenyl 6-(2,5-dioxo-2,5-dihydro-1H-pyrrol-1-yl)hexanoate Chemical Formula: C16H12F5NO4 Molecular Weight: 377.27; 6-(3,4-dibromo-2,5-dioxo-2,5-dihydro-1H-pyrrol-1-yl)hexanoic acid Chemical Formula: C10H11Br2NO4 Molecular Weight: 369.01; (2-methylcycloprop-2-en-1-yl)methyl carbamate (E)-cyclooct-4-en-1-yl (2-(2-(2-(2-aminoethoxy)ethoxy)ethoxy)ethyl)carbamate 3-(5-methylpyridin-2-yl)-6-(pyridin-2-yl)-1,2,4,5-tetrazine; ((1R,8S,9s)-bicyclo[6.1.0]non-4-yn-9-yl)methyl (2-(2-(2-aminoethoxy)ethoxy)ethyl)carbamate Chemical Formula: C17H28N2O4 Molecular Weight: 324.42; ((1R,8S,9s)-bicyclo[6.1.0]non-4-yn-9-yl)methyl (2-(2-(2-aminoethoxy)ethoxy)ethyl)carbamate Chemical Formula: C17H28N2O4 Molecular Weight: 324.42.

In other embodiments, the linker includes at least one amino acid (e.g., a peptide of at least 2, 3, 4, 5, 6, 7, 10, 15, 20, 25, 40, or 50 amino acids). In certain embodiments, the linker is a single amino acid (e.g., any naturally occurring amino acid such as Cys). In other embodiments, a glycine-rich peptide such as a peptide can be used. In some cases, the linker can be a single amino acid (e.g., any amino acid, such as Gly or Cys). Examples of suitable linkers are succinic acid, Lys, Glu, and Asp, or a dipeptide such as Gly-Lys. When the linker is succinic acid, one carboxyl group thereof may form an amide bond with an amino group of the amino acid residue, and the other carboxyl group thereof may, for example, form an amide bond with an amino group of the peptide or substituent. When the linker is Lys, Glu, or Asp, the carboxyl group thereof may form an amide bond with an amino group of the amino acid residue, and the amino group thereof may, for example, form an amide bond with a carboxyl group of the substituent. When Lys is used as the linker, a further linker may be inserted between the ε-amino group of Lys and the substituent. In one particular embodiment, the further linker is succinic acid which, e.g., forms an amide bond with the ε-amino group of Lys and with an amino group present in the substituent. In one embodiment, the further linker is Glu or Asp (e.g., which forms an amide bond with the ε-amino group of Lys and another amide bond with a carboxyl group present in the substituent), that is, the substituent is a Nε-acylated lysine residue.

In some embodiments, the anti-TM4SF1 antibody or an antigen binding fragment thereof as described herein and an oligonucleotide (e.g., a nucleic acid molecule, such as an RNA molecule or a DNA molecule) can be conjugated using various approaches, such as a genetic conjugation, an enzymatic conjugation, a chemical conjugation, or any combination thereof.

In some embodiments, the RNA molecules within the ADCs may be conjugated to the anti-TM4SF1 antibody or an antigen binding fragment thereof using an enzymatic site-specific conjugation method which involves the use of a mammalian or bacterial transglutaminase enzyme. Microbial transglutaminases (mTGs) are versatile tools in modern research and biotechnology. The availability of large quantities of relatively pure enzymes, ease of use, and lack of regulation by calcium and guanosine-5'-triphosphate (GTP) has propelled mTG to be the main cross-linking enzyme used in both the food industry and biotechnology. Currently, mTGs are used in many applications to attach proteins and peptides to small molecules, polymers, surfaces, DNA, as well as to other proteins. See, e.g., Pavel Strp, Veracity of microbial transglutaminase, Bioconjugate Chem. 25, 5, 855-862).

In some embodiments, the RNA molecules within the conjugates may be conjugated to the anti-TM4SF1 antibody or an antigen binding fragment thereof by way of a linker with direct covalent or non-covalent interactions. Linkers can be amino acid or peptide based linkers, or chemical linking agents, such as homobifunctional and heterobifunctional cross-linkers, which are available from many commercial sources. Regions available for cross-linking may be found on the anti-TM4SF1 antibody or an antigen binding fragment thereof of the disclosure. The linker may comprise a flexible arm, e.g., 2, 3, 4, 5, 6, 7, 8, 9, 10, 11, 12, 13, 14, or 15 carbon atoms. Exemplary linkers include cleavable, non-cleavable, covalent, or non-covalent linkers, or any combinations thereof. The cleavable linker, in some embodiments, comprises an acid-labile linker, a protease-sensitive linker, a photo-labile linker, or a disulfide-containing linker. In some embodiments, the linker comprises a cysteine linker or a non-cysteine linker, such as a lysine linker. In some embodiments, the anti-TM4SF1 antibody or an antigen binding fragment thereof comprises an unnatural amino acid, wherein the antibody or antibody fragment and the oligonucleotide are linked/conjugated via the unnatural amino acid.

In some embodiments, the anti-TM4SF1 antibody or an antigen binding fragment thereof comprises a natural amino acid, wherein the antibody or antibody fragment and the oligonucleotide are linked/conjugated via the natural amino acid. The unnatural amino acid may be inserted between two naturally occurring amino acids in the antibody or antibody fragment. The one or more unnatural amino acids may replace one or more naturally occurring amino acids in the antibody or antibody fragment. The one or more unnatural amino acids may be incorporated at the N terminus of the antibody or antibody fragment. The one or more unnatural amino acids may be incorporated at the C terminus of the antibody or antibody fragment. The unnatural amino acid may be incorporated distal to the binding region of antibody or antibody fragment. The unnatural amino acid may be incorporated near the binding region of the antibody or antibody fragment. The unnatural amino acid may be incorporated in the binding region of the antibody or antibody fragment.

The one or more unnatural amino acids may be encoded by a codon that does not code for one of the twenty natural amino acids. The one or more unnatural amino acids may be encoded by a nonsense codon (stop codon). The stop codon may be an amber codon. The amber codon may comprise a UAG sequence. The stop codon may be an ochre codon. The ochre codon may comprise a UAA sequence. The stop codon may be an opal or umber codon. The opal or umber codon may comprise a UGA sequence. The one or more unnatural amino acids may be encoded by a four-base codon.

The one or more unnatural amino acids may be p-acetylphenylalanine (pAcF or pAcPhe). The one or more unnatural amino acids may be selenocysteine. The one or more unnatural amino acids may be p-fluorophenylalanine (pFPhe). The one or more unnatural amino acids may be selected from the group comprising p-azidophenylalanine (pAzF),p-azidomethylphenylalanine(pAzCH2F), p-benzoylphenylalanine (pBpF), p-propargyloxyphenylalanine (pPrF), p-iodophenylalanine (pIF), p-cyanophenylalanine (pCNF), p-carboxylmethylphenylalanine (pCmF), 3-(2-naphthyl)alanine (NapA), p-boronophenylalanine (pBoF), o-nitrophenylalanine (oNiF), (8-hydroxyquinolin-3-yl)alanine (HQA), selenocysteine, and (2,2'-bipyridin-5-yl)alanine (BipyA).). The one or more unnatural amino acids may be 4-(6-methyl-s-tetrazin-3-yl)aminopheynlalanine.

The one or more unnatural amino acids may be β-amino acids (β3 and β2), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, N-methyl amino acids, or a combination thereof.

Additional examples of unnatural amino acids include, but are not limited to, 1) various substituted tyrosine and phenylalanine analogues such as O-methyl-L-tyrosine, p-amino-L-phenylalanine, 3-nitro-L-tyrosine, p-nitro-L-phenylalanine, m-methoxy-L-phenylalanine and p-isopropyl-L-phenylalanine; 2) amino acids with aryl azide and benzophenone groups that may be photo-cross-linked; 3) amino acids that have unique chemical reactivity including acetyl-L-phenylalanine and m-acetyl-L-phenylalanine, O-allyl-L-tyrosine, O-(2-propynyl)-L-tyrosine, p-ethylthiocarbonyl-L-phenylalanine and p-(3-oxobutanoyl)-L-phenylalanine; 4) heavy-atom-containing amino acids for phasing in X-ray crystallography including p-iodo and p-bromo-L-phenylalanine; 5) the redox-active amino acid dihydroxy-L-phenylalanine; 6) glycosylated amino acids including b-N-acetylglucosamine-O-serine and a-N-acetylgalactosamine-O-threonine; 7) fluorescent amino acids with naphthyl, dansyl, and 7-aminocoumarin side chains; 8) photocleavable and photoisomerizable amino acids with azobenzene and nitrobenzyl Cys, Ser, and Tyr side chains; 9) the phosphotyrosine mimetic p-carboxymethyl-L-phenylalanine; 10) the glutamine homologue homoglutamine; and 11) 2-aminooctanoic acid. The unnatural amino acid may be modified to incorporate a chemical group. The unnatural amino acid may be modified to incorporate a ketone group.

The one or more unnatural amino acids may comprise at least one oxime, carbonyl, dicarbonyl, hydroxylamine group or a combination thereof. The one or more unnatural amino acids may comprise at least one carbonyl, dicarbonyl, alkoxy-amine, hydrazine, acyclic alkene, acyclic alkyne, cyclooctyne, aryl/alkyl azide, norbomene, cyclopropene, trans-cyclooctene, or tetrazine functional group or a combination thereof.

The one or more unnatural amino acids may be incorporated into the antibody or antibody fragment by methods known in the art. Cell-based or cell-free systems may be used to alter the genetic sequence of antibody or antibody fragment, thereby producing the antibody or antibody fragment with one or more unnatural amino acids. Auxotrophic strains may be used in place of engineered tRNA and synthetase. The one or more unnatural amino acids may be produced through selective reaction of one or more natural amino acids. The selective reaction may be mediated by one or more enzymes. In one non-limiting example, the selective reaction of one or more cysteines with formylglycine generating enzyme (FGE) may produce one or more formylglycines as described in Rabuka et al., Nature Protocols 7:1052-1067 (2012).

The one or more unnatural amino acids may take part in a chemical reaction to form a linker. The chemical reaction to form the linker may be a bioorthogonal reaction. The chemical reaction to form the linker may be click chemistry.

Additional unnatural amino acids are disclosed in Liu et al. (Annu Rev Biochem, 79:413-44, 2010), Wang et al. (Angew Chem Int Ed, 44:34-66, 2005) and PCT application numbers PCT/US2012/039472, PCT/US2012/039468, PCT/US2007/088009, PCT/US2009/058668, PCT/US2007/089142, PCT/US2007/088011, PCT/US2007/001485, PCT/US2006/049397, PCT/US2006/047822 and PCT/US2006/044682, all of which are incorporated by reference in their entireties.

The one or more unnatural amino acids may replace one or more amino acids in the antibody or antibody fragment. The one or more unnatural amino acids may replace any natural amino acid in the antibody or antibody fragment.

The one or more unnatural amino acids may be incorporated in a light chain of the antibody or antibody fragment. The one or more unnatural amino acids may be incorporated in a heavy chain of the antibody or antibody fragment. The one or more unnatural amino acids may be incorporated in a heavy chain and a light chain of antibody or antibody fragment. The one or more unnatural amino acids may replace an amino acid in the light chain of the antibody or antibody fragment. The one or more unnatural amino acids may replace an amino acid in a heavy chain of the antibody or antibody fragment. The one or more unnatural amino acids may replace an amino acid in a heavy chain and a light chain of the antibody or antibody fragment.

anti-TM4SF1 antibody or an antigen binding fragment thereof anti-TM4SF1 antibody or an antigen binding fragment thereof anti-TM4SF1 antibody or an antigen binding fragment thereof anti-TM4SF1 antibody or an antigen binding fragment thereof anti-TM4SF1 antibody or an antigen binding fragment thereof anti-TM4SF1 antibody or an antigen binding fragment thereof anti-TM4SF1 antibody or an antigen binding fragment thereof In some embodiments, the linker comprises a small molecule fragment, a spacer, a non-covalent linker, or a combination thereof. In some embodiments, the linker comprises one or more of small molecule fragments. In some embodiments, the linker comprises a spacer.

In some embodiments, a linker comprises one or more of reactive moieties. In some embodiments, a linker comprises a reactive moiety selected from a Michael acceptor moiety, a leaving group moiety, or a moiety capable of forming a covalent bond with the antibody fragment and/or the therapeutic agent.

In some embodiments, a small anti-TM4SF1 antibody or an antigen binding fragment thereof anti-TM4SF1 antibody or an antigen binding fragment thereof comprises a reactive moiety. In some embodiments, a small molecule fragment comprises a reactive moiety selected from a Michael acceptor moiety, a leaving group moiety, or a moiety capable of forming a covalent bond with the thiol group of a cysteine residue.

In some embodiments, the Michael acceptor moiety comprises an alkene or an alkyne moiety. In some embodiments, a small molecule fragment is obtained from a compound library. In some embodiments, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library.

In some embodiments, a small molecule fragment comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some embodiments, a small molecule fragment comprises an alkyne or an azide group. In some embodiments, a small molecule fragment comprises an alkyne group. In some embodiments, a small molecule fragment comprises an azide group.

In some embodiments, a small molecule fragment covalently interacts with a spacer. In some embodiments, the spacer comprises an amide moiety, an ester moiety, an ether moiety, substituted or unsubstituted C1-C6alkylene moiety, substituted or unsubstituted C1-C6haloalkylene moiety, substituted or unsubstituted C1-C6heteroalkylene moiety, substituted or unsubstituted C3-C8cycloalkylene moiety, substituted or unsubstituted C2-C7heterocycloalkylene moiety, substituted or unsubstituted arylene moiety, a substituted or unsubstituted heteroarylene moiety or any combination thereof.

In some embodiments, the linker comprises MC (6-maleimidocaproyl), MCC (a maleimidomethyl cyclohexane-1-carboxylate), MP (maleimidopropanoyl), val-cit (valine-citrulline), val-ala (valine-alanine), ala-phe (alanine-phenylalanine), PAB (p-aminobenzyloxycarbonyl), SPP (N-Succinimidyl 4-(2-pyridylthio) pentanoate), SMCC (N-Succinimidyl 4-(N-maleimidomethyl)cyclohexane-1 carboxylate), SIAB (N-Succinimidyl (4-iodo-acetyl)aminobenzoate. Further examples of linkers include: BS3 ([Bis (sulfosuccinimidyl)suberate]; BS3 is a homobifunctional N-hydroxysuccinimideester that targets accessible primary amines), NHS/EDC (N-hydroxysuccinimide and N-ethyl-(dimethylaminopropyl)carbodimide; NHS/EDC allows for the conjugation of primary amine groups with carboxyl groups), sulfo-EMCS ([N-e-Maleimidocaproic acid]hydrazide; sulfo-EMCS are heterobifunctional reactive groups (maleimide and NHS-ester) that are reactive toward sulfhydryl and amino groups), hydrazide (most proteins contain exposed carbohydrates and hydrazide is a useful reagent for linking carboxyl groups to primary amines), and SATA (N-succinimidyl-S-acetylthioacetate; SATA is reactive towards amines and adds protected sulfhydryls groups). To form covalent bonds, a chemically reactive group a wide variety of active carboxyl groups (e.g., esters) where the hydroxyl moiety is physiologically acceptable at the levels required to modify the peptide. Particular agents include N-hydroxysuccinimide (NHS), N-hydroxy-sulfosuccinimide (sulfo-NHS), maleimide-benzoyl-succinimide (MBS), gamma-maleimido-butyryloxy succinimide ester (GMBS), maleimido propionic acid (MPA) maleimido hexanoic acid (MHA), and maleimido undecanoic acid (MUA). Primary amines are the principal targets for NHS esters. Accessible a-amino groups present on the N-termini of proteins and the ε-amine of lysine react with NHS esters. An amide bond is formed when the NHS ester conjugation reaction reacts with primary amines releasing N-hydroxysuccinimide. These succinimide containing reactive groups are herein referred to as succinimidyl groups. In certain embodiments of the disclosure, the functional group on the protein will be a thiol group and the chemically reactive group will be a maleimido-containing group such as gamma-maleimide-butrylamide (GMBA or MPA). Such maleimide containing groups are referred to herein as maleido groups. The maleimido group is most selective for sulfhydryl groups on peptides when the pH of the reaction mixture is 6.5-7.4. At pH 7.0, the rate of reaction of maleimido groups with sulfhydryls (e.g., thiol groups on proteins such as serum albumin or IgG) is 1000-fold faster than with amines. Thus, a stable thioether linkage between the maleimido group and the sulfhydryl can be formed.

In other embodiments, the linker includes at least one amino acid (e.g., a peptide of at least 2, 3, 4, 5, 6, 7, 10, 15, 20, 25, 40, or 50 amino acids). In certain embodiments, the linker is a single amino acid (e.g., any naturally occurring amino acid such as Cys or Lys). In other embodiments, a glycine-rich peptide such as a peptide can be used. In some cases, the linker can be a single amino acid (e.g., any amino acid, such as Gly or Cys or Lys). Examples of suitable linkers are succinic acid, Lys, Glu, and Asp, or a dipeptide such as Gly-Lys. When the linker is succinic acid, one carboxyl group thereof may form an amide bond with an amino group of the amino acid residue, and the other carboxyl group thereof may, for example, form an amide bond with an amino group of the peptide or substituent. When the linker is Lys, Glu, or Asp, the carboxyl group thereof may form an amide bond with an amino group of the amino acid residue, and the amino group thereof may, for example, form an amide bond with a carboxyl group of the substituent. When Lys is used as the linker, a further linker may be inserted between the ε-amino group of Lys and the substituent. In one particular embodiment, the further linker is succinic acid which, e.g., forms an amide bond with the ε-amino group of Lys and with an amino group present in the substituent. In one embodiment, the further linker is Glu or Asp (e.g., which forms an amide bond with the ε-amino group of Lys and another amide bond with a carboxyl group present in the substituent), that is, the substituent is a NE-acylated lysine residue. In some embodiments, a linker comprises a single-amino acid peptide consisting of a lysine. In some embodiments, a linker comprises a LysLys dipeptide. In some embodiments, a linker comprises a *Lys and/or Lys* dipeptide. In some embodiments, a linker comprises a LysLys* and/or*LysLys, Lys*Lys tripeptide. In some embodiments, a linker comprises a LysLysLys tripeptide.

In some embodiments, the conjugation of anti-TM4SF1 antibody or an antigen binding fragment thereof and the RNA molecules is carried out in a manner to produce a ring threaded molecule. In some embodiments, the spacer additionally comprises a macrocycle. In some embodiments, the macrocycle comprises a non-covalent macrocycle. In some embodiments, the macrocycle comprises a covalent macrocycle.

In some embodiments, the macrocycle comprises cucurbit[X]uril, wherein X is 5, 6, 7, 8, 9, 10, 11, 12, 13, 14, 15, 16, 17, 18, 19, or 20. In some embodiments, the macrocycle comprises cucurbit[X]uril, wherein X is 5, 6, 7, 8, 9, 10, 11, 12, 13, 14, or 15. In some embodiments, the macrocycle comprises cucurbit[X]uril, wherein X is 5, 6, 7, or 8. In some embodiments, the cucurbit[X]uril has a structure represented by:

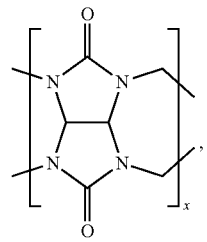

wherein x is 5, 6, 7, or 8.

In some embodiments, x is 5. In some embodiments, x is 6. In some embodiments, x is 7. In some embodiments, x is 8.

In some embodiments, the macrocycle comprises cucurbit[6]uril (CB6). In some embodiments, the macrocycle comprises cucurbit[7]uril (CB7). In some embodiments, the cucurbit[7]uril has a structure represented by:

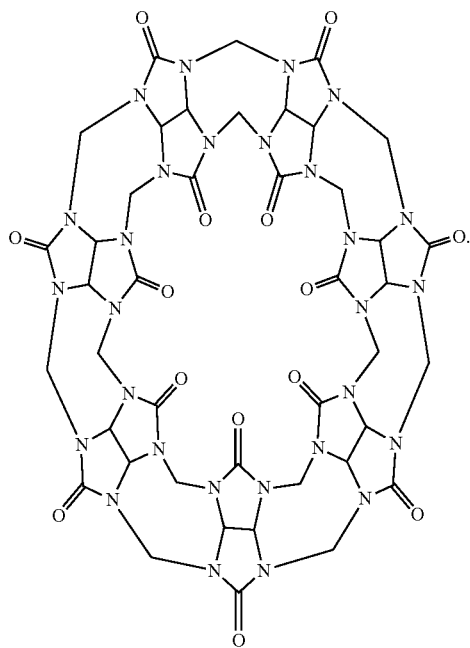

In some embodiments, the macrocycle comprises a cyclodextrin (CD). In some embodiments, the cyclodextrin has a structure represented by:

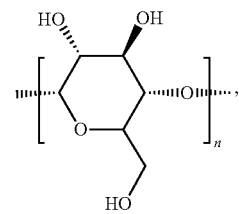

wherein n is 5, 6, 7, or 8.

In some embodiments, the macrocycle comprises a beta-cyclodextrin (n=7). In some embodiments, macrocycle comprises a gamma-cyclodextrin (n=8). In some embodiments, the beta-cyclodextrin has a structure represented by:

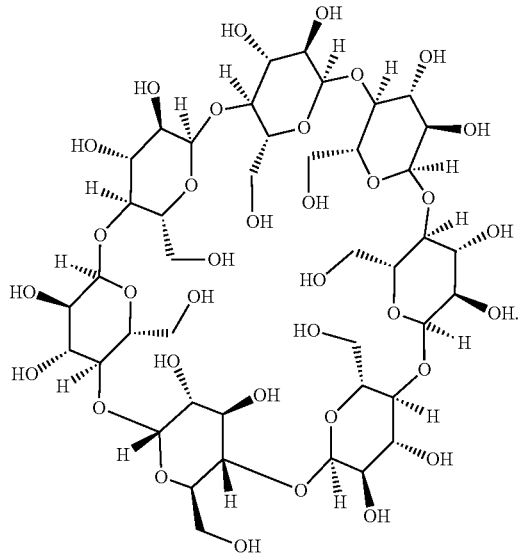

In some embodiments, the macrocycle comprises a polypeptide. In some embodiments, the polypeptide has a structure represented by:

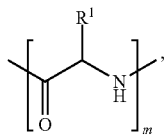

wherein $R^1$ is H, D, F, —CN, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_8$cycloalkyl, substituted or unsubstituted aryl, and substituted or unsubstituted heteroaryl; and m is 5, 6, 7, or 8.

In some embodiments, the macrocycle comprises a cycloglycine. In some embodiments, the macrocycle comprises cyclo(glycylglycylglycylglycylglycylglycylglycyl) (SEQ ID NO: 160). In some embodiments, the macrocycle comprises cyclo(glycylglycylglycylglycylglycylglycylglycylglycyl) (SEQ ID NO: 161). In some embodiments, the cyclo(glycylglycylglycylglycylglycylglycylglycylglycyl) (SEQ ID NO: 161) has a structure represented by:

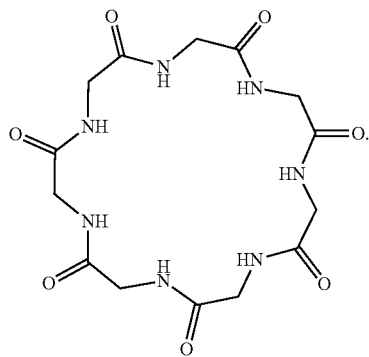 [SMILES: O=C1CNC(=O)CNC(=O)CNC(=O)CNC(=O)CNC(=O)CNC(=O)CN1]

In some embodiments, the macrocycle comprises a crown ether. In some embodiments, the crown ether is a 15-crown-5, 18-crown-6, dibenzo-18-crown-6, or diaza-18-crown-6.

In some embodiments, the macrocycle comprises a cycloalkane. In some embodiments, the cycloalkane is a cyclopentadecane, cyclohexadecane, cycloheptadecane, or cyclooctadecane.

In some embodiments, the macrocycle comprises cyclobis(paraquat-p-phenylene) ($CBPQT^{4+}$). In some embodiments, the cyclobis(paraquat-p-phenylene) ($CBPQT^{4+}$) has a structure represented by:

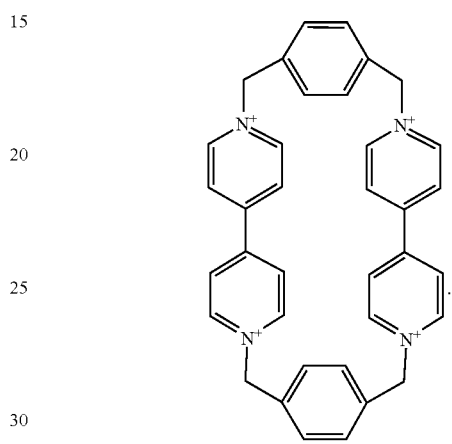

In some embodiments, a linker comprises quaternary nitrogen. In some embodiments, the linker is:

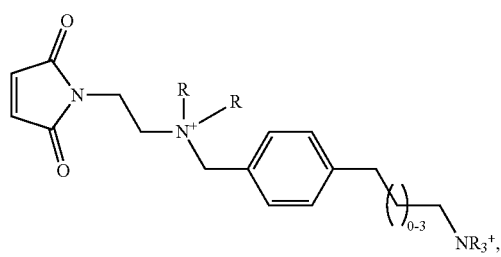

wherein each R is independently H or C1-C6 alkyl. In some embodiments, the linker is:

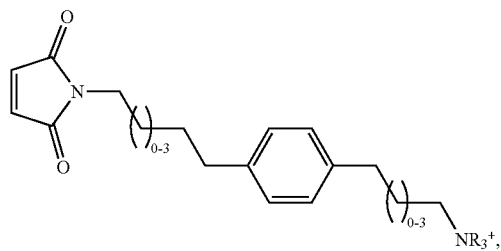

wherein each R is independently H or C1-C6 alkyl. In some embodiments, the linker is:
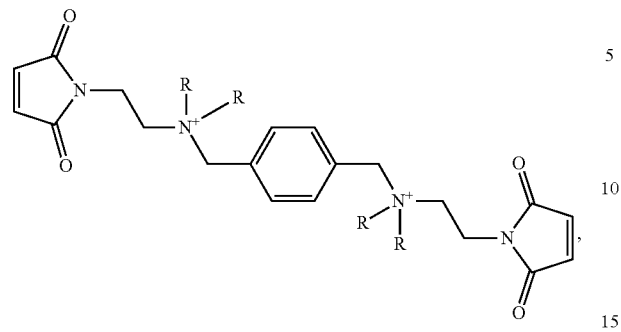
wherein each R is independently H or C1-C6 alkyl.
In some embodiments, the linker is:
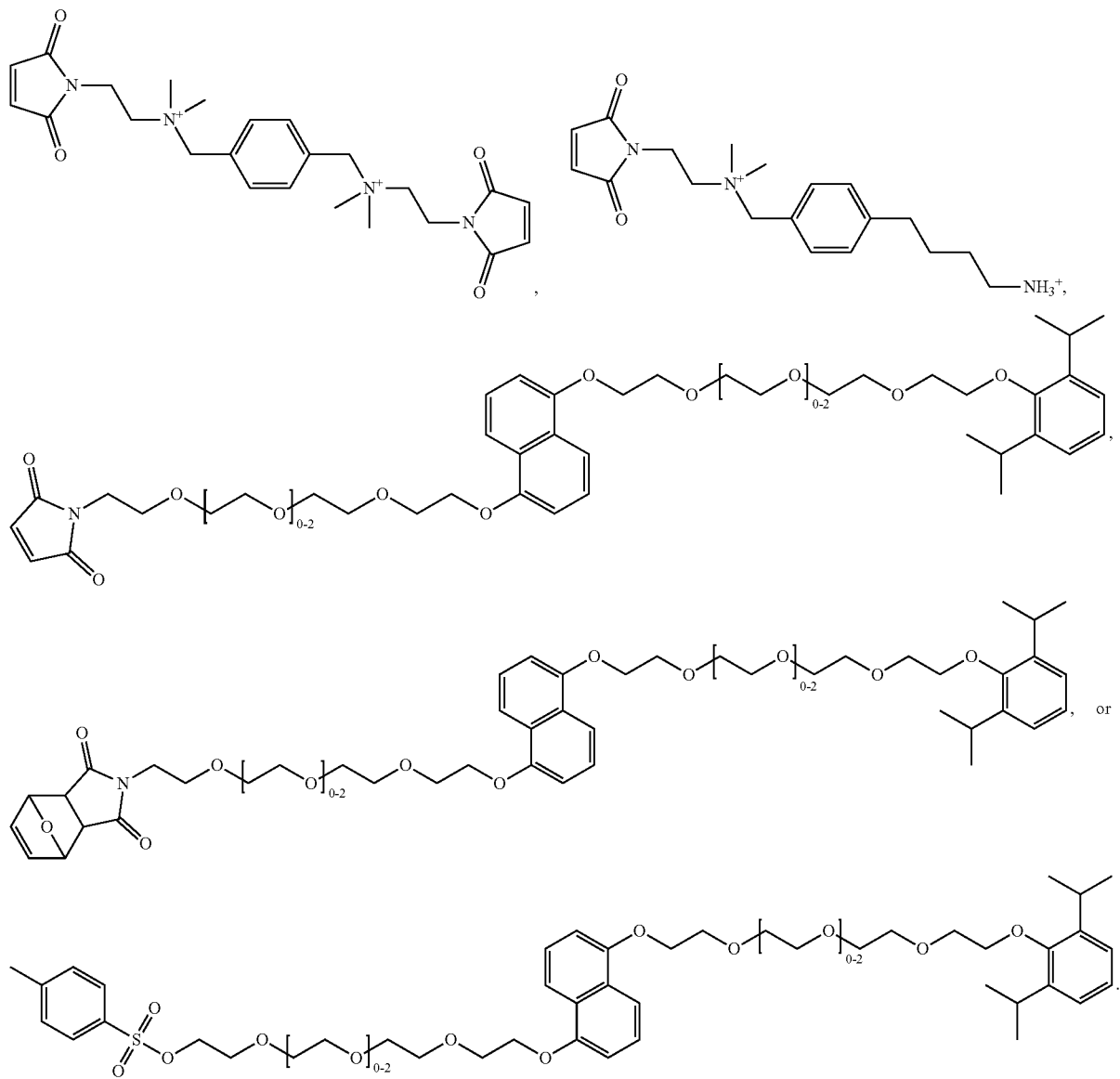

In some embodiments, the conjugates are produced by linking a first portion of the linker to the anti-TM4SF1 antibody or an antigen binding fragment thereof and a second portion of the linker to the oligonucleotide. Conjugating the linker to anti-TM4SF1 antibody or an antigen binding fragment thereof or the therapeutic molecule may comprise production of an ionic bond, a covalent bond, a non-covalent bond or a combination thereof between the linker and the antibody, antigen binding fragment thereof or therapeutic agent. Conjugating the linker to the anti-TM4SF1 antibody or an antigen binding fragment thereof or the oligonucleotide may, in some cases, be performed as described in Roberts et al., Advanced Drug Delivery Reviews 54:459-476 (2002). The linker may be selected from a bifunctional linker, a cleavable linker, a non-cleavable linker, an ethylene glycol linker, a bifunctional ethylene glycol linker, a flexible linker, or an inflexible linker. The linker may comprise a chemical group selected from a cyclooctyne, a cyclopropene, an aryl/alkyl azide, a trans-cyclooctene, a norborene, and a tetrazine. In some embodiments, a terminus of the linker comprises an alkoxy-amine. In some embodiments, a terminus of the linker comprises an azide or cyclooctyne group. In some embodiments, the antibody or antibody fragment or therapeutic agent may be coupled to the linker by a chemical group selected from a cyclooctyne, cyclopropene, aryl/alkyl azide, trans-cyclooctene, norborene, and tetrazine. Linking anti-TM4SF1 antibody or an antigen binding fragment thereof or an oligonucleotide to the linker may comprise conducting one or more copper-free reactions. Linking the antibody or antibody fragment or an oligonucleotide to the linker may comprise conducting one or more copper-containing reactions. Linking the anti-TM4SF1 antibody or an antigen binding fragment thereof or an oligonucleotide to the linker may comprise one or more cycloadditions. Linking anti-TM4SF1 antibody or an antigen binding fragment thereof or an oligonucleotide to the linker may comprise one or more Huisgen-cycloadditions. Linking the anti-TM4SF1 antibody or an antigen binding fragment thereof or an oligonucleotide to the linker may comprise one or more Diels Alder reactions. Linking anti-TM4SF1 antibody or an antigen binding fragment thereof or an oligonucleotide to the linker may comprise one or more Hetero Diels Alder reaction. In some embodiments, a terminus of the linker comprises a leaving group.

In some embodiments, a first portion of the linker covalently interacts with a cysteine containing anti-TM4SF1 antibody or an antigen binding fragment thereof, as described herein. In some embodiments, a first portion of the linker covalently interacts with a cysteine containing TM4SF1 antibody or an antigen binding fragment thereof, as described herein. In some embodiments, an oligonucleotide described herein covalently interacts with a second portion of the linker. In some embodiments, an oligonucleotide described herein non-covalently interacts with a second portion of the linker.

In some embodiments, a viral protein p19 based siRNA carrier is contemplated, which protein has been shown to have a high affinity for siRNA. See, e.g., Yang et al. Cytosolic delivery of siRNA by ultra-high affinity dsRNA binding proteins, Nucleic Acids Res. 2017 Jul. 27; 45(13): 7602-7614. In some examples, a p19-siRNA complex is generated and fused to an anti-TM4SF1 antibody or antigen-binding fragment thereof. In additional embodiments, a statistical or random conjugation methods via Cys, Lys, or Arginine residues within the antibody or antigen binding fragment thereof.

Synthesis of an ADC Comprising an Anti-TM4SF1 Antibody or an Antigen Binding Fragment Thereof and an siRNA In one embodiment, a conjugate comprising an anti-TM4SF1 antibody or an antigen binding fragment thereof and an oligonucleotide is developed by covalent conjugation of the antibody or antigen binding fragment and the RNA molecule (e.g., siRNA). As a first step of such an exemplary process, an engineered anti-TM4SF1 antibody is generated, in which a cysteine residue had been introduced in the heavy chain (thereby producing an anti-TM4SF1 HC THIOMAB). The anti-TM4SF1 thiomab, in some examples, provides at least two discrete positions for coupling with an RNA molecule, such as with an siRNA. For instance, one siRNA molecule can be coupled to each heavy chain of the anti-TM4SF1 thiomab. In a separate or subsequent step in the conjugation process, a chemically stabilized siRNA (synthesized, e.g., using siSTABLE chemistry) modified with a 3'-amine for coupling to the passenger strand with a sequence targeting peptidlyprolyl isomerase B (PPIB, cyclophilin B) is generated. The conjugation, in some embodiments, further involves a reducible N-succinimidyl-4-(2-pyridyldithio)butyrate (SPDB) or a non-reducible succinimidyl-4-[N-maleimidomethyl]cyclohexane-1-carboxylate) (SMCC) NHS (N-hydroxysuccinimide) linkers. In some embodiments, using the anti-TM4SF1 thiomab, an exemplary conjugate molecule according to this disclosure is generated in a multi step process involving at leats two primary steps: (i) reaction of an amine-tagged siRNA with an NHS-linker to form a thiol-reactive siRNA-linker adduct, and (ii) reacting the adduct with thiol groups on the THIOMAB to covalently link the siRNA via a thio-ester bond. The exemplary ADC is subsequently purified using anion exchange chromatography to remove free siRNA and then by size-exclusion chromatography to remove un-coupled antibody. Further techniques, such as gel electrophoresis and electrospray TOF mass spectrometry can then be used to assess the yield of the exemplary ADC, as well characteristics such as monomeric conjugates with one or two linked siRNAs per antibody. Additional methods that can be employed for the conjugation involve the use or chemical or peptide based linkers, chemical or enzymatic conjugation methods (e.g., using mammalian or bacterial transglutaminase), or any combinations thereof. Any of the linkers and/or methods described above can be used to couple the anti-TM4SF1 antibody or an antigen binding fragment thereof and the oligonucleotides of the conjugate.

Using appropriate coupling methods, it is possible to generate ADCs of this disclosure, which comprise, for example, an anti-TM4SF1 antibody or an antigen binding fragment thereof to oligonucleotide ratio of about 1:2, 1:3, 1:4, 1:5, 1:6, 1:7, 1:8, 1:9, or 1:10, or higher. In some embodiments, the ADC comprises an anti-TM4SF1 antibody or an antigen binding fragment thereof to oligonucleotide ratio of 1:1. This can be achieved, for example, by using an antigen binding fragment or a portion of an antibody, e.g., a half-antibody, Fab, or other fragments that comprise a THIOMAB engineered cysteine. In some examples, the ADC can be designed to comprise 1:1 ratios of an anti-TM4SF1 antibody or an antigen binding fragment thereof to oligonucleotide using a whole antibody which is conjugated to an oligonucleotide by a conjugation method that utilize a multimetallic protein (e.g., a hexa-rhodium metallopeptide) to enable modification of proteins, on the basis of molecular recognition. For example, the anti-TM4SF1 antibody or an antigen binding fragment thereof and the oligonucleotide can be conjugated using a site-specific antibody functionalization, based on molecular recognition of the Fc domain constant region of the antibody by the multimetallic protein. In some embodiments, the multimetallic protein comprises three rhodium complexes attached to specific sites of a protein that binds to the Fc domain of an antibody. Upon binding, the multimetallic protein can catalyze site-specific conjugation of the oligonucleotide to the antibody. An advantage of using the multimetallic protein can be that the antibody is minimally disrupted, such as by avoiding engineering residues within the antibody, during the conjugation.

VI. Polynucleotides

Also provided, in some embodiments, are polynucleotides encoding an anti-TM4SF1 antibody or an antigen binding fragment thereof. In some embodiments, the polynucleotide molecules are provided as a DNA construct. In other embodiments, the polynucleotide molecules are provided as a messenger RNA transcript.

In some examples, an anti-TM4SF1 antibody of the present disclosure comprises a heavy chain variable domain encoded by a nucleic acid sequence as set forth in any one of SEQ ID NOs: 4, 16, 28, 40, 52, 64, or 76. In some examples, an anti-TM4SF1 antibody of the present disclosure comprises a light chain variable domain encoded by a nucleic acid sequence as set forth in any one of SEQ ID NOs: 10, 22, 34, 46, 58, 70, or 82.

In some embodiments are provided nucleic acid sequences that are codon optimized for expression in a host cell, e.g., a bacterium, such as E. coli, or a eukaryotic cell, such as a CHO cell. In some examples, the nucleic acid sequences are codon optimized for expression in CHO cells. In some examples, an anti-TM4SF1 antibody of the present disclosure comprises a heavy chain variable domain encoded by a codon optimized nucleic acid sequence as set forth in any one of SEQ ID NOs: 5, 17, 29, 41, 53, 65, or 77. In some examples, an anti-TM4SF1 antibody of the present disclosure comprises a light chain variable domain encoded by a codon optimized nucleic acid sequence as set forth in any one of SEQ ID NOs: 11, 23, 35, 47, 59, 71, or 83. In certain instances, the nucleic acid sequence of any one of SEQ ID NOs: 5, 17, 29, 41, 53, 65, or 77 is a nucleic acid sequence codon optimized for expression in CHO cell. In certain instances, the nucleic acid sequence of any one of SEQ ID NOs: 11, 23, 35, 47, 59, 71, or 83 is a nucleic acid sequence codon optimized for expression in CHO cell.

The polynucleotide molecules are constructed by known methods such as by incorporating the genes encoding the binding proteins into a genetic construct linked to a suitable promoter, and optionally a suitable transcription terminator, and expressing it in bacteria or other appropriate expression system such as, for example CHO cells. Depending on the vector system and host utilized, any number of suitable transcription and translation elements, including constitutive and inducible promoters, may be used. The promoter is selected such that it drives the expression of the polynucleotide in the respective host cell.

In some embodiments, a polynucleotide as described herein is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described TM4SF1 binding protein. Examples of expression vectors for expression in E. coli are pSKK (Le Gall et al., J Immunol Methods. (2004) 285(1): 111-27) or pcDNA5 (Invitrogen) for expression in mammalian cells.

Thus, the TM4SF1 binding proteins as described herein, in some embodiments, are produced by introducing a vector encoding the protein as described above into a host cell and culturing said host cell under conditions whereby the protein domains are expressed, may be isolated and, optionally, further purified.

VII. Methods of Treatment

The disclosure further provides a method for inhibiting cell-cell interactions that are endothelial cell (EC) specific, for example, but not limited to EC-EC, EC-mesenchymal stem cell, EC-fibroblast, EC-smooth muscle cell, EC-tumor cell, EC-leukocyte, EC-adipose cell and EC-neuronal cell interactions. In certain embodiments, the ADCs containing the anti-TM4SF1 antibodies and fragments of the present disclosure, can be used to treat any human disease or disorder with a pathology that is characterized by abnormal EC-cell interactions. In certain embodiments, the EC-cell interaction is an EC-leukocyte interaction, where inhibition of the EC-leukocyte interaction is used to prevent inflammation.

In other embodiments, the disclosure features a method of treating or preventing a disease or disorder in a subject, wherein the disease or disorder is characterized by abnormal endothelial cell (EC)-cell interactions, said method comprising administering the antibody, or antigen-binding fragment thereof, as described herein. In certain embodiments, the EC-cell interactions include one or more of EC-mesenchymal stem cell, EC-fibroblast, EC-smooth muscle cell, EC-tumor cell, EC-leukocyte, EC-adipose cell and EC-neuronal cell interactions. In exemplary embodiments, the disease is an inflammatory disease or disorder, and the antibodies and fragments of the disclosure are used to inhibit EC-leukocyte interactions. In another exemplary embodiment, the disease or disorder is selected from an inflammatory disease or cancer. The adhesion of leukocytes to vascular endothelium is a hallmark of the inflammatory process. Accordingly, in one embodiment, an ADC containing an anti-TM4SF1 antibody, or an antigen binding fragment thereof, of the present disclosure is used to treat an inflammatory disease in which inhibiting leukocyte attachment to endothelial cells, or leukocyte transmigration across the endothelium is helpful for treatment (see, e.g. Rychly et al., Curr Pharm Des. 2006; 12(29):3799-806, incorporated by reference in its entirety herein). Examples include, but are not limited to, sepsis, inflammatory bowel disease, psoriasis or multiple sclerosis.

Each year approximately half a million patients die from cancer in the United States alone. Tumor metastasis is responsible for ~90% of these deaths. No therapy that blocks metastasis is known. The present disclosure provides antibodies, and antigen-binding fragments thereof, that can treat cancer and inhibit metastatic cells based on immunoblockade of tumor cell (TC)-endothelial cell (EC) interactions mediated by a novel target, TM4SF1.

As described above, TM4SF1 is a small, tetraspanin-like, cell surface glycoprotein originally discovered as a TC antigen with roles in TC invasion and metastasis. TM4SF1 is selectively expressed by TCs and ECs. TM4SF1 is expressed at low levels on the vascular ECs supplying normal tissues in both mice and humans. It has been shown that TM4SF1 is expressed at ~10-20 fold higher levels on the vascular ECs lining the blood vessels supplying many human cancers, and at equivalent high levels on cultured ECs. TM4SF1-enriched microdomains (TMED) recruit cell surface proteins like integrins to assist the formation of nanopodia, thin membrane channels that extend from the cell surface and mediate cell-cell interactions. Thus, in certain instances, ADCs containing anti-TM4SF1 antibodies and fragments described herein interfere with nanopodia-mediated interactions and inhibit TC interactions with EC that are necessary for TC extravasation.

ADCs of this disclosure may be formulated for treating a subject (e.g., a human) having a disorder associated with pathological angiogenesis (e.g., cancer, such as breast cancer, ovarian cancer, renal cancer, colorectal cancer, liver cancer, gastric cancer, and lung cancer; obesity; macular degeneration; diabetic retinopathy; psoriasis; rheumatoid arthritis; cellular immunity; and rosacea.

TM4SF1 is highly expressed on the surface of most epithelial TCs, and, is also highly expressed on the EC lining tumor blood vessels and on cultured EC. It is expressed at ~10-20 fold lower levels on the surface of normal vascular ECs. In mouse models, tumor metastasis to lungs is related to TM4SF1 expression on both ECs and TCs. Metastasis requires initial attachment of TC to vascular EC and their subsequent migration across ECs to enter the lung or other metastatic sites. The examples below show that, in some instances, the anti-TM4SF1 antibodies of the present disclosure interfere with TC-EC interactions in culture and can also inhibit tumor metastasis in vivo.

Thus, the ADCs of the present disclosure can be used to block one or both of the earliest steps in metastasis, namely, TC attachment to vascular ECs and/or transmigration of TCs across ECs, and thereby prevent or substantially reduce the number of metastases in at risk cancer patients.

The present disclosure further provides a method for preventing metastasis. Human tumors typically shed TCs into the blood and lymphatics at early stages of growth; hence, early treatment of primary tumors provides no guarantee that metastasis has not already taken place. Thus, immunoblockade of TM4SF1 can be used to treat or prevent hematogenous metastases or to treat or prevent lymphatic metastases.

The methods of this disclosure are, in some embodiments, directed to inhibiting metastatic cells in a subject. In one embodiment, the subject has a cancer, e.g., a cancer that is associated with metastasis or a cancer that has already metastasized. In other embodiments, the subject was already treated for cancer and is in remission or partial remission, wherein the benefits of administering ADCs containing the anti-TM4SF1 antibodies or fragments described herein are that they work to prevent metastasis and maintain remission or partial remission.

In certain embodiments, the disclosure provides a method of treating a person having a greater risk of developing metastasis, wherein administration of the ADCs containing the anti-TM4SF1 antibodies and fragments described herein can be used to inhibit or delay onset of metastasis.

Included in the disclosure is a method of blocking tumor metastasis, particularly metastasis to the lung, by administering an anti-TM4SF1 antibody to a subject in need thereof. In some examples, the anti-TM4SF1 antibody is a human anti-TM4SF1 antibody, also referred to herein as anti-hTM4SF1. In certain embodiments, the methods can include administration of an effective amount of an ADC containing an anti-hTM4SF1 antibody to a subject in need thereof, wherein the effective amount of the antibody prevents tumor cell (TC) attachment to and migration across vascular endothelial cells (ECs).

In certain embodiments, an ADC containing an anti-TM4SF1 antibody is administered to a subject having cancer or at risk of having metastasis such that the dose amount and frequency maintains long term TM4SF1 immunoblockade. The dosing regimen will maximally inhibit TM4SF1-mediated metastasis by administering an ADC containing an anti-TM4SF1 antibody to a subject in an amount sufficient to saturate TM4SF1 expressed on normal vascular ECs of the subject.

In certain embodiments, the effective amount of an ADC containing an anti-TM4SF1 antibody, or an antigen binding fragment thereof, that is administered is an amount sufficient to, at one week, achieve circulating antibody concentrations >1 µg/ml.

In certain embodiments, the effective amount of an ADC containing an anti-TM4SF1 antibody, or an antigen binding fragment thereof that is administered is an amount sufficient to maintain serum concentrations of the antibody at or above 1 µg/ml continuously for about 1 month.

In one embodiment, the disclosure provides a method of treating or preventing metastasis in a human subject comprising administering to the subject an effective amount of an ADC containing an anti-TM4SF1 antibody, or an antigen binding fragment thereof, wherein the effective amount of the antibody, or antigen binding fragment thereof, comprises 1 to 80 mg/kg of the amount of the antibody, or antigen binding fragment thereof.

The mode of administration for therapeutic use of the ADCs of the disclosure may be any suitable route that delivers the antibody to the host, such as parenteral administration, e.g., intradermal, intramuscular, intraperitoneal, intravenous or subcutaneous, pulmonary, transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

In some embodiments, the ADCs of the disclosure may be administered to a subject by any suitable route, for example parentally by intravenous (i.v.) infusion or bolus injection, intramuscularly or subcutaneously or intraperitoneally. i.v. infusion may be given over for example 15, 30, 60, 90, 120, 180, or 240 minutes, or from 1, 2, 3, 4, 5, 6, 7, 8, 9, 10, 11 or 12 hours. The dose given to a subject in some embodiments is about 0.005 mg to about 100 mg/kg, e.g., about 0.05 mg to about 30 mg/kg or about 5 mg to about 25 mg/kg, or about 4 mg/kg, about 8 mg/kg, about 16 mg/kg or about 24 mg/kg, or for example about 0.1, 0.2, 0.3, 0.4, 0.5, 0.6, 0.7, 0.8, 0.9, 1, 2, 3, 4, 5, 6, 7, 8, 9 or 10 mg/kg. In certain embodiments, the dose given to a subject is, for example about 15, 16, 17, 18, 19, 20, 21, 22, 23, 24, 25, 30, 40, 50, 60, 70, 80, 90 or 100 mg/kg. In some instances, the dose of the antibodies of the disclosure given to a subject may be about 0.1 mg/kg to 10 mg/kg via intravenous administration.

In some instances, the dose of the antibodies of the disclosure given to a subject is about 0.1 mg/kg to 10 mg/kg via subcutaneous administration. In some instances, the dose of the antibodies of the disclosure given to a subject is about 0.1 mg/kg via intravenous administration. In some instances, the dose of the antibodies of the disclosure given to a subject is about 0.1 mg/kg via subcutaneous administration. In some embodiments, the dose of the antibodies of the disclosure given to a subject is about 0.3 mg/kg via intravenous administration. In some examples, the dose of the antibodies of the disclosure given to a subject is about 0.3 mg/kg via subcutaneous administration. In some examples, the dose of the antibodies of the disclosure given to a subject is about 1.0 mg/kg via intravenous administration. In some examples, the dose of the antibodies of the disclosure given to a subject is about 1.0 mg/kg via subcutaneous administration. In some examples, the dose of the antibodies of the disclosure given to a subject is about 3.0 mg/kg via intravenous administration. In some examples, the dose of the antibodies of the disclosure given to a subject is about 3.0 mg/kg via subcutaneous administration. In some examples, the dose of the antibodies of the disclosure given to a subject may be about 10.0 mg/kg via intravenous administration. In some examples, the dose of the antibodies of the disclosure given to a subject is about 10.0 mg/kg via subcutaneous administration.

In certain embodiments, a fixed unit dose of the antibodies of the disclosure is given, for example, 50, 100, 200, 500 or 1000 mg, or the dose may be based on the patient's surface area, e.g., 500, 400, 300, 250, 200, or 100 mg/m$^2$. In some instances, between 1 and 8 doses, (e.g., 1, 2, 3, 4, 5, 6, 7 or 8) is administered to treat the patient, but 9, 10, 11, 12, 13, 14, 15, 16, 17, 18, 19, 20 or more doses are given.

The administration of the ADCs of the disclosure described herein, in some embodiments, is repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration is at the same dose or at a different dose. In some examples, the ADCs of the disclosure described herein is administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion. Alternatively, in some embodiments, the ADCs of the disclosure described herein are administered at between 0.1 mg/kg to about 10 mg/kg at weekly interval for 17 weeks. For example, in some cases the antibodies of the disclosure are provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof. In some embodiments, the antibodies of the disclosure described herein is administered prophylactically in order to reduce the risk of developing an inflammatory disease such as RA, psoriatic arthritis or psoriasis, delay the onset of the occurrence of an event in progression of the inflammatory disease such as RA, psoriatic arthritis or psoriasis. In some examples, the ADCs of the disclosure are lyophilized for storage and reconstituted in a suitable carrier prior to use. In some cases, the antibodies of the disclosure are supplied as a sterile, frozen liquid in a glass vial with stopper and aluminum seal with flip-off cap. In some examples, each vial migh contain ADC containing 3.3 mL of a 50 mg/mL solution of the antibody (including a 10% overfill) in a formulation of 10 mM histidine, 8.5% (w/v) sucrose, and 0.04% (w/v) Polysorbate 80 at pH 5.8. In some examples, the vials contain no preservatives and are for single use. Vials may be stored frozen and protected from light. To prepare for IV administration, the ADC formulations, in some examples, are filtered with a 0.22 micron filter before being diluted in sterile diluent. In some examples, diluted ADCs at volumes up to approximately 100 mL are administered by IV infusion over a period of at least 30 minutes using an in-line 0.22 micron filter. Alternatively, in some embodiments, the ADCs are administered as 1 or 2 subcutaneous injections containing about 50 mg/mL antibody in about 3.3 mL. The subcutaneous injection site may be, for example, within the abdominal area.

VIII. Pharmaceutical Compositions

The ADCs of this disclosure, can, in some embodiments, be included in compositions (e.g., pharmaceutical compositions). The pharmaceutical compositions of the disclosure may further include a pharmaceutically acceptable carrier, excipient, or diluent.

The term "pharmaceutical composition" as used herein refers to a composition containing a TM4SF1 binding protein described herein formulated with a pharmaceutically acceptable carrier, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gel cap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

The term "pharmaceutically acceptable carrier" as used herein refers to a carrier which is physiologically acceptable to a treated mammal (e.g., a human) while retaining the therapeutic properties of the protein with which it is administered. One exemplary pharmaceutically acceptable carrier is physiological saline. Other physiologically acceptable carriers and their formulations are known to one skilled in the art and described, for example, in Remington's Pharmaceutical Sciences (18th edition, A. Gennaro, 1990, Mack Publishing Company, Easton, Pa.), incorporated herein by reference.

Pharmaceutical compositions containing an ADC containing an TM4SF1 antibody or antigen-binding fragment thereof, are, in some embodiments, prepared as solutions, dispersions in glycerol, liquid polyethylene glycols, and any combinations thereof in oils, in solid dosage forms, as inhalable dosage forms, as intranasal dosage forms, as liposomal formulations, dosage forms comprising nanoparticles, dosage forms comprising microparticles, polymeric dosage forms, or any combinations thereof.

A pharmaceutically acceptable excipient is, in some examples, an excipient described in the Handbook of Pharmaceutical Excipients, American Pharmaceutical Association (1986). Non-limiting examples of suitable excipients include a buffering agent, a preservative, a stabilizer, a binder, a compaction agent, a lubricant, a chelator, a dispersion enhancer, a disintegration agent, a flavoring agent, a sweetener, a coloring agent.

In some embodiments an excipient is a buffering agent. Non-limiting examples of suitable buffering agents include sodium citrate, magnesium carbonate, magnesium bicarbonate, calcium carbonate, and calcium bicarbonate. As a buffering agent, sodium bicarbonate, potassium bicarbonate, magnesium hydroxide, magnesium lactate, magnesium glucomate, aluminium hydroxide, sodium citrate, sodium tartrate, sodium acetate, sodium carbonate, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide and other calcium salts or combinations thereof is used, in some embodiments, in a pharmaceutical composition of the present disclosure.

In some embodiments an excipient comprises a preservative. Non-limiting examples of suitable preservatives include antioxidants, such as alpha-tocopherol and ascorbate, and antimicrobials, such as parabens, chlorobutanol, and phenol. In some examples, antioxidants further include but are not limited to EDTA, citric acid, ascorbic acid, butylated hydroxytoluene (BHT), butylated hydroxy anisole (BHA), sodium sulfite, p-amino benzoic acid, glutathione, propyl gallate, cysteine, methionine, ethanol and N-acetyl cysteine. In some instances preservatives include validamycin A, TL-3, sodium ortho vanadate, sodium fluoride, N-a-tosyl-Phe-chloromethylketone, N-a-tosyl-Lys-chloromethylketone, aprotinin, phenylmethylsulfonyl fluoride, diisopropylfluorophosphate, kinase inhibitor, phosphatase inhibitor, caspase inhibitor, granzyme inhibitor, cell adhesion inhibitor, cell division inhibitor, cell cycle inhibitor, lipid signaling inhibitor, protease inhibitor, reducing agent, alkylating agent, antimicrobial agent, oxidase inhibitor, or other inhibitor.

In some embodiments a pharmaceutical composition as described herein comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof. The binders used in a pharmaceutical formulation are, in some examples, selected from starches such as potato starch, corn starch, wheat starch; sugars such as sucrose, glucose, dextrose, lactose, maltodextrin; natural and synthetic gums; gelatine; cellulose derivatives such as microcrystalline cellulose, hydroxypropyl cellulose, hydroxyethyl cellulose, hydroxypropyl methyl cellulose, carboxymethyl cellulose, methyl cellulose, ethyl cellulose; polyvinylpyrrolidone (povidone); polyethylene glycol (PEG); waxes; calcium carbonate; calcium phosphate; alcohols such as sorbitol, xylitol, mannitol and water or any combinations thereof.

In some embodiments a pharmaceutical composition as described herein comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil. The lubricants that are used in a pharmaceutical formulation, in some embodiments, are be selected from metallic stearates (such as magnesium stearate, calcium stearate, aluminium stearate), fatty acid esters (such as sodium stearyl fumarate), fatty acids (such as stearic acid), fatty alcohols, glyceryl behenate, mineral oil, paraffins, hydrogenated vegetable oils, leucine, polyethylene glycols (PEG), metallic lauryl sulphates (such as sodium lauryl sulphate, magnesium lauryl sulphate), sodium chloride, sodium benzoate, sodium acetate and talc or a combination thereof.

In some embodiments a pharmaceutical formulation comprises a dispersion enhancer as an excipient. Non-limiting examples of suitable dispersants include, in some examples, starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments a pharmaceutical composition as described herein comprises a disintegrant as an excipient. In some embodiments a disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. In some embodiments a disintegrant is an effervescent disintegrant. Non-limiting examples of suitable effervescent disintegrants include sodium bicarbonate in combination with citric acid, and sodium bicarbonate in combination with tartaric acid.

In some embodiments an excipient comprises a flavoring agent. Flavoring agents incorporated into an outer layer are, in some examples, chosen from synthetic flavor oils and flavoring aromatics; natural oils; extracts from plants, leaves, flowers, and fruits; and combinations thereof. In some embodiments a flavoring agent can be selected from the group consisting of cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In some embodiments an excipient comprises a sweetener. Non-limiting examples of suitable sweeteners include glucose (corn syrup), dextrose, invert sugar, fructose, and mixtures thereof (when not used as a carrier); saccharin and its various salts such as a sodium salt; dipeptide sweeteners such as aspartame; dihydrochalcone compounds, glycyrrhizin; Stevia Rebaudiana (Stevioside); chloro derivatives of sucrose such as sucralose; and sugar alcohols such as sorbitol, mannitol, sylitol, and the like.

In some instances, a pharmaceutical composition as described herein comprises a coloring agent. Non-limiting examples of suitable color agents include food, drug and cosmetic colors (FD&C), drug and cosmetic colors (D&C), and external drug and cosmetic colors (Ext. D&C). A coloring agents can be used as dyes or their corresponding lakes.

In some instances, a pharmaceutical composition as described herein comprises a chelator. In some cases, a chelator is a fungicidal chelator. Examples include, but are not limited to: ethylenediamine-N,N,N',N'-tetraacetic acid (EDTA); a disodium, trisodium, tetrasodium, dipotassium, tripotassium, dilithium and diammonium salt of EDTA; a barium, calcium, cobalt, copper, dysprosium, europium, iron, indium, lanthanum, magnesium, manganese, nickel, samarium, strontium, or zinc chelate of EDTA; trans-1,2-diaminocyclohexane-N,N,N',N'-tetraaceticacid monohydrate; N,N-bis(2-hydroxyethyl)glycine; 1,3-diamino-2-hydroxypropane-N,N,N',N'-tetraacetic acid; 1,3-diaminopropane-N,N,N',N'-tetraacetic acid; ethylenediamine-N,N'-diacetic acid; ethylenediamine-N,N'-dipropionic acid dihydrochloride; ethylenediamine-N,N'-bis(methylenephosphonic acid) hemihydrate; N-(2-hydroxyethyl)ethylenediamine-N,N',N'-triacetic acid; ethylenediamine-N,N,N',N'-tetrakis(methylenephosponic acid); O,O'-bis(2-aminoethyl)ethyleneglycol-N,N,N',N'-tetraacetic acid; N,N-bis(2-hydroxybenzyl)ethylenediamine-N,N-diacetic acid; 1,6-hexamethylenediamine-N,N,N',N'-tetraacetic acid; N-(2-hydroxyethyl)iminodiacetic acid; iminodiacetic acid; 1,2-diaminopropane-N,N,N',N'-tetraacetic acid; nitrilotriacetic acid; nitrilotripropionic acid; the trisodium salt of nitrilotris(methylenephosphoric acid); 7,19,30-trioxa-1,4,10,13,16,22,27,33-octaazabicyclo[11,11,11] pentatriacontane hexahydrobromide; or triethylenetetramine-N,N,N',N'',N''',N'''-hexaacetic acid.

Also contemplated are combination products that include an anti-TM4SF1 antibody as disclosed herein and one or more other antimicrobial or antifungal agents, for example, polyenes such as amphotericin B, amphotericin B lipid complex (ABCD), liposomal amphotericin B (L-AMB), and liposomal nystatin, azoles and triazoles such as voriconazole, fluconazole, ketoconazole, itraconazole, pozaconazole and the like; glucan synthase inhibitors such as caspofungin, micafungin (FK463), and V-echinocandin (LY303366); griseofulvin; allylamines such as terbinafine; flucytosine or other antifungal agents, including those described herein. In addition, it is contemplated that a peptide can be combined with topical antifungal agents such as ciclopirox olamine, haloprogin, tolnaftate, undecylenate, topical nysatin, amorolfine, butenafine, naftifine, terbinafine, and other topical agents. In some instances, a pharmaceutical composition comprises an additional agent. In some cases, an additional agent is present in a therapeutically effective amount in a pharmaceutical composition.

Under ordinary conditions of storage and use, the pharmaceutical compositions as described herein comprise a preservative to prevent the growth of microorganisms. In certain examples, the pharmaceutical compositions as described herein do not comprise a preservative. The pharmaceutical forms suitable for injectable use include sterile aqueous solutions or dispersions and sterile powders for the extemporaneous preparation of sterile injectable solutions or dispersions. The pharmaceutical compositions comprise a carrier which is a solvent or a dispersion medium containing, for example, water, ethanol, polyol (e.g., glycerol, propylene glycol, and liquid polyethylene glycol, and the like), and/or vegetable oils, or any combinations thereof. Proper fluidity is maintained, for example, by the use of a coating, such as lecithin, by the maintenance of the required particle size in the case of dispersion and by the use of surfactants. The prevention of the action of microorganisms is brought about by various antibacterial and antifungal agents, for example, parabens, chlorobutanol, phenol, sorbic acid, thimerosal, and the like. In many cases, isotonic agents are included, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the liquid dosage form is suitably buffered if necessary and the liquid diluent rendered isotonic with sufficient saline or glucose. The liquid dosage forms are especially suitable for intravenous, intramuscular, subcutaneous, intratumoral, and intraperitoneal administration. In this connection, sterile aqueous media that can be employed will be known to those of skill in the art in light of the present disclosure. For example, one dosage is dissolved, in certain cases, in 1 mL to 20 mL of isotonic NaCl solution and either added to 100 mL to 1000 mL of a fluid, e.g., sodium-bicarbonate buffered saline, or injected at the proposed site of infusion.

In certain embodiments, sterile injectable solutions is prepared by incorporating a immunotherapy agent, in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. The compositions disclosed herein are, in some instances, formulated in a neutral or salt form. Pharmaceutically-acceptable salts include, for example, the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups are, in some cases, derived from inorganic bases such as, for example, sodium, potassium, ammonium, calcium, or ferric hydroxides, and such organic bases as isopropylamine, trimethylamine, histidine, procaine and the like. Upon formulation, the pharmaceutical compositions are administered, in some embodiments, in a manner compatible with the dosage formulation and in such amount as is therapeutically effective.

In certain embodiments, a pharmaceutical composition of this disclosure comprises an effective amount of an anti-TM4SF1 antibody, as disclosed herein, combined with a pharmaceutically acceptable carrier. "Pharmaceutically acceptable," as used herein, includes any carrier which does not interfere with the effectiveness of the biological activity of the active ingredients and/or that is not toxic to the patient to whom it is administered. Non-limiting examples of suitable pharmaceutical carriers include phosphate buffered saline solutions, water, emulsions, such as oil/water emulsions, various types of wetting agents and sterile solutions. Additional non-limiting examples of pharmaceutically compatible carriers can include gels, bioadsorbable matrix materials, implantation elements containing the immunotherapeutic agents or any other suitable vehicle, delivery or dispensing means or material. Such carriers are formulated, for example, by conventional methods and administered to the subject at an effective amount.

IX. Combination Therapies

In certain embodiments, the methods of this disclosure comprise administering an ADC as disclosed herein, followed by, preceded by or in combination with one or more further therapy. Examples of the further therapy can include, but are not limited to, chemotherapy, radiation, an anti-cancer agent, or any combinations thereof. The further therapy can be administered concurrently or sequentially with respect to administration of the immunotherapy. In certain embodiments, the methods of this disclosure comprise administering an immunotherapy as disclosed herein, followed by, preceded by, or in combination with one or more anti-cancer agents or cancer therapies. Anti-cancer agents include, but are not limited to, chemotherapeutic agents, radiotherapeutic agents, cytokines, immune checkpoint inhibitors, anti-angiogenic agents, apoptosis-inducing agents, anti-cancer antibodies and/or anti-cyclin-dependent kinase agents. In certain embodiments, the cancer therapies include chemotherapy, biological therapy, radiotherapy, immunotherapy, hormone therapy, anti-vascular therapy, cryotherapy, toxin therapy and/or surgery or combinations thereof. In certain embodiments, the methods of this disclosure include administering an immunotherapy, as disclosed herein, followed by, preceded by or in combination with one or more further immunomodulatory agents. An immunomodulatory agent includes, in some examples, any compound, molecule or substance capable of suppressing antiviral immunity associated with a tumor or cancer. Non-limiting examples of the further immunomodulatory agents include anti-CD33 antibody or variable region thereof, an anti-CD11b antibody or variable region thereof, a COX2 inhibitor, e.g., celecoxib, cytokines, such as IL-12, GM-CSF, IL-2, IFN3 and 1FNy, and chemokines, such as MIP-1, MCP-1 and IL-8.

In certain examples, where the further therapy is radiation exemplary doses are 5,000 Rads (50 Gy) to 100,000 Rads (1000 Gy), or 50,000 Rads (500 Gy), or other appropriate doses within the recited ranges. Alternatively, the radiation dose are about 30 to 60 Gy, about 40 to about 50 Gy, about 40 to 48 Gy, or about 44 Gy, or other appropriate doses within the recited ranges, with the dose determined, example, by means of a dosimetry study as described above. "Gy" as used herein can refer to a unit for a specific absorbed dose of radiation equal to 100 Rads. Gy is the abbreviation for "Gray."

In certain examples, where the further therapy is chemotherapy, exemplary chemotherapeutic agents include without limitation alkylating agents (e.g., nitrogen mustard derivatives, ethylenimines, alkylsulfonates, hydrazines and triazines, nitrosureas, and metal salts), plant alkaloids (e.g., vinca alkaloids, taxanes, podophyllotoxins, and camptothecan analogs), antitumor antibiotics (e.g., anthracyclines, chromomycins, and the like), antimetabolites (e.g., folic acid antagonists, pyrimidine antagonists, purine antagonists, and adenosine deaminase inhibitors), topoisomerase I inhibitors, topoisomerase II inhibitors, and miscellaneous antineoplastics (e.g., ribonucleotide reductase inhibitors, adrenocortical steroid inhibitors, enzymes, antimicrotubule agents, and retinoids). Exemplary chemotherapeutic agents can include, without limitation, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®), Ibrutinib, idelalisib, and brentuximab vedotin.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines can include, without limitation, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors can, but are not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoac etamido)-4-phenylbutanamido)-pentanamide); marizomib (NPI-0052);

ixazomib citrate (MLN-9708); delanzomib (CEP-18770); and O-Methyl-N-[(2-methyl-5-thiazolyl)carbonyl]-L-seryl-O-methyl-N-[1S)-2-[(2R)-2-methyl-2-oxiranyl]-2-oxo-1-(phenylmethyl)ethyl]-L-serinamide (ONX-0912).

"In combination with," as used herein, means that the anti-TM4SF1 antibody and the further therapy are administered to a subject as part of a treatment regimen or plan. In certain embodiments, being used in combination does not require that the anti-TM4SF1 antibody and the further therapy are physically combined prior to administration or that they be administered over the same time frame. For example, and not by way of limitation, the anti-TM4SF1 antibody and the one or more agents are administered concurrently to the subject being treated, or are administered at the same time or sequentially in any order or at different points in time.

X. Kits

In some embodiments, the disclosure provides kits that include a composition (e.g., a pharmaceutical composition) of the disclosure (e.g., a composition including an ADC containing an anti-TM4SF1 antibody or antigen binding fragment thereof). The kits include instructions to allow a clinician (e.g., a physician or nurse) to administer the composition contained therein to a subject to treat a disorder associated with pathological angiogenesis (e.g., cancer).

In certain embodiments, the kits include a package of a single-dose pharmaceutical composition(s) containing an effective amount of an antibody of the disclosure. Optionally, instruments or devices necessary for administering the pharmaceutical composition(s) may be included in the kits. For instance, a kit of this disclosure may provide one or more pre-filled syringes containing an effective amount of a vaccine, vector, stabilized trimer, or optimized viral polypeptide of the disclosure. Furthermore, the kits may also include additional components such as instructions regarding administration schedules for a subject having a disorder associated with pathological angiogenesis (e.g., cancer) to use the pharmaceutical composition(s) containing a TM4SF1 binding protein or polynucleotide of the disclosure.

EXAMPLES

Example 1: Characterization of Exemplary Anti-TM4SF1 Antibodies

Affinity

Figure 3:
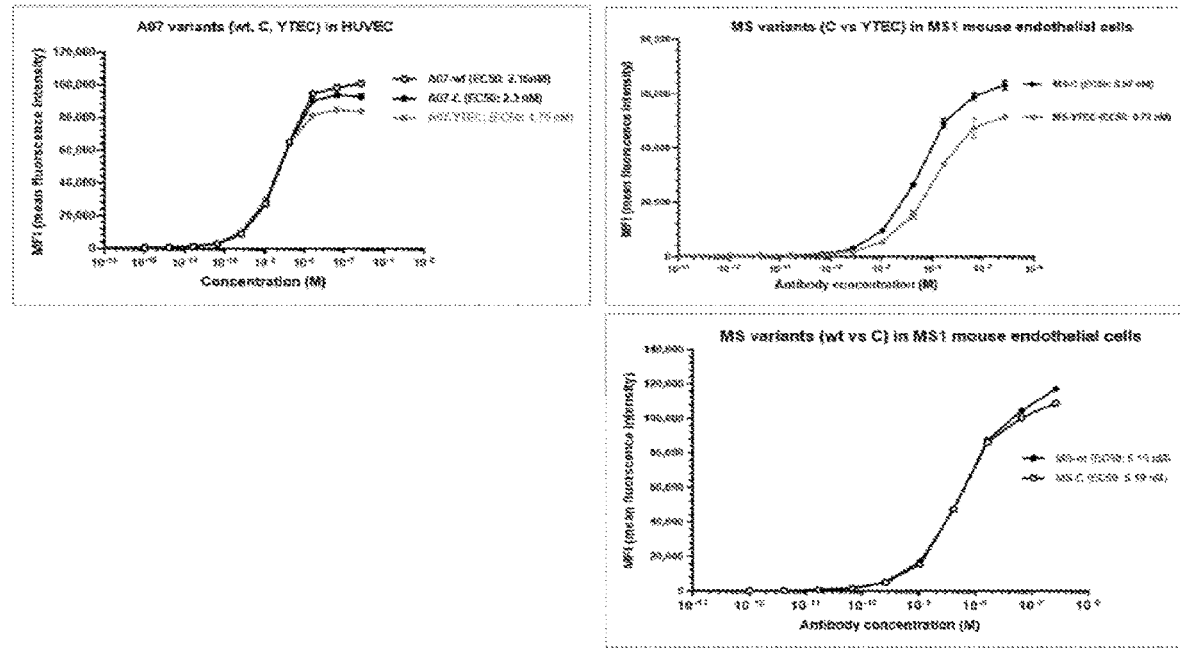
FIG. 3 illustrates the results of a study assessing the affinity of exemplary anti-TM4SF1 antibodies, in various endothelial cells.

Antigen binding affinities of anti-TM4SF1 antibodies comprising various Fc mutations were tested, via a cell-based flow cytometry assay. Variants of an exemplary anti-TM4SF1 antibody AGX-A07, comprising Fc region mutation N297C (the "C" variant) or N297C in combination with the mutations M252Y, S254T, and T256E (the "YTEC" variant), were tested using HUVEC cells (Primary Umbilical Vein Endothelial Cells; ATCC® PCS-100-010™) The $EC_{50}$ values for binding are shown in FIG. 3 (top left panel), where A07-wt corresponds to the AGX-A07 antibody without Fc region mutations. Similarly, a "C" variant and an "YTEC" variant of a murine surrogate (referred to as "MS" in the figures), were tested in immortalized mouse endothelial cell MS-1 cells (MILE SVEN 1; ATCC® CRL-2279™) The $EC_{50}$ values for binding are shown in FIG. 3 (top right panel and bottom right panel), where MS-wt corresponds to the murine surrogate antibody without the Fc region mutations.

Tissue Distribution

In this study, in vivo tissue distribution of the murine surrogate (MS) anti-TM4SF1 antibody "C" and "YTEC" variants was determined, in mice. Murine surrogate "C" variant conjugated to Alexa Fluor™ 647 (MS-C-647) and murine surrogate "YTEC" variant conjugated to Alexa Fluor™ 488 (MS-YTEC-488) were intraperitoneally co-injected to LLC (Lewis lung carcinoma) tumor bearing C57BL/6 (8 weeks old) mice, at a dose of 30 mg/kg (30 mpk). Major organs were harvest 24 or 48 hours after the injection and were fixed in 4% paraformaldehyde for embedding in OCT mounting media and sectioning. The MS-C-647 and MS-YTEC-488 antibody signals in tissue sections were captured via confocal microscope and the tissue distribution differences were examined.

Figure 4:
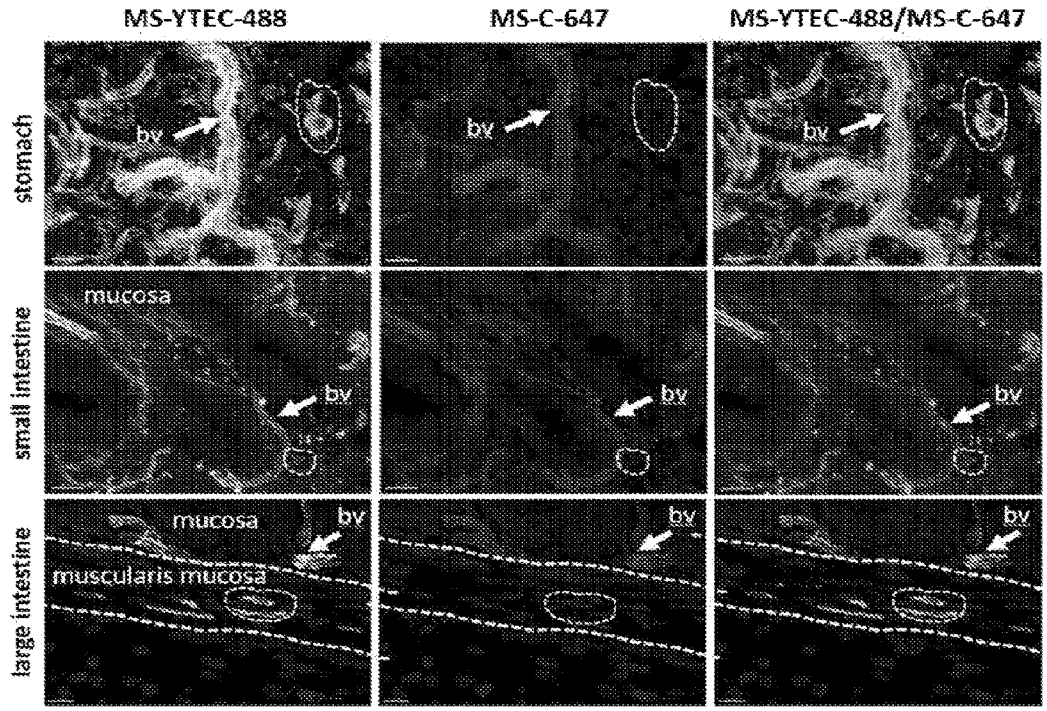
FIG. 4 illustrates in vivo tissue distribution (large intestine, small intestine, stomach) of exemplary anti-TM4SF1 antibodies (murine surrogate, MS) containing various Fc mutations.
Figure 5:
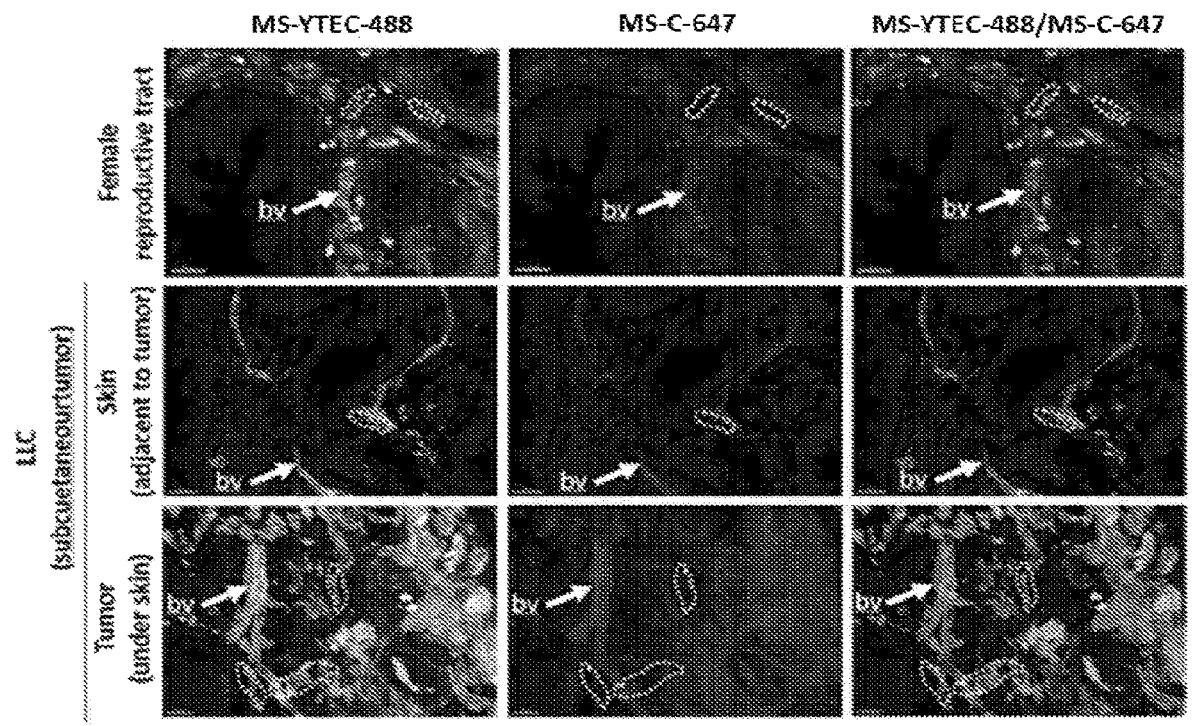
FIG. 5 illustrates in vivo tissue distribution (female reproductive tract, skin adjacent to a tumor, and tumor under the skin) of exemplary anti-TM4SF1 antibodies (murine surrogate, MS) containing various Fc mutations.

All blood vessels were found to be positive for both MS-C-647 and MS-YTEC-488 signals. In some organs, tissue resident mast cells and/or pericytes also strongly interacted with the MS-YTEC-488 but not with the MS-C-647. These results suggested that the MS-YTEC-488 can readily be transcytosed from endothelium to tissues for their interaction with leukocyte via antibody constant region or pericytes via antigen binding. The overall tissue distribution observations are summarized in below table and also shown in FIGS. 4 and 5 (bv=blood vessel).

TABLE 1

Tissue distribution of MS-C and MS-YTEC

| Mouse organs | Blood vessel staining | Tissue resident mast cell or pericyte staining |
|---|---|---|
| Brain | | no |
| Stomach | Comparable | Yes for MS-YTEC |
| Small Intestine | between | Yes for MS-YTEC |
| Large Intestine | MS-C and | Yes for MS-YTEC |
| Eye | MS-YTEC | No |
| Female Reproductive System | | Yes for MS-YTEC |
| Heart | | No |
| Kidney | | No |
| Liver | | No |
| Lung | | No |
| Pancreas | | No |
| Skin + tumor | | Yes for MS-YTEC |

Hydrophobicity

Figure 6:
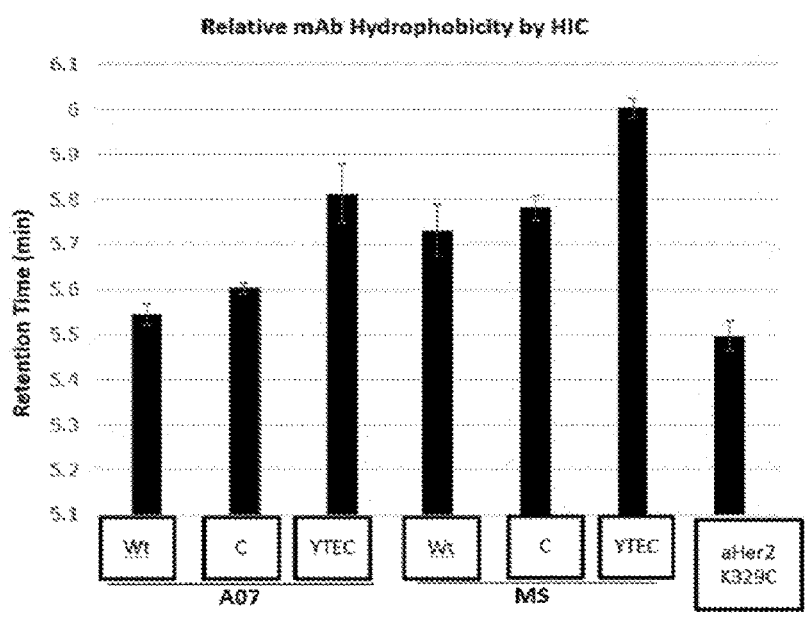
FIG. 6 illustrates hydrophobicity of exemplary anti-TM4SF1 antibodies (murine surrogate, MS; and anti-human AGX-A07), assessed by hydrophobic interaction chromatography (HIC).

The hydrophobicity of exemplary anti-TM4SF1 antibodies, and their Fc mutation containing variants were assessed in this study, using hydrophobic interaction chromatography. The tested antibodies were AGX-A07 (the "wt," "C," and "YTEC"); MS (the "wt," "C," and "YTEC"). An anti-Her2 antibody with an Fc mutation was used as a control. Results are plotted in FIG. 6 and also summarized in Table 2. Both in case of AGX-A07 and the murine surrogate anti-TM4SF1 antibody, it was observed that the hydrophobicity increased with the "C" and "YTEC" mutations.

TABLE 2

Hydrophobicity summary

| | Run 1 | Run 2 | Run 3 | Average | StD |
|---|---|---|---|---|---|
| A07-wt | 5.547 | 5.523 | 5.568 | 5.55 | 0.023 |
| A07C | 5.614 | 5.591 | 5.606 | 5.60 | 0.0012 |
| A07-YTEC | 5.781 | 5.77 | 5.888 | 5.81 | 0.065 |
| MS-wt | 5.697 | 5.7 | 5.797 | 5.73 | 0.057 |
| MS-C | 5.807 | 5.784 | 5.752 | 5.78 | 0.028 |

TABLE 2-continued

Hydrophobicity summary

| | Run 1 | Run 2 | Run 3 | Average | StD |
|---|---|---|---|---|---|
| MS-YTEC | 6.017 | 5.978 | 6.017 | 6.00 | 0.023 |
| anti-Her2 K392C | 5.496 | 5.467 | 5.532 | 5.5 | 0.033 |

Example 2: Antibody Drug Conjugates Containing Exemplary Anti-TM4SF1 Antibodies

Figure 1:
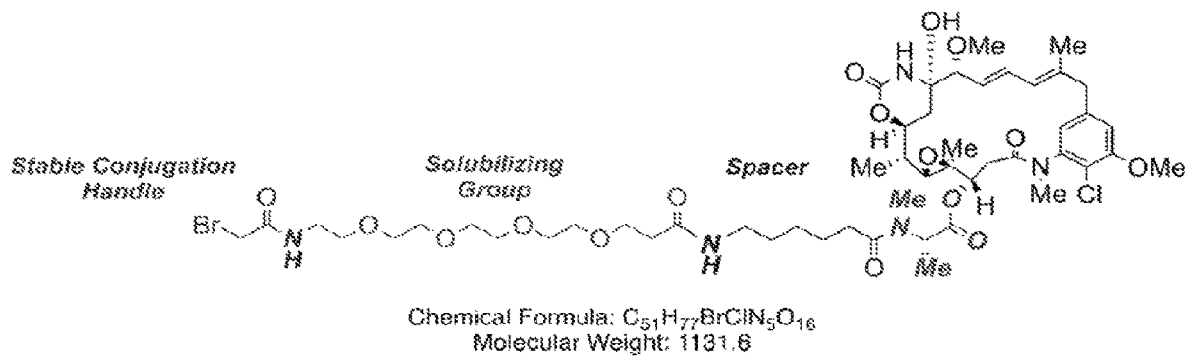
FIG. 1 illustrates an exemplary antibody drug conjugate (ADC), using bromoacetamide conjugation.
Figure 2:
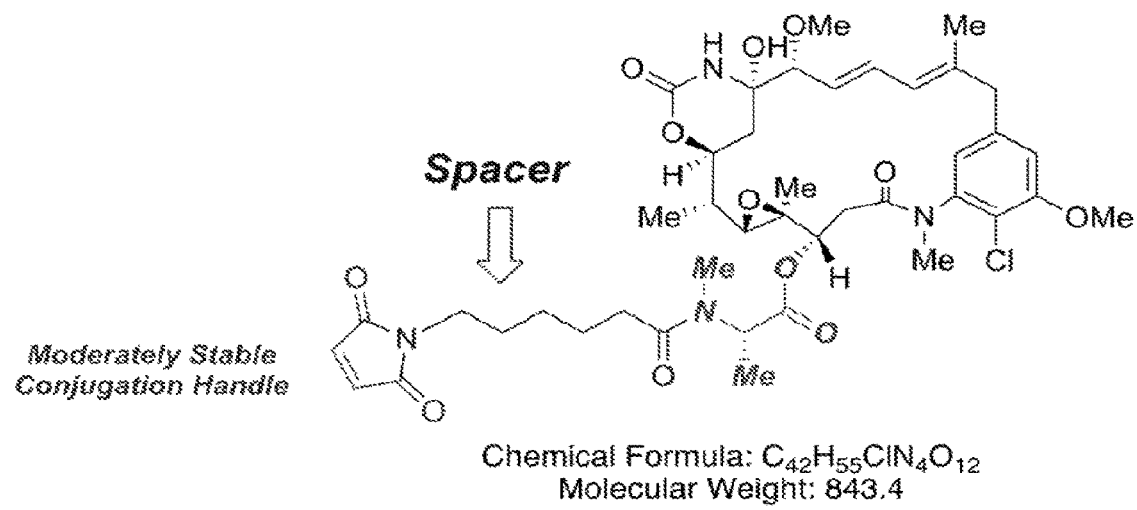
FIG. 2 illustrates an exemplary ADC, using maleimide conjugation.

Antibody drug conjugates (ADCs) containing exemplary anti-TM4SF1 antibodies were prepared and tested in in vitro and in vivo studies. FIGS. 1 and 2 provide the structures of the ADCs, prepared using maleimide conjugation (FIG. 2) or bromoacetamide conjugation (FIG. 1); $1^4S, 1^6S, 3^2S, 3^3S, 2R, 4S, 10E, 12E, 14R)-8^6$-chloro-14-hydroxy-$8^5$,14-dimethoxy-$3^3$,2,7,10-tetramethyl-$1^2$,6-dioxo-7-aza-1(6,4)-oxazinana-3(2,3)-oxirana-8(1,3)-benzenacyclotetradecaphane-10,12-dien-4-yl N-(6-(2,5-dioxo-2,5-dihydro-1H-pyrrol-1-yl)hexanoyl)-N-methyl-L-alaninate and $1^4S, 1^6S, 3^2S, 3^3S, 2R, 4S, 10E, 12E, 14R)-8^6$-chloro-$1^4$-hydroxy-$8^5$,14-dimethoxy-$3^3$,2,7,10-tetramethyl-$1^2$,6-dioxo-7-aza-1(6,4)-oxazinana-3(2,3)-oxirana-8(1,3)-benzenacyclotetradecaphane-10,12-dien-4-yl (S)-1-bromo-26,27-dimethyl-2,18,25-trioxo-6,9,12,15-tetraoxa-3,19,26-triazaoctacosan-28-oate.

In Vivo Tolerance

Figure 7:
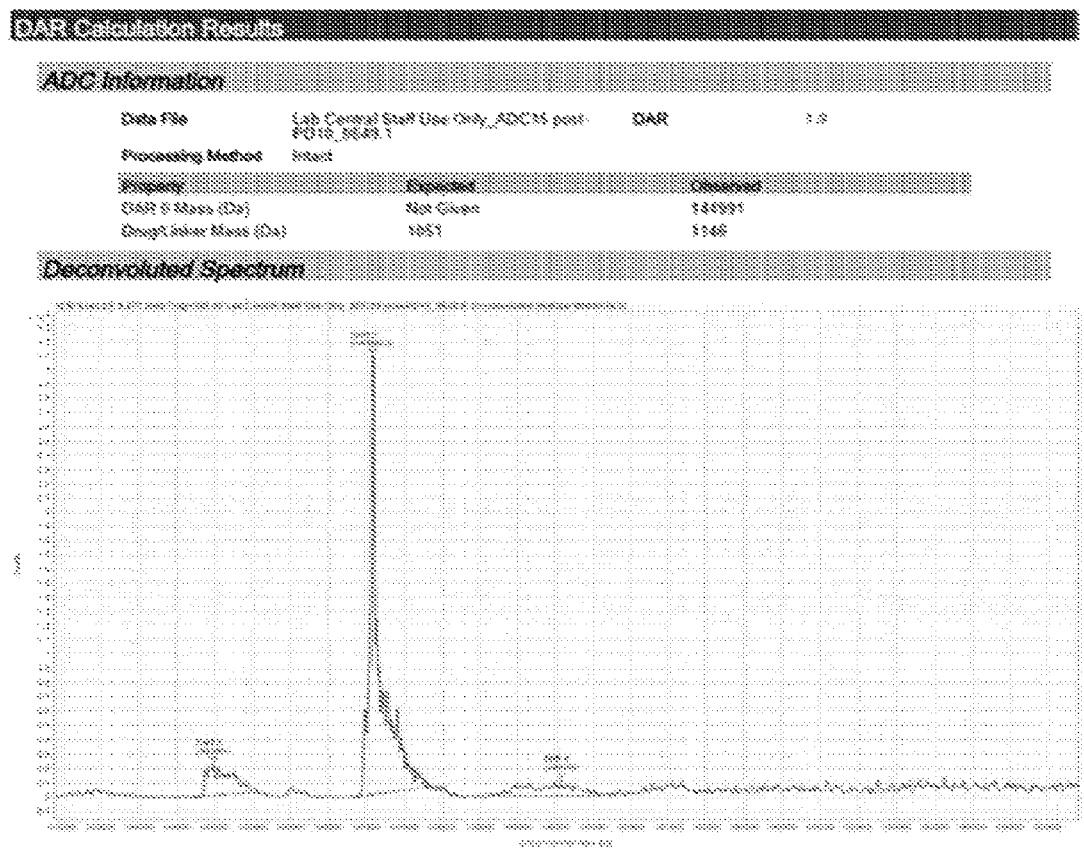
FIG. 7 provides a spectrum showing drug to antibody (DAR) ratio of an exemplary anti-TM4SF1 antibody (murine surrogate, MS).

Eight weeks old C57Bl/6 mice were administered an ADC (MS-C-mc-DM1) containing the murine surrogate "C" variant (MS-C) conjugated to maytansine, prepared using maleimide conjugation, at various doses (40 mg/kg, 50 mg/kg, and 60 mg/kg). The DAR for the ADC was about 2.0 (deconvoluted spectrum shown in FIG. 7).

Figure 8:
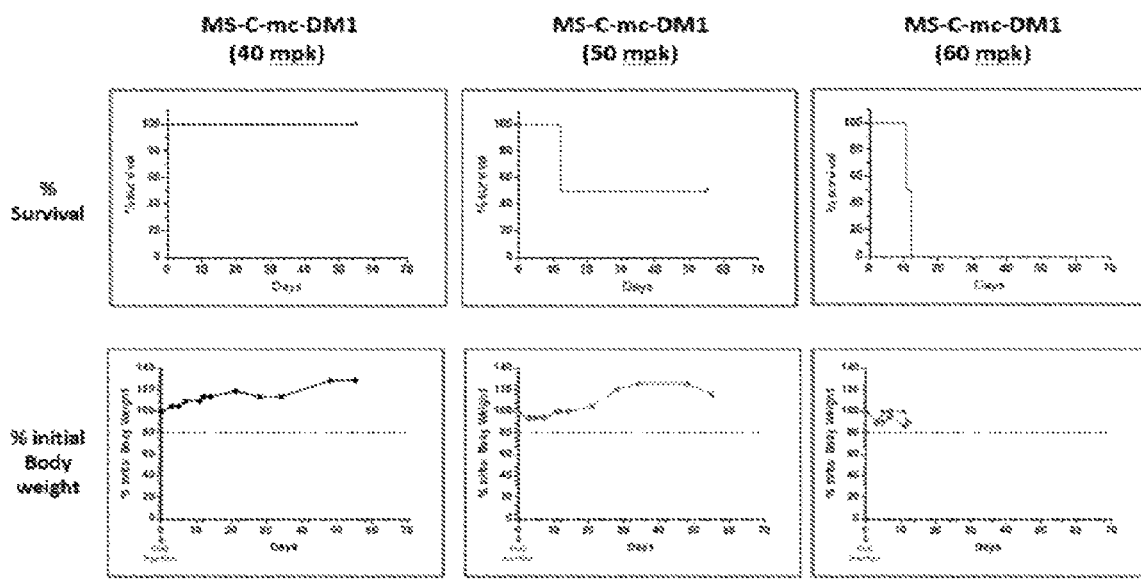
FIG. 8 provides the results of a study assessing in vivo tolerance of exemplary ADCs (maleimide conjugation) containing anti-TM4SF1 antibody (murine surrogate, MS), in mice, following administration at varying doses (40 mg/kg—left panel; 50 mg/kg—middle panel; and 60 mg/kg—right panel). The top half of the figure shows survival percentage and the bottom half shows body weight change, following administration of the ADC.

The ADC was tolerated at 40 mg/kg dose but not at the 50 mg/kg dose, as shown in FIG. 8. In addition, mice showed chest cavity fluid accumulation at day 10-12 with the 60 mg/kg dose of the MS-C-mc-DM1.

In further studies, mice of different ages were administered either (i) the MS-C-BA-DM1 ADC (containing the murine surrogate "C" variant conjugated to maytansine, prepared using bromoacetamide conjugation), or (ii) the MS-YTEC-BA-DM1 ADC (containing the murine surrogate "YTEC" variant conjugated to maytansine, prepared using bromoacetamide conjugation). It was observed that in general, the MS ADCs were better tolerated in the older mice (4-9 months) than in the younger mice (8 weeks). At a dose of 60 mg/kg, mice tolerated the MS-YTEC-BA-DM1 better than the MS-C-BA-DM1. Also, unlike the maleimide-conjugated ADCs, no obvious chest cavity fluid accumulation was observed with the BA-DM1 conjugated MS-C and MS-YTEC antibodies. This was an improvement over the maleimide-conjugated ADCs which had no survival at 60 mg/kg (see FIG. 8).

Figure 9:
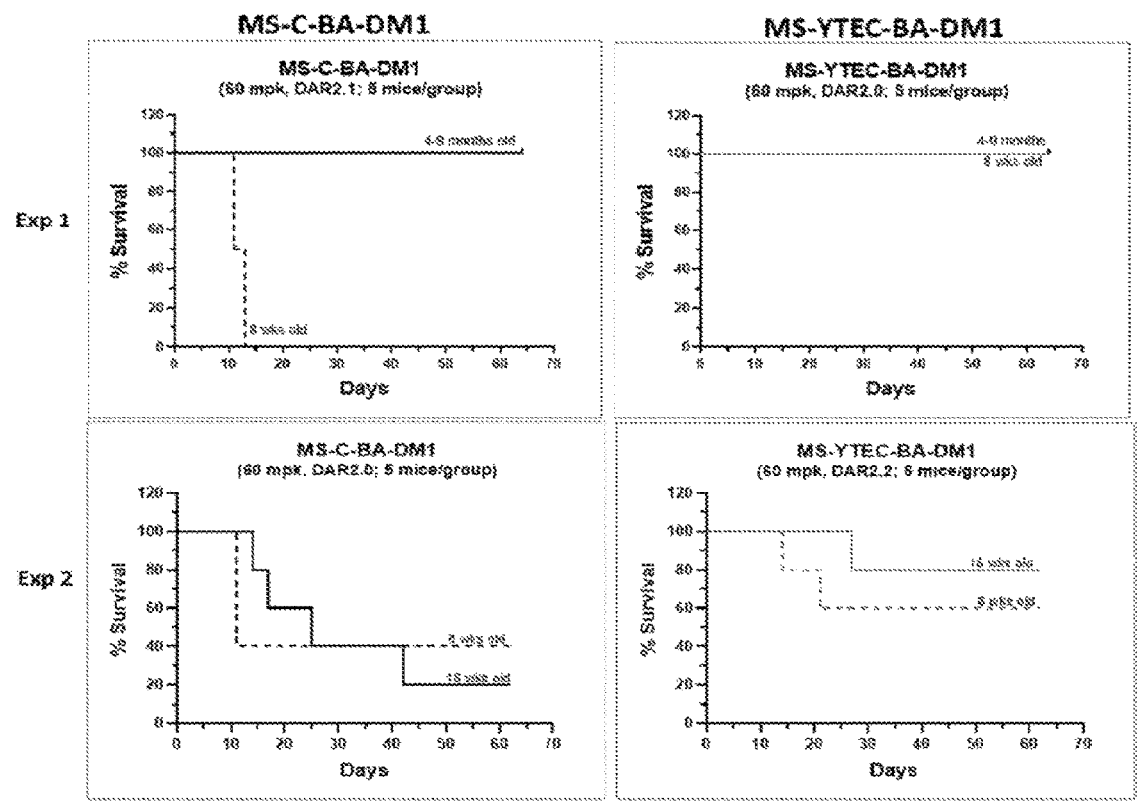
FIG. 9 provides the results of a study assessing in vivo tolerance of exemplary ADCs (bromoacetamide conjugation) containing anti-TM4SF1 antibodies (murine surrogate, MS), in mice, following administration at 60 mg/kg.

Results for the bromoacetamide-conjugated ADCs is shown in FIG. 9. Experiments 1 and 2 were carried out with two groups of animals. The survival rate at the 60 mg/kg dose is summarized in below table.

TABLE 3

Survival rate

| | Survival Rate (%) at 60 mg/kg | |
|---|---|---|
| Age | MS-C-BA-DM1 | MS-YTEC-BA-DM1 |
| 4-9 months | 60 | 90 |
| 8 weeks | 20 | 80 |

Toxicity Studies in Cynomolgus Monkeys

In this study the animals were randomly divided into various groups and administered either (i) an ADC (AGX-A07-C-BA-DM1) containing the AGX-A07 "C" variant (A07-C) conjugated to maytansine, at 5 mg/kg, 10 mg/kg, 20 mg/kg, or 40 mg/kg; or (ii) an ADC (AGX-A07-BA-YTEC-DM1) containing the AGX-A07 "YTEC" (A07-YTEC) conjugated to maytansine, at 40 mg/kg. Table 4 provides the details regarding animals tested.

TABLE 4

A non-GLP single dose study of ADCs containing exemplary anti-human TM4SF1 antibodies, by intravenous injection or infusion in cynomolgus monkeys

| Group No. | Test Material | Dose Level (mg/kg) | Body weight (kg) | Amount Ab injected (mg) | No. of Female Animals (2 years 3 months to 3 years 1 month) |
|---|---|---|---|---|---|
| 1 | AGX-A07-C-BA-DM1 | 5 | 2.05 | 10.25 | 1 |
| 2 | | 10 | 2.45 | 24.50 | 1 |
| 3 | | 20 | 2.20 | 44.00 | 1 |
| 4 | | 40 | 1.95 | 78.00 | 1 |
| 5 | AGX-A07-YTEC-BA-DM1 | 40 | 2.40 | 96.00 | 1 |

Summary of macroscopic and microscopic pathological observations from the monkey study is provided in Table 5.

TABLE 5

Macroscopic/Microscopic pathology reports at termination (42 days after 1 injection of test article)

| | | A07-C-BA-DM1 | A07-YTEC-BA-DM1 |
|---|---|---|---|
| Macroscopic | | | There were no test article-related macroscopic findings at terminal euthanasia |
| Microscopic | pleura of the lungs (thickening of lungs and expansion by fibrosis, multiple small vessels, mixed inflammatory cells, and proliferating fibroblasts; adhesion/inflammation/fibrosis) | mild at 40 mg/kg | minimal at 40 mg/kg (also evidenced a mild edema of the alveoli and interstitium) |
| | lung edema | mild 40 mg/kg | minimal at 40 mg/kg |

TABLE 5-continued

Macroscopic/Microscopic pathology reports at termination
(42 days after 1 injection of test article)

|  | A07-C-BA-DM1 | A07-YTEC-BA-DM1 |
|---|---|---|
| intimal proliferation of the aortic arch (with no other vessels affected) | (no mention) | minimal at 40 mg/kg |
| endocardial hyperplasia (characterized by a loose expansion of the endocardium and sub-endocardium by fibrillar to homogenous amphophilic to lightly basophilic acellular material and slightly increased cellularity. When affected, this was seen in both ventricles, and in the most affected animal extended from the base to the apex of the heart, possibly extending into the atria or large vessels. However, valves were not seemingly affected.) | in animals at all doses ≥10 mg/kg in a non-dose dependent pattern; moderate thickening seen at 10 mg/kg, mild at 20 mg/kg, minimal at 40 mg/kg. | minimal thickening of the vascular endothelium was seen in the aorta, at the aortic arch. |
| epicardial adhesion/inflammation/fibrosis (characterized by thickening of the atrial and heart base epicardium by fibrosis, fibroblasts, mixed inflammatory cells, and proliferating mesothelium) | minimal at 40 mg/kg | minimal at 40 mg/kg |
| other microscopic observations (spontaneously occurring findings, they were low/isolated in frequency and/or distributed randomly among groups, or their appearance was similar to findings in controls from this and/or previous studies.) | considered incidental | considered incidental |

Pharmacokinetic Studies in Mice and Cynomolgus Monkeys

In this study, various concentrations of exemplary anti-TM4SF1 antibodies and ADCs containing the same were assessed, in mouse and cynomolgus monkeys. Surrogate anti-mouse TM4SF1 antibodies (MS-C and MS-YTEC) cleared much faster in mice than the clearance of the anti-human TM4SF1 antibodies (A07-C and A07-YTEC) in monkey. The MS-YTEC cleared much faster than the MS-C in mice, when administered at the same dose of 60 mg/kg. In case of the exemplary anti-human TM4SF1 antibodies, A07-C-BA-DM1 and A07-YTEC-BA-DM1 were cleared in a similar pace in monkey, when administered at the same dose of 40 mg/kg.

Figure 10:
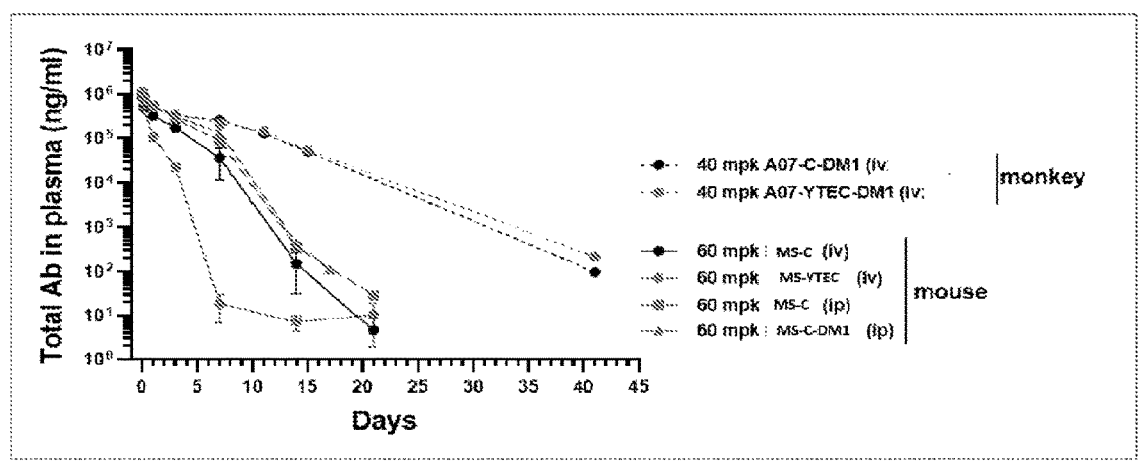
FIG. 10 provides the results of a pharmacokinetic study using ADCs containing exemplary anti-human TM4SF1 antibodies (AGX-A07) or murine surrogate (MS) TM4SF1 antibodies. The AGX-A07 containing ADCs were tested in cynomolgus monkeys and the MS containing ADCs were tested in mice.

Different injection route, intravenous (iv) and intraperitoneal (ip), showed very similar level of the murine surrogate antibodies in circulation in mice regardless whether the antibody was a naked antibody or conjugated with a DM1 payload. Results for this study are shown in FIG. 10.

Efficacy

In this study, the efficacy of murine surrogate anti-TM4SF1 antibodies conjugated to payload DM1, using bromoacetamide conjugation, MS-C-BA-DM1 and MS-YTEC-BA-DM1, in reducing tumor volume, were tested.

Briefly, eight weeks old C57/Bl6 mice that were previously implanted with B16-F10 tumor cells (ATCC® CRL-6475™—mouse skin melanoma cells) were randomized into groups and injected with a control or ADCs as follows: (i) MS-C-BA-DM1 (DAR 2.2) at 12 mg/kg or 20 mg/kg; or (ii) MS-YTEC-BA-DM1 (DAR 2.1) at 12 mg/kg or 20 mg/kg.

Figure 11:
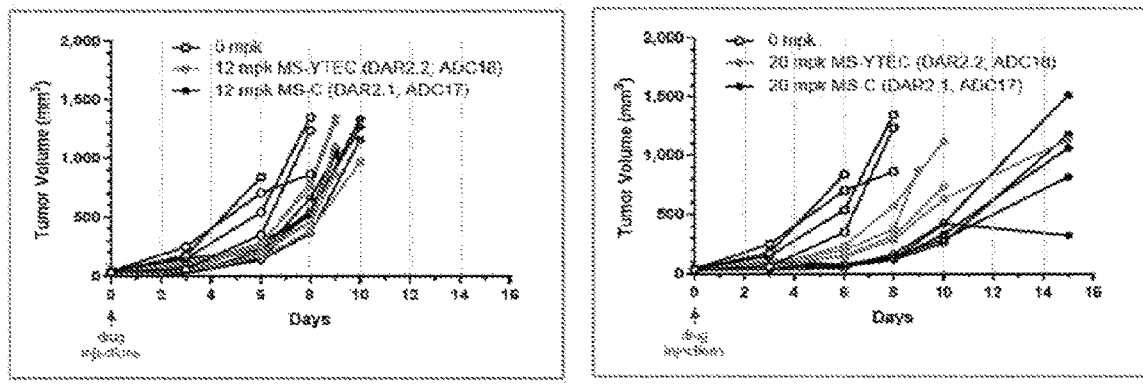
FIG. 11 provides the results of an in vivo study assessing the efficacy of exemplary ADCs containing anti-TM4SF1 antibodies (murine surrogate, MS) containing various Fc region mutations, administered at two doses (12 mg/kg and 20 mg/kg), in regression of tumor growth in mice.

Tumor volumes for a period of about 16 days, following injection, were measured and the results are shown in FIG. 11. At 12 mg/kg dosage, MS-C-BA-DM1 and MS-YTEC-BA-DM1 showed very similar B16-F10 tumor regression efficacy. Whereas, at 20 mg/kg dosage, MS-C-BA-DM1 showed better B16-F10 tumor regression efficacy than the MS-YTEC-BA-DM1.

Figure 12:
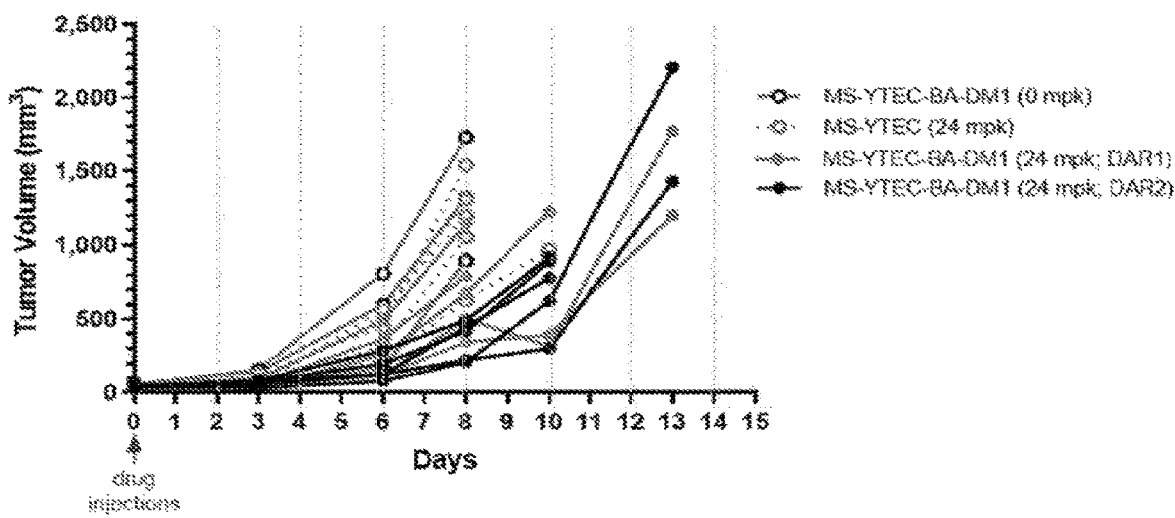
FIG. 12 provides the results of an in vivo study assessing the efficacy of exemplary ADCs containing anti-TM4SF1 antibodies (murine surrogate, MS) containing various Fc region mutations, administered at 24 mg/kg, in regressing of tumor growth in mice.

Next, the tumor regression property of MS-YTEC-BA-DM1 (at DAR of about 2 or about 1) was assessed using a 24 mg/kg single injection, in eight weeks old C57/Bl6 mice that were previously implanted with B16-F10 tumor cells, as described above. The MS-YTEC-BA-DM1 at DAR1 and DAR2 conjugation showed very similar B16F10 tumor regression efficacy. Results are shown in FIG. 12.

A further efficacy study was carried out using a MiaPaca 2 (ATCC® CRL-1420™—pancreatic carcinoma) xenograft tumor model. Briefly, eight weeks old athymic nude mice were randomized into groups and injected with a control or ADCs as follows: (i) MS-C-BA-DM1 at 12 mg/kg (single injection) or MS-YTEC-BA-DM1 at 12 mg/kg (single injection) (FIG. 13—top left panel); (ii) A07-C-BA-DM1 at 12 mg/kg (single injection) or A07-YTEC-BA-DM1 at 12 mg/kg (single injection) (FIG. 13—top right panel); (iii) MS-C-BA-DM1 at 12 mg/kg, single injection in combination with A07-C-BA-DM1 at 12 mg/kg, single injection or MS-YTEC-BA-DM1 at 12 mg/kg, single injection in combination with A07-YTEC-BA-DM1 at 12 mg/kg (FIG. 13—bottom left panel); (iv) MS-C-BA-DM1 at 3 mg/kg (q7d4—weekly for four times) in combination with A07-C-BA-DM1 at 3 mg/kg, q7d4 or MS-YTEC-BA-DM1 at 3 mg/kg, q7d4 in combination with A07-YTEC-BA-DM1 at 3 mg/kg, q7d4 (FIG. 13—bottom right panel).

MS-C-BA-DM1 and MS-YTEC-BA-DM1 show very similar efficacy of MiaPaca2 tumor regression. In combination therapy of MS+A07, MiaPaca2 tumor regression was better with the single injection of the higher dose (12 mg/kg), compared to the smaller dose (3 mg/kg) that was injected weekly for 4 times.

It will be apparent to those skilled in the art that various modifications and variations can be made in the compositions, methods, and kits of the present disclosure without departing from the spirit or scope of the disclosure. Thus, it is intended that the present disclosure cover the modifications and variations of this disclosure provided they come within the scope of the appended claims and their equivalents.

TABLE 6

SEQUENCE DESCRIPTION

| SEQ ID NO | Description | Sequence |
|---|---|---|
| | Antibody AGX-A01 | |
| 1 | AGX-A01 Variable heavy (VH) chain-amino acid | EVILVESGGGLVKPGGSLKLSCAASGFTFSSF AMSWVRQTPEKRLEWVATISSGSIYIYYTDG VKGRFTISRDNAKNTVHLQMSSLRSEDTAM YYCARRGIYYGYDGYAMDYWGQGTSVTVS |
| 2 | AGX-A01 Variable light (VL) chain-amino acid | AVVMTQTPLSLPVSLGDQASISCRSSQSLVHS NGNTYLHWYMQKPGQSPKVLIYKVSNRFSG VPDRFSGSGSGTDFTLKISRVEADDLGIYFCS QSTHIPLAFGAGTKLELK |
| | Antibody AGX-A03 | |
| 3 | AGX-A03 Variable heavy (VH) chain-amino acid | QIQLVQSGPELKKPGETVKISCKASGYSFRDY GMNWVKQAPGRTFKWMGWINTYTGAPVY AADFKGRFAFSLDTSASAAFLQINNLKNEDT ATYFCARWVSYGNNRNWFFDFWGAGTTVT VSS |
| 4 | AGX-A03 Variable heavy (VH) chain-nucleic acid | CAGATCCAGTTGGTGCAGTCTGGACCTGAG CTGAAGAAGCCTGGAGAGACAGTCAAGAT CTCCTGCAAGGCTTCTGGGTATTCCTTCAG AGACTATGGAATGAACTGGGTGAAGCAGG CTCCAGGAAGGACTTTTAAGTGGATGGGCT GGATAAACACCTACACTGGAGCGCCAGTA TATGCTGCTGACTTCAAGGGACGGTTTGCC TTCTCTTTGGACACCTCTGCCAGCGCTGCC TTTTTGCAGATCAACAACCTCAAAAATGAA GACACGGCTACATATTTCTGTGCAAGATGG GTCTCCTACGGTAATAACCGCAACTGGTTC TTCGATTTTTGGGGCGCAGGGACCACGGTC ACCGTCTCCTCA |
| 5 | AGX-A03 Variable heavy (VH) chain-codon optimized nucleic acid | CAAATTCAGTTGGTTCAATCCGGCCCTGAG CTCAAGAAGCCTGGAGAGACAGTGAAGAT AAGTTGTAAGGCTAGTGGCTATTCATTTCG AGATTATGGGATGAATTGGGTCAAGCAGG CCCCAGGGCGGACCTTCAAATGGATGGGG TGGATCAATACTTACACTGGCGCACCAGTA TATGCAGCTGATTTTAAGGGTCGCTTTGCA TTTTCACTTGATACTTCAGCCAGTGCCGCT TTTTTGCAAATCAACAATCTCAAAAATGAA GACACTGCTACATATTTCTGCGCCAGGTGG GTGAGCTATGGCAATAACAGAAATTGGTT CTTTGACTTTTGGGGCGCAGGCACCACCGT CACTGTCTCATCA |
| 6 | VH-CDR1 | GYSFRDYGMN |
| 7 | VH-CDR2 | WINTYTGAPVYAADFKG |
| 8 | VH-CDR3 | WVSYGNNRNWFFDF |
| 9 | AGX-A03 Variable light (VL) chain-amino acid | DVLMTQTPLSLPVRLGDQASISCRSSQTLVHS NGNTYLEWYLQKPGQSPKLLIYKVSNRLSG VPDRFSGSGSGTDFTLKISRVETEDLGVYYCF QGSHGPWTFGGGTKLEIK |
| 10 | AGX-A03 Variable light (VL) chain-nucleic acid | GATGTTTTGATGACCCAAACTCCACTCTCC CTGCCTGTCCGTCTTGGAGATCAGGCCTCC ATCTCTTGTAGATCTAGTCAGACCCTTGTA CATAGTAATGGAAACACCTATTTAGAATG GTACCTGCAGAAACCAGGCCAGTCTCCAA AACTCTTGATCTACAAAGTTTCCAATCGAC TTTCTGGGGTCCCAGACAGGTTCAGTGGCA GTGGATCAGGGACAGATTTCACACTCAAG ATCAGCAGAGTGGAGACTGAGGATCTGGG AGTTTATTACTGCTTTCAAGGTTCACATGG TCCGTGGACGTTCGGTGGAGGCACCAAGC TGGAAATCAAA |

TABLE 6-continued

SEQUENCE DESCRIPTION

| SEQ ID NO | Description | Sequence |
|---|---|---|
| 11 | AGX-A03 Variable light (VL) chain-codon optimized nucleic acid | GACGTACTTATGACACAAACTCCCTTGAGC TTGCCAGTACGGCTTGGCGATCAAGCTTCA ATTTCATGTCGTTCTTCTCAAACACTTGTCC ACTCAAATGGGAATACATATTTGGAATGGT ATCTCCAAAAGCCCGGCCAATCCCCAAAA TTGTTGATTTACAAGGTGTCTAATCGACTC TCAGGCGTCCCCGACCGATTCTCCGGGAGC GGGTCCGGTACAGACTTCACCTTGAAAATC TCCAGGGTAGAAACTGAAGACCTCGGAGT CTACTATTGTTTCCAGGGGTCACACGGCCC CTGGACATTTGGAGGAGGAACTAAGCTCG AGATCAAA |
| 12 | VL-CDR1 | RSSQTLVHSNGNTYLE |
| 13 | VL-CDR2 | KVSNRLS |
| 14 | VL-CDR3 | FQGSHGPWT |

Antibody AGX-A04

| 15 | AGX-A04 Variable heavy (VH) chain-amino acid | EVQLQQSGPELVKPGASVKISCKTSGYTFTD YTMHWVRQSHGKSLEWIGSFNPNNGGLTNY NQKFKGKATLTVDKSSSTVYMDLRSLTSEDS AVYYCTRIRATGFDSWGQGTTLTVSS |
| 16 | AGX-A04 Variable heavy (VH) chain-nucleic acid | GAGGTCCAGCTGCAACAGTCTGGACCTGA GCTGGTGAAGCCTGGGGCTTCAGTGAAGA TATCCTGCAAGACTTCTGGATACACATTCA CTGATTACACCATGCACTGGGTGAGGCAG AGCCATGGAAAGAGCCTTGAGTGGATTGG AAGTTTTAATCCTAACAATGGTGGTCTTAC TAACTACAACCAGAAGTTCAAGGGCAAGG CCACATTGACTGTGGACAAGTCTTCCAGCA CAGTGTACATGGACCTCCGCAGCCTGACAT CTGAGGATTCTGCAGTCTATTACTGTACAA GAATCCGGGCTACGGGCTTTGACTCCTGGG GCCAGGGCACCACTCTCACAGTCTCCTCA |
| 17 | AGX-A04 Variable heavy (VH) chain-codon optimized nucleic acid | GAGGTACAACTGCAACAGAGTGGACCTGA ACTTGTCAAACCTGGAGCAAGTGTGAAGA TTAGCTGTAAAACCAGTGGCTACACATTTA CCGATTATACTATGCACTGGGTAAGACAG AGCCACGGAAAATCACTGGAGTGGATTGG TAGTTTCAATCCTAACAACGGAGGATTGAC AAATTACAACCAGAAGTTCAAAGGGAAAG CCACCTTGACAGTTGATAAGTCCTCAAGTA CCGTGTATATGGATCTGCGTTCTCTCACAA GTGAAGATAGCGCAGTTTACTACTGTACCC GCATCCGAGCCACCGGGTTCGATTCATGGG GTCAGGGGACAACACTGACTGTTTCTTCT |
| 18 | VH-CDR1 | GYTFTDYTMH |
| 19 | VH-CDR2 | SFNPNNGGLTNYNQKFKG |
| 20 | VH-CDR3 | IRATGFDS |
| 21 | AGX-A04 Variable light (VL) chain-amino acid | DIVMSQSPSSLAVSAGEKVTMSCKSSQSLLN SRTRKNYLAWYQQKPGQSPKLLIYWASTRE SGVPDRFTGSGSGTDFTLTISNVQAEDLTVY YCKQSYNPPWTFGGGTKLEIK |
| 22 | AGX-A04 Variable light (VL) chain-nucleic acid | GACATTGTGATGTCACAGTCTCCATCCTCC CTGGCTGTGTCAGCAGGAGAGAAGGTCAC TATGAGCTGCAAATCCAGTCAGAGTCTGCT CAACAGTAGAACCCGAAAGAACTACTTGG CTTGGTACCAGCAGAAACCAGGGCAGTCT CCTAAACTGCTGATCTACTGGGCATCCACT AGGGAATCTGGGGTCCCTGATCGCTTCACA GGCAGTGGATCTGGGACAGATTTCACTCTC ACCATCAGCAATGTGCAGGCTGAAGACCT GACAGTTTATTACTGCAAGCAATCTTATAA TCCTCCGTGGACGTTCGGTGGAGGCACCAA GCTGGAAATCAAA |
| 23 | AGX-A04 Variable light (VL) chain-codon optimized nucleic acid | GACATAGTTATGTCCCAGTCTCCATCCAGC TTGGCTGTCAGCGCCGGAGAGAAAGTGAC TATGAGTTGTAAATCTTCCCAGTCCCTGCT TAACTCACGTACTCGGAAGAATTATCTTGC CTGGTATCAACAAAAGCCAGGTCAAAGTC CTAAGCTCCTTATTTACTGGGCCTCAACAC GGGAGTCAGGTGTCCCCGATCGCTTCACAG GTAGTGGGAGTGGTACTGACTTCACTCTCA |

TABLE 6-continued

| SEQ ID NO | Description | Sequence |
|---|---|---|
| | | CCATTTCAAATGTCCAAGCAGAAGACTTGA<br>CTGTGTATTACTGTAAGCAGAGTTACAACC<br>CTCCTTGGACCTTTGGTGGGGGGACCAAAC<br>TGGAGATCAAG |
| 24 | VL-CDR1 | KSSQSLLNSRTRKNYLA |
| 25 | VL-CDR2 | WASTRES |
| 26 | VL-CDR3 | KQSYNPPWT |
| | Antibody AGX-A05 | |
| 27 | AGX-A05<br>Variable heavy (VH) chain-<br>amino acid | EVQVQQSGPELVKPGASVKMSCKASGYTFT<br>SYVMHWVKQKPGQGLEWIGYINPNNDNINY<br>NEKFKGKASLTSDKSSNTVYMELSSLTSEDS<br>AVYYCAGYGNSGANWGQGTLVTVSA |
| 28 | AGX-A05<br>Variable heavy (VH) chain-<br>nucleic acid | GAGGTCCAGGTACAGCAGTCTGGACCTGA<br>ACTGGTAAAGCCTGGGGCTTCAGTGAAGA<br>TGTCCTGTAAGGCTTCTGGATACACATTCA<br>CTAGCTATGTCATGCACTGGGTGAAGCAG<br>AAGCCTGGGCAGGGCCTTGAGTGGATTGG<br>ATATATTAATCCTAACAATGATAATATTAA<br>CTACAATGAGAAGTTCAAAGGCAAGGCCT<br>CACTGACTTCAGACAAATCCTCCAACACAG<br>TCTACATGGAGCTCAGCAGCCTGACCTCTG<br>AGGACTCTGCGGTCTATTACTGTGCAGGCT<br>ATGGTAACTCCGGAGCTAACTGGGGCCAA<br>GGGACTCTGGTCACTGTCTCTGCA |
| 29 | AGX-A05<br>Variable heavy (VH) chain-<br>codon optimized nucleic acid | GAAGTTCAAGTTCAGCAAAGCGGGCCTGA<br>GCTTGTCAAGCCAGGCGCATCAGTCAAAA<br>TGAGCTGTAAGGCTTCCGGGTACACCTTCA<br>CCAGTTATGTCATGCATTGGGTAAAACAAA<br>AGCCAGGACAGGGACTCGAGTGGATAGGA<br>TACATTAACCCAAATAACGACAACATTAA<br>CTACAACGAGAAATTCAAGGGCAAAGCAT<br>CATTGACTTCCGATAAATCCTCTAACACCG<br>TGTACATGGAGCTGAGTTCATTGACCAGCG<br>AGGATTCTGCCGTGTACTACTGTGCAGGTT<br>ATGGCAACTCTGGTGCTAACTGGGGGCAG<br>GGGACTCTGGTCACAGTCAGCGCA |
| 30 | VH-CDR1 | GYTFTSYVMH |
| 31 | VH-CDR2 | YINPNNDNINYNEKFKG |
| 32 | VH-CDR3 | YGNSGAN |
| 33 | AGX-A05<br>Variable light (VL) chain-amino<br>acid | DIQMTQSPASLSASVGETVTITCRTSKNIFNFL<br>AWYHQKQGRSPRLLVSHTKTLAAGVPSRFS<br>GSGSGTQFSLKINSLQPEDFGIYYCQHHYGTP<br>WTFGGGTKLEIK |
| 34 | AGX-A05<br>Variable light (VL) chain-<br>nucleic acid | GACATCCAGATGACTCAGTCTCCAGCCTCC<br>CTATCTGCATCTGTGGGAGAAACTGTCACC<br>ATCACATGTCGAACAAGTAAAAATATTTTC<br>AATTTTTTAGCATGGTATCACCAGAAACAG<br>GGAAGATCTCCTCGACTCCTGGTCTCTCAT<br>ACAAAAACCTTAGCAGCAGGTGTGCCATC<br>AAGGTTCAGTGGCAGTGGCTCAGGCACAC<br>AGTTTTCTCTGAAGATCAACAGCCTGCAGC<br>CTGAAGATTTTGGGATTTATTACTGTCAAC<br>ATCATTATGGTACTCCGTGGACGTTCGGTG<br>GAGGCACCAAACTGGAAATCAAA |
| 35 | AGX-A05<br>Variable light (VL) chain-codon<br>optimized nucleic acid | GACATTCAGATGACCCAGTCACCAGCATCT<br>TTGAGCGCATCCGTTGGGGAGACTGTGAC<br>AATCACATGCCGAACCAGTAAGAACATCT<br>TCAACTTCCTCGCATGGTACCATCAAAAGC<br>AGGGCAGGTCTCCCAGACTGCTTGTCTCTC<br>ACACCAAGACACTGGCAGCAGGCGTCCCC<br>AGCCGGTTTAGTGGTAGTGGATCTGGCACA<br>CAGTTTAGTTTGAAAATCAATTCCCTGCAA<br>CCCGAAGACTTCGGCATATACTATTGCCAG<br>CACCACTATGGGACACCTTGGACTTTCGGA<br>GGTGGTACTAAACTTGAGATTAAA |
| 36 | VL-CDR1 | RTSKNIFNFLA |
| 37 | VL-CDR2 | HTKTLAA |
| 38 | VL-CDR3 | QHHYGTPWT |

TABLE 6-continued

SEQUENCE DESCRIPTION

| SEQ ID NO | Description | Sequence |
|---|---|---|
| | Antibody AGX-A07 | |
| 39 | AGX-A07 Variable heavy (VH) chain-amino acid | QIQLVQSGPELKKPGETVKISCKASGYTFTNY GVKWVKQAPGKDLKWMGWINTYTGNPIYA ADFKGRFAFSLETSASTAFLQINNLKNEDTAT YFCVRFQYGDYRYFDVWGAGTTVTSS |
| 40 | AGX-A07 Variable heavy (VH) chain-nucleic acid | CAGATCCAGTTGGTGCAGTCTGGACCTGAG CTGAAGAAGCCTGGAGAGACAGTCAAGAT CTCCTGCAAGGCTTCTGGGTATACCTTCAC AAACTATGGAGTGAAGTGGGTGAAGCAGG CTCCAGGAAAGGATTTAAAGTGGATGGGC TGGATAAACACCTACACTGGAAATCCAATT TATGCTGCTGACTTCAAGGGACGGTTTGCC TTCTCTTTGGAGACCTCTGCCAGCACTGCC TTTTTGCAGATCAACAACCTCAAAAATGAG GACACGGCTACATATTTCTGTGTAAGATTC CAATATGGCGATTACCGGTACTTCGATGTC TGGGGCGCAGGGACCACGGTCACCGTCTC CTCA |
| 41 | AGX-A07 Variable heavy (VH) chain-codon optimized nucleic acid | CAAATCCAACTTGTCCAGAGCGGTCCCGA GTTGAAGAAGCCTGGCGAAACCGTGAAAA TCTCATGCAAGGCCAGTGGATATACATTTA CAAACTATGGCGTCAAGTGGGTGAAACAA GCCCCAGGTAAAGACTTGAAATGGATGGG ATGGATCAACACATACACAGGGAATCCTA TCTATGCAGCCGACTTTAAAGGCAGATTTG CCTTCAGTTTGGAGACATCTGCCTCCACCG CTTTCCTGCAAATAAATAACCTGAAAAATG AAGATACCGCTACATACTTCTGTGTACGGT TCCAGTACGGAGATTACCGCTATTTCGATG TGTGGGGCGCAGGTACCACAGTAACCGTC TCCTCA |
| 42 | VH-CDR1 | GYTFTNYGVK |
| 43 | VH-CDR2 | WINTYTGNPIYAADFKG |
| 44 | VH-CDR3 | FQYGDYRYFDV |
| 45 | AGX-A07 Variable light (VL) chain-amino acid | QIILSQSPAILSASPGEKVTMTCRANSGISFIN WYQQKPGSSPKPWIYGTANLASGVPARFGG SGSGTSYSLTISRVEAEDAATYYCQQWSSNP LTFGAGTKLELR |
| 46 | AGX-A07 Variable light (VL) chain-nucleic acid | CAAATTATTCTCTCCCAGTCTCCAGCAATC CTGTCTGCATCTCCAGGGGAGAAGGTCAC GATGACTTGCAGGGCCAACTCAGGTATTA GTTTCATCAACTGGTACCAGCAGAAGCCA GGATCCTCCCCCAAACCCTGGATTTATGGC ACAGCCAACCTGGCTTCTGGAGTCCCTGCT CGCTTCGGTGGCAGTGGGTCTGGGACTTCT TACTCTCTCACAATCAGCAGAGTGGAGGCT GAAGACGCTGCCACTTATTACTGCCAGCAG TGGAGTAGTAACCCGCTCACGTTCGGTGCT GGGACCAAGCTGGAGTTGAGA |
| 47 | AGX-A07 Variable light (VL) chain-codon optimized nucleic acid | CAAATAATTCTGTCACAGTCCCCCGCTATA CTTAGTGCTTCACCAGGAGAAAAAGTGAC CATGACTTGTAGAGCTAATTCTGGCATATC ATTCATCAACTGGTATCAACAAAAGCCAG GTTCCTCCCCCAAGCCATGGATTTACGGGA CCGCCAACCTTGCTTCTGGGGTACCCGCTC GTTTCGGCGGATCAGGTTCAGGAACTTCCT ATAGCCTCACTATCAGTCGGGTTGAAGCTG AGGATGCCGCTACATATTACTGCCAGCAAT GGTCTAGTAATCCACTTACCTTTGGAGCTG GCACCAAATTGGAACTTCGT |
| 48 | VL-CDR1 | RANSGISFIN |
| 49 | VL-CDR2 | GTANLAS |
| 50 | VL-CDR3 | QQWSSNPLT |
| | Antibody AGX-A08 | |
| 51 | AGX-A08 Variable heavy (VH) chain-amino acid | EVQLQQSGPELVKPGASVKLSCKASGYTVTS YVMHWVKQKPGQGLEWIGYINPYSDVTNC NEKFKGKATLTSDKTSSTAYMELSSLTSEDS AVYYCSSYGGGFAYWGQGTLVTVSA |
| 52 | AGX-A08 Variable heavy (VH) chain-nucleic acid | GAGGTCCAGCTGCAGCAGTCTGGACCTGA GCTGGTAAAGCCTGGGGCTTCAGTGAAGC TGTCCTGCAAGGCTTCTGGATACACAGTCA CTAGCTATGTTATGCACTGGGTGAAGCAGA |

TABLE 6-continued

SEQUENCE DESCRIPTION

| SEQ ID NO | Description | Sequence |
|---|---|---|
| 53 | AGX-A08 Variable heavy (VH) chain-codon optimized nucleic acid | AGCCTGGGCAGGGCCTTGAGTGGATTGGA TATATTAATCCTTACAGTGATGTTACTAAC TGCAATGAGAAGTTCAAAGGCAAGGCCAC ACTGACTTCAGACAAAACCTCCAGCACAG CCTACATGGAGCTCAGCAGCCTGACCTCTG AGGACTCTGCGGTCTATTACTGTTCCTCCT ACGGTGGGGGGTTTGCTTACTGGGGCCAA GGGACTCTGGTCACTGTCTCTGCA GAAGTCCAGCTTCAGCAATCCGGCCCAGA ACTGGTAAAACCAGGCGCAAGTGTTAAGT TGAGTTGCAAAGCCAGTGGTTATACCGTTA CTTCATACGTCATGCATTGGGTAAAACAAA AGCCCGGCCAAGGGCTTGAATGGATCGGC TACATCAACCCCTTACTCTGACGTCACCAAC TGCAACGAGAAATTCAAAGGGAAAGCCAC ATTGACCTCTGACAAGACAAGCAGTACCG CCTACATGGAGCTTTCTAGTTTGACTTCTG AAGACTCTGCTGTCTACTACTGTAGCAGCT ACGGCGGCGGCTTTGCTTACTGGGGCCAG GGTACATTGGTGACTGTGAGTGCA |
| 54 | VH-CDR1 | GYTVTSYVMH |
| 55 | VH-CDR2 | YINPYSDVTNCNEKFKG |
| 56 | VH-CDR3 | YGGGFAY |
| 57 | AGX-A08 Variable light chain(VL)-amino acid | DIQMTQSPASLSASVGEPVTITCRASKNIYTY LAWYHQKQGKSPQFLVYNARTLAGGVPSRL SGSGSVTQFSLNINTLHREDLGTYFCQHHYD TPYTFGGGTNLEIK |
| 58 | AGX-A08 Variable light (VL) chain-nucleic acid | GACATCCAGATGACTCAGTCTCCAGCCTCC CTATCTGCATCTGTGGGAGAACCTGTCACC ATCACATGTCGAGCAAGTAAGAATATTTAC ACATATTTAGCATGGTATCACCAGAAACA GGGAAAATCTCCTCAGTTCCTGGTCTATAA TGCAAGAACCTTAGCAGGAGGTGTGCCAT CAAGGCTCAGTGGCAGTGGATCAGTCACG CAGTTTTCTCTAAACATCAACACCTTGCAT CGAGAAGATTTAGGGACTTACTTCTGTCAA CATCATTATGATACTCCGTACACGTTCGGA GGGGGGACCAACCTGGAAATAAAA |
| 59 | AGX-A08 Variable light (VL) chain-codon optimized nucleic acid | GACATCCAGATGACACAGTCACCAGCATC CCTGTCCGCCTCAGTTGGGGAGCCTGTTAC CATAACTTGTCGGGCAAGCAAAAACATAT ACACCTATTTGGCTTGGTATCACCAAAAGC AAGGTAAGTCACCTCAGTTTCTTGTATATA ATGCCCGCACACTTGCTGGCGGAGTACCCT CTCGATTGTCTGGATCTGGCAGCGTTACCC AATTCAGCCTGAACATCAACACCCTCCATC GGGAAGATTTGGGTACCTATTTCTGTCAAC ATCACTACGACACCCCATACACCTTCGGAG GCGGCACAAATTTGGAAATTAAA |
| 60 | VL-CDR1 | RASKNIYTYLA |
| 61 | VL-CDR2 | NARTLAG |
| 62 | VL-CDR3 | QHHYDTPYT |

Antibody AGX-A09

| 63 | AGX-A09 Variable heavy (VH) chain-amino acid | EVQLQQSGPELVKPGASVKMSCKASGYTFSS YVMHWVKQKPGQGLEWIGYINPYSDVTNY NEKFKGKATLTSDRSSNTAYMELSSLTSEDS AVYYCARNYFDWGRGTLVTVSA |
| 64 | AGX-A09 Variable heavy (VH) chain-nucleic acid | GAGGTCCAGCTGCAGCAGTCTGGACCTGA GCTGGTAAAGCCTGGGGCTTCAGTGAAGA TGTCCTGCAAGGCTTCTGGATACACATTCT CTAGCTATGTTATGCACTGGGTGAAGCAGA AGCCTGGGCAGGGCCTTGAGTGGATTGGA TATATTAATCCTTACAGTGATGTCACTAAC TACAATGAGAAGTTCAAAGGCAAGGCCAC ACTGACTTCAGACAGATCCTCCAACACAGC CTACATGGAACTCAGCAGCCTGACCTCTGA GGACTCTGCGGTCTATTACTGTGCAAGAA TTACTTCGACTGGGGCCAGGGACTCTGGT CACAGTCTCTGCA |
| 65 | AGX-A09 Variable heavy (VH) chain-codon optimized nucleic acid | GAGGTACAGCTTCAGCAGAGTGGTCCAGA ACTCGTCAAGCCTGGGGCAAGCGTTAAGA TGAGTTGTAAAGCATCCGGTTACACATTCA GTAGCTATGTTATGCACTGGGTCAAACAGA AGCCTGGGCAGGGGTGGAGTGGATCGGA |

TABLE 6-continued

SEQUENCE DESCRIPTION

| SEQ ID NO | Description | Sequence |
|---|---|---|
| | | TATATAAATCCCTATTCAGACGTAACTAAT TATAATGAAAAGTTCAAGGGGAAAGCAAC CTTGACAAGTGACCGGTCATCTAATACCGC ATACATGGAGCTGAGCTCATTGACAAGTG AGGACTCTGCTGTGTATTACTGTGCCCGGA ACTACTTCGACTGGGGTAGGGGCACACTG GTAACTGTTAGTGCA |
| 66 | VH-CDR1 | GYTFSSYVMH |
| 67 | VH-CDR2 | YINPYSDVTNYNEKFKG |
| 68 | VH-CDR3 | NYFD |
| 69 | AGX-A09 Variable light (VL) chain-amino acid | DIQMTQSPASLSASVGETVTITCRASKNVYS YLAWFQQKQGKSPQLLVYNAKTLAEGVPSR FSGGGSGTQFSLKINSLQPADFGSYYCQHHY NIPFTFGSGTKLEIK |
| 70 | AGX-A09 Variable light (VL) chain-nucleic acid | GACATCCAGATGACTCAGTCTCCAGCCTCC CTATCTGCATCTGTGGGAGAAACTGTCACC ATCACATGTCGAGCAAGTAAAAATGTTTAC AGTTATTTAGCATGGTTTCAACAGAAACAG GGGAAATCTCCTCAGCTCCTGGTCTATAAT GCTAAAACCTTAGCAGAAGGTGTGCCATC AAGGTTCAGTGGCGGGGGATCAGGCACAC AGTTTTCTCTGAAGATCAACAGCCTGCAGC CTGCAGATTTTGGGAGTTATTACTGTCAAC ATCATTATAATATTCCATTCACGTTCGGCT CGGGGACAAAGTTGGAAATAAAA |
| 71 | AGX-A09 Variable light (VL) chain-codon optimized nucleic acid | GACATACAAATGACACAAAGTCCCGCTAG TCTTTCAGCCAGTGTTGGTGAGACTGTGAC AATAACCTGTAGAGCTAGCAAAAATGTCT ACTCCTATCTGGCTTGGTTCCAGCAGAAAC AAGGAAAGAGTCCTCAGTTGCTCGTATATA ATGCTAAAACTTTGGCAGAAGGCGTCCCTT CTCGTTTCAGTGGCGGAGGAAGTGGGACT CAATTCTCACTGAAGATCAATAGCCTCCAG CCCGCCGACTTTGGGAGCTACTATTGCCAA CATCATTACAACATACCATTCACCTTTGGC TCAGGTACTAAACTCGAAATTAAA |
| 72 | VL-CDR1 | RASKNVYSYLA |
| 73 | VL-CDR2 | NAKTLAE |
| 74 | VL-CDR3 | QHHYNIPFT |

Antibody AGX-A11

| SEQ ID NO | Description | Sequence |
|---|---|---|
| 75 | AGX-A11 Variable heavy (VH) chain-amino acid | QIQLVQSGPELKKPGETVKISCKASGFTFTNY PMHWVKQAPGKGLKWMGWINTYSGVPTY ADDFKGRFAFSLETSASTAYLQINNLKNEDM ATYFCARGGYDGSREFAYWGQGTLVTVS |
| 76 | AGX-A11 Variable heavy (VH) chain-nucleic acid | CAGATCCAGTTGGTGCAGTCTGGACCTGAG CTGAAGAAGCCTGGAGAGACAGTCAAGAT CTCCTGCAAGGCTTCTGGGTTTACCTTCAC AAACTATCCAATGCACTGGGTGAAGCAGG CTCCAGGAAAGGGTTTAAAGTGGATGGGC TGGATAAACACCTACTCTGGAGTGCCAAC ATATGCAGATGACTTCAAGGGACGGTTTGC CTTCTCTTTGGAAACCTCTGCCAGCACTGC ATATTTGCAGATCAACAACCTCAAAAATG AGGACATGGCTACATATTTCTGTGCAAGAG GGGGCTACGATGGTAGCAGGGAGTTTGCT TACTGGGGCCAAGGGACTCTGGTCACTGTC TCT |
| 77 | AGX-A11 Variable heavy (VH) chain-codon optimized nucleic acid | CAGATACAACTCGTCCAGTCAGGTCCAGA GTTGAAGAAACCCGGAGAAACTGTGAAGA TATCCTGTAAAGCCAGCGGCTTTACTTTCA CAAACTACCCCATGCATTGGGTGAAGCAG GCCCCCGGAAAAGGACTCAAATGGATGGG ATGGATCAACACATACAGTGGGGTGCCTA CTTACGCAGACGATTTCAAAGGAAGGTTC GCATTTAGCTTGGAAACTAGCGCATCTACA GCATATCTCCAGATTAACAATCTTAAAAAT GAGGATATGGCAACATACTTCTGCGCTAG GGGAGGTTACGATGGGAGCAGGGAGTTCG CTTATTGGGGCAAGGGACTCTTGTGACTG TAAGT |

TABLE 6-continued

SEQUENCE DESCRIPTION

| SEQ ID NO | Description | Sequence |
|---|---|---|
| 78 | VH-CDR1 | GFTFTNYPMH |
| 79 | VH-CDR2 | WINTYSGVPTYADDFKG |
| 80 | VH-CDR3 | GGYDGSREFAY |
| 81 | AGX-A11<br>Variable light (VL) chain-amino acid | DIVLTQSPASLAASLGQRATTSYRASKSVSTS<br>GYSYMHWNQQKPGQPPRLLIYLVSNLESGV<br>PARFSGSGSGTDFTLNIHPVEEEDAATYYCQ<br>HIRELTTFGGGTKLEIK |
| 82 | AGX-A11<br>Variable light (VL) chain-<br>nucleic acid | GACATTGTGCTGACACAGTCTCCTGCTTCC<br>TTAGCTGCATCTCTGGGGCAGAGGGCCACC<br>ACCTCATACAGGGCCAGCAAAAGTGTCAG<br>TACATCTGGCTATAGTTATATGCACTGGAA<br>CCAACAGAAACCAGGACAGCCACCCAGAC<br>TCCTCATCTATCTTGTATCCAACCTAGAAT<br>CTGGGGTCCCTGCCAGGTTCAGTGGCAGTG<br>GGTCTGGGACAGACTTCACCCTCAACATCC<br>ATCCTGTGGAGGAGGAGGATGCTGCAACC<br>TATTACTGTCAGCACATTAGGGAGCTTACC<br>ACGTTCGGAGGGGGGACCAAGCTGGAAAT<br>AAAA |
| 83 | AGX-A11<br>Variable light (VL) chain-codon optimized nucleic acid | GACATAGTGCTCACTCAGAGCCCTGCATCC<br>CTTGCCGCCTCCCTCGGACAACGAGCTACT<br>ACAAGCTACCGGGCATCAAAGTCCGTTAG<br>CACATCAGGATACAGCTATATGCACTGGA<br>ATCAGCAAAAGCCAGGCCAACCACCCCGT<br>CTTCTCATCTACCTCGTAAGTAATCTGGAA<br>TCAGGCGTGCCAGCCCGATTCAGTGGGTCA<br>GGGTCTGGGACAGATTTCACCCTCAACATC<br>CATCCAGTAGAGGAAGAGGACGCAGCAAC<br>ATATTACTGCCAACACATTAGAGAACTTAC<br>CACTTTCGGAGGAGGAACTAAATTGGAGA<br>TCAAA |
| 84 | VL-CDR1 | RASKSVSTSGYSYMH |
| 85 | VL-CDR2 | LVSNLES |
| 86 | VL-CDR3 | QHIRELTT |

Constant Region Sequences

| SEQ ID NO | Description | Sequence |
|---|---|---|
| 87 | IgG1 Glm17* (heavy chain constant region)<br>*with L234A/L235A/G237A mutations<br>SEQ ID NO: 88 is sequence without the terminal lysine | ASTKGPSVFPLAPSSKSTSGGTAALGCLVKD<br>YFPEPVTVSWNSGALTSGVHTFPAVLQSSGL<br>YSLSSVVTVPSSSLGTQTYICNVNHKPSNTKV<br>DKKVEPKSCDKTHTCPPCPAPEAAGAPSVFL<br>FPPKPKDTLMISRTPEVTCVVVDVSHEDPEV<br>KFNWYVDGVEVHNAKTKPREEQYNSTYRV<br>VSVLTVLHQDWLNGKEYKCKVSNKALPAPI<br>EKTISKAKGQPREPQVYTLPPSREEMTKNQV<br>SLTCLVKGFYPSDIAVEWESNGQPENNYKTT<br>PPVLDSDGSFFLYSKLTVDKSRWQQGNVFSC<br>SVMHEALHNHYTQKSLSLSPGK |
| 88 | IgG1 Glm17* (heavy chain constant region)<br>*with L234A/L235A/G237A mutations | ASTKGPSVFPLAPSSKSTSGGTAALGCLVKD<br>YFPEPVTVSWNSGALTSGVHTFPAVLQSSGL<br>YSLSSVVTVPSSSLGTQTYICNVNHKPSNTKV<br>DKKVEPKSCDKTHTCPPCPAPEAAGAPSVFL<br>FPPKPKDTLMISRTPEVTCVVVDVSHEDPEV<br>KFNWYVDGVEVHNAKTKPREEQYNSTYRV<br>VSVLTVLHQDWLNGKEYKCKVSNKALPAPI<br>EKTISKAKGQPREPQVYTLPPSREEMTKNQV<br>SLTCLVKGFYPSDIAVEWESNGQPENNYKTT<br>PPVLDSDGSFFLYSKLTVDKSRWQQGNVFSC<br>SVMHEALHNHYTQKSLSLSPG |
| 89 | IgG1 Km3 (light chain constant region) | RTVAAPSVFIFPPSDEQLKSGTASVVCLLNNF<br>YPREAKVQWKVDNALQSGNSQESVTEQDSK<br>DSTYSLSSTLTLSKADYEKHKVYACEVTHQG<br>LSSPVTKSFNRGEC |

Humanized AGX-A07 sequences

| SEQ ID NO | Description | Sequence |
|---|---|---|
| 90 | AGX-A07 (humanized) H2<br>Heavy chain amino acid | QVQLVQSGAEVKKPGASVKVSCKASGYTFT<br>NYGVKWVRQAPGQDLEWMGWINTYTGNPI<br>YAADFKGRVTMTTDTSTSTAFMELRSLRSD<br>DTAVYYCVRFQYGDYRYFDVWGQGTLVTV<br>SSASTKGPSVFPLAPSSKSTSGGTAALGCLVK<br>DYFPEPVTVSWNSGALTSGVHTFPAVLQSSG<br>LYSLSSWTVPSSSLGTQTYICNVNHKPSNTK<br>VDKKVEPKSCDKTHTCPPCPAPEAAGAPSVF<br>LFPPKPKDTLMISRTPEVTCVVVDVSHEDPE<br>VKFNWYVDGVEVHNAKTKPREEQYNSTYR |

TABLE 6-continued

| SEQ ID NO | Description | Sequence |
|---|---|---|
| | | VVSVLTVLHQDWLNGKEYKCKVSNKALPAP IEKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |
| 91 | AGX-A07 (humanized) H2 Heavy chain nucleic acid | TCTACCGGACAGGTGCAGTTGGTTCAGTCT GGCGCCGAAGTGAAGAAACCTGGCGCTTC TGTGAAGGTGTCCTGCAAGGCCTCTGGCTA CACCTTTACCAACTACGGCGTGAAATGGGT CCGACAGGCTCCTGGACAGGATCTGGAAT GGATGGGCTGGATCAACACCTACACCGGC AATCCTATCTACGCCGCCGACTTCAAGGGC AGAGTGACCATGACCACCGACACCTCTAC CTCCACCGCCTTCATGGAACTGCGGTCCCT GAGATCTGACGACACCGCCGTGTACTACTG CGTGCGGTTTCAGTACGGCGACTACCGGTA CTTTGATGTGTGGGGCCAGGGCACACTGGT CACCGTTTCTTCCGCTTCTACCAAGGGACC CAGCGTGTTCCCTCTGGCTCCTTCCTCTAA ATCCACCTCTGGCGGAACCGCTGCTCTGGG CTGTCTGGTCAAGGATTACTTCCCTGAGCC TGTGACCGTGTCCTGGAACTCTGGTGCTCT GACATCCGGCGTGCACACCTTTCCAGCTGT GCTGCAGTCCTCTGGCCTGTACTCTCTGTC CTCTGTCGTGACCGTGCCTTCTAGCTCTCT GGGCACCCAGACCTACATCTGCAACGTGA ACCACAAGCCTTCCAACACCAAGGTGGAC AAGAAGGTGGAACCCAAGTCCTGCGACAA GACCCACACCTGTCCTCCATGTCCTGCTCC AGAAGCTGCTGGCGCTCCCTCTGTGTTCCT GTTTCCTCCAAAGCCTAAGGACACCCTGAT GATCTCTCGGACCCCTGAAGTGACCTGCGT GGTGGTGGATGTGTCTCACGAGGACCCAG AAGTGAAGTTCAATTGGTACGTGGACGGC GTGGAAGTGCACAACGCCAAGACCAAGCC TAGAGAGGAACAGTACAACTCCACCTACA GAGTGGTGTCCGTGCTGACCGTGCTGCACC AGGATTGGCTGAACGGCAAAGAGTACAAG TGCAAGGTGTCCAACAAGGCACTGCCCGC TCCTATCGAAAAGACCATCTCCAAGGCTAA GGGCCAGCCTCGGGAACCTCAGGTTTACA CCCTGCCTCCATCTCGGGAAGAGATGACCA AGAACCAGGTGTCCCTGACCTGCCTCGTGA AGGGCTTCTACCCTTCCGATATCGCCGTGG AATGGGAGTCCAATGGCCAGCCTGAGAAC AACTACAAGACAACCCCTCCTGTGCTGGAC TCCGACGGCTCATTCTTCCTGTACTCCAAG CTGACAGTGGACAAGTCTCGGTGGCAGCA GGGCAACGTGTTCTCCTGTTCTGTGATGCA CGAGGCCCTGCACAACCACTACACACAGA AGTCCCTGTCTCTGTCCCCTGGCAAGTGA |
| 92 | AGX-A07 H2v1 Heavy chain amino acid | EVQLVQSGAEVKKPGASVKVSCKASGYTFT NYGVKWVRQAPGQGLEWMGWINTYTGNPI YAADFKGRVTMTTDTSTSTAYMELRSLRSD DTAVYYCVRFQYGDYRYFDVWGQGTLVTV SSASTKGPSVFPLAPSSKSTSGGTAALGCLVK DYFPEPVTVSWNSGALTSGVHTFPAVLQSSG LYSLSSWTVPSSSLGTQTYICNVNHKPSNTK VDKKVEPKSCDKTHTCPPCPAPEAAGAPSVF LFPPKPKDTLMISRTPEVTCVVVDVSHEDPE VKFNWYVDGVEVHNAKTKPREEQYNSTYR VVSVLTVLHQDWLNGKEYKCKVSNKALPAP IEKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |
| 93 | AGX-A07 H2v1 Heavy chain nucleic acid | GAAGTGCAGTTGGTGCAGTCTGGCGCCGA AGTGAAGAAACCTGGCGCTTCTGTGAAGG TGTCCTGCAAGGCCTCTGGCTACACCTTTA CCAACTACGGCGTGAAATGGGTCCGACAG GCTCCTGGACAAGGCCTGGAATGGATGGG CTGGATCAACACCTACACCGGCAATCCTAT CTACGCCGCCGACTTCAAGGGCAGAGTGA CCATGACCACCGACACCTCTACCTCCACCG CCTACATGGAACTGCGGTCCCTGAGATCTG ACGACACCGCCGTGTACTACTGCGTGCGGT |

TABLE 6-continued

SEQUENCE DESCRIPTION

| SEQ ID NO | Description | Sequence |
|---|---|---|
| | | TTCAGTACGGCGACTACCGGTACTTTGATG
TGTGGGGCCAGGGCACACTGGTCACCGTTT
CTTCCGCTTCTACCAAGGGACCCAGCGTGT
TCCCTCTGGCTCCTTCCTCTAAATCCACCTC
TGGCGGAACCGCTGCTCTGGGCTGTCTGGT
CAAGGATTACTTCCCTGAGCCTGTGACCGT
GTCCTGGAATTCTGGTGCTCTGACATCCGG
CGTGCACACCTTTCCAGCTGTGCTGCAGTC
CTCTGGCCTGTACTCTCTGTCCTCTGTCGTG
ACCGTGCCTTCTAGCTCTCTGGGCACCCAG
ACCTACATCTGCAACGTGAACCACAAGCCT
TCCAACACCAAGGTGGACAAGAAGGTGGA
ACCCAAGTCCTGCGACAAGACCCACACCT
GTCCTCCATGTCCTGCTCCAGAAGCTGCTG
GCGCTCCCTCTGTGTTCCTGTTTCCTCCAAA
GCCTAAGGACACCCTGATGATCTCTCGGAC
CCCTGAAGTGACCTGCGTGGTGGTGGATGT
GTCTCACGAGGACCCAGAAGTGAAGTTCA
ATTGGTACGTGGACGGCGTGGAAGTGCAC
AACGCCAAGACCAAGCCTAGAGAGGAACA
GTACAACTCCACCTACAGAGTGGTGTCCGT
GCTGACCGTGCTGCACCAGGATTGGCTGA
ACGGCAAAGAGTACAAGTGCAAGGTGTCC
AACAAGGCACTGCCCGCTCCTATCGAAAA
GACCATCTCCAAGGCTAAGGGCCAGCCTC
GGGAACCTCAGGTTTACACCCTGCCTCCAT
CTCGGGAAGAGATGACCAAGAACCAGGTG
TCCCTGACCTGCCTCGTGAAGGGCTTCTAC
CCTTCCGATATCGCCGTGGAATGGGAGTCC
AATGCCAGCCTGAGAACAACTACAAGAC
AACCCCTCCTGTGCTGGACTCCGACGGCTC
ATTCTTCCTGTACTCCAAGCTGACAGTGGA
CAAGTCTCGGTGGCAGCAGGGCAACGTGT
TCTCCTGTTCTGTGATGCACGAGGCCCTGC
ACAACCACTACACACAGAAGTCCCTGTCTC
TGTCCCCTGGCAAGTGA |
| 94 | VH-CDR1 | GYTFTNYGVK |
| 95 | VH-CDR2 | WINTYTGNPIYAADFK |
| 96 | VH-CDR3 | FQYGDYRYFDV |
| 97 | AGX-A07 L5
Light chain amino acid | EIILTQSPATLSLSPGERATLSCRANSGISFIN
WYQQKPGQAPRLLIYGTANLASGIPARFGGS
GSGRDFTLTISSLEPEDFAVYYCQQWSSNPLT
FGGGTKVEIKRTVAAPSVFIFPPSDEQLKSGT
ASVVCLLNNFYPREAKVQWKVDNALQSGNS
QESVTEQDSKDSTYSLSSTLTLSKADYEKHK
VYACEVTHQGLSSPVTKSFNRGEC |
| 98 | AGX-A07 L5
Light chain nucleic acid | AAGCTTGCCACCATGGAAACCGACACACT
GCTGCTGTGGGTGCTGTTGTTGTGGGTGCC
AGGATCTACCGGAGAGATCATCCTGACAC
AGAGCCCCGCCACATTGTCTCTGAGTCCTG
GCGAGAGAGCTACCCTGTCCTGTAGAGCC
AACTCCGGCATCTCCTTCATCAACTGGTAT
CAGCAGAAGCCCGGCCAGGCTCCTAGACT
GCTGATCTATGGCACCGCTAACCTGGCCTC
TGGCATCCCTGCTAGATTTGGCGGCTCTGG
CTCTGGCAGAGACTTCACCCTGACCATCTC
TAGCCTGGAACCTGAGGACTTCGCCGTGTA
CTACTGCCAGCAGTGGTCTAGCAACCCTCT
GACCTTTGGCGGAGGCACCAAGGTGGAAA
TCAAGAGAACCGTGGCCGCTCCTTCCGTGT
TCATCTTCCCACCATCTGACGAGCAGCTGA
AGTCTGGCACAGCCTCTGTCGTGTGCCTGC
TGAACAACTTCTACCCTCGGGAAGCCAAG
GTGCAGTGGAAGGTGGACAATGCCCTGCA
GTCCGGCAACTCCCAAGAGTCTGTGACCG
AGCAGGACTCCAAGGACTCTACCTACAGC
CTGTCCTCCACACTGACCCTGTCTAAGGCC
GACTACGAGAAGCACAAGGTGTACGCCTG
TGAAGTGACCCACCAGGGACTGTCTAGCC
CCGTGACCAAGTCTTTCAACCGGGGCGAGT
GCTGA |
| 99 | AGX-A07 L5v1
Light chain amino acid | EIVLTQSPATLSLSPGERATLSCRANSGISFIN
WYQQKPGQAPRLLIYGTANLASGIPARFSGS
GSGRDFTLTISSLEPEDFAVYYCQQWSSNPLT
FGGGTKVEIKRTVAAPSVFIFPPSDEQLKSGT |

TABLE 6-continued

SEQUENCE DESCRIPTION

| SEQ ID NO | Description | Sequence |
|---|---|---|
| | | ASVVCLLNNFYPREAKVQWKVDNALQSGNS QESVTEQDSKDSTYSLSSTLTLSKADYEKHK VYACEVTHQGLSSPVTKSFNRGEC |
| 100 | AGX-A07 L5v1 Light chain nucleic acid | TCTACAGGCGAGATCGTGCTGACCCAGTCT CCTGCCACATTGTCTCTGAGTCCTGGCGAG AGAGCTACCCTGTCCTGTAGAGCCAACTCC GGCATCTCCTTCATCAACTGGTATCAGCAG AAGCCCGGCCAGGCTCCTAGACTGCTGATC TATGGCACCGCTAACCTGGCCTCTGGCATC CCTGCTAGATTTTCCGGCTCTGGCTCTGGC AGAGACTTCACCCTGACCATCTCTAGCCTG GAACCTGAGGACTTCGCCGTGTACTACTGC CAGCAGTGGTCTAGCAACCCTCTGACCTTT GGCGGAGGCACCAAGGTGGAAATCAAGAG AACCGTGGCCGCTCCTTCCGTGTTCATCTT CCCACCATCTGACGAGCAGCTGAAGTCTG GCACAGCCTCTGTCGTGTGCCTGCTGAACA ACTTCTACCCTCGGGAAGCCAAGGTGCAGT GGAAGGTGGACAATGCCCTGCAGTCCGGC AACTCCCAAGAGTCTGTGACCGAGCAGGA CTCCAAGGACTCTACCTACAGCCTGTCCTC CACACTGACCCTGTCTAAGGCCGACTACGA GAAGCACAAGGTGTACGCCTGTGAAGTGA CCCACCAGGGACTGTCTAGCCCCGTGACCA AGTCTTTCAACCGGGGCGAGTGCTGA |
| 101 | AGX-A07 L5v2 Light chain amino acid | EIVLTQSPATLSLSPGERATLSCRAQSGISFIN WYQQKPGQAPRLLIYGTANLASGIPARFSGS GSGRDFTLTISSLEPEDFAVYYCQQWSSNPLT FGGGTKVEIKRTVAAPSVFIFPPSDEQLKSGT ASVVCLLNNFYPREAKVQWKVDNALQSGNS QESVTEQDSKDSTYSLSSTLTLSKADYEKHK VYACEVTHQGLSSPVTKSFNRGEC |
| 102 | AGX-A07 L5v2 Light chain nucleic acid | TCTACAGGCGAGATCGTGCTGACCCAGTCT CCTGCCACATTGTCTCTGAGTCCTGGCGAG AGAGCTACCCTGTCTTGTAGAGCCCAGTCC GGCATCTCCTTCATCAACTGGTATCAGCAG AAGCCCGGCCAGGCTCCTAGACTGCTGATC TATGGCACCGCTAACCTGGCCTCTGGCATC CCTGCTAGATTTTCCGGCTCTGGCTCTGGC AGAGACTTCACCCTGACCATCTCTAGCCTG GAACCTGAGGACTTCGCCGTGTACTACTGC CAGCAGTGGTCTAGCAACCCTCTGACCTTT GGCGGAGGCACCAAGGTGGAAATCAAGAG AACCGTGGCCGCTCCTTCCGTGTTCATCTT CCCACCATCTGACGAGCAGCTGAAGTCTG GCACAGCCTCTGTCGTGTGCCTGCTGAACA ACTTCTACCCTCGGGAAGCCAAGGTGCAGT GGAAGGTGGACAATGCCCTGCAGTCTGGC AACTCCCAAGAGTCTGTGACCGAGCAGGA CTCCAAGGACTCTACCTACAGCCTGTCCTC CACACTGACCCTGTCTAAGGCCGACTACGA GAAGCACAAGGTGTACGCCTGTGAAGTGA CCCACCAGGGACTGTCTAGCCCCGTGACCA AGTCTTTCAACCGGGGCGAGTGCTGA |
| 103 | AGX-A07 L5v3 Light chain amino acid | EIVLTQSPATLSLSPGERATLSCRANSGISFIN WYQQKPGQAPRLLIYGTANLASGIPARFSGS GSGRDFTLTISSLEPEDFAVYYCQQYSSNPLT FGGGTKVEIKRTVAAPSVFIFPPSDEQLKSGT ASVVCLLNNFYPREAKVQWKVDNALQSGNS QESVTEQDSKDSTYSLSSTLTLSKADYEKHK VYACEVTHQGLSSPVTKSFNRGEC |
| 104 | AGX-A07 L5v3 Light chain nucleic acid | TCTACAGGCGAGATCGTGCTGACCCAGTCT CCTGCCACATTGTCTCTGAGTCCTGGCGAG AGAGCTACCCTGTCCTGTAGAGCCAACTCC GGCATCTCCTTCATCAACTGGTATCAGCAG AAGCCCGGCCAGGCTCCTAGACTGCTGATC TATGGCACCGCTAACCTGGCCTCTGGCATC CCTGCTAGATTTTCCGGCTCTGGCTCTGGC AGAGACTTCACCCTGACCATCTCTAGCCTG GAACCTGAGGACTTCGCCGTGTACTACTGC CAGCAGTACAGCAGCAACCCTCTGACCTTT GGCGGAGGCACCAAGGTGGAAATCAAGAG AACCGTGGCCGCTCCTTCCGTGTTCATCTT CCCACCATCTGACGAGCAGCTGAAGTCTG GCACAGCCTCTGTCGTGTGCCTGCTGAACA ACTTCTACCCTCGGGAAGCCAAGGTGCAGT |

TABLE 6-continued

SEQUENCE DESCRIPTION

| SEQ ID NO | Description | Sequence |
|---|---|---|
| | | GGAAGGTGGACAATGCCCTGCAGTCCGGC<br>AACTCCCAAGAGTCTGTGACCGAGCAGGA<br>CTCCAAGGACTCTACCTACAGCCTGTCCTC<br>CACACTGACCCTGTCTAAGGCCGACTACGA<br>GAAGCACAAGGTGTACGCCTGTGAAGTGA<br>CCCACCAGGGACTGTCTAGCCCCGTGACCA<br>AGTCTTTCAACCGGGGCGAGTGCTGA |
| 105 | AGX-A07 L5v4<br>Light chain amino acid | EIVLTQSPATLSLSPGERATLSCRAQSGISFIN<br>WYQQKPGQAPRLLIYGTANLASGIPARFSGS<br>GSGRDFTLTISSLEPEDFAVYYCQQYSSNPLT<br>FGGGTKVEIKRTVAAPSVFIFPPSDEQLKSGT<br>ASVVCLLNNFYPREAKVQWKVDNALQSGNS<br>QESVTEQDSKDSTYSLSSTLTLSKADYEKHK<br>VYACEVTHQGLSSPVTKSFNRGEC |
| 106 | AGX-A07 L5v4<br>Light chain nucleic acid | TCTACAGGCGAGATCGTGCTGACCCAGTCT<br>CCTGCCACATTGTCTCTGAGTCCTGGCGAG<br>AGAGCTACCCTGTCTTGTAGAGCCCAGTCC<br>GGCATCTCCTTCATCAACTGGTATCAGCAG<br>AAGCCCGGCCAGGCTCCTAGACTGCTGATC<br>TATGGCACCGCTAACCTGGCCTCTGGCATC<br>CCTGCTAGATTTTCCGGCTCTGGCTCTGGC<br>AGAGACTTCACCCTGACCATCTCTAGCCTG<br>GAACCTGAGGACTTCGCCGTGTACTACTGC<br>CAGCAGTACAGCAGCAACCCTCTGACCTTT<br>GGCGGAGGCACCAAGGTGGAAATCAAGAG<br>AACCGTGGCCGCTCCTTCCGTGTTCATCTT<br>CCCACCATCTGACGAGCAGCTGAAGTCTG<br>GCACAGCCTCTGTCGTGTGCCTGCTGAACA<br>ACTTCTACCCTCGGGAAGCCAAGGTGCAGT<br>GGAAGGTGGACAATGCCCTGCAGTCTGGC<br>AACTCCCAAGAGTCTGTGACCGAGCAGGA<br>CTCCAAGGACTCTACCTACAGCCTGTCCTC<br>CACACTGACCCTGTCTAAGGCCGACTACGA<br>GAAGCACAAGGTGTACGCCTGTGAAGTGA<br>CCCACCAGGGACTGTCTAGCCCCGTGACCA<br>AGTCTTTCAACCGGGGCGAGTGCTGA |
| 107 | VL-CDR1 (variant 1) | RANSGISFIN |
| 108 | VL-CDR1 (variant 2) | RAQSGISFIN |
| 109 | VL-CDR2 | GTANLAS |
| 110 | VL-CDR3 (variant 1) | QQWSSNPLT |
| 111 | VL-CDR3 (variant 2) | QQYSSNPLT |
| Humanized AGX-A01 sequences | | |
| 112 | AGX-A01 H1<br>Heavy chain amino acid | EVQLVESGGGLVKPGGSLRLSCAASGFTFSS<br>FAMSWVRQAPGKGLEWVSTISSGSIYIYYTD<br>GVKGRFTISRDNAKNSLYLQMNSLRAEDTA<br>VYYCARRGIYYGYDGYAMDYWGQGTLVTV<br>SSASTKGPSVFPLAPSSKSTSGGTAALGCLVK<br>DYFPEPVTVSWNSGALTSGVHTFPAVLQSSG<br>LYSLSSWTVPSSSLGTQTYICNVNHKPSNTK<br>VDKKVEPKSCDKTHTCPPCPAPEAAGAPSVF<br>LFPPKPKDTLMISRTPEVTCVVVDVSHEDPE<br>VKFNWYVDGVEVHNAKTKPREEQYNSTYR<br>VVSVLTVLHQDWLNGKEYKCKVSNKALPAP<br>IEKTISKAKGQPREPQVYTLPPSREEMTKNQV<br>SLTCLVKGFYPSDIAVEWESNGQPENNYKTT<br>PPVLDSDGSFFLYSKLTVDKSRWQQGNVFSC<br>SVMHEALHNHYTQKSLSLSPGK |
| 113 | AGX-A01 H1<br>Heavy chain nucleic acid | GAGGTGCAGCTGGTTGAATCTGGCGGAGG<br>ACTTGTGAAGCCTGGCGGCTCTCTGAGACT<br>GTCTTGTGCCGCCTCTGGCTTCACCTTCTCC<br>AGCTTTGCCATGTCCTGGGTCCGACAGGCT<br>CCTGGCAAAGGACTGGAATGGGTGTCCAC<br>CATCTCCTCCGGCTCCATCTACATCTACTA<br>CACCGACGGCGTGAAGGGCAGATTCACCA<br>TCAGCAGAGACAACGCCAAGAACTCCCTG<br>TACCTGCAGATGAACAGCCTGAGAGCCGA<br>GGACACCGCCGTGTACTATTGTGCCAGACG<br>GGGCATCTACTATGGCTACGACGGCTACGC<br>TATGGACTATTGGGGACAGGGCACACTGG<br>TCACCGTGTCCTCTGCTTCTACCAAGGGAC<br>CCAGCGTGTTCCCTCTGGCTCCTTCCTCTA<br>AATCCACCTCTGGCGGAACCGCTGCTCTGG<br>GCTGTCTGGTCAAGGATTACTTCCCTGAGC<br>CTGTGACCGTGTCCTGGAACTCTGGTGCTC |

TABLE 6-continued

SEQUENCE DESCRIPTION

| SEQ ID NO | Description | Sequence |
|---|---|---|
| | | TGACATCCGGCGTGCACACCTTTCCAGCTG<br>TGCTGCAGTCCTCTGGCCTGTACTCTCTGT<br>CCTCTGTCGTGACCGTGCCTTCTAGCTCTCT<br>GGGCACCCAGACCTACATCTGCAACGTGA<br>ACCACAAGCCTTCCAACACCAAGGTGGAC<br>AAGAAGGTGGAACCCAAGTCCTGCGACAA<br>GACCCACACCTGTCCTCCATGTCCTGCTCC<br>AGAAGCTGCTGGCGCTCCCTCTGTGTTCCT<br>GTTTCCTCCAAAGCCTAAGGACACCCTGAT<br>GATCTCTCGGACCCCTGAAGTGACCTGCGT<br>GGTGGTGGATGTGTCTCACGAGGACCCAG<br>AAGTGAAGTTCAATTGGTACGTGGACGGC<br>GTGGAAGTGCACAACGCCAAGACCAAGCC<br>TAGAGAGGAACAGTACAACTCCACCTACA<br>GAGTGGTGTCCGTGCTGACCGTGCTGCACC<br>AGGATTGGCTGAACGGCAAAGAGTACAAG<br>TGCAAGGTGTCCAACAAGGCACTGCCCGC<br>TCCTATCGAAAAGACCATCTCCAAGGCTAA<br>GGGCCAGCCTCGGGAACCTCAGGTTTACA<br>CCCTGCCTCCATCTCGGGAAGAGATGACCA<br>AGAACCAGGTGTCCCTGACCTGCCTCGTGA<br>AGGGCTTCTACCCTTCCGATATCGCCGTGG<br>AATGGGAGTCCAATGGCCAGCCTGAGAAC<br>AACTACAAGACAACCCCTCCTGTGCTGGAC<br>TCCGACGGCTCATTCTTCCTGTACTCCAAG<br>CTGACAGTGGACAAGTCTCGGTGGCAGCA<br>GGGCAACGTGTTCTCCTGTTCTGTGATGCA<br>CGAGGCCCTGCACAACCACTACACACAGA<br>AGTCCCTGTCTCTGTCCCCTGGCAAGTGA |
| 114 | AGX-A01 H1v1<br>Heavy chain amino acid | EVQLVESGGGLVKPGGSLRLSCAASGFTFSS<br>FAMSWVRQAPGKGLEWVSTISSGSIYIYYTD<br>SVKGRFTISRDNAKNSLYLQMNSLRAEDTAV<br>YYCARRGIYYGYEGYAMDYWGQGTLVTVS<br>SASTKGPSVFPLAPSSKSTSGGTAALGCLVK<br>DYFPEPVTVSWNSGALTSGVHTFPAVLQSSG<br>LYSLSSWTVPSSSLGTQTYICNVNHKPSNTK<br>VDKKVEPKSCDKTHTCPPCPAPEAAGAPSVF<br>LFPPKPKDTLMISRTPEVTCVVVDVSHEDPE<br>VKFNWYVDGVEVHNAKTKPREEQYNSTYR<br>VVSVLTVLHQDWLNGKEYKCKVSNKALPAP<br>IEKTISKAKGQPREPQVYTLPPSREEMTKNQV<br>SLTCLVKGFYPSDIAVEWESNGQPENNYKTT<br>PPVLDSDGSFFLYSKLTVDKSRWQQGNVFSC<br>SVMHEALHNHYTQKSLSLSPGK |
| 115 | VH-CDR1 | GFTFSSFAMS |
| 116 | VH-CDR2 (variant 1) | TISSGSIYIYYTDGVKG |
| 117 | VH-CDR2 (variant 2) | TISSGSIYIYYTDSVKG |
| 118 | VH-CDR3 (variant 1) | RGIYYGYDGYAMDY |
| 119 | VH-CDR3 (variant 2) | RGIYYGYEGYAMDY |
| 120 | VH-CDR3 (variant 3) | RGIYYGYSGYAMDY |
| 121 | VH-CDR3 (variant 4) | RGIYYGYAGYAMDY |
| 122 | AGX-A01 L10<br>Light chain amino acid | AIVLTQSPGTLSLSPGERATLSCRSSQSLVHS<br>NGNTYLHWYMQKPGQAPRVLIYKVSNRFSG<br>IPDRFSGSGSGTDFTLTISRLEPDDFAIYYCSQ<br>STHIPLAFGQGTKLEIKRTVAAPSVFIFPPSDE<br>QLKSGTASVVCLLNNFYPREAKVQWKVDN<br>ALQSGNSQESVTEQDSKDSTYSLSSTLTLSKA<br>DYEKHKVYACEVTHQGLSSPVTKSFNRGEC |
| 123 | AGX-A01 L10<br>Light chain nucleic acid | GCCATCGTGTTGACCCAGTCTCCAGGCACA<br>TTGTCTCTGAGCCCTGGCGAGAGAGCTACC<br>CTGTCCTGCAGATCTTCTCAGTCCCTGGTG<br>CACTCCAACGGCAACACCTACCTGCACTGG<br>TACATGCAGAAGCCCGGACAGGCTCCCAG<br>AGTGCTGATCTACAAGGTGTCCAACCGGTT<br>CTCTGGCATCCCCGACAGATTTTCCGGCTC<br>TGGCTCTGGCACCGACTTCACCCTGACCAT<br>CTCTAGACTGGAACCCGACGACTTCGCCAT<br>CTACTACTGCTCCCAGTCCACACACATCCC<br>TCTGGCTTTTGGCCAGGGCACCAAGCTGGA<br>AATCAAGAGAACCGTGGCCGCTCCTTCCGT<br>GTTCATCTTCCCACCATCTGACGAGCAGCT<br>GAAGTCCGGCACAGCTTCTGTCGTGTGCCT<br>GCTGAACAACTTCTACCCTCGGGAAGCCA<br>AGGTGCAGTGGAAGGTGGACAATGCCCTG<br>CAGTCCGGCAACTCCCAAGAGTCTGTGACC<br>GAGCAGGACTCCAAGGACTCTACCTACAG |

TABLE 6-continued

| SEQ ID NO | Description | Sequence |
|---|---|---|
| | | CCTGTCCTCCACACTGACCCTGTCTAAGGC |
| | | CGACTACGAGAAGCACAAGGTGTACGCCT |
| | | GTGAAGTGACCCACCAGGGCCTGTCTAGC |
| | | CCTGTGACCAAGTCTTTCAACCGGGGCGAG |
| | | TGTTGA |
| 124 | VL-CDR1 (variant 1) | RSSQSLVHSNGNTYLH |
| 125 | VL-CDR1 (variant 2) | RSSQSLVHSSGNTYLH |
| 126 | VL-CDR1 (variant 3) | RSSQSLVHSTGNTYLH |
| 127 | VL-CDR1 (variant 4) | RSSQSLVHSQGNTYLH |
| 128 | VL-CDR2 | KVSNRFS |
| 129 | VL-CDR3 | SQSTHIPLA |

Humanized AGX-A07 H2v1L5v2

| SEQ ID NO | Description | Sequence |
|---|---|---|
| 130 | AGX-A07 H2v1 Heavy chain variable region amino acid | EVQLVQSGAEVKKPGASVKVSCKASGYTFT NYGVKWVRQAPGQGLEWMGWINTYTGNPI YAADFKGRVTMTTDTSTSTAYMELRSLRSD DTAVYYCVRFQYGDYRYFDVWGQGTLVTV SS |
| 131 | AGX-A07 H2v1L5v2 Light chain variable region amino acid | EIVLTQSPATLSLSPGERATLSCRAQSGISFIN WYQQKPGQAPRLLIYGTANLASGIPARFSGS GSGRDFTLTISSLEPEDFAVYYCQQWSSNPLT FGGGTKVEIK |

Humanized AGX-A07 H2L5

| SEQ ID NO | Description | Sequence |
|---|---|---|
| 132 | AGX-A07 H2 Heavy chain variable region amino acid | QVQLVQSGAEVKKPGASVKVSCKASGYTFT NYGVKWVRQAPGQDLEWMGWINTYTGNPI YAADFKGRVTMTTDTSTSTAFMELRSLRSD DTAVYYCVRFQYGDYRYFDVWGQGTLVTV SS |
| 133 | AGX-A07 L5 Light chain variable region amino acid | EIILTQSPATLSLSPGERATLSCRANSGISFIN WYQQKPGQAPRLLIYGTANLASGIPARFGGS GSGRDFTLTISSLEPEDFAVYYCQQWSSNPLT FGGGTKVEIK |

Fc Region Sequences

| SEQ ID NO | Description | Sequence |
|---|---|---|
| 135 | IgG1 L234A/L235A/G237A | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAPEAAGAPSVFL FPPKPKDTLMISRTPEVTCVVVDVSHEDPEV KFNWYVDGVEVHNAKTKPREEQYNSTYRV VSVLTVLHQDWLNGKEYKCKVSNKALPAPI EKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |
| 136 | IgG1 L234A/L235A/G237A + N297C | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAPEAAGAPSVFL FPPKPKDTLMISRTPEVTCVVVDVSHEDPEV KFNWYVDGVEVHNAKTKPREEQCSTYRV VSVLTVLHQDWLNGKEYKCKVSNKALPAPI EKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |
| 137 | IgG1 L234A/L235A/G237A + P331G | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAPEAAGAPSVFL FPPKPKDTLMISRTPEVTCVVVDVSHEDPEV KFNWYVDGVEVHNAKTKPREEQYNSTYRV VSVLTVLHQDWLNGKEYKCKVSNKALPAGI EKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |
| 138 | IgG1 L234A/L235A/G237A + N297C/P331G | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAPEAAGAPSVFL FPPKPKDTLMISRTPEVTCVVVDVSHEDPEV |

TABLE 6-continued

SEQUENCE DESCRIPTION

| SEQ ID NO | Description | Sequence |
|---|---|---|
| | | KFNWYVDGVEVHNAKTKPREEQY*C*STYRV VSVLTVLHQDWLNGKEYKCKVSNKALPA*G*I EKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |
| 139 | IgG1 L234A/L235A/G237A + K322A/P331G | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAPE*AAGA*PSVFL FPPKPKDTLMISRTPEVTCVVVDVSHEDPEV KFNWYVDGVEVHNAKTKPREEQYNSTYRV VSVLTVLHQDWLNGKEYKC*A*VSNKALPA*G*I EKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |
| 140 | IgG1 L234A/L235A/G237A + E233P/P331G | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAP*PAAGA*PSVFL FPPKPKDTLMISRTPEVTCVVVDVSHEDPEV KFNWYVDGVEVHNAKTKPREEQYNSTYRV VSVLTVLHQDWLNGKEYKCKVSNKALPA*G*I EKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |
| 141 | IgG1 L234A/L235A/G237A + E233P/N297C | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAP*EAAGA*PSVFL FPPKPKDTLMISRTPEVTCVVVDVSHEDPEV KFNWYVDGVEVHNAKTKPREEQY*C*STYRV VSVLTVLHQDWLNGKEYKCKVSNKALPAPI EKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |
| 142 | IgG1 L234A/L235A/G237A + N297C/K322A/P331G | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAP*EAAGA*PSVFL FPPKPKDTLMISRTPEVTCVVVDVSHEDPEV KFNWYVDGVEVHNAKTKPREEQY*C*STYRV VSVLTVLHQDWLNGKEYKC*A*VSNKALPA*G*I EKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |
| 143 | IgG1 L234A/L235A/G237A + E233P/N297C/P331G | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAP*EAAGA*PSVFL FPPKPKDTLMISRTPEVTCVVVDVSHEDPEV KFNWYVDGVEVHNAKTKPREEQY*C*STYRV VSVLTVLHQDWLNGKEYKCKVSNKALPA*G*I EKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |
| 144 | IgG1 L234A/L235A/G237A + E233P/D265A/N297C/K322A/P331G | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAP*EAAGA*PSVFL FPPKPKDTLMISRTPEVTCVVVAVSHEDPEV KFNWYVDGVEVHNAKTKPREEQY*C*STYRV VSVLTVLHQDWLNGKEYKC*A*VSNKALPA*G*I EKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |

TABLE 6-continued

| SEQ ID NO | Description | Sequence |
|---|---|---|
| 145 | IgG1 L234A/L235A/G237A + E233P/D265A/N297C/K322A/P331G-PGKKP(SEQ ID NO: 162) | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAP*EAAGA*PSVFL FPPKPKDTLMISRTPEVTCVVVDVSHEDPEV KFNWYVDGVEVHNAKTKPREEQY*C*STYRV VSVLTVLHQDWLNGKEYKC*A*VSNKALPA*G*I EKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGKKP |
| 146 | IgG4 S228P(sequence includes AGX-A07 H2v1 heavy chain variable region amino acid) | EVQLVQSGAEVKKPGASVKVSCKASGYTFT NYGVKWVRQAPGQGLEWMGWINTYTGNPI YAADFKGRVTMTTDTSTSTAYMELRSLRSD DTAVYYCVRFQYGDYRYFDVWGQGTLVTV SSASTKGPSVFPLAPCSRSTSESTAALGCLVK DYFPEPVTVSWNSGALTSGVHTFPAVLQSSG LYSLSSVVTVPSSSLGTKTYTCNVDHKPSNT KVDKRVESKYGPPCP*P*CPAPEFLGGPSVFLFP PKPKDTLMISRTPEVTCVVVDVSQEDPEVQF NWYVDGVEVHNAKTKPREEQFNSTYRVVS VLTVLHQDWLNGKEYKCKVSNKGLPSSIEK TISKAKGQPREPQVYTLPPSQEEMTKNQVSL TCLVKGFYPSDIAVEWESNGQPENNYKTTPP VLDSDGSFFLYSRLTVDKSRWQEGNVFSCSV MHEALHNHYTQKSLSLSLGK |
| 147 | IgG4 S228P/L235E (sequence includes AGX-A07 H2v1 heavy chain variable region amino acid) | EVQLVQSGAEVKKPGASVKVSCKASGYTFT NYGVKWVRQAPGQGLEWMGWINTYTGNPI YAADFKGRVTMTTDTSTSTAYMELRSLRSD DTAVYYCVRFQYGDYRYFDVWGQGTLVTV SSASTKGPSVFPLAPCSRSTSESTAALGCLVK DYFPEPVTVSWNSGALTSGVHTFPAVLQSSG LYSLSSVVTVPSSSLGTKTYTCNVDHKPSNT KVDKRVESKYGPPCP*P*CPAPEF*E*GGPSVFLFP PKPKDTLMISRTPEVTCVVVDVSQEDPEVQF NWYVDGVEVHNAKTKPREEQFNSTYRVVS VLTVLHQDWLNGKEYKCKVSNKGLPSSIEK TISKAKGQPREPQVYTLPPSQEEMTKNQVSL TCLVKGFYPSDIAVEWESNGQPENNYKTTPP VLDSDGSFFLYSRLTVDKSRWQEGNVFSCSV MHEALHNHYTQKSLSLSLGK |
| 148 | IgG4 S228P/L235E/N297C (sequence includes AGX-A07 H2v1 heavy chain variable region amino acid) | EVQLVQSGAEVKKPGASVKVSCKASGYTFT NYGVKWVRQAPGQGLEWMGWINTYTGNPI YAADFKGRVTMTTDTSTSTAYMELRSLRSD DTAVYYCVRFQYGDYRYFDVWGQGTLVTV SSASTKGPSVFPLAPCSRSTSESTAALGCLVK DYFPEPVTVSWNSGALTSGVHTFPAVLQSSG LYSLSSVVTVPSSSLGTKTYTCNVDHKPSNT KVDKRVESKYGPPCP*P*CPAPEF*E*GGPSVFLFP PKPKDTLMISRTPEVTCVVVDVSQEDPEVQF NWYVDGVEVHNAKTKPREEQF*C*STYRVVSV LTVLHQDWLNGKEYKCKVSNKGLPSSIEKTI SKAKGQPREPQVYTLPPSQEEMTKNQVSLTC LVKGFYPSDIAVEWESNGQPENNYKTTPPVL DSDGSFFLYSRLTVDKSRWQEGNVFSCSVM HEALHNHYTQKSLSLSLGK |
| 149 | IgG4 S228P/F234A/L235E/N297C (sequence includes AGX-A07 H2v1 heavy chain variable region amino acid) | EVQLVQSGAEVKKPGASVKVSCKASGYTFT NYGVKWVRQAPGQGLEWMGWINTYTGNPI YAADFKGRVTMTTDTSTSTAYMELRSLRSD DTAVYYCVRFQYGDYRYFDVWGQGTLVTV SSASTKGPSVFPLAPCSRSTSESTAALGCLVK DYFPEPVTVSWNSGALTSGVHTFPAVLQSSG LYSLSSVVTVPSSSLGTKTYTCNVDHKPSNT KVDKRVESKYGPPCP*P*CPAPE*AE*GGPSVFLF PPKPKDTLMISRTPEVTCVVVDVSQEDPEVQ FNWYVDGVEVHNAKTKPREEQF*C*STYRVVS VLTVLHQDWLNGKEYKCKVSNKGLPSSIEK TISKAKGQPREPQVYTLPPSQEEMTKNQVSL TCLVKGFYPSDIAVEWESNGQPENNYKTTPP VLDSDGSFFLYSRLTVDKSRWQEGNVFSCSV MHEALHNHYTQKSLSLSLGK |

TABLE 6-continued

SEQUENCE DESCRIPTION

| SEQ ID NO | Description | Sequence |
|---|---|---|
| 150 | IgG4 S228P/L235E/N297C-LGKKP (SEQ ID NO: 163) (sequence includes AGX-A07 H2v1 heavy chain variable region amino acid) | EVQLVQSGAEVKKPGASVKVSCKASGYTFT NYGVKWVRQAPGQGLEWMGWINTYTGNPI YAADFKGRVTMTTDTSTSTAYMELRSLRSD DTAVYYCVRFQYGDYRYFDVWGQGTLVTV SSASTKGPSVFPLAPCSRSTSESTAALGCLVK DYFPEPVTVSWNSGALTSGVHTFPAVLQSSG LYSLSSVVTVPSSSLGTKTYTCNVDHKPSNT KVDKRVESKYGPPCP*P*CPAPEF*E*GGPSVFLFP PKPKDTLMISRTPEVTCVVVDVSQEDPEVQF NWYVDGVEVHNAKTKPREEQF*C*STYRVVSV LTVLHQDWLNGKEYKCKVSNKGLPSSIEKTI SKAKGQPREPQVYTLPPSQEEMTKNQVSLTC LVKGFYPSDIAVEWESNGQPENNYKTTPPVL DSDGSFFLYSRLTVDKSRWQEGNVFSCSVM HEALHNHYTQKSLSLSLGKK*P* |
| 151 | IgG1 M252Y/S254T/T256E | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAPELLGGPSVFLF PPKPKDTL*YITRE*PEVTCVVVDVSHEDPEVKF NWYVDGVEVHNAKTKPREEQYNSTYRVVS VLTVLHQDWLNGKEYKCKVSNKALPAPIEK TISKAKGQPREPQVYTLPPSREEMTKNQVSL TCLVKGFYPSDIAVEWESNGQPENNYKTTPP VLDSDGSFFLYSKLTVDKSRWQQGNVFSCS VMHEALHNHYTQKSLSLSPGK |
| 152 | IgG1 T252Q/M428L | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAPELLGGPSVFLF PPKPKD*Q*LMISRTPEVTCVVVDVSHEDPEVK FNWYVDGVEVHNAKTKPREEQYNSTYRVV SVLTVLHQDWLNGKEYKCKVSNKALPAPIE KTISKAKGQPREPQVYTLPPSREEMTKNQVS LTCLVKGFYPSDIAVEWESNGQPENNYKTTP PVLDSDGSFFLYSKLTVDKSRWQQGNVFSCS V*L*HEALHNHYTQKSLSLSPGK |
| 153 | IgG1 M428L/N434S | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAPELLGGPSVFLF PPKPKDTLMISRTPEVTCVVVDVSHEDPEVK FNWYVDGVEVHNAKTKPREEQYNSTYRVV SVLTVLHQDWLNGKEYKCKVSNKALPAPIE KTISKAKGQPREPQVYTLPPSREEMTKNQVS LTCLVKGFYPSDIAVEWESNGQPENNYKTTP PVLDSDGSFFLYSKLTVDKSRWQQGNVFSCS V*L*HEALH*S*HYTQKSLSLSPGK |
| 154 | IgG4 T250Q/M428L (sequence includes AGX-A07 H2v1 heavy chain variable region amino acid) | EVQLVQSGAEVKKPGASVKVSCKASGYTFT NYGVKWVRQAPGQGLEWMGWINTYTGNPI YAADFKGRVTMTTDTSTSTAYMELRSLRSD DTAVYYCVRFQYGDYRYFDVWGQGTLVTV SSASTKGPSVFPLAPCSRSTSESTAALGCLVK DYFPEPVTVSWNSGALTSGVHTFPAVLQSSG LYSLSSVVTVPSSSLGTKTYTCNVDHKPSNT KVDKRVESKYGPPCPSCPAPEFLGGPSVFLFP PKPKD*Q*LMISRTPEVTCVVVDVSQEDPEVQF NWYVDGVEVHNAKTKPREEQFNSTYRVVS VLTVLHQDWLNGKEYKCKVSNKGLPSSIEK TISKAKGQPREPQVYTLPPSQEEMTKNQVSL TCLVKGFYPSDIAVEWESNGQPENNYKTTPP VLDSDGSFFLYSRLTVDKSRWQEGNVFSCSV *L*HEALHNHYTQKSLSLSLGK |
| 155 | IgG4 M428L/N434S (sequence includes AGX-A07 H2v1 heavy chain region amino acid) | EVQLVQSGAEVKKPGASVKVSCKASGYTFT NYGVKWVRQAPGQGLEWMGWINTYTGNPI YAADFKGRVTMTTDTSTSTAYMELRSLRSD DTAVYYCVRFQYGDYRYFDVWGQGTLVTV SSASTKGPSVFPLAPCSRSTSESTAALGCLVK DYFPEPVTVSWNSGALTSGVHTFPAVLQSSG LYSLSSVVTVPSSSLGTKTYTCNVDHKPSNT KVDKRVESKYGPPCPSCPAPEFLGGPSVFLFP PKPKDTLMISRTPEVTCVVVDVSQEDPEVQF NWYVDGVEVHNAKTKPREEQFNSTYRVVS VLTVLHQDWLNGKEYKCKVSNKGLPSSIEK TISKAKGQPREPQVYTLPPSQEEMTKNQVSL TCLVKGFYPSDIAVEWESNGQPENNYKTTPP |

TABLE 6-continued

SEQUENCE DESCRIPTION

| SEQ ID NO | Description | Sequence |
|---|---|---|
| 156 | IgG1 M252Y/S254T/T256E (sequence includes AGXA07 H2v1 heavy chain variable region amino acid) | VLDSDGSFFLYSRLTVDKSRWQEGNVFSCSV LHEALHSHYTQKSLSLSLGK EVQLVQSGAEVKKPGASVKVSCKASGYTFT NYGVKWVRQAPGQGLEWMGWINTYTGNPI YAADFKGRVTMTTDTSTSTAYMELRSLRSD DTAVYYCVRFQYGDYRYFDVWGQGTLVTV SSASTKGPSVFPLAPSSKSTSGGTAALGCLVK DYFPEPVTVSWNSGALTSGVHTFPAVLQSSG LYSLSSWTVPSSSLGTQTYICNVNHKPSNTK VDKKVEPKSCDKTHTCPPCPAPELLGGPSVF LFPPKPKDTLYITRE PEVTCVVVDVSHEDPEV KFNWYVDGVEVHNAKTKPREEQYNSTYRV VSVLTVLHQDWLNGKEYKCKVSNKALPAPI EKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. An antibody-drug conjugate comprising (1) an anti-transmembrane 4 L six family member 1 (TM4SF1) antibody or an antigen binding fragment thereof conjugated to (2) a therapeutic molecule via a linker, wherein the anti-TMA4SF1 antibody or the antigen binding fragment thereof comprises a human IgG1 Fc region comprising (1) a cysteine residue at position N297, or (2) a cysteine residue at position N297 and one or more mutations selected from the group consisting of M252Y, S254T, and T256E; as numbered by the EU index as set forth in Kabat, wherein the linker comprises (1) acetamide and (2) a spacer of C6 alkylene, wherein the therapeutic molecule is conjugated to the cysteine at position 297, and wherein the anti-TM4SF1 antibody or the antigen binding fragment thereof comprises:

(a) a heavy chain comprising a CDR1, CDR2, and CDR3 domain comprising the amino acid sequence of SEQ ID NOs: 6, 7, and 8, respectively; and a light chain comprising a CDR1, CDR2, and CDR3 domain comprising the amino acid sequence of SEQ ID NOs: 12, 13, and 14, respectively;

(b) a heavy chain comprising a CDR1, CDR2, and CDR3 domain comprising the amino acid sequence of SEQ ID NOs: 18, 19, and 20, respectively; and a light chain comprising a CDR1, CDR2, and CDR3 domain comprising the amino acid sequence of SEQ ID NOs: 24, 25, and 26, respectively;

(c) a heavy chain comprising a CDR1, CDR2, and CDR3 domain comprising the amino acid sequence of SEQ ID NOs: 30, 31, and 32, respectively; and a light chain comprising a CDR1, CDR2, and CDR3 domain comprising the amino acid sequence of SEQ ID NOs: 36, 37, and 38, respectively;

(d) a heavy chain comprising a CDR1, CDR2, and CDR3 domain comprising the amino acid sequence of SEQ ID NOs: 42, 43, and 44, respectively; and a light chain comprising a CDR1, CDR2, and CDR3 domain comprising the amino acid sequence of SEQ ID NOs: 48, 49, and 50, respectively;

(e) a heavy chain comprising a CDR1, CDR2, and CDR3 domain comprising the amino acid sequence of SEQ ID NOs: 54, 55, and 56, respectively; and a light chain comprising a CDR1, CDR2, and CDR3 domain comprising the amino acid sequence of SEQ ID NOs: 60, 61, and 62, respectively;

(f) a heavy chain comprising a CDR1, CDR2, and CDR3 domain comprising the amino acid sequence of SEQ ID NOs: 66, 67, and 68, respectively; and a light chain comprising a CDR1, CDR2, and CDR3 domain comprising the amino acid sequence of SEQ ID NOs: 72, 73, and 74, respectively;

(g) a heavy chain comprising a CDR1, CDR2, and CDR3 domain comprising the amino acid sequence of SEQ ID NOs: 78, 79, and 80, respectively; and a light chain comprising a CDR1, CDR2, and CDR3 domain comprising the amino acid sequence of SEQ ID NOs: 84, 85, and 86, respectively;

(h) a heavy chain comprising a CDR1, CDR2, and CDR3 domain comprising the amino acid sequence of SEQ ID NOs: 94, 95, and 96, respectively; and a light chain comprising a CDR1 comprising the amino acid sequence of SEQ ID NOs: 107 or 108, a CDR2 comprising the amino acid sequence of SEQ ID NO: 109, a CDR3 comprising the amino acid sequence of SEQ ID NOs: 110 or 111; or (i) a heavy chain comprising a CDR1 domain comprising the amino acid sequence of SEQ ID NO: 115, a CDR2 domain comprising the amino acid sequence of SEQ ID NOs: 116 or 117, a CDR3 domain comprising the amino acid sequence of SEQ ID NOs: 118, 119, 120, or 121; and a light chain comprising a CDR1 domain comprising the amino acid sequence of SEQ ID NOs: 124, 125, 126, or 127, a CDR2 domain comprising the amino acid sequence of SEQ ID NO: 128, a CDR3 domain comprising the amino acid sequence of SEQ ID NO: 129.

2. The antibody-drug conjugate of claim 1, wherein the anti-TM4SF1 antibody or the antigen binding fragment thereof comprises:

(A) the heavy chain in (a) comprising the amino acid sequence of SEQ ID NO: 3, and the light chain in (a) comprising the amino acid sequence of SEQ ID NO: 9;

(B) the heavy chain in (b) comprising the amino acid sequence of SEQ ID NO: 15, and the light chain in (b) comprising the amino acid sequence of SEQ ID NO: 21;

(C) the heavy chain in (c) comprising the amino acid sequence of SEQ ID NO: 27, and the light chain in (c) comprising the amino acid sequence of SEQ ID NO: 33;

(D) the heavy chain in (d) comprising the amino acid sequence of SEQ ID NO: 39, and the light chain in (d) comprising the amino acid sequence of SEQ ID NO: 45;

(E) the heavy chain in (e) comprising the amino acid sequence of SEQ ID NO: 51, and the light chain in (e) comprising the amino acid sequence of SEQ ID NO: 57;

(F) the heavy chain in (f) comprising the amino acid sequence of SEQ ID NO: 63, and the light chain in (f) comprising the amino acid sequence of SEQ ID NO: 69;

(G) the heavy chain in (g) comprising the amino acid sequence of SEQ ID NO: 75, and the light chain in (g) comprising the amino acid sequence of SEQ ID NO: 81;

(H) the heavy chain in (h) comprising the amino acid sequence of SEQ ID NO: 90, 92, 130, or 132, and the light chain in (h) comprising the amino acid sequence of SEQ ID NO: 97, 99, 101, 103, 105, 131, or 133; or (I) the heavy chain in (i) comprising the amino acid sequence of SEQ ID NO: 1, 112, or 114, and the light chain in (i) comprising the amino acid sequence of SEQ ID NO: 2 or 122.

3. The antibody-drug conjugate of claim 1 or claim 2, wherein the therapeutic molecule comprises a radioactive isotope, a cytotoxic agent, a chemotherapeutic agent, a prodrug activating enzyme, an anti-hormonal agent, or any combination thereof.

4. The antibody-drug conjugate of claim 1 or claim 2, wherein the therapeutic molecule comprises at least one of a V-ATPase inhibitor, a pro-apoptotic agent, a B-cell lymphoma 2 (Bcl2) inhibitor, a myeloid cell leukemia 1 (MCL1) inhibitor, a HSP90 inhibitor, an inhibitor of apoptosis protein (IAP) inhibitor, an mTor inhibitor, a microtubule stabilizer, a microtubule destabilizer, an auristatin, a dolastatin, a maytansinoid, a MetAP (methionine aminopeptidase), an inhibitor of nuclear export of protein chromosome region maintenance 1 (CRM1), a dipeptidyl peptidase IV (DPPIV) inhibitor, a proteasome inhibitor, an inhibitor of phosphoryl transfer reactions in mitochondria, a protein synthesis inhibitor, a kinase inhibitor, a cyclin-dependent kinase 2 (CDK2) inhibitor, a cyclin-dependent kinase 9 (CDK9) inhibitor, a kinesin inhibitor, an histone deacetylase (HDAC) inhibitor, a DNA damaging agent, a DNA alkylating agent, a DNA intercalator, a DNA minor groove binder, a dihydrofolate reductase (DHFR) inhibitor, a CRISPR enzyme, or any combination thereof.

5. The antibody-drug conjugate of claim 1 or claim 2, wherein the anti-TM4SF1 antibody or the antigen binding fragment thereof and the therapeutic molecule are conjugated by the linker in a single or a multistep protocol.

6. The antibody-drug conjugate of claim 1 or claim 2, wherein the linker comprises a MC (6-maleimidocaproyl), a MCC (a maleimidomethyl cyclohexane-1-carboxylate), a MP (maleimidopropanoyl), a val-cit (valine-citrulline), a val-ala (valine-alanine), an ala-phe (alanine-phenylalanine), a PAB (p-aminobenzyloxycarbonyl), a SPP (N-Succinimidyl 4-(2-pyridylthio)pentanoate), 2,5-dioxopyrrolidin-1-yl 4-(pyridin-2-ylthio)hexanoate, 2,5-dioxopyrrolidin-1-yl 5-methyl-4-(pyridin-2-ylthio)hexanoate, 2,5-dioxopyrrolidin-1-yl 5-methyl-4-(pyridin-2-ylthio)heptanoate, 2,5-dioxopyrrolidin-1-yl 5-ethyl-4-(pyridin-2-ylthio)heptanoate, 2,5-dioxopyrrolidin-1-yl 4-cyclopropyl-4-(pyridin-2-ylthio)butanoate, 2,5-dioxopyrrolidin-1-yl 4-5-cyclobutyl-4-(pyridin-2-ylthio)butanoate, 2,5-dioxopyrrolidin-1-yl 4-cyclopentyl-4-(pyridin-2-ylthio)butanoate, 2,5-dioxopyrrolidin-1-yl 4-cyclohexyl-4-(pyridin-2-ylthio)butanoate, a SMCC (N-Succinimidyl 4-(N-maleimidomethyl)cyclohexane-1 carboxylate), a SIAB (N-Succinimidyl (4-iodo-acetyl)aminobenzoate), or a spacer comprising an amide, an ester, an ether, substituted or unsubstituted $C_1$-$C_6$ alkylene, substituted or unsubstituted $C_1$-$C_6$ haloalkylene, substituted or unsubstituted $C_1$-$C_6$ heteroalkylene, substituted or unsubstituted $C_3$-$C_8$ cycloalkylene, substituted or unsubstituted $C_2$-$C_7$ heterocycloalkylene, substituted or unsubstituted arylene, a substituted or unsubstituted heteroarylene, or any combination thereof.

7. The antibody-drug conjugate of claim 1 or claim 2, wherein the linker is a cross-linking reagent that comprises iodoacetamide, bromoacetamide, vinyl pyridine, disulfide, pyridyl disulfide, isocyanate, isothiocyanate, N-succinimidyl-3-(2-pyridyldithio)propionate (SPDP), 2,5-dioxopyrrolidin-1-yl 3-cyclopropyl-3-(pyridin-2-yldisulfaneyl)propanoate, 2,5-dioxopyrrolidin-1-yl 3-cyclobutyl-3-(pyridin-2-yldisulfaneyl)propanoate, N-succinimidyl 4-(2-pyridyldithio)pentanoate (SPP), 2,5-dioxopyrrolidin-1-yl 4-cyclopropyl-4-(pyridin-2-yldisulfaneyl)butanoate, 2,5-dioxopyrrolidin-1-yl 4-cyclobutyl-4-(pyridin-2-yldisulfaneyl)butanoate, N-succinimidyl 4-(2-pyridyldithio)butanoate (SPDB), 2,5-dioxopyrrolidin-1-yl 4-cyclopropyl-4-(pyridin-2-yldisulfaneyl)butanoate, 2,5-dioxopyrrolidin-1-yl 4-cyclobutyl-4-(pyridin-2-yldisulfaneyl)butanoate, N-succinimidyl-4-(2-pyridyldithio)-2-sulfo-butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl) cyclohexanecarboxylate (SMCC), N-sulfosuccinimidyl 4-(maleimidomethyl) cyclohexanecarboxylate (sulfo-SMCC), or 2,5-dioxopyrrolidin-1-yl 17-(2,5-dioxo-2, 5-dihydro-1 H-pyrrol-1-yl)-5,8, 11,14-tetraoxo-4,7,10,13-tetraazaheptadecan-1-oate (CX1-1).

* * * * *